US008349565B2

(12) United States Patent
Kokoris et al.

(10) Patent No.: US 8,349,565 B2
(45) Date of Patent: *Jan. 8, 2013

(54) HIGH THROUGHPUT NUCLEIC ACID SEQUENCING BY EXPANSION

(75) Inventors: Mark Stamatios Kokoris, Bothell, WA (US); Robert N. McRuer, Mercer Island, WA (US)

(73) Assignee: Stratos Genomics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/075,864

(22) Filed: Mar. 30, 2011

(65) Prior Publication Data

US 2011/0251079 A1      Oct. 13, 2011

Related U.S. Application Data

(63) Continuation of application No. 12/142,221, filed on Jun. 19, 2008, now Pat. No. 7,939,259.

(60) Provisional application No. 60/945,031, filed on Jun. 19, 2007, provisional application No. 60/981,916, filed on Oct. 23, 2007, provisional application No. 61/000,305, filed on Oct. 25, 2007.

(51) Int. Cl.
*C12Q 1/68* (2006.01)
*C12P 19/34* (2006.01)
*C07H 21/04* (2006.01)

(52) U.S. Cl. ............... 435/6.12; 435/91.2; 536/24.31; 536/24.32

(58) Field of Classification Search ................... None
See application file for complete search history.

(56) References Cited

U.S. PATENT DOCUMENTS

| | | | | |
|---|---|---|---|---|
| 4,415,732 | A | 11/1983 | Caruthers et al. | 536/27 |
| 4,458,066 | A | 7/1984 | Caruthers et al. | 536/27 |
| 5,378,825 | A | 1/1995 | Cook et al. | 536/25.34 |
| 5,432,272 | A | 7/1995 | Benner | 536/25.3 |
| 5,770,713 | A | 6/1998 | Imbach et al. | 536/22.1 |
| 5,804,375 | A | 9/1998 | Gelfand et al. | 435/6 |
| 5,844,106 | A | 12/1998 | Seela et al. | 536/22.1 |
| 6,150,510 | A | 11/2000 | Seela et al. | 536/22.1 |
| 6,242,589 | B1 | 6/2001 | Cook et al. | 536/24.5 |
| 6,329,178 | B1 | 12/2001 | Patel et al. | 435/91.1 |
| 6,395,524 | B2 | 5/2002 | Loeb et al. | 435/193 |
| 6,465,193 | B2 | 10/2002 | Akeson et al. | 435/7.1 |
| 6,602,695 | B2 | 8/2003 | Patel et al. | 435/194 |
| 6,627,067 | B1 | 9/2003 | Branton et al. | 205/778 |
| 6,723,513 | B2 | 4/2004 | Lexow | 435/6 |
| 6,951,720 | B2 | 10/2005 | Burgin, Jr. et al. | 435/6 |
| 7,060,440 | B1 | 6/2006 | Kless | 435/6 |
| 7,060,507 | B2 | 6/2006 | Akeson et al. | 436/518 |
| 7,371,851 | B1 | 5/2008 | Lexow | 536/25.3 |
| 7,939,259 | B2* | 5/2011 | Kokoris et al. | 435/6.1 |
| 2002/0028458 | A1 | 3/2002 | Lexow | 435/6 |
| 2002/0182601 | A1 | 12/2002 | Sampson et al. | 435/6 |
| 2005/0032053 | A1 | 2/2005 | Sampson | 435/6 |
| 2007/0048748 | A1 | 3/2007 | Williams et al. | 435/6 |
| 2007/0254280 | A1 | 11/2007 | Lexow et al. | 435/6 |
| 2009/0181385 | A1 | 7/2009 | McKernan et al. | 435/6 |

FOREIGN PATENT DOCUMENTS

| | | |
|---|---|---|
| WO | WO 92/02258 A1 | 2/1992 |
| WO | WO 93/10820 A1 | 6/1993 |
| WO | WO 94/22892 A1 | 10/1994 |
| WO | WO 94/24144 A2 | 10/1994 |
| WO | WO 00/79257 A1 | 12/2000 |
| WO | WO 2004/094663 A2 | 11/2004 |

OTHER PUBLICATIONS

Abramova et al., "A facile and effective synthesis of dinucleotide 5'-triphosphates", *Bioorg Med Chem* 15: 6549-6555, 2007.
Agrawal, "Functionalization of Oligonucleotides with Amino Groups and Attachment of Amino Specific Reporter Groups", *Methods in Molecular Biology*, vol. 26: *Protocols for Oligonucleotide Conjugates*, Agrawal, ed., Humana Press Inc., Totowa, NJ, 1994, pp. 93-120.
Agrawal et al., "Oliogodeoxynucleoside phosphoramidates and phosphorothioates as inhibitors of human immunodeficiency virus", *PNAS* 85: 7079-83, Oct. 1988.
Agrawal et al., "Site specific functionalization of oligonucleotides for attaching two different reporter groups", *Nucleic Acids Research* 18(18): 5419-5423, 1990.
Benoiton, "Chemistry of Peptide Synthesis", CRC Press, Ottawa, Ontario, Canada, 2005.
Branton et al., "The potential and challenges of nanopore sequencing," *Nature Biotechnology* 26(10): 1146-1153, Oct. 2008.
Burgess and Cook, "Syntheses of Nucleoside Triphosphates", *Chem. Rev.* 100(6): 2047-2059, 2000.
de Lange et al., "Cell biology beyond the diffraction limit: near-field scanning optical microscopy," *J. Cell Sci.* 114: 4153-60, 2001.
DeMattei et al., "Designed Dendrimer Syntheses by Self-Assembly of Single-Site, ssDNA Functionalized Dendrons", *Nano Letters* 4(5):771-77, 2004.
De Mesmaeker et al., "Amide Backbone Modifications for Antisense Oligonucleotides Carrying Potential Intercalating Substituents: Influence on the Thermodynamic Stability of the Corresponding Duplexes with RNA- and DNA- Complements", *Bioorganic & Medicinal Chemistry Letters* 7(14): 1869-1874, 1997.

(Continued)

*Primary Examiner* — Prabha Chunduru
(74) *Attorney, Agent, or Firm* — Seed IP Law Group PLLC

(57) ABSTRACT

Nucleic acid sequencing methods and related products are disclosed. Methods for sequencing a target nucleic acid comprise providing a daughter strand produced by a template-directed synthesis, the daughter strand comprising a plurality of subunits coupled in a sequence corresponding to a contiguous nucleotide sequence of all or a portion of the target nucleic acid, wherein the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand, the Xpandomer comprising the tethers and reporter elements for parsing genetic information in a sequence corresponding to the contiguous nucleotide sequence of all or a portion of the target nucleic acid. Reporter elements of the Xpandomer are then detected. Corresponding products, including Xpandomers and oligomeric and monomeric substrate constructs are also disclosed.

30 Claims, 75 Drawing Sheets

OTHER PUBLICATIONS

Efimov et al., "Synthesis of polyacrylamides N-substituted with PNA-like oligonucleotide mimics for molecular diagnostic applications," *Nucleic Acids Res. 27*(22): 4416-4426, 1999.

Fathi et al., "Oligonucleotides with novel, cationic backbone substituents: aminoethylphosphonates", *Nucleic Acids Research 22*(24): 5416-5424, 1994.

Ferree et al., "Electrokinetic Stretching of Tethered DNA", *Biophysical Journal 85*: 2539-2546, Oct. 2003.

Gellman, "Foldamers: a manifesto", *Acc Chem Res 31*(4): 173-80, 1998.

Gish et al., "DNA and RNA Sequence Determination Based on Phosphorothioate Chemistry", *Science 240*(4858): 1520-1522, Jun. 10, 1988.

Holmes et al., "Reagents for Combinatorial Organic Synthesis: Development of a New o-Nitrobenzyl Photolabile Linker for Solid Phase Synthesis", *J Org Chem, 60*(8): 2318-19, 1995.

Hong et al., "DNA microarrays on nanoscale-controlled surface", *Nucleic Acids Research 33*(12): e106(1-8), 2005.

Igloi et al., "Enzymatic Addition of Fluorescein- or Biotin-RiboUTP to Oligonucleotides Results in Primers Suitable for DNA Sequencing and PCR", *BioTechniques 15*(3): 486-497, 1993.

Jo et al., "A single-molecule barcoding system using nanoslits for DNA analysis", *PNAS 104*(8): 2673-2678, Feb. 20, 2007.

Ju et al., "Four-color DNA sequencing by synthesis using cleavable fluorescent nucleotide reversible terminators", *PNAS 103*(52): 19635-19640, Dec. 26, 2006.

Kayushin et al., "A convenient approach to the synthesis of trinucleotide phosphoramidites—synthons for the generation of oligonucleotide/ peptide libraries," *Nucl Acids Res 24*(19): 3748-55, 1996.

Kenney et al., "Mutation Typing Using Electrophoresis and Gel-Immobilized Acrydite™ Probes", *BioTechniques 25*(3): 516-21, 1998.

Lee, "Ligase Chain Reaction", *Biologicals 24*(3): 197-199, 1996.

Lee, "Nanoelectrode-Gated Detection of Individual Molecules with Potential for Rapid DNA Sequencing", *Solid State Phenomena 121-123*: 1379-1386, 2007.

Lee and Meller, "Rapid DNA Sequencing by Direct Nanoscale Reading of Nucleotide Bases on Individual DNA Chains," Chapter 8 in *New High Throughput Technologies for DNA Sequencing and Genomics*, vol. 2 (*Perspectives in Bioanalysis*), Mitchelson, ed., Elsevier B.V., Amsterdam, The Netherlands, 2007, pp. 245-263.

Levene et al., "Zero-Mode Waveguides for Single-Molecule Analysis at High Concentrations," *Science 299*: 682-86, Jan. 31, 2003.

Mag et al., "Synthesis and selective cleavage of an oligodeoxynucleotide containing a bridged internucleotide 5'-phosphorothioate linkage", *Nucleic Acids Research 19*(7): 1437-1441, 1991.

Mag et al., "Synthesis and selective cleavage of oligodeoxyribonucleotides containing non-chiral internucleotide phosphoramidate linkages", *Nucleic Acids Research 17*(15): 5973-5988, 1989.

Matsukura et al., "Phosphorothioate analogs of oligodeoxynucleotides: Inhibitors of replication and cytopathic effects of human immunodeficiency virus", *PNAS 84*: 7706-7710, Nov. 1987.

Meagher et al., "End-labeled free-solution electrophoresis of DNA", *Electrophoresis 26*: 331-350, 2005.

Merrifield, "Solid Phase Peptide Synthesis. I. The Synthesis of a Tetrapeptide", *J. Am. Chem. Soc. 85*: 2149-2154, Jul. 20, 1963.

Metzker et al., "Termination of DNA synthesis by novel 3'-modified-deoxyribonucleoside 5'-triphosphates," *Nucleic Acids Res. 22*(20): 4259-4267, 1994.

Miles, "Scanning Probe Microscopy—Probing the Future," *Science 277*: 1845-1847, Sep. 19, 1997.

Montoliu et al., "Visualization of Large DNA Molecules by Electron Microscopy with Polyamines: Application to the Analysis of Yeast Endogenous and artificial Chromosomes", *J. Mol. Biol. 246*: 486-92, 1995.

Nauwelaerts et al., "Cleavage of DNA without loss of genetic information by incorporation of a disaccharide nucleoside", *Nucleic Acids Research 31*(23): 6758-6769, 2003.

Obika et al., "Acid-Mediated Cleavage of Oligonucleotide P3'→N5' Phosphoramidates Triggered by Sequence-Specific Triplex Formation", *Nucleosides, Nucleotides and Nucleic Acids 26*(8): 893-896, 2007.

Ordoukhanian et al., "Design and Synthesis of a Versatile Photocleavable DNA Building Block, Application to Phototriggered Hybridization", *J. Am. Chem. Soc. 117*: 9570 (7 pgs.), 1995.

Proudnikov et al., "Immobilization of DNA in Polyacrylamide Gel for the Manufacture of DNA and DNA-Oligonucleotide Microchips", *Analytical Biochemistry 259*: 34-41, 1998.

Ruparel et al., "Design and synthesis of a 3'-O-allyl photocleavable fluorescent nucleotide as a reversible terminator for DNA sequencing by synthesis", *PNAS 102*(17): 5932-5937, Apr. 26, 2005.

Sauer et al., "A novel procedure for efficient genotyping of single nucleotide polymorphisms", *Nucleic Acids Research 28*(5): e13(i-viii), 2000.

Sauer et al., "MALDI mass spectrometry analysis of single nucleotide polymorphisms by photocleavage and charge-tagging", *Nucleic Acids Research 31*(11): e63(1-10), 2003.

Sayers et al., "Inhibition of restriction endonuclease hydrolysis by phosphorothioate-containing DNA", *Nucleic Acids Research 17*(22): 9495, Nov. 22, 1989.

Semkin et al., "Synthesis of peptides on a resin by the mixed anhydride method", *Chemistry of Natural Compounds 3*(3): 182-183, May-Jun. 1967.

Seo et al., "Four-color DNA sequencing by synthesis on a chip using photocleavable fluorescent nucleotides," *PNAS 102*(17): 5926-5931, Apr. 26, 2005.

Singer, "Alkyl Bases, Nucleosides, and Nucleotides: UV Spectral Characteristics and Acidic Dissociation Constants of 280 Alkyl Bases, Nucleosides, and Nucleotides," in *Practical Handbook of Biochemistry and Molecular Biology*, Fasman, ed., CRC Press, Boca Raton, LA, 1989, pp. 385-394.

Sinyakov et al., "Functionalization of the Oligonucleotides Containing an Internucleotide Phosphoramidate Bond", *Russian J Bioorganic Chem 29*(1): 88-90, 2003.

Spagna et al., "Stabilization of a β-glucosidase from *Aspergillus niger* by binding to an amine agarose gel", *J Molecular Catalysis B: Enzymatic 11*: 63-69, 2000.

Starr et al., "Total Internal Reflection with Fluorescence Correlation Spectroscopy: Combined Surface Reaction and Solution Diffusion," *Biophys J 80*: 1575-84, Mar. 2001.

Stewart et al., "A quantitative assay for assessing allelic proportions by iterative gap ligation", *Nucleic Acids Research 26*(4): 961-966, 1998.

Summers et al., "Boranophosphates as Mimics of Natural Phosphodiesters in DNA", *Curr Med Chem. 8*(10): 1147-55, 2001.

Vallone et al., "Genotyping SNPs Using a UV-Photocleavable Oligonucleotide in MALDI-TOF MS", Chapter 12 in *Methods in Molecular Biology*, vol. 297: *Forensic DNA Typing Protocols*, Carracedo, ed., Humana Press Inc., Totowa NJ, 2004, pp. 169-178.

Vyle et al., "Sequence- and Strand-Specific Cleavage in Oligodeoxyribonucleotides and DNA Containing 3'-Thiothymidine", *Biochemistry 31*(11): 3012-3018, 1992.

Wiedmann et al., "Ligase Chain Reaction (LCR)—Overview and Applications," *PCR Methods Appl 3*: S51-S64, 1994.

* cited by examiner

FIG. 6

| Reporter Code | Fluorescence (F) | Reporter Code | Fluorescence (F) |
|---|---|---|---|
| 1 | RED | 12 | RED-blue |
| 2 | GREEN | 13 | green-blue |
| 3 | BLUE | 14 | GREEN-blue |
| 4 | red | 15 | green-Blue |
| 5 | green | 16 | red-green-blue |
| 6 | blue | 17 | RED-green-blue |
| 7 | red-green | 18 | red-GREEN-blue |
| 8 | red-blue | 19 | red-green-BLUE |
| 9 | red-GREEN | 20 | RED-GREEN-blue |
| 10 | red-BLUE | 21 | red-GREEN-BLUE |
| 11 | RED-green | 22 | RED-green-BLUE |

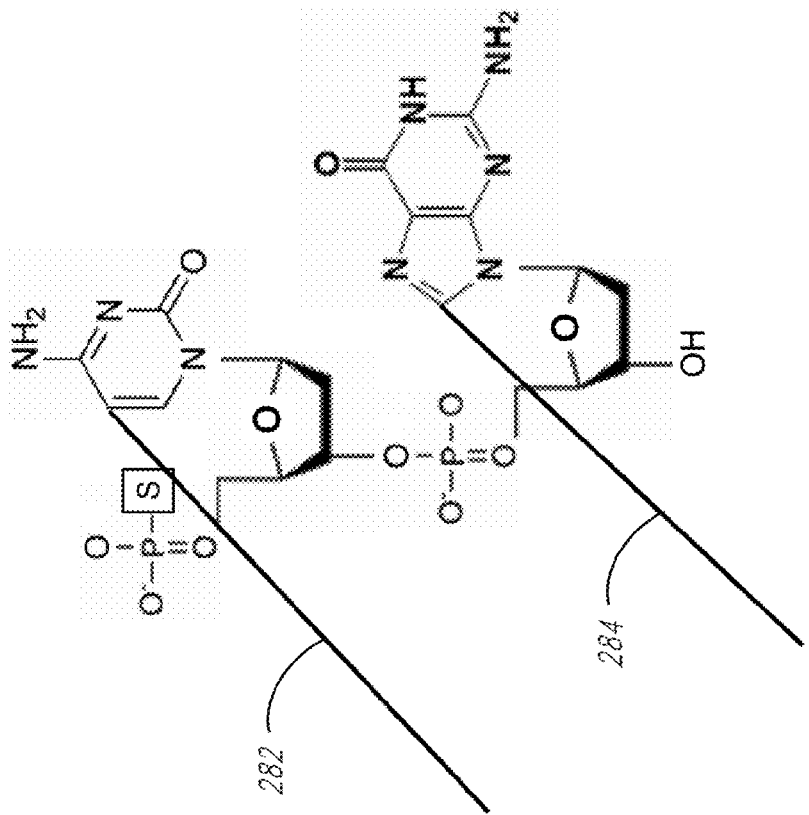
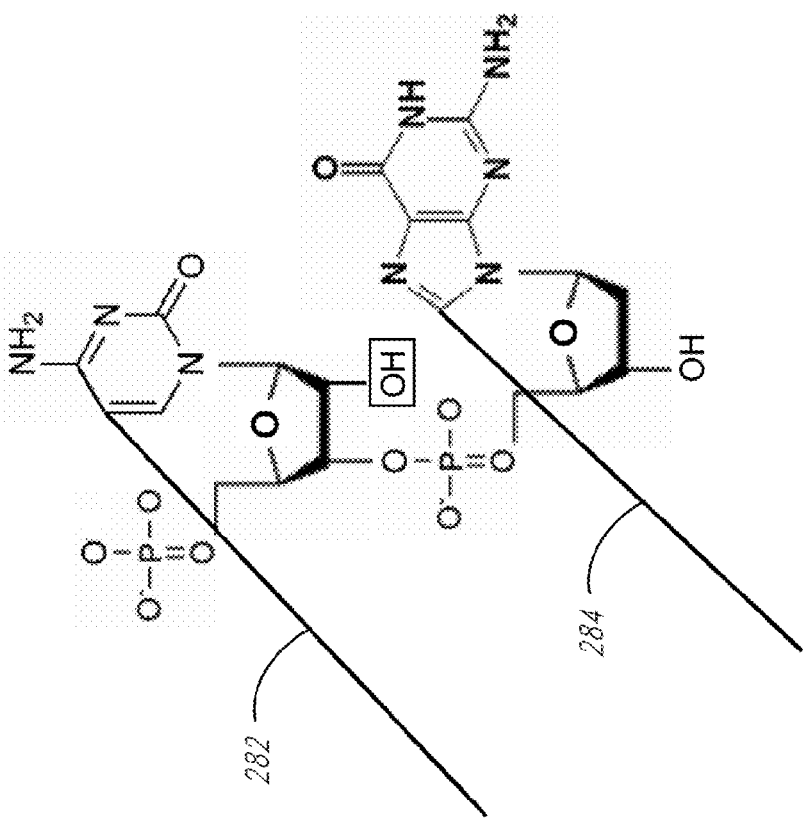

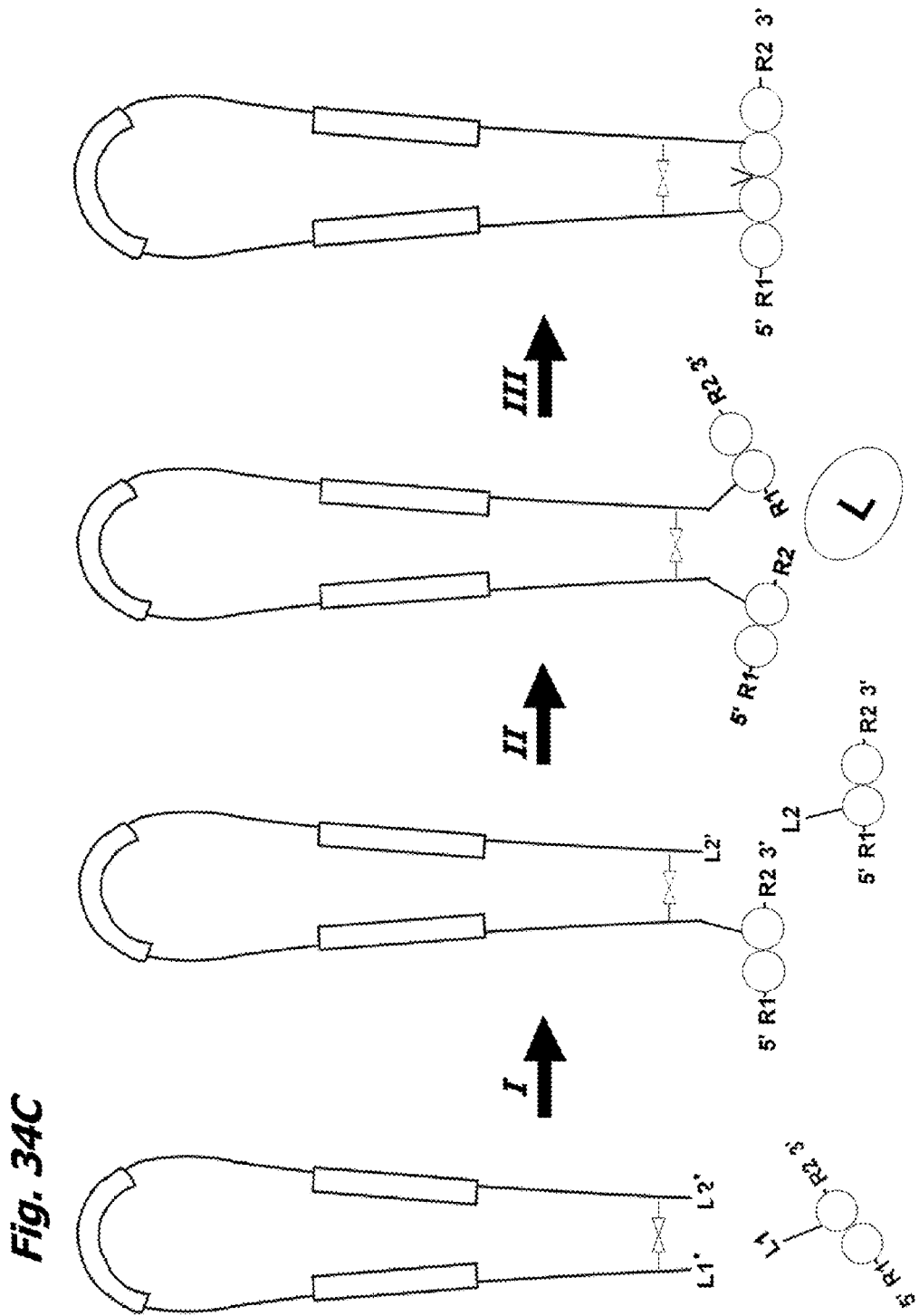

Fig. 37

| Label Identity | Mass (M) | Fluorescence (F) | Chemical Linkers | |
|---|---|---|---|---|
| 1 | M1 | RED | HYDRAZINE | - |
| 2 | M2 | GREEN | AMINE | - |
| 3 | M3 | BLUE | CARBOXYL | - |
| 4 | m1 | red | hydrazine | - |
| 5 | m2 | green | amine | - |
| 6 | m3 | blue | carboxyl | - |
| 7 | m1-m2 | red-green | hydrazine | amine |
| 8 | m1-m3 | red-blue | hydrazine | carboxyl |
| 9 | m1-M2 | red-GREEN | AMINE | - |
| 10 | m1-M3 | red-BLUE | hydrazine | CARBOXYL |
| 11 | M1-m2 | RED-green | HYDRAZINE | amine |
| 12 | M1-m3 | RED-blue | HYDRAZINE | carboxyl |
| 13 | m2-m3 | green-blue | - | amine |
| 14 | M2-m3 | GREEN-blue | - | AMINE |
| 15 | m2-M3 | green-Blue | - | amine |
| 16 | m1-m2-m3 | red-green-blue | hydrazine | amine carboxyl |
| 17 | M1-m2-m3 | RED-green-blue | HYDRAZINE | amine carboxyl |
| 18 | m1-M2-m3 | red-GREEN-blue | hydrazine | AMINE carboxyl |
| 19 | m1-m2-M3 | red-green-BLUE | hydrazine | amine CARBOXYL |
| 20 | M1-M2-m3 | RED-GREEN-blue | HYDRAZINE | AMINE carboxyl |
| 21 | m1-M2-M3 | red-GREEN-BLUE | hydrazine | AMINE CARBOXYL |
| 22 | M1-m2-M3 | RED-green-BLUE | HYDRAZINE | amine CARBOXYL |

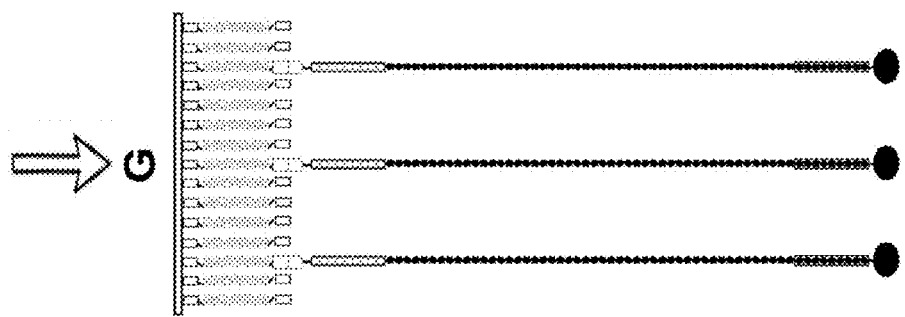
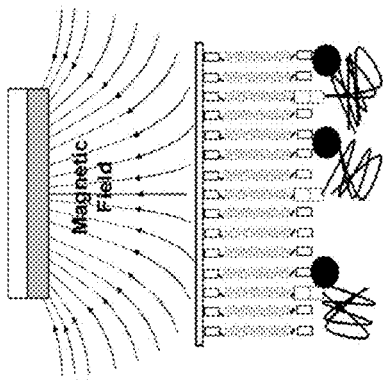
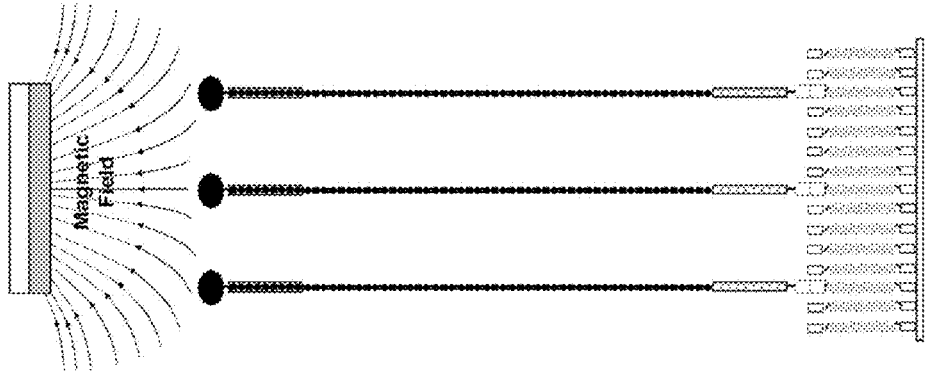

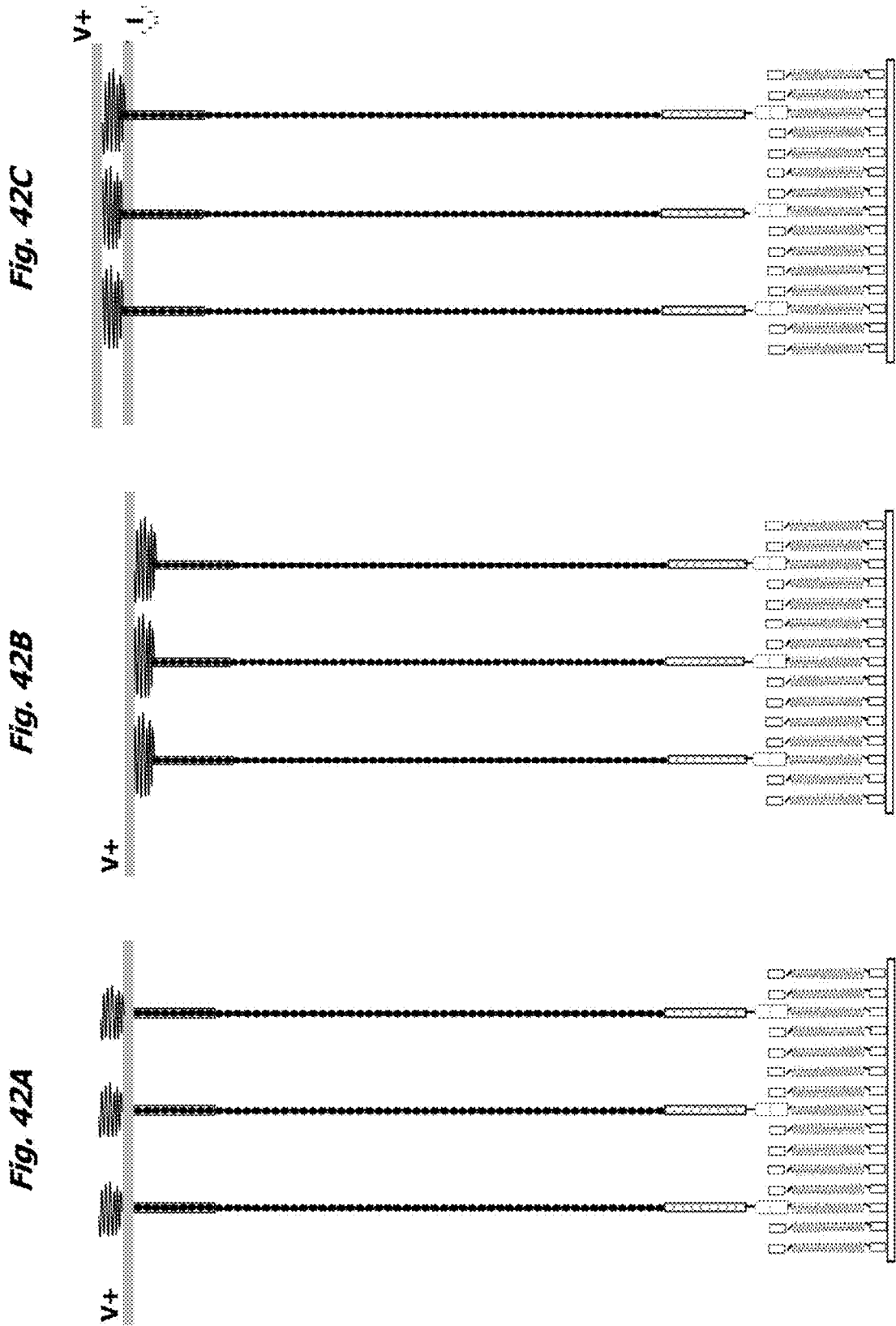

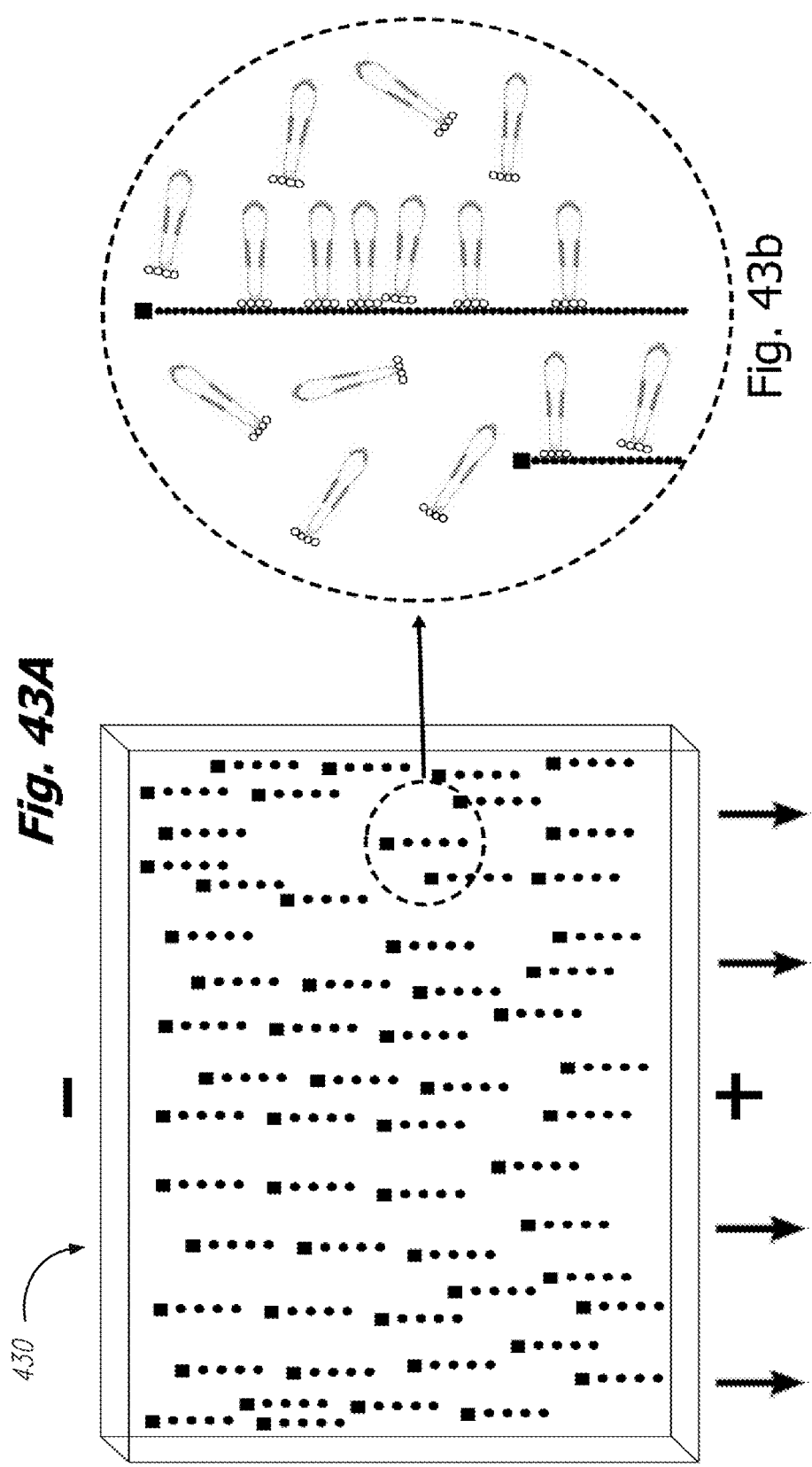

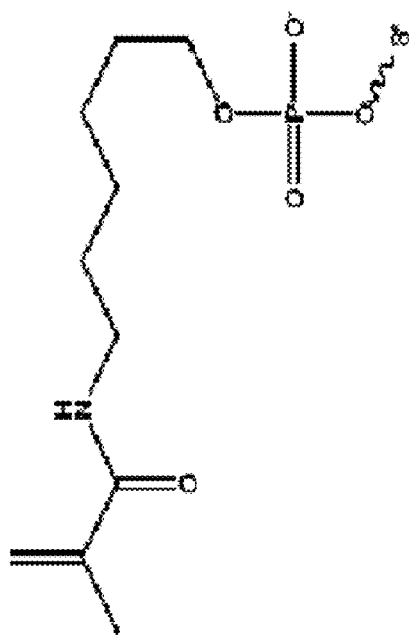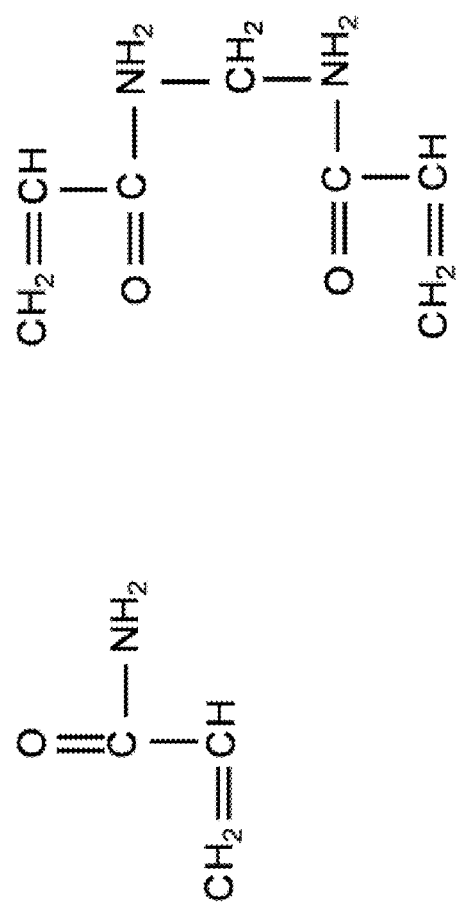
Fig. 43C

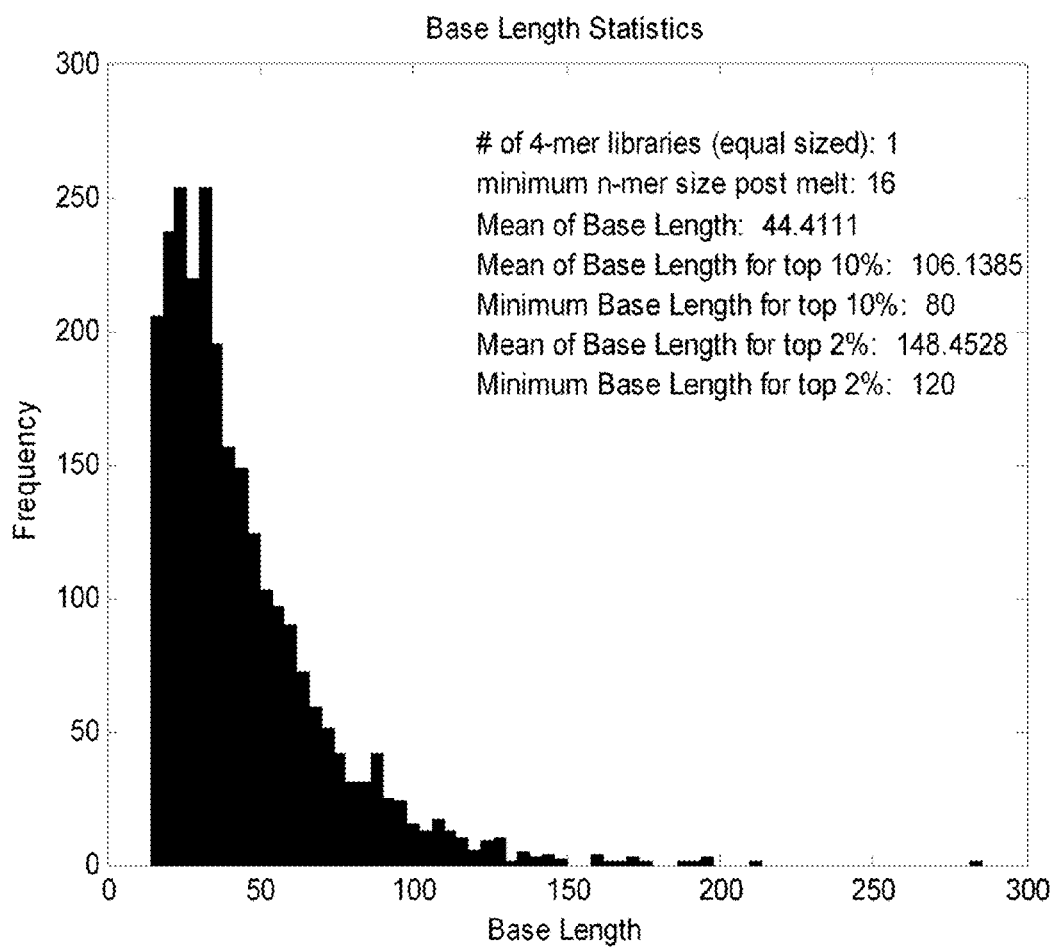

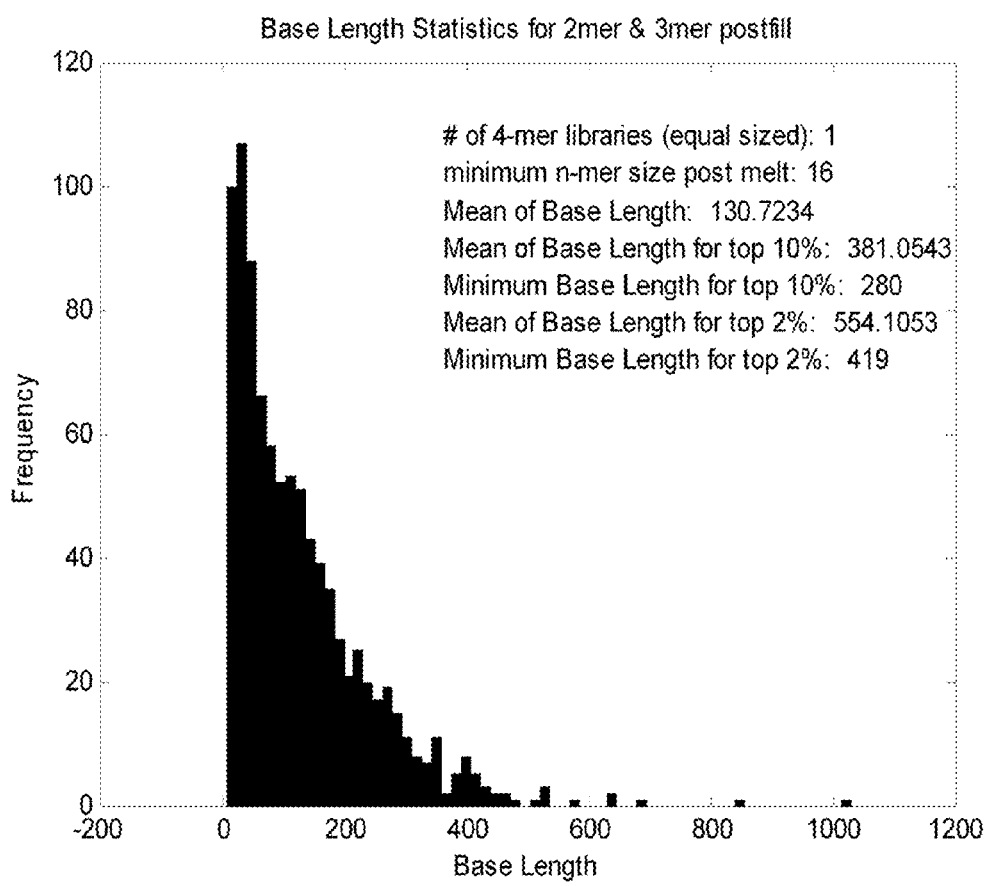

*Fig. 53*
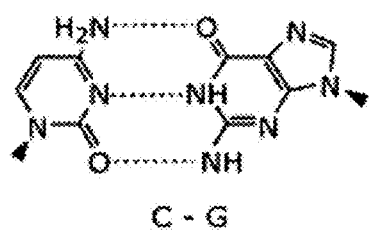
C - G
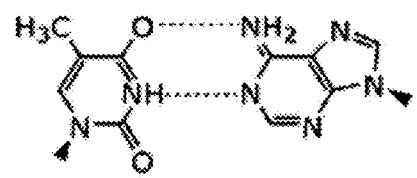
T (or U) - A
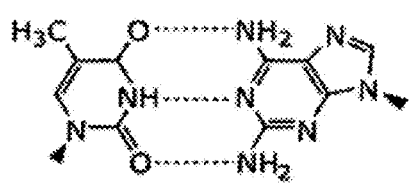
T (or U) - 2-amino A
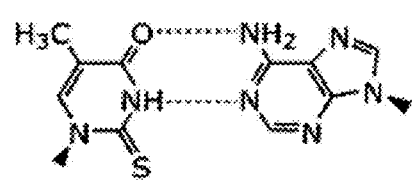
2-thio T (or U) - A
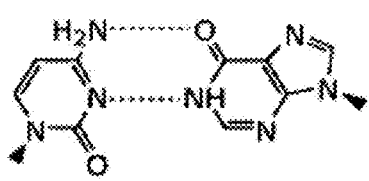
C - I
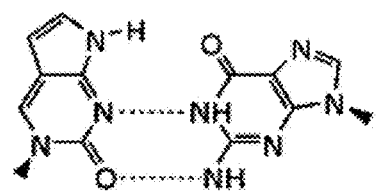
PyrroloPyr - G
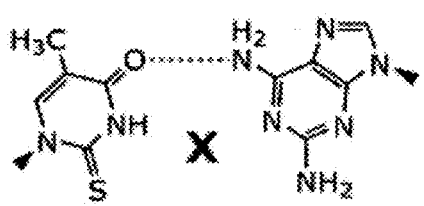
2-thio T (or U) - 2-amino A
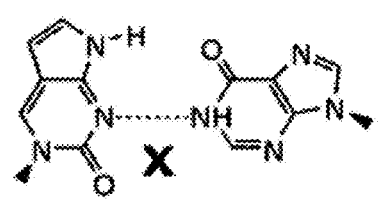
PyrroloPyr - I
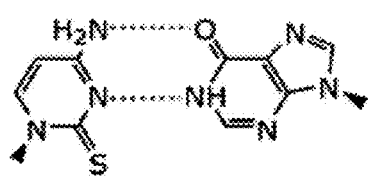
2-thio C - I
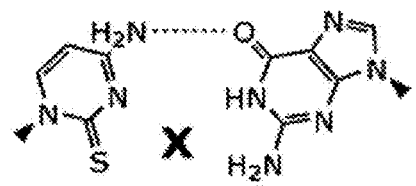
2-thio C - G

HIGH THROUGHPUT NUCLEIC ACID SEQUENCING BY EXPANSION

CROSS-REFERENCES TO RELATED APPLICATIONS

This application is a continuation of U.S. patent application Ser. No. 12/142,221, filed Jun. 19, 2008 (allowed); which claims the benefit under 35 U.S.C. §119(e) of U.S. Provisional Patent Application No. 60/945,031 filed on Jun. 19, 2007; U.S. Provisional Patent Application No. 60/981,916 filed on Oct. 23, 2007; and U.S. Provisional Patent Application No. 61/000,305 filed on Oct. 25, 2007; all of which are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 870225_401C1_SEQUENCE_LISTING.txt. The text file is 2 KB, was created on Jun. 9, 2011, and is being submitted electronically via EFS-Web.

BACKGROUND

1. Technical Field

This invention is generally related to nucleic acid sequencing, as well as methods and products relating to the same.

2. Description of the Related Art

Nucleic acid sequences encode the necessary information for living things to function and reproduce, and are essentially a blueprint for life. Determining such sequences is therefore a tool useful in pure research into how and where organisms live, as well as in applied sciences such drug development. In medicine, sequencing tools can be used for diagnosis and to develop treatments for a variety of pathologies, including cancer, heart disease, autoimmune disorders, multiple sclerosis, or obesity. In industry, sequencing can be used to design improved enzymatic processes or synthetic organisms. In biology, such tools can be used to study the health of ecosystems, for example, and thus have a broad range of utility.

An individual's unique DNA sequence provides valuable information concerning their susceptibility to certain diseases. The sequence will provide patients with the opportunity to screen for early detection and to receive preventative treatment. Furthermore, given a patient's individual blueprint, clinicians will be capable of administering personalized therapy to maximize drug efficacy and to minimize the risk of an adverse drug response. Similarly, determining the blueprint of pathogenic organisms can lead to new treatments for infectious diseases and more robust pathogen surveillance. Whole genome DNA sequencing will provide the foundation for modern medicine.

DNA sequencing is the process of determining the order of the chemical constituents of a given DNA polymer. These chemical constituents, which are called nucleotides, exist in DNA in four common forms: deoxyadenosine (A), deoxyguanosine (G), deoxycytidine (C), and deoxythymidine (T). Sequencing of a diploid human genome requires determining the sequential order of approximately 6 billion nucleotides.

Currently, most DNA sequencing is performed using the chain termination method developed by Frederick Sanger. This technique, termed Sanger Sequencing, uses sequence specific termination of DNA synthesis and fluorescently modified nucleotide reporter substrates to derive sequence information. This method sequences a target nucleic acid strand, or read length, of up to 1000 bases long by using a modified polymerase chain reaction. In this modified reaction the sequencing is randomly interrupted at select base types (A, C, G or T) and the lengths of the interrupted sequences are determined by capillary gel electrophoresis. The length then determines what base type is located at that length. Many overlapping read lengths are produced and their sequences are overlaid using data processing to determine the most reliable fit of the data. This process of producing read lengths of sequence is very laborious and expensive and is now being superseded by new methods that have higher efficiency.

The Sanger method was used to provide most of the sequence data in the Humane Genome Project which generated the first complete sequence of the human genome. This project took over 10 years and nearly $3B to complete. Given these significant throughput and cost limitations, it is clear that DNA sequencing technologies will need to improve drastically in order to achieve the stated goals put forth by the scientific community. To that end, a number of second generation technologies, which far exceed the throughput and cost per base limitations of Sanger sequencing, are gaining an increasing share of the sequencing market. Still, these "sequencing by synthesis" methods fall short of achieving the throughput, cost, and quality targets required by markets such as whole genome sequencing for personalized medicine.

For example, 454 Life Sciences is producing instruments (e.g., the Genome Sequencer) that can process 100 million bases in 7.5 hours with an average read length of 200 nucleotides. Their approach uses a variation of Polymerase Chain Reaction ("PCR") to produce a homogeneous colony of target nucleic acid, hundreds of bases in length, on the surface of a bead. This process is termed emulsion PCR. Hundreds of thousands of such beads are then arranged on a "picotiter plate". The plate is then prepared for an additional sequencing whereby each nucleic acid base type is sequentially washed over the plate. Beads with target that incorporate the base produce a pyrophosphate byproduct that can be used to catalyze a light producing reaction that is then detected with a camera.

Illumina Inc. has a similar process that uses reversibly terminating nucleotides and fluorescent labels to perform nucleic acid sequencing. The average read length for Illumina's 1G Analyzer is less than 40 nucleotides. Instead of using emulsion PCR to amplify sequence targets, Illumina has an approach for amplifying PCR colonies on an array surface. Both the 454 and Illumina approaches use a complicating polymerase amplification to increase signal strength, perform base measurements during the rate limiting sequence extension cycle, and have limited read lengths because of incorporation errors that degrade the measurement signal to noise proportionally to the read length.

Applied Biosystems uses reversible terminating ligation rather than sequencing-by-synthesis to read the DNA. Like 454's Genome Sequencer, the technology uses bead-based emulsion PCR to amplify the sample. Since the majority of the beads do not carry PCR products, the researchers next use an enrichment step to select beads coated with DNA. The biotin-coated beads are spread and immobilized on a glass slide array covered with streptavidin. The immobilized beads are then run through a process of 8-mer probe hybridization (each labeled with four different fluorescent dyes), ligation, and cleavage (between the 5th and 6th bases to create a site for the next round of ligation). Each probe interrogates two bases, at positions 4 and 5 using a 2-base encoding system, which is recorded by a camera. Similar to Illumina's approach, the average read length for Applied Biosystems' SOLiD platform is less than 40 nucleotides.

Other approaches are being developed to avoid the time and expense of the polymerase amplification step by measuring single molecules of DNA directly. Visigen Biotechnologies, Inc. is measuring fluorescently labeled bases as they are sequenced by incorporating a second fluorophore into an engineered DNA polymerase and using Forster Resonance Energy Transfer (FRET) for nucleotide identification. This technique is faced with the challenges of separating the signals of bases that are separated by less than a nanometer and by a polymerase incorporation action that will have very large statistical variation.

A process being developed by LingVitae sequences cDNA inserted into immobilized plasmid vectors. The process uses a Class IIS restriction enzyme to cleave the target nucleic acid and ligate an oligomer into the target. Typically, one or two nucleotides in the terminal 5' or 3' overhang generated by the restriction enzyme determine which of a library of oligomers in the ligation mix will be added to the sticky, cut end of the target. Each oligomer contains "signal" sequences that uniquely identify the nucleotide(s) it replaces. The process of cleavage and ligation is then repeated. The new molecule is then sequenced using tags specific for the various oligomers. The product of this process is termed a "Design Polymer" and always consists of a nucleic acid longer than the one it replaces (e.g., a dinucleotide target sequence is replaced by a "magnified" polynucleotide sequence of as many as 100 base pairs). An advantage of this process is that the duplex product strand can be amplified if desired. A disadvantage is that the process is necessarily cyclical and the continuity of the template would be lost if simultaneous multiple restriction cuts were made.

U.S. Pat. No. 7,060,440 to Kless describes a sequencing process that involves incorporating oligomers by polymerization with a polymerase. A modification of the Sanger method, with end-terminated oligomers as substrates, is used to build sequencing ladders by gel electrophoresis or capillary chromatography. While coupling of oligomers by end ligation is well known, the use of a polymerase to couple oligomers in a template-directed process was utilized to new advantage.

Polymerization techniques are expected to grow in power as modified polymerases (and ligases) become available through genetic engineering and bioprospecting, and methods for elimination of exonuclease activity by polymerase modification are already known. For example, Published U.S. Patent Application 2007/0048748 to Williams describes the use of mutant polymerases for incorporating dye-labeled and other modified nucleotides. Substrates for these polymerases also include γ-phosphate labeled nucleotides. Both increased speed of incorporation and reduction in error rate were found with chimeric and mutant polymerases.

In addition, a large effort has been made by both academic and industrial teams to sequence native DNA using non-synthetic methods. For example, Agilent Technologies, Inc. along with university collaborators are developing a single molecule detection method that threads the DNA through a nanopore to make measurements as it passes through. As with Visigen and LingVitae, this method must overcome the problem of efficiently and accurately obtaining distinct signals from individual nucleobases separated by sub-nanometer dimensions, as well as the problem of developing reproducible pore sizes of similar size. As such, direct sequencing of DNA by detection of its constituent parts has yet to be achieved in a high-throughput process due to the small size of the nucleotides in the chain (about 4 Angstroms center-to-center) and the corresponding signal to noise and signal resolution limitations therein. Direct detection is further complicated by the inherent secondary structure of DNA, which does not easily elongate into a perfectly linear polymer.

While significant advances have been made in the field of DNA sequencing, there continues to be a need in the art for new and improved methods. The present invention fulfills these needs and provides further related advantages.

BRIEF SUMMARY

In general terms, methods and corresponding devices and products are disclosed that overcome the spatial resolution challenges presented by existing high throughput nucleic acid sequencing techniques. This is achieved by encoding the nucleic acid information on a surrogate polymer of extended length which is easier to detect. The surrogate polymer (referred to herein as an "Xpandomer") is formed by template directed synthesis which preserves the original genetic information of the target nucleic acid, while also increasing linear separation of the individual elements of the sequence data.

In one embodiment, a method is disclosed for sequencing a target nucleic acid, comprising: a) providing a daughter strand produced by a template-directed synthesis, the daughter strand comprising a plurality of subunits coupled in a sequence corresponding to a contiguous nucleotide sequence of all or a portion of the target nucleic acid, wherein the individual subunits comprise a tether, at least one probe or nucleobase residue, and at least one selectively cleavable bond; b) cleaving the at least one selectively cleavable bond to yield an Xpandomer of a length longer than the plurality of the subunits of the daughter strand, the Xpandomer comprising the tethers and reporter elements for parsing genetic information in a sequence corresponding to the contiguous nucleotide sequence of all or a portion of the target nucleic acid; and c) detecting the reporter elements of the Xpandomer.

In more specific embodiments, the reporter elements for parsing the genetic information may be associated with the tethers of the Xpandomer, with the daughter strand prior to cleavage of the at least one selectively cleavable bond, and/or with the Xpandomer after cleavage of the at least one selectively cleavable bond. The Xpandomer may further comprise all or a portion of the at least one probe or nucleobase residue, and the reporter elements for parsing the genetic information may be associated with the at least one probe or nucleobase residue or may be the probe or nucleobase residues themselves. Further, the selectively cleavable bond may be a covalent bond, an intra-tether bond, a bond between or within probes or nucleobase residues of the daughter strand, and/or a bond between the probes or nucleobase residues of the daughter strand and a target template.

In further embodiments, Xpandomers have the following structures (I) through (X):

Structure (I):

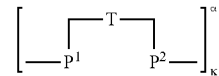

wherein

T represents the tether;

$P^1$ represents a first probe moiety;

$P^2$ represents a second probe moiety;

κ represents the $κ^{th}$ subunit in a chain of m subunits, where m is an integer greater than three; and α represents a species of a subunit motif selected from a library of subunit motifs, wherein each of the species comprises sequence information of the contiguous nucleotide sequence of a portion of the target nucleic acid.

Structure (II):

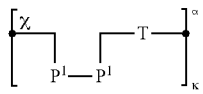

wherein
T represents the tether;
P$^1$ represents a first probe moiety;
P$^2$ represents a second probe moiety;
κ represents the κ$^{th}$ subunit in a chain of m subunits, where m is an integer greater than three;
α represents a species of a subunit motif selected from a library of subunit motifs, wherein each of the species comprises sequence information of the contiguous nucleotide sequence of a portion of the target nucleic acid; and
χ represents a bond with the tether of an adjacent subunit.

Structure (III):

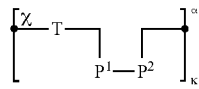

wherein
T represents the tether;
P$^1$ represents a first probe moiety;
P$^2$ represents a second probe moiety;
κ represents the κ$^{th}$ subunit in a chain of m subunits, where m is an integer greater than three;
α represents a species of a subunit motif selected from a library of subunit motifs, wherein each of the species comprises sequence information of the contiguous nucleotide sequence of a portion of the target nucleic acid; and
χ represents a bond with the tether of an adjacent subunit.

Structure (IV):

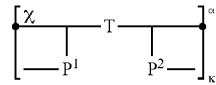

wherein
T represents the tether;
P$^1$ represents a first probe moiety;
P$^2$ represents a second probe moiety;
κ represents the κ$^{th}$ subunit in a chain of m subunits, where m is an integer greater than three;
α represents a species of a subunit motif selected from a library of subunit motifs, wherein each of the species comprises sequence information of the contiguous nucleotide sequence of a portion of the target nucleic acid; and
χ represents a bond with the tether of an adjacent subunit.

Structure (V):

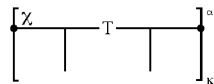

wherein
T represents the tether;
κ represents the κ$^{th}$ subunit in a chain of m subunits, where m is an integer greater than three;
α represents a species of a subunit motif selected from a library of subunit motifs, wherein each of the species comprises sequence information of the contiguous nucleotide sequence of a portion of the target nucleic acid; and
χ represents a bond with the tether of an adjacent subunit.

Structure (VI):

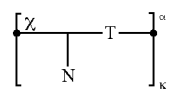

wherein
T represents the tether;
N represents a nucleobase residue;
κ represents the κ$^{th}$ subunit in a chain of m subunits, where m is an integer greater than ten;
α represents a species of a subunit motif selected from a library of subunit motifs, wherein each of the species comprises sequence information of the contiguous nucleotide sequence of a portion of the target nucleic acid; and
χ represents a bond with the tether of an adjacent subunit.

Structure (VII):

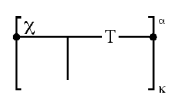

wherein
T represents the tether;
κ represents the κ$^{th}$ subunit in a chain of m subunits, where m is an integer greater than ten;
α represents a species of a subunit motif selected from a library of subunit motifs, wherein each of the species comprises sequence information of the contiguous nucleotide sequence of a portion of the target nucleic acid; and
χ represents a bond with the tether of an adjacent subunit.

Structure (VIII):

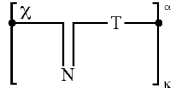

wherein
T represents the tether;
N represents a nucleobase residue;

κ represents the κ$^{th}$ subunit in a chain of m subunits, where m is an integer greater than ten;

α represents a species of a subunit motif selected from a library of subunit motifs, wherein each of the species comprises sequence information of the contiguous nucleotide sequence of a portion of the target nucleic acid; and χ represents a bond with the tether of an adjacent subunit.

Structure (IX):

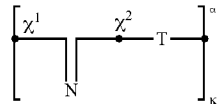

wherein

T represents the tether;

N represents a nucleobase residue;

κ represents the κ$^{th}$ subunit in a chain of m subunits, where m is an integer greater than ten;

α represents a species of a subunit motif selected from a library of subunit motifs, wherein each of the species comprises sequence information of the contiguous nucleotide sequence of a portion of the target nucleic acid;

χ$^1$ represents a bond with the tether of an adjacent subunit; and

χ$^2$ represents an inter-tether bond.

Structure (X):

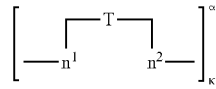

wherein

T represents the tether;

n$^1$ and n$^2$ represents a first portion and a second portion, respectively, of a nucleobase residue;

κ represents the κ$^{th}$ subunit in a chain of m subunits, where m is an integer greater than ten; and α represents a species of a subunit motif selected from a library of subunit motifs, wherein each of the species comprises sequence information of the contiguous nucleotide sequence of a portion of the target nucleic acid.

In further embodiments, oligomer substrate constructs for use in a template directed synthesis for sequencing a target nucleic acid are disclosed. Oligomer substrate constructs comprise a first probe moiety joined to a second probe moiety, each of the first and second probe moieties having an end group suitable for the template directed synthesis, and a tether having a first end and a second end with at least the first end of the tether joined to at least one of the first and second probe moieties, wherein the oligomer substrate construct when used in the template directed synthesis is capable of forming a daughter strand comprising a constrained Xpandomer and having a plurality of subunits coupled in a sequence corresponding to the contiguous nucleotide sequence of all or a portion of the target nucleic acid, wherein the individual subunits comprise a tether, the first and second probe moieties and at least one selectively cleavable bond.

In another embodiment, monomer substrate constructs for use in a template directed synthesis for sequencing a target nucleic acid are disclosed. Monomer substrate constructs comprise a nucleobase residue with end groups suitable for the template directed synthesis, and a tether having a first end and a second end with at least the first end of the tether joined to the nucleobase residue, wherein the monomer substrate construct when used in the template directed synthesis is capable of forming a daughter strand comprising a constrained Xpandomer and having a plurality of subunits coupled in a sequence corresponding to the contiguous nucleotide sequence of all or a portion of the target nucleic acid, wherein the individual subunits comprise a tether, the nucleobase residue and at least one selectively cleavable bond.

In yet further embodiments, template-daughter strand duplexes are disclosed comprising a daughter strand duplexed with a template strand, as well as to methods for forming the same from the template strand and the oligomer or monomer substrate constructs.

These and other aspects of the invention will be apparent upon reference to the attached drawings and following detailed description. To this end, various references are set forth herein which describe in more detail certain procedures, compounds and/or compositions, and are hereby incorporated by reference in their entirety.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

FIG. 6 is a look-up table from which the data of FIG. 5 is derived.

FIGS. 28A through 28D illustrate in more detail Class I-IV substrates of the invention, here showing examples of selectively cleavable bond cleavage sites in the probe backbone and indicating loop end linkages bridging the cleavage sites.

FIGS. 34A through 34C illustrate selected methods of tether loop closure integrated with reporter construct assembly from segments.

FIG. 37 is a table showing composition and chemical methods for assembling reporter constructs and their corresponding reporter codes.

FIGS. 41A through 41E illustrate selected physical stretching methods.

FIGS. 42A through 42C illustrate selected electrostretching methods.

FIGS. 43A through 43D illustrate methods, reagents, and adaptors for stretching in gel matrices.

FIGS. 50A and B describe gap filling simulations using combinations of 2 mers and 3 mers.

FIG. 53 describes nucleotide substitutions used to reduce secondary structure.

DETAILED DESCRIPTION

Figure 1A:
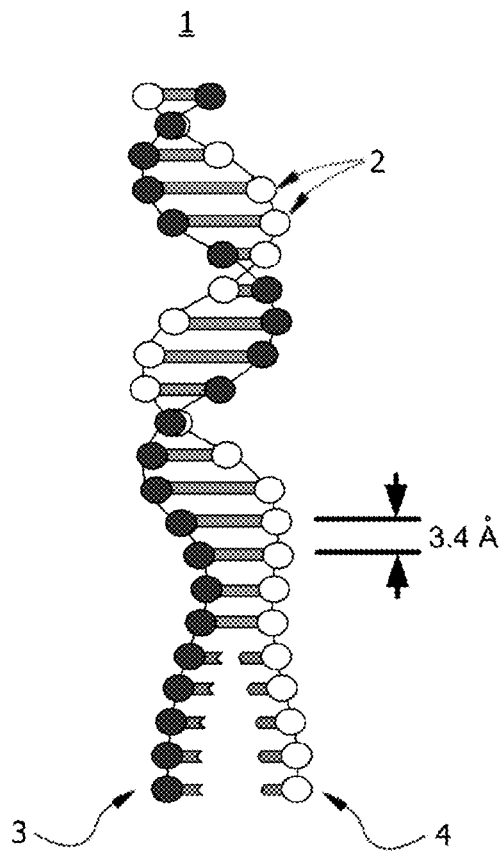
FIGS. 1A and 1B illustrate the limited separation between nucleobases that must be resolved in order to determine the sequence of nucleotides in a nucleic acid target.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Definitions

As used herein, and unless the context dictates otherwise, the following terms have the meanings as specified below.

"Nucleobase" is a heterocyclic base such as adenine, guanine, cytosine, thymine, uracil, inosine, xanthine, hypoxanthine, or a heterocyclic derivative, analog, or tautomer thereof. A nucleobase can be naturally occurring or synthetic. Non-limiting examples of nucleobases are adenine, guanine, thymine, cytosine, uracil, xanthine, hypoxanthine, 8-azapurine, purines substituted at the 8 position with methyl or bromine, 9-oxo-N6-methyladenine, 2-aminoadenine, 7-deazaxanthine, 7-deazaguanine, 7-deaza-adenine, N4-ethanocytosine, 2,6-diaminopurine, N6-ethano-2,6-diaminopurine, 5-methylcytosine, 5-(C3-C6)-alkynylcytosine, 5-fluorouracil, 5-bromouracil, thiouracil, pseudoisocytosine, 2-hydroxy-5-methyl-4-triazolopyridine, isocytosine, isoguanine, inosine, 7,8-dimethylalloxazine, 6-dihydrothymine, 5,6-dihydrouracil, 4-methyl-indole, ethenoadenine and the non-naturally occurring nucleobases described in U.S. Pat. Nos. 5,432,272 and 6,150,510 and PCT applications WO 92/002258, WO 93/10820, WO 94/22892, and WO 94/24144, and Fasman ("Practical Handbook of Biochemistry and Molecular Biology", pp. 385-394, 1989, CRC Press, Boca Raton, La.), all herein incorporated by reference in their entireties.

"Nucleobase residue" includes nucleotides, nucleosides, fragments thereof, and related molecules having the property of binding to a complementary nucleotide. Deoxynucleotides and ribonucleotides, and their various analogs, are contemplated within the scope of this definition. Nucleobase residues may be members of oligomers and probes. "Nucleobase" and "nucleobase residue" may be used interchangeably herein and are generally synonymous unless context dictates otherwise.

"Polynucleotides", also called nucleic acids, are covalently linked series of nucleotides in which the 3' position of the pentose of one nucleotide is joined by a phosphodiester group to the 5' position of the next. DNA (deoxyribonucleic acid) and RNA (ribonucleic acid) are biologically occurring polynucleotides in which the nucleotide residues are linked in a specific sequence by phosphodiester linkages. As used herein, the terms "polynucleotide" or "oligonucleotide" encompass any polymer compound having a linear backbone of nucleotides. Oligonucleotides, also termed oligomers, are generally shorter chained polynucleotides.

"Complementary" generally refers to specific nucleotide duplexing to form canonical Watson-Crick base pairs, as is understood by those skilled in the art. However, complementary as referred to herein also includes base-pairing of nucleotide analogs, which include, but are not limited to, 2'-deoxyinosine and 5-nitroindole-2'-deoxyriboside, which are capable of universal base-pairing with A, T, G or C nucleotides and locked nucleic acids, which enhance the thermal stability of duplexes. One skilled in the art will recognize that hybridization stringency is a determinant in the degree of match or mismatch in the duplex formed by hybridization.

"Nucleic acid" is a polynucleotide or an oligonucleotide. A nucleic acid molecule can be deoxyribonucleic acid (DNA), ribonucleic acid (RNA), or a combination of both. Nucleic acids are generally referred to as "target nucleic acids" or "target sequence" if targeted for sequencing. Nucleic acids can be mixtures or pools of molecules targeted for sequencing.

"Probe" is a short strand of nucleobase residues, referring generally to two or more contiguous nucleobase residues which are generally single-stranded and complementary to a target sequence of a nucleic acid. As embodied in "Substrate Members" and "Substrate Constructs", probes can be up to 20 nucleobase residues in length. Probes may include modified nucleobase residues and modified intra-nucleobase bonds in any combination. Backbones of probes can be linked together by any of a number of types of covalent bonds, including, but not limited to, ester, phosphodiester, phosphoramide, phosphonate, phosphorothioate, phosphorothiolate, amide bond and any combination thereof. The probe may also have 5' and 3' end linkages that include, but are not limited to, the following moieties: monophosphate, triphosphate, hydroxyl, hydrogen, ester, ether, glycol, amine, amide, and thioester.

"Selective hybridization" refers to specific complementary binding. Polynucleotides, oligonucleotides, probes, nucleobase residues, and fragments thereof selectively hybridize to target nucleic acid strands, under hybridization and wash conditions that minimize nonspecific binding. As known in the art, high stringency conditions can be used to achieve selective hybridization conditions favoring a perfect match. Conditions for hybridization such as salt concentration, temperature, detergents, PEG, and GC neutralizing agents such as betaine can be varied to increase the stringency of hybridization, that is, the requirement for exact matches of C to base pair with G, and A to base pair with T or U, along a contiguous strand of a duplex nucleic acid.

"Template-directed synthesis", "template-directed assembly", "template-directed hybridization", "template-directed binding" and any other template-directed processes, refer to a process whereby nucleobase residues or probes bind selectively to a complementary target nucleic acid, and are incorporated into a nascent daughter strand. A daughter strand produced by a template-directed synthesis is complementary to the single-stranded target from which it is synthesized. It should be noted that the corresponding sequence of a target strand can be inferred from the sequence of its daughter strand, if that is known. "Template-directed polymerization" and "template-directed ligation" are special cases of template-directed synthesis whereby the resulting daughter strand is polymerized or ligated, respectively.

"Contiguous" indicates that a sequence continues without interruption or missed nucleobase. The contiguous sequence of nucleotides of the template strand is said to be complementary to the contiguous sequence of the daughter strand.

"Substrates" or "substrate members" are oligomers, probes or nucleobase residues that have binding specificity to the target template. The substrates are generally combined with tethers to form substrate constructs. Substrates of substrate constructs that form the primary backbone of the daughter strand are also substrates or substrate members of the daughter strand.

"Substrate constructs" are reagents for template-directed synthesis of daughter strands, and are generally provided in the form of libraries. Substrate constructs generally contain a substrate member for complementary binding to a target template and either a tether member or tether attachment sites to which a tether may be bonded. Substrate constructs are provided in a variety of forms adapted to the invention. Substrate constructs include both "oligomeric substrate constructs" (also termed "probe substrate constructs") and "monomeric substrate constructs" (also termed "nucleobase substrate constructs").

"Subunit motif" or "motif" refers to a repeating subunit of a polymer backbone, the subunit having an overall form characteristic of the repeating subunits, but also having species-specific elements that encode genetic information. Motifs of complementary nucleobase residues are represented in libraries of substrate constructs according to the number of possible combinations of the basic complementary sequence binding nucleobase elements in each motif. If the nucleobase binding elements are four (e.g., A, C, G, and T), the number of possible motifs of combinations of four elements is $4^x$, where x is the number of nucleobase residues in the motif. However, other motifs based on degenerate pairing bases, on the substitution of uracil for thymidine in ribonucleobase residues or other sets of nucleobase residues, can lead to larger libraries (or smaller libraries) of motif-bearing substrate constructs. Motifs are also represented by species-specific reporter constructs, such as the reporters making up a reporter tether. Generally there is a one-to-one correlation between the reporter construct motif identifying a particular substrate species and the binding complementarity and specificity of the motif.

"Xpandomer intermediate" is an intermediate product (also referred to herein as a "daughter strand") assembled from substrate constructs, and is formed by a template-directed assembly of substrate constructs using a target nucleic acid template. Optionally, other linkages between abutted substrate constructs are formed which may include polymerization or ligation of the substrates, tether-to-tether linkages or tether-to-substrate linkages. The Xpandomer intermediate contains two structures; namely, the constrained Xpandomer and the primary backbone. The constrained Xpandomer comprises all of the tethers in the daughter strand but may comprise all, a portion or none of the substrate as required by the method. The primary backbone comprises all of the abutted substrates. Under the process step in which the primary backbone is fragmented or dissociated, the constrained Xpandomer is no longer constrained and is the Xpandomer product which is extended as the tethers are stretched out. "Duplex daughter strand" refers to an Xpandomer intermediate that is hybridized or duplexed to the target template.

"Primary backbone" refers to a contiguous or segmented backbone of substrates of the daughter strand. A commonly encountered primary backbone is the ribosyl 5'-3' phosphodiester backbone of a native polynucleotide. However, the primary backbone of an daughter strand may contain analogs of nucleobases and analogs of oligomers not linked by phosphodiester bonds or linked by a mixture of phosphodiester bonds and other backbone bonds, which include, but are not limited to following linkages: phosphorothioate, phosphorothiolate, phosphonate, phosphoramidate, and peptide nucleic acid "PNA" backbone bonds which include phosphono-PNA, serine-PNA, hydroxyproline-PNA, and combinations thereof. Where the daughter strand is in its duplex form (i.e., duplex daughter strand), and substrates are not covalently bonded between the subunits, the substrates are nevertheless contiguous and form the primary backbone of the daughter strand.

"Constrained Xpandomer" is an Xpandomer in a configuration before it has been expanded. The constrained Xpandomer comprises all tether members of the daughter strand. It is constrained from expanding by at least one bond or linkage per tether attaching to the primary backbone. During the expansion process, the primary backbone of the daughter strand is fragmented or dissociated to transform the constrained Xpandomer into an Xpandomer.

"Constrained Xpandomer backbone" refers to the backbone of the constrained Xpandomer. It is a synthetic covalent backbone co-assembled along with the primary backbone in the formation of the daughter strand. In some cases both backbones may not be discrete but may both have the same substrate or portions of the substrate in their composition. The constrained Xpandomer backbone always comprises the tethers whereas the primary backbone comprises no tether members.

"Xpandomer" or "Xpandomer product" is a synthetic molecular construct produced by expansion of a constrained Xpandomer, which is itself synthesized by template-directed assembly of substrate constructs. The Xpandomer is elongated relative to the target template it was produced from. It is composed of a concatenation of subunits, each subunit a motif, each motif a member of a library, comprising sequence information, a tether and optionally, a portion, or all of the substrate, all of which are derived from the formative substrate construct. The Xpandomer is designed to expand to be longer than the target template thereby lowering the linear density of the sequence information of the target template along its length. In addition, the Xpandomer optionally provides a platform for increasing the size and abundance of reporters which in turn improves signal to noise for detection. Lower linear information density and stronger signals increase the resolution and reduce sensitivity requirements to detect and decode the sequence of the template strand.

"Selectively cleavable bond" refers to a bond which can be broken under controlled conditions such as, for example, conditions for selective cleavage of a phosphorothiolate bond, a photocleavable bond, a phosphoramide bond, a 3'-O—B-D-ribofuranosyl-2' bond, a thioether bond, a selenoether bond, a sulfoxide bond, a disulfide bond, deoxyribosyl-5'-3' phosphodiester bond, or a ribosyl-5'-3' phosphodiester bond, as well as other cleavable bonds known in the art. A selectively cleavable bond can be an intra-tether bond or between or within a probe or a nucleobase residue or can be the bond formed by hybridization between a probe and a template strand. Selectively cleavable bonds are not limited to covalent bonds, and can be non-covalent bonds or associations, such as those based on hydrogen bonds, hydrophobic bonds, ionic bonds, pi-bond ring stacking interactions, Van der Waals interactions, and the like.

"Moiety" is one of two or more parts into which something may be divided, such as, for example, the various parts of a tether, a molecule or a probe.

"Tether" or "tether member" refers to a polymer or molecular construct having a generally linear dimension and with an end moiety at each of two opposing ends. A tether is attached to a substrate with a linkage in at least one end moiety to form a substrate construct. The end moieties of the tether may be connected to cleavable linkages to the substrate or cleavable intra-tether linkages that serve to constrain the tether in a "constrained configuration". After the daughter strand is synthesized, each end moiety has an end linkage that couples directly or indirectly to other tethers. The coupled tethers comprise the constrained Xpandomer that further comprises the daughter strand. Tethers have a "constrained configuration" and an "expanded configuration". The constrained configuration is found in substrate constructs and in the daughter strand. The constrained configuration of the tether is the precursor to the expanded configuration, as found in Xpandomer products. The transition from the constrained configuration to the expanded configuration results cleaving of selectively cleavable bonds that may be within the primary backbone of the daughter strand or intra-tether linkages. A tether in a constrained configuration is also used where a tether is added to form the daughter strand after assembly of the "primary backbone". Tethers can optionally comprise one or more reporters or reporter constructs along its length that can encode sequence information of substrates. The tether provides a means to expand the length of the Xpandomer and thereby lower the sequence information linear density.

"Tether constructs" are tethers or tether precursors composed of one or more tether segments or other architectural components for assembling tethers such as reporter constructs, or reporter precursors, including polymers, graft copolymers, block copolymers, affinity ligands, oligomers, haptens, aptamers, dendrimers, linkage groups or affinity binding group (e.g., biotin).

"Tether element" or "tether segment" is a polymer having a generally linear dimension with two terminal ends, where the ends form end-linkages for concatenating the tether elements. Tether elements may be segments of tether constructs. Such polymers can include, but are not limited to: polyethylene glycols, polyglycols, polypyridines, polyisocyanides, polyisocyanates, poly(triarylmethyl)methacrylates, polyaldehydes, polypyrrolinones, polyureas, polyglycol phosphodiesters, polyacrylates, polymethacrylates, polyacrylamides, polyvinyl esters, polystyrenes, polyamides, polyurethanes, polycarbonates, polybutyrates, polybutadienes, polybutyrolactones, polypyrrolidinones, polyvinylphosphonates, polyacetamides, polysaccharides, polyhyaluranates, polyamides, polyimides, polyesters, polyethylenes, polypropylenes, polystyrenes, polycarbonates, polyterephthalates, polysilanes, polyurethanes, polyethers, polyamino acids, polyglycines, polyprolines, N-substituted polylysine, polypeptides, side-chain N-substituted peptides, poly-N-substituted glycine, peptoids, side-chain carboxyl-substituted peptides, homopeptides, oligonucleotides, ribonucleic acid oligonucleotides, deoxynucleic acid oligonucleotides, oligonucleotides modified to prevent Watson-Crick base pairing, oligonucleotide analogs, polycytidylic acid, polyadenylic acid, polyuridylic acid, polythymidine, polyphosphate, polynucleotides, polyribonucleotides, polyethylene glycol-phosphodiesters, peptide polynucleotide analogues, threosyl-polynucleotide analogues, glycol-polynucleotide analogues, morpholino-polynucleotide analogues, locked nucleotide oligomer analogues, polypeptide analogues, branched polymers, comb polymers, star polymers, dendritic polymers, random, gradient and block copolymers, anionic polymers, cationic polymers, polymers forming stem-loops, rigid segments and flexible segments.

"Peptide nucleic acid" or "PNA" is a nucleic acid analog having nucleobase residues suitable for hybridization to a nucleic acid, but with a backbone that comprises amino acids or derivatives or analogs thereof.

"Phosphono-peptide nucleic acid" or "pPNA" is a peptide nucleic acid in which the backbone comprises amino acid analogs, such as N-(2-hydroxyethyl)phosphonoglycine or N-(2-aminoethyl)phosphonoglycine, and the linkages between nucleobase units are through phosphonoester or phosphonoamide bonds.

"Serine nucleic acid" or "SerNA" is a peptide nucleic acid in which the backbone comprises serine residues. Such residues can be linked through amide or ester linkages.

"Hydroxyproline nucleic acid" or "HypNA" is a peptide nucleic acid in which the backbone comprises 4-hydroxyproline residues. Such residues can be linked through amide or ester linkages.

"Reporter element" is a signaling element, molecular complex, compound, molecule or atom that is also comprised of an associated "reporter detection characteristic". Other reporter elements include, but are not limited to, FRET resonant donor or acceptor, dye, quantum dot, bead, dendrimer, up-converting fluorophore, magnet particle, electron scatterer (e.g., boron), mass, gold bead, magnetic resonance, ionizable group, polar group, hydrophobic group. Still others are fluorescent labels, such as but not limited to, ethidium bromide, SYBR Green, Texas Red, acridine orange, pyrene, 4-nitro-1,8-naphthalimide, TOTO-1, YOYO-1, cyanine 3 (Cy3), cyanine 5 (Cy5), phycoerythrin, phycocyanin, allophycocyanin, FITC, rhodamine, 5(6)-carboxyfluorescein, fluorescent proteins, DOXYL (N-oxyl-4,4-dimethyloxazolidine), PROXYL (N-oxyl-2,2,5,5-tetramethylpyrrolidine), TEMPO (N-oxyl-2,2,6,6-tetramethylpiperidine), dinitrophenyl, acridines, coumarins, Cy3 and Cy5 (Biological Detection Systems, Inc.), erytrosine, coumaric acid, umbelliferone, texas red rhodaine, tetramethyl rhodamin, Rox, 7-nitrobenzo-1-oxa-1-diazole (NBD), oxazole, thiazole, pyrene, fluorescein or lanthamides; also radioisotopes (such as $^{33}$P, $^{3}$H, $^{14}$C, $^{35}$S, $^{125}$I, $^{32}$P or $^{131}$I), ethidium, Europium, Ruthenium, and Samarium or other radioisotopes; or mass tags, such as, for example, pyrimidines modified at the C5 position or purines modified at the N7 position, wherein mass modifying groups can be, for examples, halogen, ether or polyether, alkyl, ester or polyester, or of the general type XR, wherein X is a linking group and R is a mass-modifying group, chemiluminescent labels, spin labels, enzymes (such as peroxidases, alkaline phosphatases, beta-galactosidases, and oxidases), antibody fragments, and affinity ligands (such as an oligomer, hapten, and aptamer). Association of the reporter element with the tether can be covalent or non-covalent, and direct or indirect. Representative covalent associations include linker and zero-linker bonds. Included are bonds to the tether backbone or to a tether-bonded element such as a dendrimer or sidechain. Representative non-covalent bonds include hydrogen bonds, hydrophobic bonds, ionic bonds, pi-bond ring stacking, Van der Waals interactions, and the like. Ligands, for example, are associated by specific affinity binding with binding sites on the reporter element. Direct association can take place at the time of tether synthesis, after tether synthesis, and before or after Xpandomer synthesis.

A "reporter" is composed of one or more reporter elements. Reporters include what are known as "tags" and "labels." The probe or nucleobase residue of the Xpandomer can be considered a reporter. Reporters serve to parse the genetic information of the target nucleic acid.

"Reporter construct" comprises one or more reporters that can produce a detectable signal(s), wherein the detectable signal(s) generally contain sequence information. This signal information is termed the "reporter code" and is subsequently decoded into genetic sequence data. A reporter construct may also comprise tether segments or other architectural components including polymers, graft copolymers, block copolymers, affinity ligands, oligomers, haptens, aptamers, dendrimers, linkage groups or affinity binding group (e.g., biotin).

"Reporter detection characteristic" referred to as the "signal" describes all possible measurable or detectable elements, properties or characteristics used to communicate the genetic sequence information of a reporter directly or indirectly to a measurement device. These include, but are not limited to, fluorescence, multi-wavelength fluorescence, emission spectrum fluorescence quenching, FRET, emission, absorbance, reflectance, dye emission, quantum dot emission, bead image, molecular complex image, magnetic susceptibility, electron scattering, ion mass, magnetic resonance, molecular complex dimension, molecular complex impedance, molecular charge, induced dipole, impedance, molecular mass, quantum state, charge capacity, magnetic spin state, inducible polarity, nuclear decay, resonance, or complementarity.

"Reporter Code" is the genetic information from a measured signal of a reporter construct. The reporter code is decoded to provide sequence-specific genetic information data.

"Xprobe" is an expandable oligomeric substrate construct. Each Xprobe has a probe member and a tether member. The tether member generally having one or more reporter constructs. Xprobes with 5'-monophosphate modifications are compatible with enzymatic ligation-based methods for Xpandomer synthesis. Xprobes with 5' and 3' linker modifications are compatible with chemical ligation-based methods for Xpandomer synthesis.

"Xmer" is an expandable oligomeric substrate construct. Each Xmer has an oligomeric substrate member and a tether member, the tether member generally having one or more reporter constructs. Xmers are 5'-triphosphates compatible with polymerase-based methods for synthesizing Xpandomers.

"RT-NTP" is an expandable, 5' triphosphate-modified nucleotide substrate construct ("monomeric substrate") compatible with template dependant enzymatic polymerization. An RT-NTP has a modified deoxyribonucleotide triphosphate ("DNTP"), ribonucleotide triphosphate ("RNTP"), or a functionally equivalent analog substrate, collectively referred to as the nucleotide triphosphate substrate ("NTPS"). An RT-NTP has two distinct functional components; namely, a nucleobase 5'-triphosphate and a tether or tether precursor. After formation of the daughter strand the tether is attached between each nucleotide at positions that allow for controlled RT expansion. In one class of RT-NTP (e.g., Class IX), the tether is attached after RT-NTP polymerization. In some cases, the RT-NTP has a reversible end terminator and a tether that selectively crosslinks directly to adjacent tethers. Each tether can be uniquely encoded with reporters that specifically identify the nucleotide to which it is tethered.

"XNTP" is an expandable, 5' triphosphate modified nucleotide substrate compatible with template dependent enzymatic polymerization. An XNTP has two distinct functional components; namely, a nucleobase 5'-triphosphate and a tether or tether precursor that is attached within each nucleotide at positions that allow for controlled RT expansion by intra-nucleotide cleavage.

"Processive" refers to a process of coupling of substrates which is generally continuous and proceeds with directionality. While not bound by theory, both ligases and polymerases, for example, exhibit processive behavior if substrates are added to a nascent daughter strand incrementally without interruption. The steps of hybridization and ligation, or hybridization and polymerization, are not seen as independent steps if the net effect is processive growth of the nascent daughter strand. Some but not all primer-dependent processes are processive.

"Promiscuous" refers to a process of coupling of substrates that proceeds from multiple points on a template at once, and is not primer dependent, and indicates that chain extension occurs in parallel (simultaneously) from more than one point of origin.

"Single-base extension" refers to a cyclical stepwise process in which monomeric substrates are added one by one. Generally the coupling reaction is restrained from proceeding beyond single substrate extension in any one step by use of reversible blocking groups.

"Single-probe extension" refers to a cyclical stepwise process in which oligomeric substrates are added one by one. Generally the coupling reaction is restrained from proceeding beyond single substrate extension in any one step by use of reversible blocking groups.

"Corresponds to" or "corresponding" is used here in reference to a contiguous single-stranded sequence of a probe, oligonucleotide, oligonucleotide analog, or daughter strand that is complementary to, and thus "corresponds to", all or a portion of a target nucleic acid sequence. The complementary sequence of a probe can be said to correspond to its target. Unless otherwise stated, both the complementary sequence of the probe and the complementary sequence of the target are individually contiguous sequences.

"Nuclease-resistant" refers to is a bond that is resistant to a nuclease enzyme under conditions where a DNA or RNA phosphodiester bond will generally be cleaved. Nuclease enzymes include, but are not limited to, DNase I, Exonuclease III, Mung Bean Nuclease, RNase I, and RNase H. One skilled in this field can readily evaluate the relative nuclease resistance of a given bond.

"Ligase" is an enzyme generally for joining 3'-OH 5'-monophosphate nucleotides, oligomers, and their analogs. Ligases include, but are not limited to, $NAD^+$-dependent ligases including tRNA ligase, Taq DNA ligase, *Thermus filiformis* DNA ligase, *Escherichia coli* DNA ligase, Tth DNA ligase, *Thermus scotoductus* DNA ligase, thermostable ligase, Ampligase thermostable DNA ligase, VanC-type ligase, 9° N DNA Ligase, Tsp DNA ligase, and novel ligases discovered by bioprospecting. Ligases also include, but are not limited to, ATP-dependent ligases including T4 RNA ligase, T4 DNA ligase, T7 DNA ligase, Pfu DNA ligase, DNA ligase I, DNA ligase III, DNA ligase IV, and novel ligases discovered by bioprospecting. These ligases include wild-type, mutant isoforms, and genetically engineered variants.

"Polymerase" is an enzyme generally for joining 3'-OH 5'-triphosphate nucleotides, oligomers, and their analogs. Polymerases include, but are not limited to, DNA-dependent DNA polymerases, DNA-dependent RNA polymerases, RNA-dependent DNA polymerases, RNA-dependent RNA polymerases, T7 DNA polymerase, T3 DNA polymerase, T4 DNA polymerase, T7 RNA polymerase, T3 RNA polymerase, SP6 RNA polymerase, DNA polymerase I, Klenow fragment, *Thermophilus aquaticus* DNA polymerase, Tth DNA polymerase, VentR® DNA polymerase (New England Biolabs), Deep VentR® DNA polymerase (New England Biolabs), Bst DNA Polymerase Large Fragment, Stoeffel Fragment, 9° N DNA Polymerase, 9° N DNA polymerase, Pfu DNA Polymerase, Tfl DNA Polymerase, Tth DNA Polymerase, RepliPHI Phi29 Polymerase, Tli DNA polymerase, eukaryotic DNA polymerase beta, telomerase, Therminator™ polymerase (New England Biolabs), KOD HiFi™ DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting, and polymerases cited in US 2007/0048748, U.S. Pat. No. 6,329,178, U.S. Pat. No. 6,602,695, and U.S. Pat. No. 6,395,524 (incorporated by reference). These polymerases include wild-type, mutant isoforms, and genetically engineered variants.

"Encode" or "parse" are verbs referring to transferring from one format to another, and refers to transferring the genetic information of target template base sequence into an arrangement of reporters.

"Extragenetic" refers to any structure in the daughter strand that is not part of the primary backbone; for example, an extragenetic reporter is not the nucleobase itself that lies in the primary backbone.

"Hetero-copolymer" is a material formed by combining differing units (e.g., monomer subunit species) into chains of a "copolymer". Hetero-copolymers are built from discrete "subunit" constructs. A "subunit" is a region of a polymer composed a well-defined motif, where each motif is a species and carries genetic information. The term hetero-copolymer is also used herein to describe a polymer in which all the blocks are blocks constructed of repeating motifs, each motif having species-specific elements. The daughter strand and the Xpandomer are both hetero-copolymers whereby each subunit motif encodes 1 or more bases of the target template sequence and the entire target sequence is defined further with the sequence of motifs.

"Solid support" is a solid material having a surface for attachment of molecules, compounds, cells, or other entities. The surface of a solid support can be flat or not flat. A solid support can be porous or non-porous. A solid support can be a chip or array that comprises a surface, and that may comprise glass, silicon, nylon, polymers, plastics, ceramics, or metals. A solid support can also be a membrane, such as a nylon, nitrocellulose, or polymeric membrane, or a plate or dish and can be comprised of glass, ceramics, metals, or plastics, such as, for example, polystyrene, polypropylene, polycarbonate, or polyallomer. A solid support can also be a bead, resin or particle of any shape. Such particles or beads can be comprised of any suitable material, such as glass or ceramics, and/or one or more polymers, such as, for example, nylon, polytetrafluoroethylene, TEFLON™, polystyrene, polyacrylamide, sepaharose, agarose, cellulose, cellulose derivatives, or dextran, and/or can comprise metals, particularly paramagnetic metals, such as iron.

"Reversibly blocking" or "terminator" refers to a chemical group that when bound to a second chemical group on a moiety prevents the second chemical group from entering into particular chemical reactions. A wide range of protecting groups are known in synthetic organic and bioorganic chemistry that are suitable for particular chemical groups and are compatible with particular chemical processes, meaning that they will protect particular groups during those processes and may be subsequently removed or modified (see, e.g., Metzker et al. *Nucleic Acids Res.* 22(20): 4259, 1994).

"Linker" is a molecule or moiety that joins two molecules or moieties, and provides spacing between the two molecules or moieties such that they are able to function in their intended manner. For example, a linker can comprise a diamine hydrocarbon chain that is covalently bound through a reactive group on one end to an oligonucleotide analog molecule and through a reactive group on another end to a solid support, such as, for example, a bead surface. Coupling of linkers to nucleotides and substrate constructs of interest can be accomplished through the use of coupling reagents that are known in the art (see, e.g., Efimov et al., *Nucleic Acids Res.* 27: 4416-4426, 1999). Methods of derivatizing and coupling organic molecules are well known in the arts of organic and bioorganic chemistry. A linker may also be cleavable or reversible.

General Overview

In general terms, methods and corresponding devices and products are described for replicating single-molecule target nucleic acids. Such methods utilize "Xpandomers" which permit sequencing of the target nucleic acid with increased throughput and accuracy. An Xpandomer encodes (parses) the nucleotide sequence data of the target nucleic acid in a linearly expanded format, thereby improving spatial resolution, optionally with amplification of signal strength. These processes are referred to herein as "Sequencing by Expansion" or "SBX".

As shown in FIG. 1A, native duplex nucleic acids have an extremely compact linear data density; about a 3.4 Å center-to-center separation between sequential stacked bases (2) of each strand of the double helix (1), and are therefore tremendously difficult to directly image or sequence with any accuracy and speed. When the double-stranded form is denatured to form single stranded polynucleotides (3,4), the resulting base-to-base separation distances are similar, but the problem becomes compounded by domains of secondary structure.

Figure 1B:
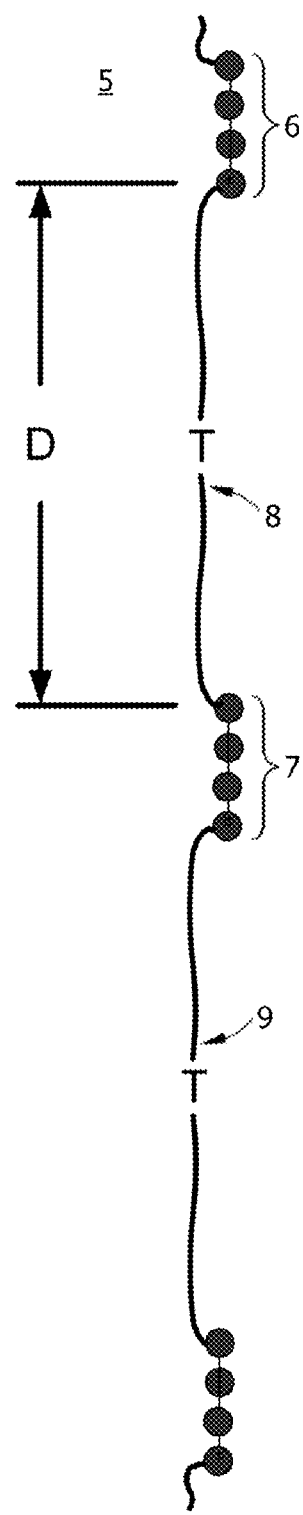

As shown in FIG. 1B, Xpandomer (5), here illustrated as a concatenation of short oligomers (6,7) held together by extragenetic tethers T (8,9), is a synthetic replacement or "surrogate" for the nucleic acid target to be sequenced. Bases complementary to the template are incorporated into the Xpandomer, but the regularly spaced tethers serve to increase the distance between the short oligomers (here each shown with four nucleobases depicted by circles). The Xpandomer is made by a process in which a synthetic duplex intermediate is first formed by replicating a template strand. The daughter strand is unique in that it has both a linear backbone formed by the oligomers and a constrained Xpandomer backbone comprised of folded tethers. The tethers are then opened up or "expanded" to transform the product into a chain of elongated tethers. Figuratively, the daughter strand can be viewed as having two superimposed backbones: one linear (primary backbone) and the other with "accordion" folds (constrained Xpandomer). Selective cleavage of bonds in the daughter strand allows the accordion folds to expand to produce an Xpandomer product. This process will be explained in more detail below, but it should be noted that the choice of four nucleobases per oligomer and particulars of the tether as shown in FIG. 1B is for purpose of illustration only, and in no way should be construed to limit the invention.

The separation distance "D" between neighboring oligomers in the Xpandomer is now a process-dependent variable and is determined by the length of the tether T. As will be shown, the length of the tether T is designed into the substrate constructs, the building blocks from which the Xpandomer is made. The separation distance D can be selected to be greater than 0.5 nm, or greater than 2 nm, or greater than 5 nm, or greater than 10 nm, or greater than 50 nm, for example. As the separation distance increases, the process of discriminating or "resolving" the individual oligomers becomes progressively easier. This would also be true if, instead of oligomers, individual nucleobases of another Xpandomer species were strung together on a chain of tethers.

Referring again to FIG. 1A, native DNA replicates by a process of semi-conservative replication; each new DNA molecule is a "duplex" of a template strand (3) and a native daughter strand (4). The sequence information is passed from the template to the native daughter strand by a process of "template-directed synthesis" that preserves the genetic information inherent in the sequence of the base pairs. The native daughter strand in turn becomes a template for a next generation native daughter strand, and so forth. Xpandomers are formed by a similar process of template-directed synthesis, which can be an enzymatic or a chemical coupling process. However, unlike native DNA, once formed, Xpandomers cannot be replicated by a biological process of semi-conservative replication and are not suitable for amplification by processes such as PCR. The Xpandomer product is designed to limit unwanted secondary structure.

Figure 2A:
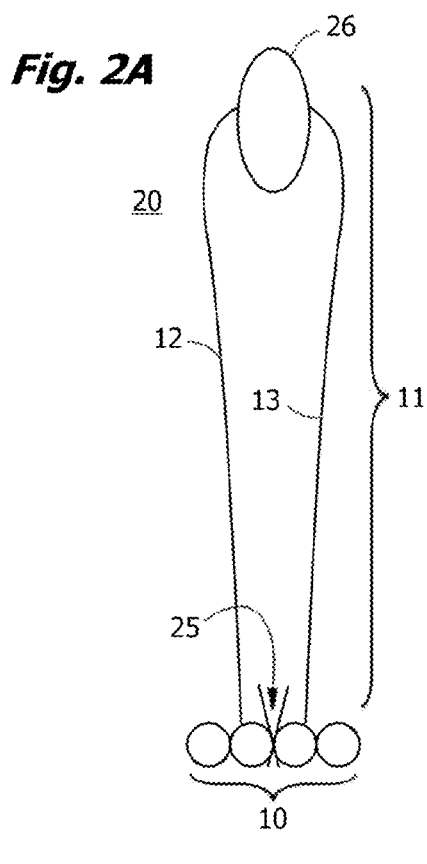
FIGS. 2A through 2D illustrate schematically several representative structures of substrates useful in the invention.
Figure 2B:
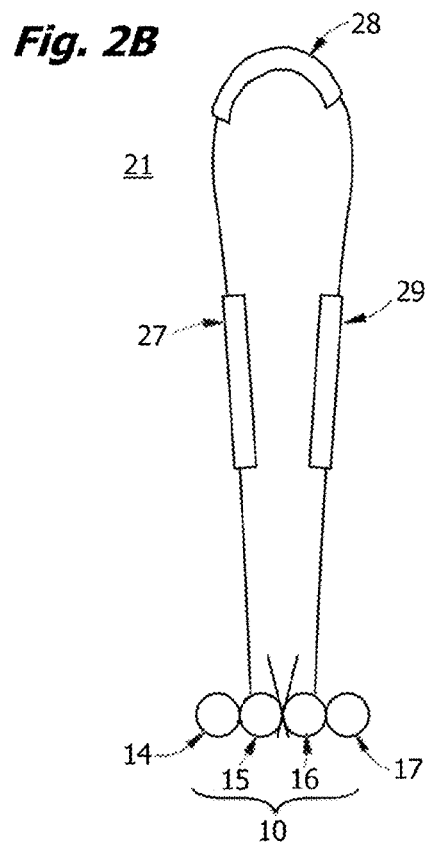

FIGS. 2A through 2D show representative Class I Xpandomer substrates (20,21,22,23). These are the building blocks from which Xpandomers are synthesized. Other Xpandomer substrates (ten classes are disclosed herein) are addressed in the subsequent sections. The Xpandomer substrate constructs shown here have two functional components; namely, a probe member (10) and a "tether" member (11) in a loop configuration. The loop forms the elongated tether "T" of the final product. Solely for convenience in explanation, the probe member is again depicted with four nucleobase residues (14, 15,16,17) as shown in FIG. 2B.

These substrate constructs can be end modified with R-groups, for example as a 5'-monophosphate, 3'-OH suitable for use with a ligase (herein termed an "Xprobe") or as a 5'-triphosphate, 3'-OH suitable for use with a polymerase (herein termed an "Xmer"). Other R groups may be of use in various protocols. In the first example shown in FIG. 3B, we present the use of Xprobes in synthesis of an Xpandomer from a template strand of a target nucleic acid by a ligase-dependent process.

The four nucleobase residues (14,15,16,17) of the probe member (10) are selected to be complementary to a contiguous sequence of four nucleotides of the template. Each "probe" is thus designed to hybridize with the template at a complementary sequence of four nucleotides. By supplying a library of many such probe sequences, a contiguous complementary replica of the template can be formed. This daughter strand is termed an "Xpandomer intermediate". Xpandomer intermediates have duplex or single-stranded forms.

The tether loop is joined to the probe member (10) at the second and third nucleobase residues (15,16). The second and third nucleobase residues (15,16) are also joined to each other by a "selectively cleavable bond" (25) depicted by a "V". Cleavage of this cleavable bond enables the tether loop to expand. The linearized tether can be said to "bridge" the selectively cleavable bond site of the primary polynucleotide backbone of a daughter strand. Cleaving these bonds breaks up the primary backbone and forms the longer Xpandomer.

Selective cleavage of the selectively cleavable bonds (25) can be done in a variety of ways including, but not limited to, chemical cleavage of phosphorothiolate bonds, ribonuclease digestion of ribosyl 5'-3' phosphodiester linkages, cleavage of photocleavable bonds, and the like, as discussed is greater detail below.

Figure 2C:
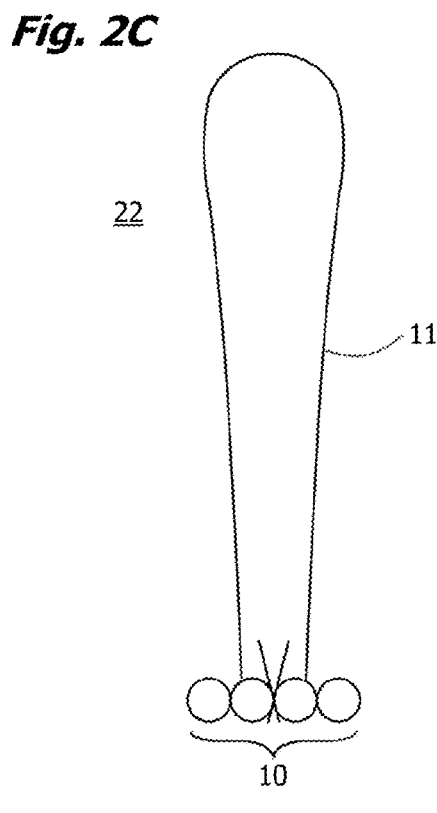
Figure 2D:
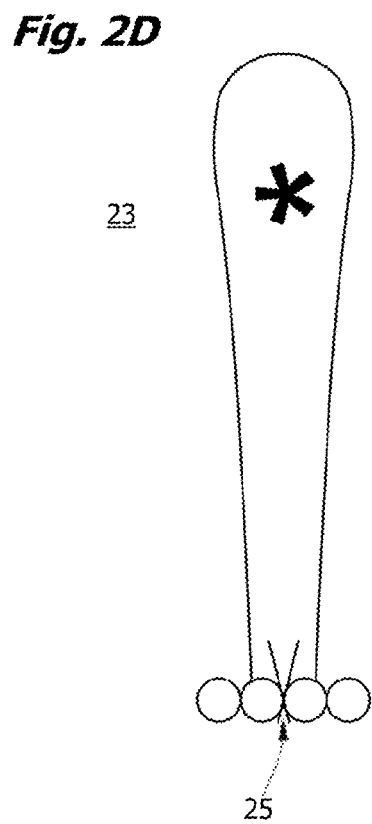

The substrate construct (20) shown in FIG. 2A has a single tether segment, represented here by an ellipse (26), for attachment of reporter elements. This segment is flanked with spacer tether segments (12,13), all of which collectively form the tether construct. One to many dendrimer(s), polymer(s), branched polymer(s) or combinations therein can be used, for example, to construct the tether segment. For the substrate construct (21) of FIG. 2B, the tether construct is composed of three tether segments for attachment of reporter elements (27,28,29), each of which is flanked with a spacer tether segment. The combination of reporter elements collectively form a "reporter construct" to produce a unique digital reporter code (for probe sequence identification). These reporter elements include, but are not limited to, fluorophores, FRET tags, beads, ligands, aptamers, peptides, haptens, oligomers, polynucleotides, dendrimers, stem-loop structures, affinity labels, mass tags, and the like. The tether loop (11) of the substrate construct (22) in FIG. 2C is "naked". The genetic information encoded in this construct is not encoded on the tether, but is associated with the probe (10), for example, in the form of tagged nucleotides. The substrate construct (23) of FIG. 2D illustrates the general principal: as indicated by the asterisk (*), the sequence information of the probe is encoded or "parsed" in the substrate construct in a modified form more readily detected in a sequencing protocol. Because the sequence data is physically better resolved after cleavage of the selectively cleavable bond (25) to form the linearly elongated Xpandomer polymer, the asterisk (*) represents any form of encoded genetic information for which this is a benefit. The bioinformatic element or elements (*) of the substrate construct, whatever their form, can be detectable directly or can be precursors to which detectable elements are added in a post-assembly labeling step. In some instances, the genetic information is encoded in a molecular property of the substrate construct itself, for example a multi-state mass tag. In other instances, the genetic information is encoded by one or more fluorophores of FRET donor:acceptor pairs, or a nanomolecular barcode, or a ligand or combination of ligands, or in the form of some other labeling technique drawn from the art. Various embodiments will be discussed in more detail below.

The tether generally serves a number of functions: (1) to sequentially link, directly or indirectly, to adjacent tethers forming the Xpandomer intermediate; (2) to stretch out and expand to form an elongated chain of tethers upon cleavage of selected bonds in the primary backbone or within the tether (see FIG. 1B); and/or (3) to provide a molecular construct for incorporating reporter elements, also termed "tags" or "labels", that encode the nucleobase residue sequence information of its associated substrate. The tether can be designed to optimize the encoding function by adjusting spatial separations, abundance, informational density, and signal strength of its constituent reporter elements. A broad range of reporter properties are useful for amplifying the signal strength of the genetic information encoded within the substrate construct. The literature directed to reporters, molecular bar codes, affinity binding, molecular tagging and other reporter elements is well known to one skilled in this field.

It can be seen that if each substrate of a substrate construct contains x nucleobases, then a library representing all possible sequential combinations of x nucleobases would contain 4ˣ probes (when selecting the nucleobases from A, T, C or G). Fewer or more combinations can be needed if other bases are used. These substrate libraries are designed so that each substrate construct contains (1) a probe (or at least one nucleobase residue) complementary to any one of the possible target sequences of the nucleic acid to be sequenced and (2) a unique reporter construct that encodes the identity of the target sequence which that particular probe (or nucleobase) is complementary to. A library of probes containing two nucleobases would have 16 unique members; a library of probes containing three nucleobases would have 64 unique members, and so forth. A representative library would have the four individual nucleobases themselves, but configured to accommodate a tethering means.

Figure 3A:
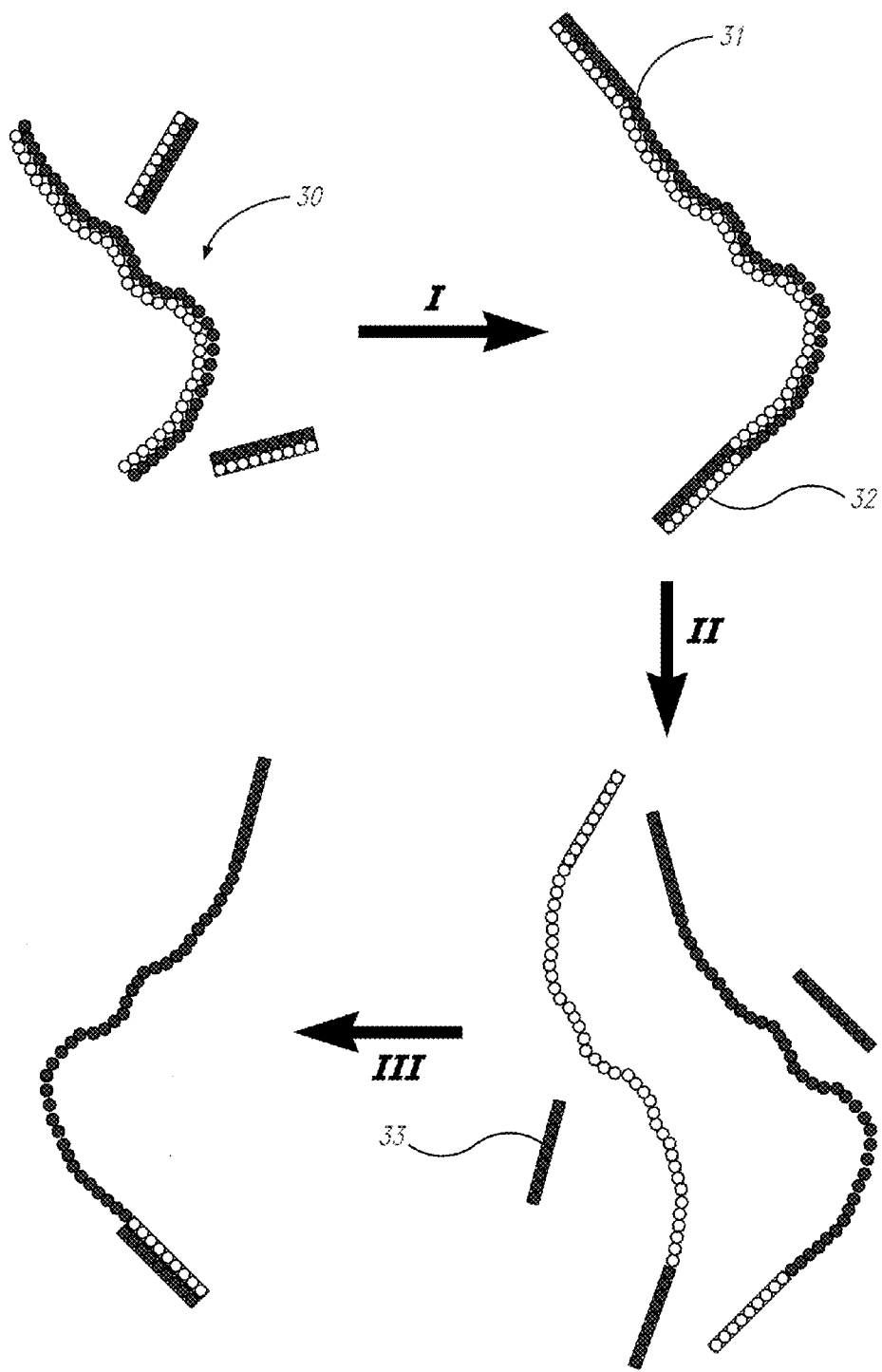
FIGS. 3A, 3B and 3C are schematics illustrating simplified steps for synthesizing an Xpandomer from a target nucleic acid.
Figure 3B:
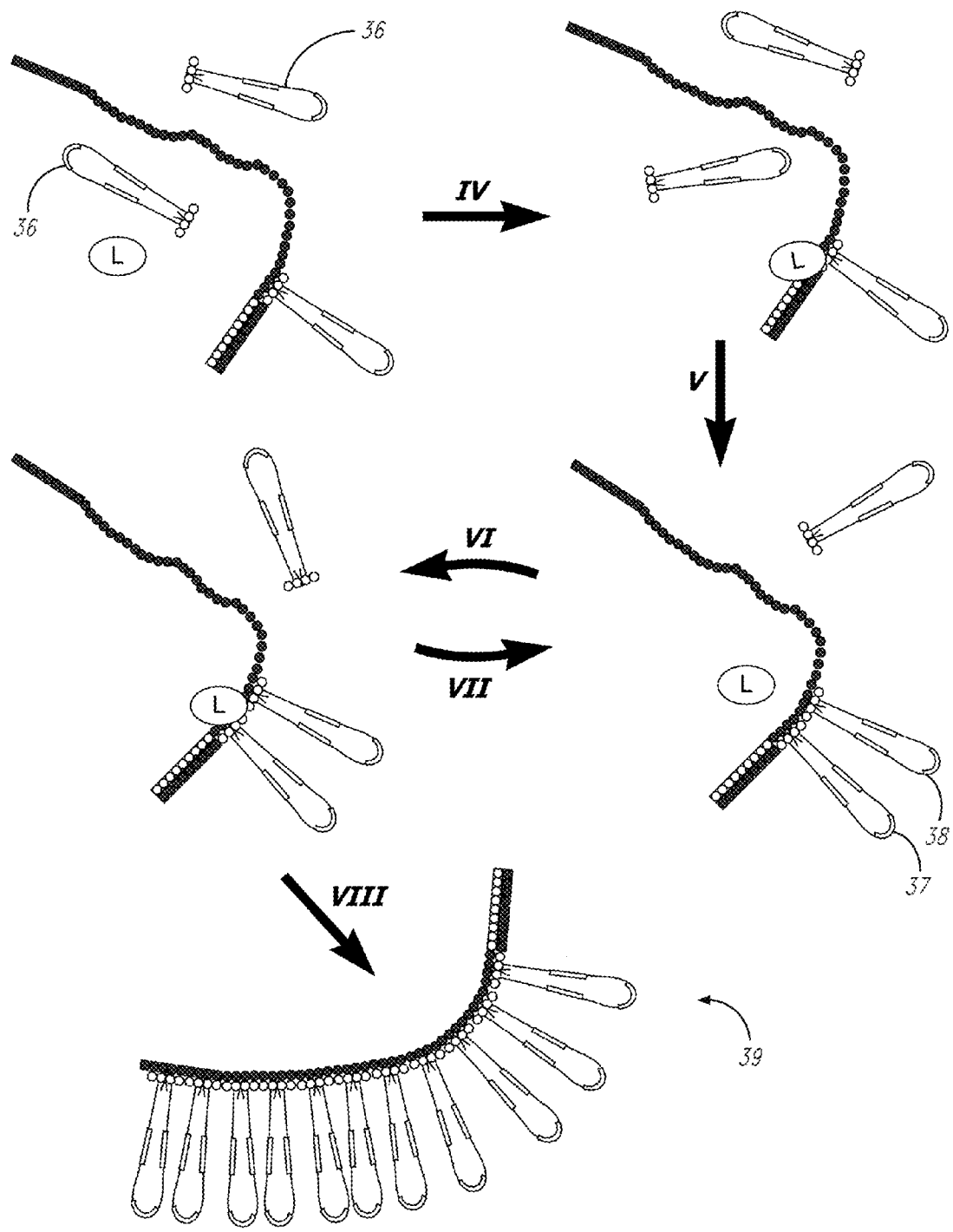
Figure 3C:
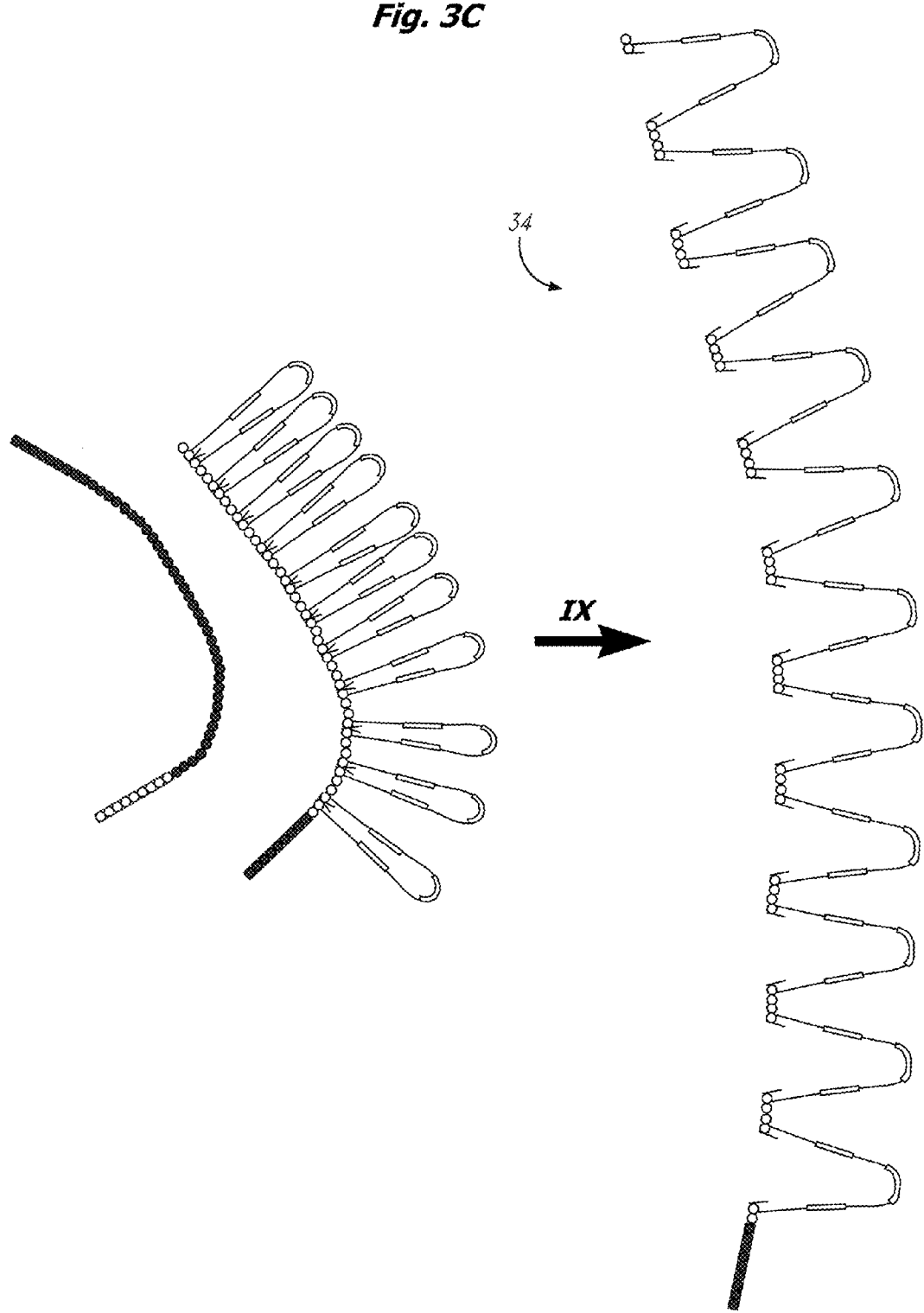

Synthesis of an Xpandomer is illustrated in FIGS. 3A through 3C. The substrate depicted here is an Xprobe and the method can be described as hybridization with primer-dependent processive ligation in free solution.

Many well known molecular biological protocols, such as protocols for fragmenting the target DNA and ligating end adaptors, can be adapted for use in sequencing methods and are used here to prepare the target DNA (30) for sequencing. Here we illustrate, in broad terms that would be familiar to those skilled in the art, processes for polishing the ends of the fragments and blunt-ended ligation of adaptors (31,32) designed for use with sequencing primers. These actions are shown in Step I of FIG. 3A. In Steps II and III, the target nucleic acid is denatured and annealed with suitable primers (33) complementary to the adaptors.

In FIG. 3B, the primed template strand of Step III is contacted with a library of substrate constructs (36) and ligase (L), and in Step IV conditions are adjusted to favor hybridization followed by ligation at a free 3'-OH of a primer-template duplex. Optionally in Step V the ligase dissociates, and in Steps VI and VII, the process of hybridization and ligation can be recognized to result in extension by cumulative addition of substrates (37,38) to the primer end. Although priming can occur from adaptors at both ends of a single stranded template, the growth of a nascent Xpandomer daughter strand is shown here to proceed from a single primer, solely for simplicity. Extension of the daughter strand is represented in Steps VI and VII, which, are continuously repeated (incrementally, without interruption). These reactions occur in free solution and proceed until a sufficient amount of product has been synthesized. In Step VIII, formation of a completed Xpandomer intermediate (39) is shown.

Relatively long lengths of contiguous nucleotide sequence can be efficiently replicated in this manner to form Xpandomer intermediates. It can be seen that continuous read lengths ("contigs") corresponding to long template strand fragments can be achieved with this technology. It will be apparent to one skilled in the art that billions of these single molecule SBX reactions can be done simultaneously in an efficient batch process in a single tube. Subsequently, the shotgun products of these syntheses can be sequenced.

In FIG. 3C, the next steps of the SBX process are depicted. Step IX shows denaturation of the duplex Xpandomer intermediate followed by cleavage of selectively cleavable bonds in the backbone, with the selectively cleavable bonds designed so that the tether loops "open up", forming the linearly elongated Xpandomer product (34). Such selective cleavage may be achieved by any number of techniques known to one skilled in the art, including, but not limited to, phosphorothiolate cleavage with metal cations as disclosed by Mag et al. ("Synthesis and selective cleavage of an oligodeoxynucleotide containing a bridged internucleotide 5'-phosphorothioate linkage", *Nucleic Acids Research* 19(7): 1437-1441, 1991), acid catalyzed cleavage of phosphoramidate as disclosed by Mag et al. ("Synthesis and selective cleavage of oligodeoxyribonucleotides containing non-chiral internucleotide phosphoramidate linkages", *Nucleic Acids Research* 17(15): 5973-5988, 1989), selective nuclease cleavage of phosphodiester linkages as disclosed by Gut et al. ("A novel procedure for efficient genotyping of single nucleotide polymorphisms", *Nucleic Acids Research* 28(5): E13, 2000) and separately by Eckstein et al. ("Inhibition of restriction endonuclease hydrolysis by phosphorothioate-containing DNA", *Nucleic Acids Research* 25; 17(22): 9495, 1989), and selective cleavage of photocleavable linker modified phosphodiester backbone as disclosed by Sauer et al. ("MALDI mass spectrometry analysis of single nucleotide polymorphisms by photocleavage and charge-tagging", *Nucleic Acids Research* 31, 11 e63, 2003), Vallone et al. ("Genotyping SNPs using a UV-photocleavable oligonucleotide in MALDI-TOF MS", *Methods Mol. Bio.* 297:169-78, 2005), and Ordoukhanian et al. ("Design and synthesis of a versatile photocleavable DNA building block, application to phototriggered hybridization", *J. Am. Chem. Soc.* 117: 9570-9571, 1995).

Refinements of the basic process, such as wash steps and adjustment of conditions of stringency are well within the skill of an experienced molecular biologist. Variants on this process, include for example immobilization and parsing of the target strands, stretching and other techniques to reduce secondary structure during synthesis of the Xpandomer, post-expansion labeling, end-functionalization, and alternatives to ligase for linking the substrates will be discussed in the materials that follow.

Synthesis of Xpandomers is done to facilitate the detection and sequencing of nucleic acids, and is applicable to nucleic acids of all kinds. The process is a method for "expanding" or "elongating" the length of backbone elements (or subunits) encoding the sequence information (expanded relative to the small nucleotide-to-nucleotide distances of native nucleic acids) and optionally also serves to increase signal intensity (relative to the nearly indistinguishable, low-intensity signals observed for native nucleotides). As such, the reporter elements incorporated in the expanded synthetic backbone of an Xpandomer can be detected and processed using a variety of detection methods, including detection methods well known in the art (for example, a CCD camera, an atomic force microscope, or a gated mass spectrometer), as well as by methods such as a massively parallel nanopore sensor array, or a combination of methods. Detection techniques are selected on the basis of optimal signal to noise, throughput, cost, and like factors.

Figure 4:
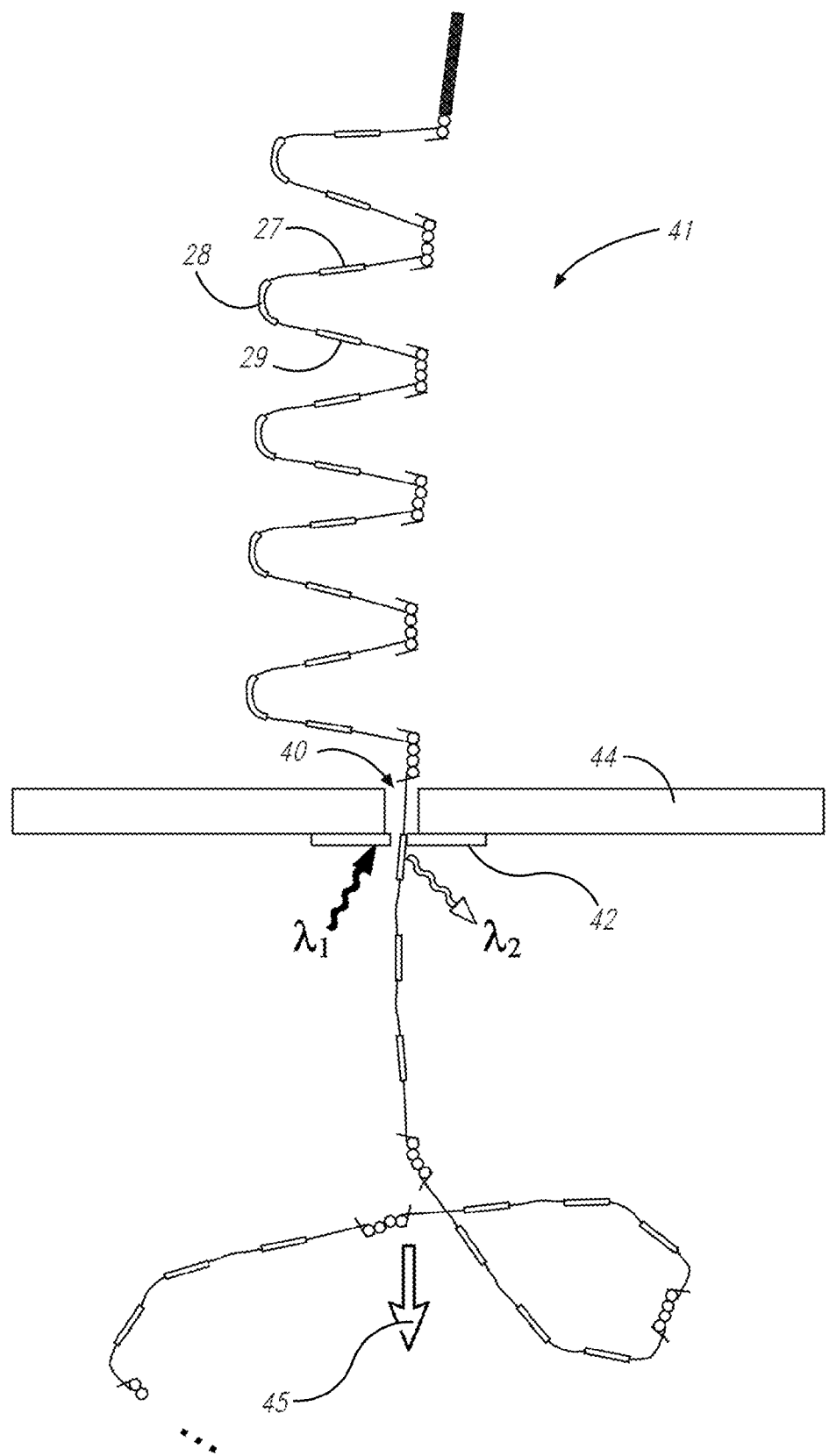
FIG. 4 is a simple model illustrating a FRET nanopore-type device for sequencing an Xpandomer.

Turning to FIG. 4, a simple model of a detection technology is shown; namely, a nanopore (40) with FRET donor (42) in a membrane (44), which is excited by light of $\lambda_1$ wavelength. As the Xpandomer product (41) elongates and is conveyed through the nanopore (40) in the direction of arrow (45), serial bursts of emission of wavelength $\lambda_2$ from excited fluorophores, in the proximity of the pore, are detected. The emission wavelengths ($\lambda_2$) are temporally spaced as a function of the length of the tether and the speed of the Xpandomer passing through the nanopore. By capturing these analog signals and digitally processing them, the sequence information can be read directly from the Xpandomer. It should be noted that in this detection method, the nanopore and membrane can have many paths through which the Xpandomer may translocate. The FRET detection requires there be at least one excited FRET donor along each path. In contrast, a Coulter counter based nanopore can only have an additional translocation hole at the cost of signal-to-noise.

In the nanopore-based detection technique of FIG. 4, which depicts chains of Xprobes of the structure shown in FIG. 2B, the tether constructs contain multi-element reporter constructs, as indicated by the box-like reporter members (27,28,29) disposed along the tether. Relevant nanopore sequencing technology is disclosed, for example, by Branton et al. in U.S. Pat. No. 6,627,067 and by Lee et al. (Lee, J W and A Meller. 2007. Rapid sequencing by direct nanoscale reading of nucleotide bases in individual DNA chains. In "New High Throughput Technologies for DNA Sequencing and Genomics, 2", Elsevier).

Figure 5:
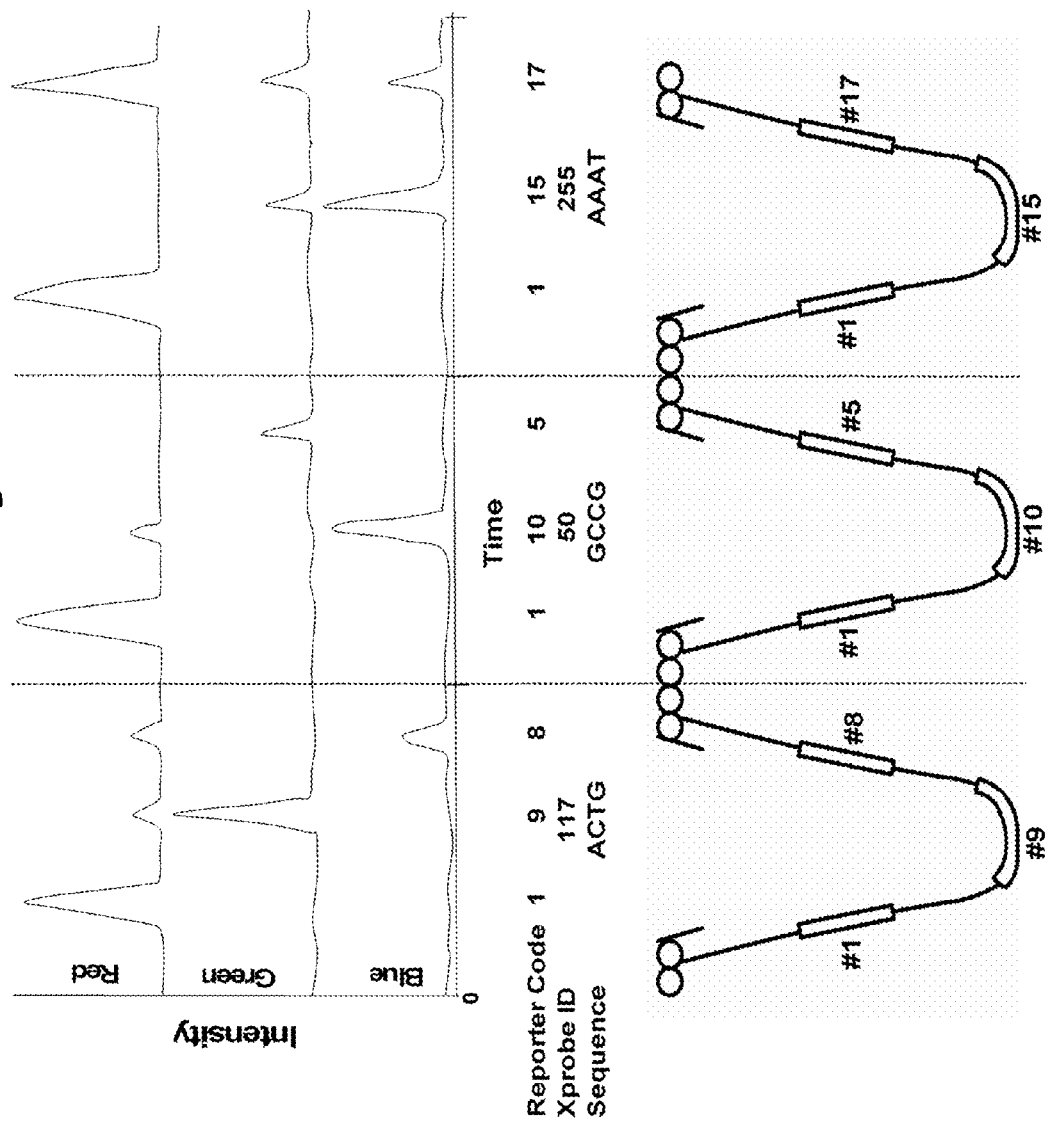
FIG. 5 is a plot with channels for red, green, and blue fluorescence emissions, and illustrates how analog signals can be decoded into digital information that corresponds to the genetic sequence information encoded in an Xpandomer. The accompanying table (FIG. 6) shows how the data is decoded. By employing three multi-state fluorophores, the sequence of bases can be read with high resolution in digital form from a single molecule in real time as the Xpandomer spools through the nanopore.

FIG. 5 demonstrates how multi-element reporter constructs, here comprised of FRET acceptor fluorophores, appear to a detector positioned at the FRET gate. It can be seen in this multi-channel plot of emissions, that analog signals are generated at generally regular time intervals and can be parsed as a type of digital code (here termed a reporter code, and, for this example, an Xprobe ID) revealing the identity and order of the Xprobe subunits and thus the genetic sequence of the illustrated Xpandomer. Various combinations of reporters can be used to create a library of reporter codes that sequentially encode any 4-base combination of A, T, G or C of the described Xprobe. In this example, combinations of three fluorophores are used to produce twenty-two reporter codes. In this way, the sequence ACTG is seen to be followed by GCCG; followed by AAAT. Vertically placed dotted lines separate the fluorimetry data and the corresponding subunits of the Xpandomer (shown schematically). An interpretive algorithm immediately below the plot shows how the regularly spaced analog signals are transformed into a readable genetic sequence.

The Xprobe substrate construct illustrated in FIG. 5, which uses a multi-element tether construct composed of three reporter labeled segments, each of which is flanked with spacer tether segments, to encode the sequence identity of the substrate, is further elaborated. The first tether segment is reporter code #1 (reading from left to right), and is read as a high signal in the red channel. The second tether segment is reporter code #9, and is read as a high green signal and a low red signal. The third tether segment is reporter code #8, and is read as a low blue signal and a low red signal. Reporter code #1 is used as a clock or synchronization signal; reporter code #9 encodes the first probe moiety "AC"; reporter code number #8 encodes the second moiety "TG" of the probe. Taken together, the sequential reporter code of "1-9-8" corresponds to a particular species of Xprobe (Xprobe ID 117), which in turn corresponds by design to the sequence fragment "ACTG". Three Xprobe IDs encode the entire contiguous 1 sequence shown in the plot, "ACTGGCCGAAAT" (SEQ ID NO:1). The fluorophore emissions, the table for decoding reporter codes and sequence fragments, and the corresponding physical representations of the reporter constructs are separated by the dotted lines of the figures according to structural subunits of the Xpandomer so that it can readily be seen how the sequence information is decoded and digitized.

FIG. 6 is a table of fluorophore labels from which the example of FIG. 5 was prepared. This illustrates more generally the use of combinations of multi-state reporter codes to parse information in the form of detectable signals. Fluorophores having twenty-two possible emission states are used to form the reporter constructs of this example. Three fluorophore labels per oligomer are more than adequate to code all possible 4 mer combinations of A, T, C and G. By increasing the length of the tether, the resolution between the fluorophore label emissions is improved, benefiting the accuracy of the detection step, a principle that is generally applicable.

Reporters useable with tether constructs of this kind are of many types, not merely fluorophores, and can be measured using a corresponding broad range of high throughput and accurate detection technologies, technologies that might not otherwise be useful to sequence native nucleic acids because of limited resolution. Massively parallel, state of the art detection methods, such as nanopore sensor arrays, are facilitated by the more measurable characteristics of Xpandomers. Inefficiencies in sequencing detection processes can be reduced by pre-purifying batches of Xpandomers to eliminate incomplete or short reaction products. Methods for end-modifying synthesized Xpandomers are provided that can be utilized for both purification and as a means of facilitating Xpandomer presentation to the detector. Furthermore, the reading process is not constrained by limitation to capping, uncapping, nucleotide extension, labeling, or other concurrent processing methods.

Figure 7A:
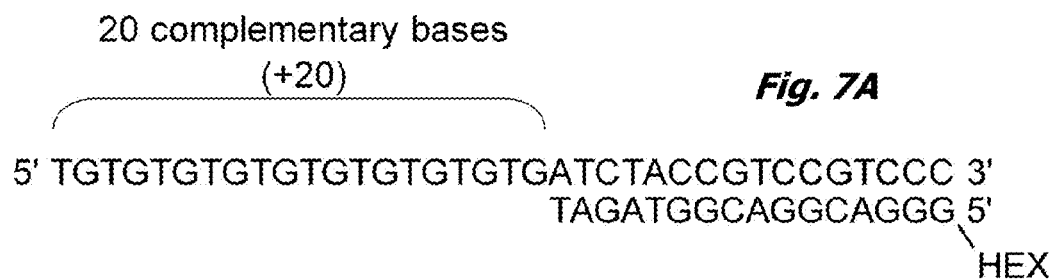
FIGS. 7A-E are gels of ligation products.
Figure 7B:
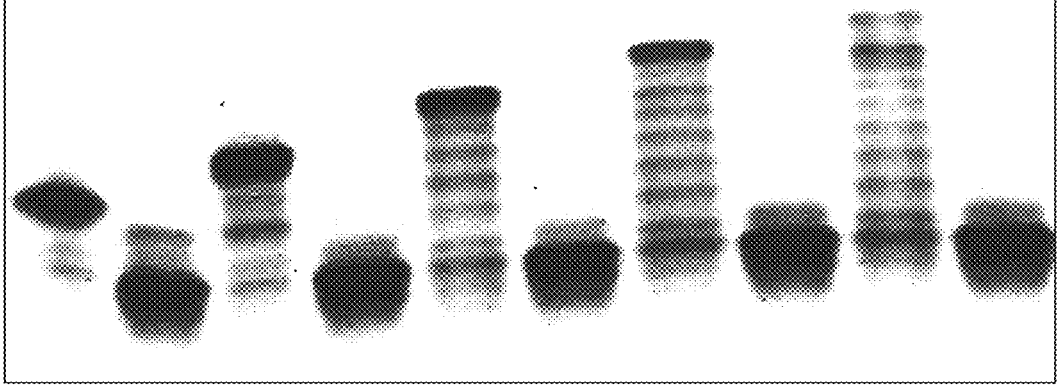

FIG. 7A describes a partial duplex template (SEQ ID NO:2) designed with a twenty base 5' overhang to demonstrate processive ligation of substrates and primer-initiated (SEQ ID NO:3) template-directed ligation in free solution. FIG. 7B is a photograph of a gel demonstrating ligation of the substrates using the primer-template format described in FIG. 7A. For this example, dinucleotide oligomeric substrates of the sequence 5' phosphate CA 3' are hybridized to the template in the presence of a primer and T4 DNA ligase. The unduplexed end-overhang (if any) is then nuclease digested and the ligation products are separated on a 20% acrylamide gel. The ligation results in product polymers containing demonstrably ligated subunits. As indicated by the banding pattern, the ligase positive reactions run out in lanes 1, 3, 5, 7 and 9, which contain progressively longer templates (4, 8, 12, 16, and 20 bases, respectively), clearly demonstrate sequential ligation of 2 mer substrates (increased lengths of exonuclease protected duplexes). Lanes 2, 4, 6, 8 and 10 are negative controls containing no ligase and show complete exonuclease digestion of unligated products.

Figure 7C:
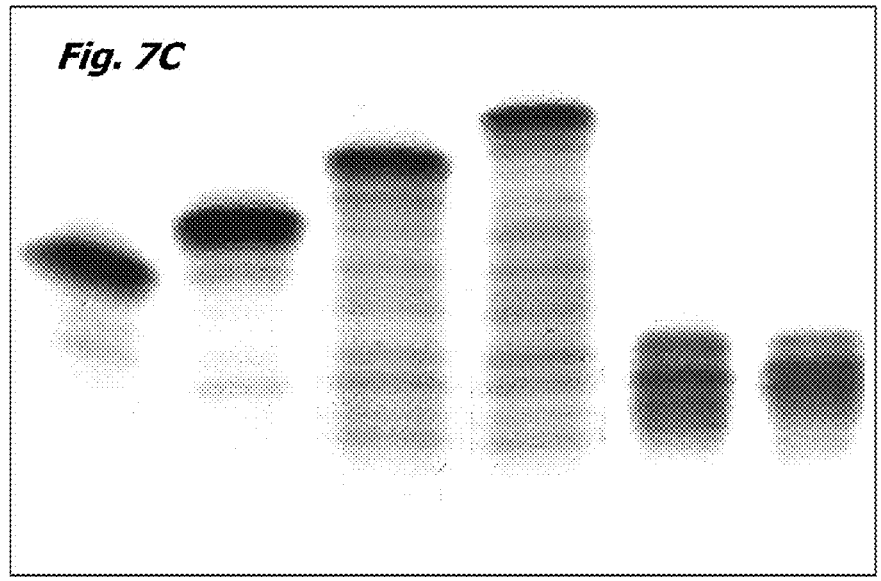

FIG. 7C is a second gel showing template-directed ligation of substrates. Four progressively longer positive control templates, again duplexed with an extension primer, were assayed (4, 8, 12, and 16 template bases, respectively). Again, dinucleotide oligomeric substrates of the sequence 5' phosphate CA 3' are hybridized to the template in the presence of a primer and T4 DNA ligase. The unduplexed end-overhang (if any) is then nuclease digested and the ligation products are separated on a 20% acrylamide gel. Oligomeric substrates (again 2 mers) are seen to ligate to the template in lanes 1, 2, 3 and 4, but not in lanes 5 and 6, where the template strands contain a mismatch with the 5' (phosphate) CA 3' dinucleotide (Lane 5 template—5' CGCG 3'; Lane 6 template—5' GGGG 3').

Figure 7D:
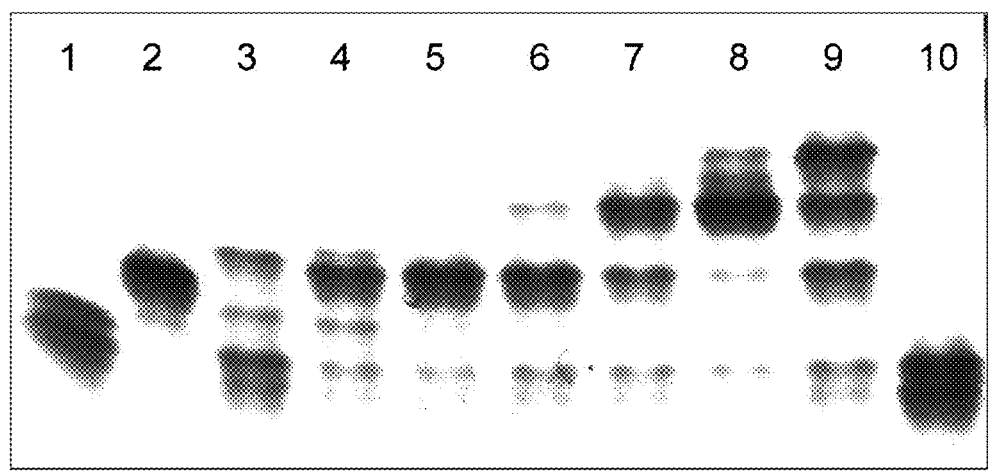

The gel results shown in FIG. 7D demonstrate multiple, template-directed ligations of a Bis(aminomodified) tetranucleotide probe. The aliphatic amino modifiers were of the linkage and composition described in FIG. 26. For this example, a tetranucleotide oligomeric substrate of the sequence 5' (phosphate) C (amino)A (amino)C A 3' was hybridized to a range of progressively longer complimentary templates (duplexed with an extension primer) in the presence of a primer and T4 DNA ligase. The unduplexed end-overhang (if any) was then nuclease digested and the ligation products are separated on a 20% acrylamide gel. The ligation results in product polymers containing demonstrably ligated subunits. Lanes 1 and 2 represent 16 mer and 20 mer size controls. Lanes 3, 4, 5, 6, 7, 8, and 9 show ligation products for progressively longer complementary templates (4, 6, 8, 12, 16, 18, and 20 template bases, respectively). Multiple tetramer ligations are observed for longer templates reactions (Lanes 6-9). Lane 10 shows essentially complete ligase inhibition due to template-probe mismatch (template—5' CGCG 3').

Figure 7E:
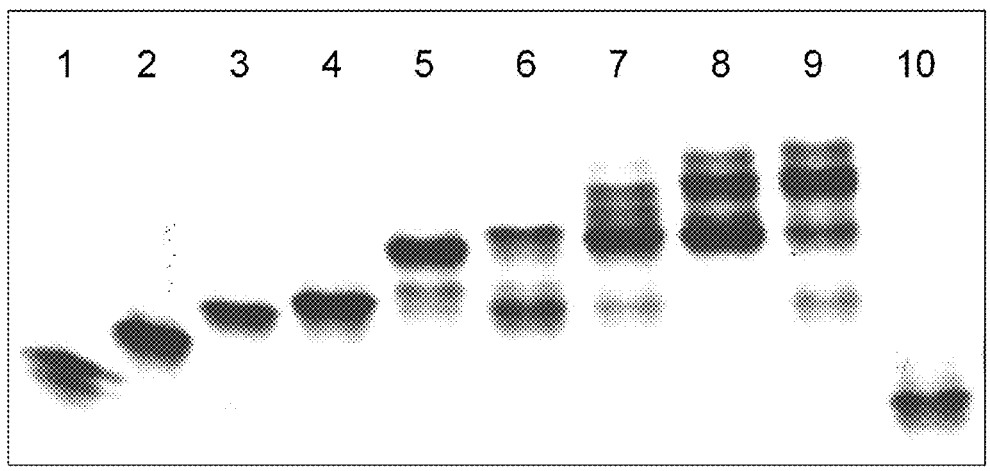

The gel results shown in FIG. 7E demonstrate multiple, template-directed ligations of a Bis(aminomodified) hexanucleotide probe. The aliphatic amino modifiers were of the linkage and composition described in FIG. 26. For this example, a hexanucleotide oligomeric substrate of the sequence 5' (phosphate) C A (amino)C (amino)A C A 3' was hybridized to a range of progressively longer complimentary templates (duplexed with an extension primer) in the presence of a primer and T4 DNA ligase. The unduplexed end-overhang (if any) was then nuclease digested and the ligation products are separated on a 20% acrylamide gel. The ligation results in product polymers containing demonstrably ligated subunits. Lanes 1 and 2 represent 16 mer and 20 mer size controls. Lanes 3, 4, 5, 6, 7, 8 and 9 show ligation products for progressively longer complementary templates (4, 6, 8, 12, 16, 18, and 20 template bases, respectively). Multiple tetramer ligations are observed for longer templates reactions (Lanes 5-9). Lane 10 shows nearly complete ligase inhibition due to template-probe mismatch (template—5' CGCGCG 3').

Figure 8:
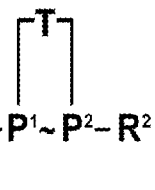
FIG. 8 is an overview of oligomeric Xpandomers.
Figure 9:
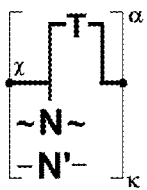
FIG. 9 is an overview of monomeric Xpandomers.

Substrates include both probe members (i.e., oligomers as template-specific binding members for assembling the Xpandomer intermediate), and monomers (i.e., individual nucleobase members as the template-specific binding elements). We term the first "probe-type" substrates and the second "monomer-type" substrates. As illustrated in FIG. 8, probe-type Xpandomers have five basic subgenera, while FIG. 9 illustrates five basic subgenera of monomer-type Xpandomers. The tables of FIGS. 8 and 9 include three columns: the first describing substrate constructs, the second Xpandomer intermediates, and the third the Xpandomer products characteristic of the subgenus (by row). The tables are provided here as an overview, with methods making and using the same being disclosed in greater detail herein below. In FIGS. 8 and 9, "P" refers to a probe member, "T" to a tether member (or loop tether or tether arm precursor), "N" to a monomer (an individual nucleobase or nucleobase residue), and "R" to an end group.

More specifically, in the table of FIG. 8 the following nomenclature is used:

P is a probe substrate member and is composed of $P^1$-$P^2$, where $P^1$ is a first probe moiety and $P^2$ is a second probe moiety;

T is a tether;

Brackets indicate a subunit of the daughter strand, wherein each subunit is a subunit motif having a species-specific probe member, further wherein said probe members of said subunit motifs are serially complementary to the corresponding contiguous nucleotide sequence of the template strand, denoted here $P^{1'}$-$P^{2'}$, and form a primary backbone of the Xpandomer intermediate, and wherein the tether members, optionally in combination with the probe moieties, form a constrained Xpandomer backbone. Cleavage of one or more selectively cleavable bonds within the Xpandomer intermediate enables expansion of the subunits to produce an Xpandomer product, the subunits of which are also indicated with brackets;

α denotes a species of subunit motif selected from a library of subunit motifs;

ε is a first linker group attached to a first terminus or moiety of a probe member or tether; under controlled conditions, ε is capable of selectively reacting with, directly or via crosslinkers, linker group δ of an abutting terminus of an adjacent subunit to form covalent or equivalently durable linkages;

δ is a second linker group attached to a first terminus or moiety of a probe member or tether; under controlled conditions, δ is capable of selectively reacting with, directly or via crosslinkers, linker group ε of an abutting terminus of an adjacent subunit to form covalent or equivalently durable linkages;

χ represents a bond with an adjacent subunit and is the product linkage of the reaction of linker groups δ and ε;

~ denotes a selectively cleavable bond, which may be the same or different when multiple selectively cleavable bonds are present;

$R^1$ includes, but is not limited to, hydroxyl, hydrogen, triphosphate, monophosphate, ester, ether, glycol, amine, amide, and thioester;

$R^2$ includes, but is not limited to, hydroxyl, hydrogen, triphosphate, monophosphate, ester, ether, glycol, amine, amide, and thioester; and κ denotes the $κ^{th}$ subunit in a chain of m subunits, where κ=1, 2, . . . to m, where m>3, and generally m>20, and preferably m>50, and more preferentially m>1000.

More specifically, and in context of the table FIG. 9, the following nomenclature is used:

N is a nucleobase residue;

T is a tether;

Brackets indicate a subunit of the daughter strand, wherein each subunit is a subunit motif having a species-specific nucleobase residue, further wherein said nucleobase residues of said subunit motifs are serially complementary to the corresponding contiguous nucleotide sequence of the template strand, denoted here N', and form a primary backbone of the Xpandomer intermediate, and wherein the tether members, optionally in combination with the nucleobase residues, form a constrained Xpandomer backbone. Cleavage of one or more selectively cleavable bonds within the Xpandomer intermediate enables expansion of the subunits to produce an Xpandomer product, the subunits of which are also indicated with brackets;

$n^1$ is a first portion of a nucleobase residue;

$n^2$ is a second portion of a nucleobase residue;

ε is a first linker group attached to a first terminus or moiety of a probe member or tether; under controlled conditions, ε is capable of selectively reacting with, directly or via crosslinkers, linker group δ of an abutting terminus of an adjacent subunit to form covalent or equivalently durable linkages;

δ is a second linker group attached to a first terminus or moiety of a probe member or tether; under controlled conditions, δ is capable of selectively reacting with, directly or via crosslinkers, linker group ε of an abutting terminus of an adjacent subunit to form covalent or equivalently durable linkages;

χ represents a bond with an adjacent subunit and is the product linkage of the reaction of linkage groups δ and ε;

$χ^1$ is the product linkage of the reaction of linkage groups $δ^1$ and $ε^1$;

$χ^2$ is the product linkage of the reaction of linkage groups $δ^2$ and $ε^2$;

~ denotes a selectively cleavable bond, which may be the same or different when multiple selectively cleavable bonds are present;

$R^1$ includes, but is not limited to, hydroxyl, hydrogen, triphosphate, monophosphate, ester, ether, glycol, amine, amide, and thioester;

$R^2$ includes, but is not limited to, hydroxyl, hydrogen, triphosphate, monophosphate, ester, ether, glycol, amine, amide, and thioester; and κ denotes the $κ^{th}$ subunit in a chain of m subunits, where κ=1, 2, ... to m, where m>10, and generally m>50, and typically m>500 or >5,000.

Oligomeric Constructs

Xpandomer precursors and constructs can be divided into two categories based upon the substrate (oligomeric or monomeric) used for template directed assembly. The Xpandomer structure, precursors and synthesis methods for those based upon the oligomer substrates are discussed below.

The substrate constructs are reagent precursors to the Xpandomer and generally have a tether member and a substrate. The substrate discussed here is an oligomer substrate or probe, generally made up of a plurality of nucleobase residues. By generating combinatorial-type libraries of two to twenty nucleobase residues per probe, generally 2 to 10 and typically 2, 3, 4, 5 or 6 nucleobase residues per probe, probe libraries useful as reagents in the synthesis of Xpandomers precursors (substrate constructs) are generated.

The probe is generally described below as having two probe moieties, $P^1$ and $P^2$. These probe moieties are generally depicted in the figures as dinucleotides, but in general $P^1$ and $P^2$ have each at least one nucleobase residue. In the example of a probe with two nucleobase residues, the probe moieties $P^1$ and $P^2$ would be single nucleobase residues. The number of nucleobase residues for each is chosen, appropriately, for the Xpandomer synthesis method and may not be equal in $P^1$ and $P^2$.

For the substrate constructs where ε and δ linker groups are used to create inter-subunit linkages, a broad range of suitable commercially available chemistries (Pierce, Thermo Fisher Scientific, USA) can be adapted for this purpose. Common linker chemistries include, for example, NHS-esters with amines, maleimides with sulfhydryls, imidoesters with amines, EDC with carboxyls for reactions with amines, pyridyl disulfides with sulfhydryls, and the like. Other embodiments involve the use of functional groups like hydrazide (HZ) and 4-formylbenzoate (4FB) which can then be further reacted to form linkages. More specifically, a wide range of crosslinkers (hetero- and homo-bifunctional) are broadly available (Pierce) which include, but are not limited to, Sulfo-SMCC (Sulfosuccinimidyl 4-[N-maleimidomethyl]cyclohexane-1-carboxylate), SIA (N-Succinimidyl iodoacetate), Sulfo-EMCS ([N-e-Maleimidocaproyloxy]sulfosuccinimide ester), Sulfo-GMBS (N-[g-Maleimido butyryloxy]sulfosuccinimide ester), AMAS N-(a-Maleimidoacetoxy)succinimide ester), BMPS(N EMCA (N-e-Maleimidocaproic acid)-[β-Maleimidopropyloxy] succinimide ester), EDC (1-Ethyl-3-[3-dimethylaminopropyl]carbodiimide Hydrochloride), SANPAH (N-Succinimidyl-6-[4'-azido-2'-nitrophenylamino]hexanoate), SADP (N-Succinimidyl(4-azidophenyl)-1,3'-dithiopropionate), PMPI (N-[p-Maleimidophenyl] isocy, BMPH (N-[β-Maleimidopropionic acid]hydrazide, trifluoroacetic acid salt)anate), EMCH ([N-e-Maleimidocaproic acid]hydrazide, trifluoroacetic acid salt), SANH (succinimidyl 4-hydrazinonicotinate acetone hydrazone), SHTH (succinimidyl 4-hydrazidoterephthalate hydrochloride), and C6-SFB (C6-succinimidyl 4-formylbenzoate). Also, the method disclosed by Letsinger et al. ("Phosphorothioate oligonucleotides having modified internucleoside linkages", U.S. Pat. No. 6,242,589) can be adapted to form phosphorothiolate linkages.

Further, well established protection/deprotection chemistries are broadly available for common linker moieties (Benoiton, "Chemistry of Peptide Synthesis", CRC Press, 2005). Amino protection include, but are not limited to, 9-Fluorenylmethyl carbamate (Fmoc-NRR'), t-Butyl carbamate (Boc-NRR'), Benzyl carbamate (Z—NRR', Cbz-NRR'), Acetamide Trifluoroacetamide, Phthalimide, Benzylamine (Bn-NRR'), Triphenylmethylamine (Tr-NRR'), and Benzylideneamine p-Toluenesulfonamide (Ts-NRR'). Carboxyl protection include, but are not limited to, Methyl ester, t-Butyl ester, Benzyl ester, S-t-Butyl ester, and 2-Alkyl-1,3-oxazoline. Carbonyl include, but are not limited to, Dimethyl acetal 1,3-Dioxane, and 1,3-Dithiane N,N-Dimethylhydrazone. Hydroxyl protection include, but are not limited to, Methoxymethyl ether (MOM-OR), Tetrahydropyranyl ether (THP-OR), t-Butyl ether, Allyl ether, Benzyl ether (Bn-OR), t-Butyldimethylsilyl ether (TBDMS-OR), t-Butyldiphenylsilyl ether (TBDPS-OR), Acetic acid ester, Pivalic acid ester, and Benzoic acid ester.

While the tether is often depicted as a reporter construct with three reporter groups, various reporter configurations can be arrayed on the tether, and can comprise single reporters that identify probe constituents, single reporters that identify probe species, molecular barcodes that identify probe species, or the tether may be naked polymer (having no reporters). In the case of the naked polymer, the reporters may be the probe itself, or may be on a second tether attached to the probe. In some cases, one or more reporter precursors are arrayed on the tether, and reporters are affinity bound or covalently bound following assembly of the Xpandomer product.

As discussed above, FIG. 8 provides an overview of oligomeric constructs of the invention, with five classes being distinguished: Classes I, II, III, IV, and V. These classes apply to both Xprobes and Xmers. Each class will be discussed individually below.

Class I Oligomeric Constructs

Turning to FIG. 10, Class I oligomeric constructs are described in more detail. FIGS. 10A through 10C employ a notation adapted for showing these molecules as substrates and as hetero-copolymer products of the SBX process. The figures are read from left to right, showing first the probe substrate construct (oligomeric precursor of Xpandomer), then the intermediate duplex daughter strand in the center, and on the right the Xpandomer product prepared for sequencing.

Figure 10A:
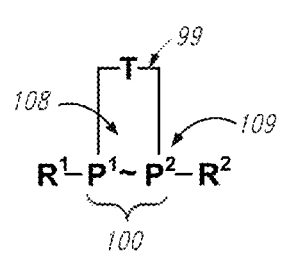
FIGS. 10A through 10E depict Class I Xpandomers, intermediates and precursors in a symbolic and graphical form. These precursors are termed Xprobes if monophosphates and Xmers if triphosphates.

As shown in FIG. 10A, a Class I substrate construct has an oligomeric probe member (-$P^1$~$P^2$-)) (100) and a tether member, T (99). The tether is attached by two end linkages (108, 109) to probe moieties $P^1$ and $P^2$. These constraints prevent the tether from elongating or expanding and thus in a constrained configuration. Under template-directed assembly, substrates form a duplex with the target template such that the substrates are abutted.

$R^1$ and $R^2$ are end groups configured as appropriate for the synthesis protocol in which the substrate construct is used. For example, $R^1$=5'-phosphate and $R^2$=3'-OH, would find use in a ligation protocol, and $R^1$=5'-triphosphate and $R^2$=3'-OH for a polymerase protocol. Optionally, $R^2$ can be configured with a reversible blocking group for cyclical single-substrate addition. Alternatively, $R^1$ and $R^2$ can be configured with linker end groups for chemical coupling or with no linker groups for a hybridization only protocol. $R^1$ and $R^2$ can be of the general type XR, wherein X is a linking group and R is a functional group.

Figure 10B:
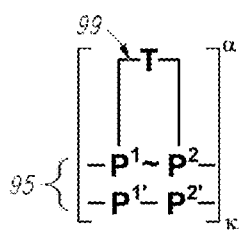

The tilde (~) in FIGS. 10A and 10B denotes a selectively cleavable bond separating two moieties of the probe member. The end linkages of the tether are attached to the two moieties of the probe member that are separated by the selectively cleavable bond. The tether links the first probe moiety to the second probe moiety, forming a loop bridging the selectively cleavable bond. When the probe member is intact (uncleaved), the probe member can bind with high-fidelity to the template sequence and the tether is looped in the "constrained configuration". When this bond is cleaved, the tether loop can open and the tether is in the "expanded configuration".

Substrate constructs are reagents used for template-dependent assembly of a daughter strand, which is an intermediate composition for producing Xpandomers. FIG. 10B shows the duplex daughter strand, a hetero-copolymer with repeating subunits, (shown in brackets). Shown are the daughter strand primary backbone (-$P^1$~$P^2$-) and the target template strand (-$P^{1'}$~$P^{2'}$-) as a duplex (95). Each subunit of the daughter strand is a repeating motif composed of a probe member and a tether member, T (99), the tether member in constrained configuration. The motifs have species-specific variability, indicated here by the "a" superscript. Each particular subunit in the daughter strand is selected from a library of motifs by a template-directed process and its probe binds to a corresponding sequence of complementary nucleotides on the template strand. In this way, the sequence of nucleobase residues of the probes forms a contiguous, complementary copy of the target template strand.

The daughter strand is composed of an Xpandomer precursor called the "constrained Xpandomer" which is further composed of tethers in the "constrained configuration". When the tethers (99) convert to their "expanded configuration", the constrained Xpandomer converts to the Xpandomer product.

The daughter strand can be seen to have two backbones, a "primary backbone", and the backbone of the "constrained Xpandomer. The primary backbone is composed of contiguously abutted probe substrates. The "constrained Xpandomer backbone" bypasses the selectively cleavable linkage between probe moieties $P^1$ and $P^2$ and is formed by linked backbone moieties, each backbone moiety being a linear linkage of $P^1$ to the tether to $P^2$, and where $P^2$ can further link to the $P^1$ of next backbone moiety. It can be seen that the constrained Xpandomer backbone bridges or loops over the selectively cleavable bonds of the primary backbone, and will remain covalently intact when these selectively cleavable bonds are cleaved and the primary backbone is fragmented.

Figure 10C:
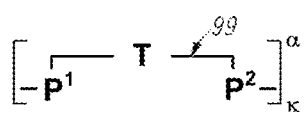

FIG. 10C is a representation of the Class I Xpandomer product after dissociation of the template strand and after cleavage of the selectively cleavable bonds of the primary backbone. Methods for dissociation of the template strand include heat denaturation, or selective digestion with a nuclease, or chemical degradation. The Xpandomer product strand contains a plurality of subunits κ, where κ denotes the $κ^{th}$ subunit in a chain of m subunits making up the daughter strand, where κ=1, 2, 3 to m, where m>3, and generally m>20, and preferably m>50, and more preferentially m>1000. Each subunit is formed of a tether (99) and probe moieties $P^1$ and $P^2$. The tether member T, now in "expanded configuration", is seen stretched to its length between the cleaved probe moieties $P^1$ and $P^2$, which remain covalently linked to the adjacent subunits. Each subunit, a subunit motif α, contains species-specific genetic information established by template directed assembly of the Xpandomer intermediate (daughter strand).

Figure 10D:
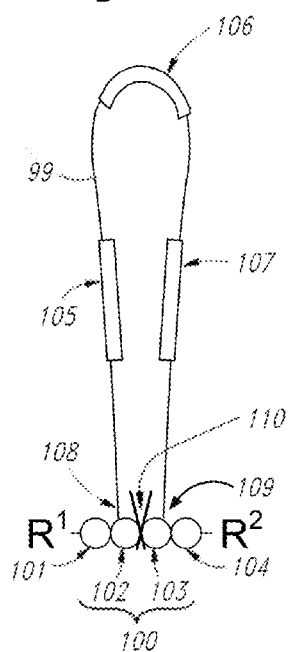

FIG. 10D shows the substrate construct of FIG. 10A as a molecular model, where the probe member (100) is arbitrarily represented with four nucleobase residues (101,102,103,104), two of which (102,103) are joined to the tether (99) by end linkages (108,109). Between the two end linkages of the tether is a selectively cleavable bond, shown as the "V" (110) in probe member (100). This bond joins probe moieties $P^1$ and $P^2$ referred to in FIG. 10A. The tether loop shown here has three reporters (105,106,107), which can also be motif species specific.

Figure 10E:
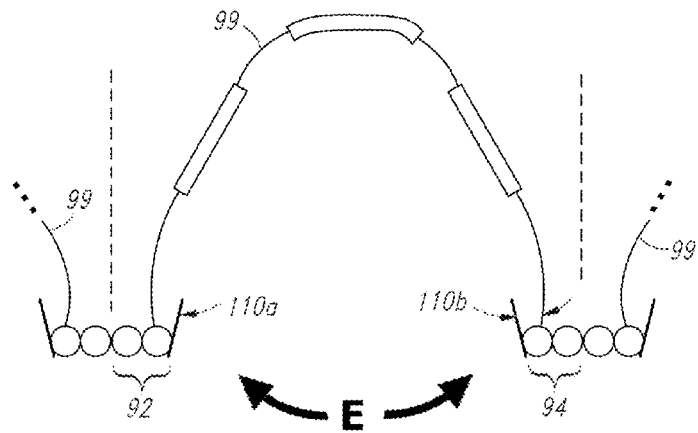

FIG. 10E shows the product Xpandomer after cleavage of the selectively cleavable bonds in the substrate. Cleavage results in expansion of the constrained Xpandomer and is denoted by "E" (dark arrows). The residues (110a,110b) of the selectively Cleavable bond mark the cleavage event. The subunit is indicated by dotted lines vertically bracketing the repeating subunit, as represented by brackets in the accompanying FIG. 10C.

In the Xpandomer product (FIG. 10E) the primary backbone is now fragmented and not covalently intact because the probe members have been cleaved, separating each $P^1$ (92) and $P^2$ (94). Through the cleavage process, the constrained Xpandomer is released to become the Xpandomer product. The Xpandomer includes each concatenated subunit in sequence. Linked within each subunit are the probe moiety $P^1$, the tether, and probe moiety $P^2$. The tether members (99) of the Xpandomer, which were formerly in constrained configuration, are now in expanded configuration, thereby functioning to linearly stretch out the sequence information of the template target. Expanding the tethers lowers the linear density of the sequence information along the Xpandomer and provides a platform for increasing the size and abundance of reporters which in turn improves signal to noise for detection and decoding of the template sequence.

Figure 11:
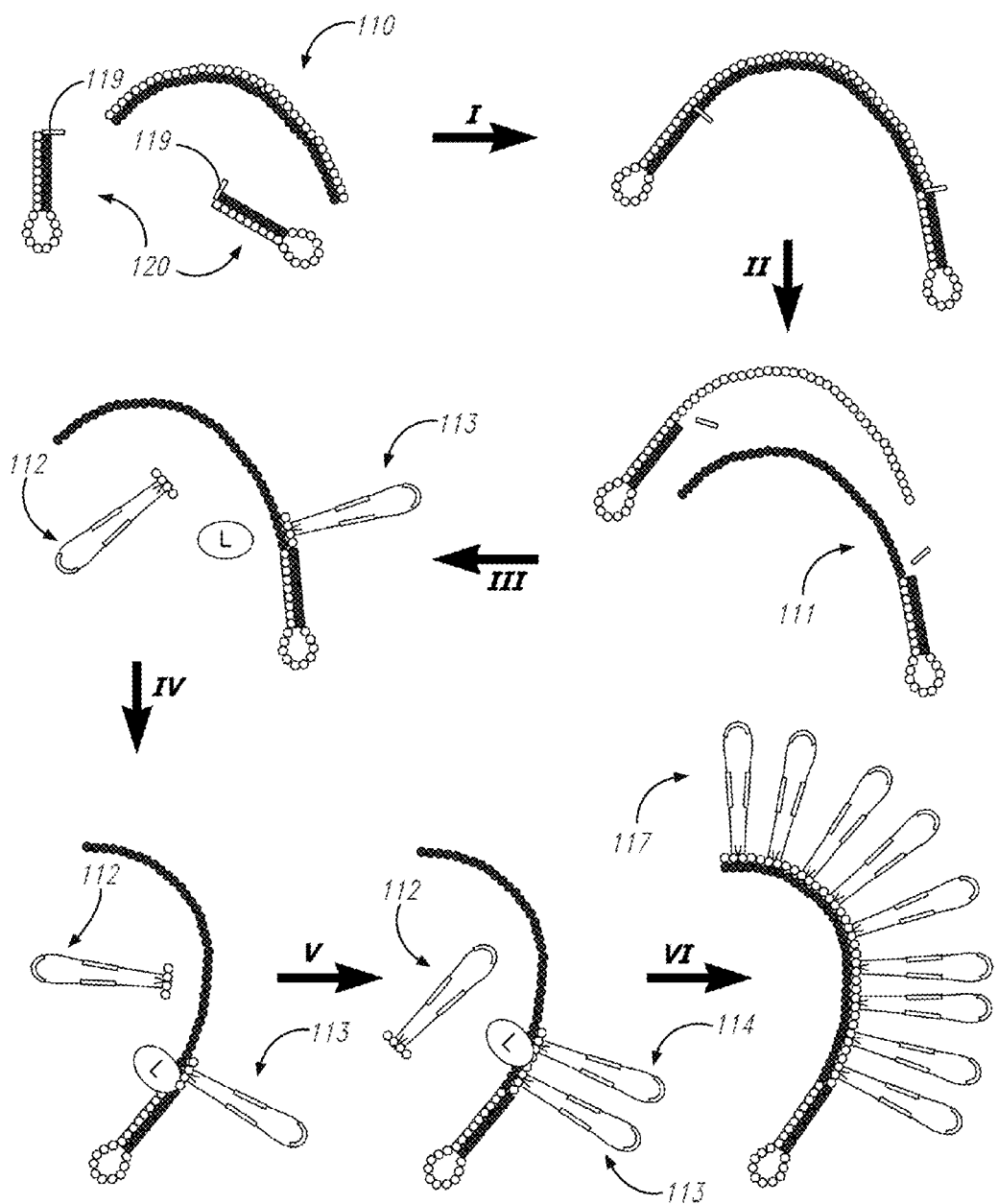
FIG. 11 is a condensed schematic of a method for synthesis of an Xpandomer by solution ligation using an end-terminated hairpin primer and Class I substrate constructs.

FIG. 11 depicts a condensed schematic of a method for making a an embodiment of a Class I Xpandomer; the method illustrates the making and using of substrates and products shown in FIGS. 10D and 10E. The method may be performed in free solution and is described using a ligase (L) to covalently couple abutting Xprobes. Methods for relieving secondary structure in the template are discussed in a subsequent section. Conditions adapted for hybridization and ligation are well known in the art and such conditions can be readily optimized by one of ordinary skill in this field.

Ligases include, but are not limited to, $NAD^+$-dependent ligases including tRNA ligase, Taq DNA ligase, *Thermus filiformis* DNA ligase, *Escherichia coli* DNA ligase, Tth DNA ligase, *Thermus scotoductus* DNA ligase, thermostable ligase, Ampligase thermostable DNA ligase, VanC-type ligase, 9° N DNA Ligase, Tsp DNA ligase, and novel ligases discovered by bioprospecting. Ligases also include, but are not limited to, ATP-dependent ligases including T4 RNA ligase, T4 DNA ligase, T7 DNA ligase, Pfu DNA ligase, DNA ligase I, DNA ligase III, DNA ligase IV, and novel ligases discovered by bioprospecting. These ligases include wild-type, mutant isoforms, and genetically engineered variants.

Referring to FIG. 11, and in preparation for the synthesis, a target nucleic acid (110) is provided and the ends are polished in preparation for blunt-ended ligation of adaptors. Step I shows the ligation of hairpin primers (120) to the target nucleic acid. The free 5' end of the primers are blocked with a removable blocking group (119). The primers will prime both strands of the target nucleic acid. The adaptors are generally added in excess. The blocking groups on the hot ends of the primers are removed in Step II, and the two strands of the template are separated by denaturation. In Step III, the primed single-stranded template (111) is contacted with a substrate construct library (as represented by construct (112) for purpose of illustration) and with ligase, L, under conditions permissible for hybridization of complementary probe substrate (113) and ligation at the reactive end of the primer, as is shown in Step IV. Generally, hybridization and ligation is performed at a temperature greater than the melting temperature of the substrate to reduce non-specific side reactions. Each substrate construct in this example contains a tether arrayed with three reporters. Each probe substrate has a selectively cleavable bond (indicated with a "V") between the two tether attachment sites. In Step V, a second substrate construct (114) is added by template-directed hybridization and ligation, and so forth. In Step VI, formation of a fully extended Xpandomer intermediate (117) is demonstrated. This intermediate can be denatured from the template strand and selectively cleaved at the cleavage sites shown, thereby forming a product Xpandomer suitable for sequencing. In some embodiments, denaturation is not needed and the template strand can be digested in place.

Figure 12:
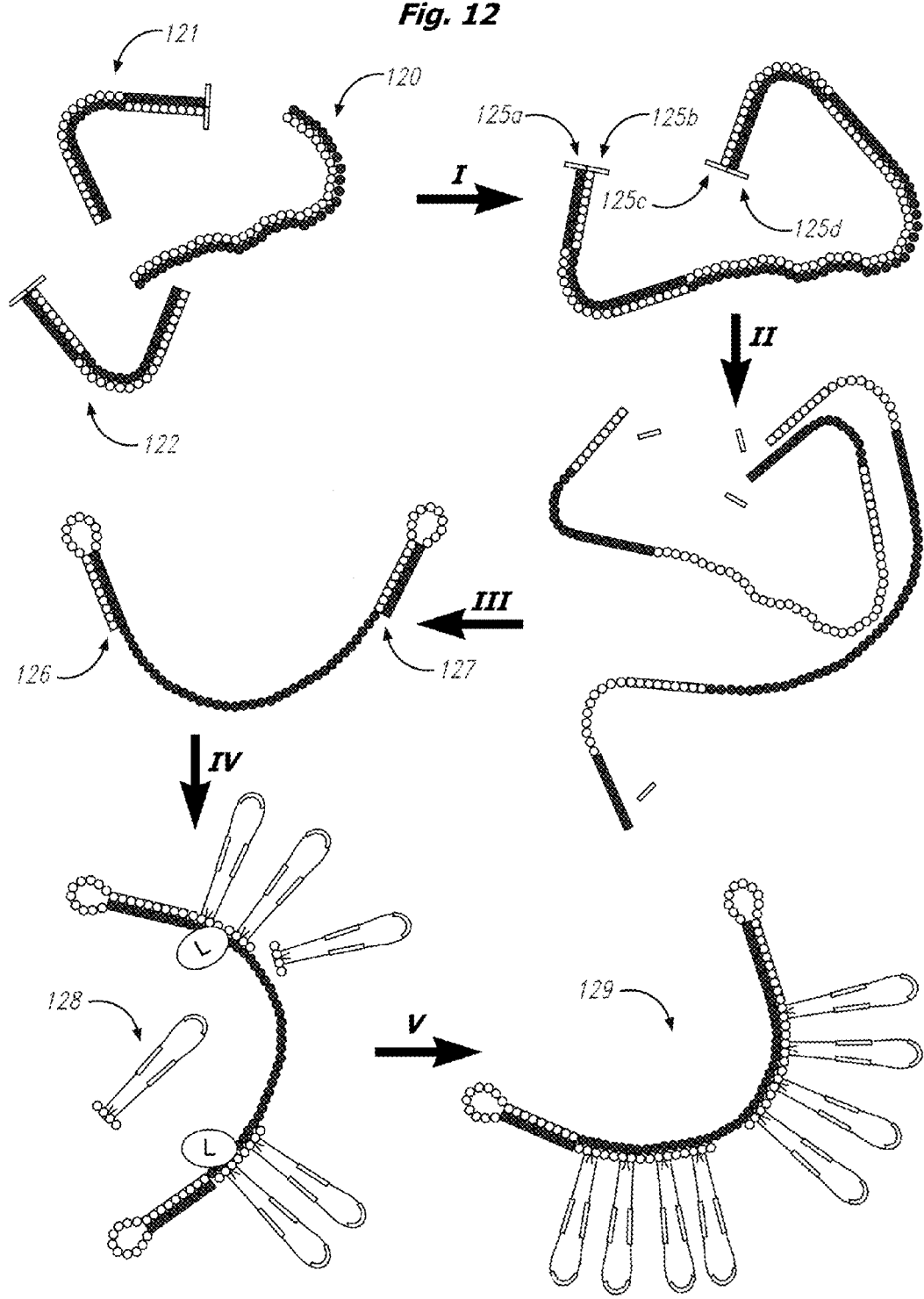
FIG. 12 is a condensed schematic of a method for synthesis of an Xpandomer by solution ligation using a double-ended hairpin primer and Class I substrate constructs.

FIG. 12 is a condensed schematic of a second method, here for making another embodiment of a Class I Xpandomer. In preparation for the synthesis, a target nucleic acid (120) is provided and the ends are polished in preparation for blunt-ended ligation of adaptors (121,122). Step I shows the ligation of doubly-blocked hairpin primer precursors to the target nucleic acid. One end of the duplex hairpin primers is blocked with removable blocking groups (125a,125b,125c,125d) intended to prevent ligation and concatenation of the template strands or adaptors. The adaptors are generally added in excess. The blocking groups are removed in Step II, and the two strands of the template are separated by denaturation. In Step III, the hairpin primers self-anneal, forming priming sites (126,127) for the subsequent ligation of substrate constructs, which can proceed bi-directionally, i.e., both in a '3 to 5' and a 5' to 3' direction. In Step IV, the primed templates are contacted with a substrate construct library (128) under conditions permissible for hybridization of complementary probe substrates and ligation. Ligation proceeds incrementally (i.e., extending the growing ends with apparent processivity) by a process of hybridization of complementary probe substrates and ligation at the ends of the nascent daughter strands. Each substrate construct in this example contains a tether loop arrayed with reporter groups. In Step V, formation of a completed Xpandomer intermediate (129) is depicted. Optionally the template strand can be removed by nuclease digestion, freeing the Xpandomer. The intermediate can be selectively cleaved at the cleavage sites shown, thereby forming a product Xpandomer suitable for sequencing. The product Xpandomers are formed in free solution.

Figure 13:
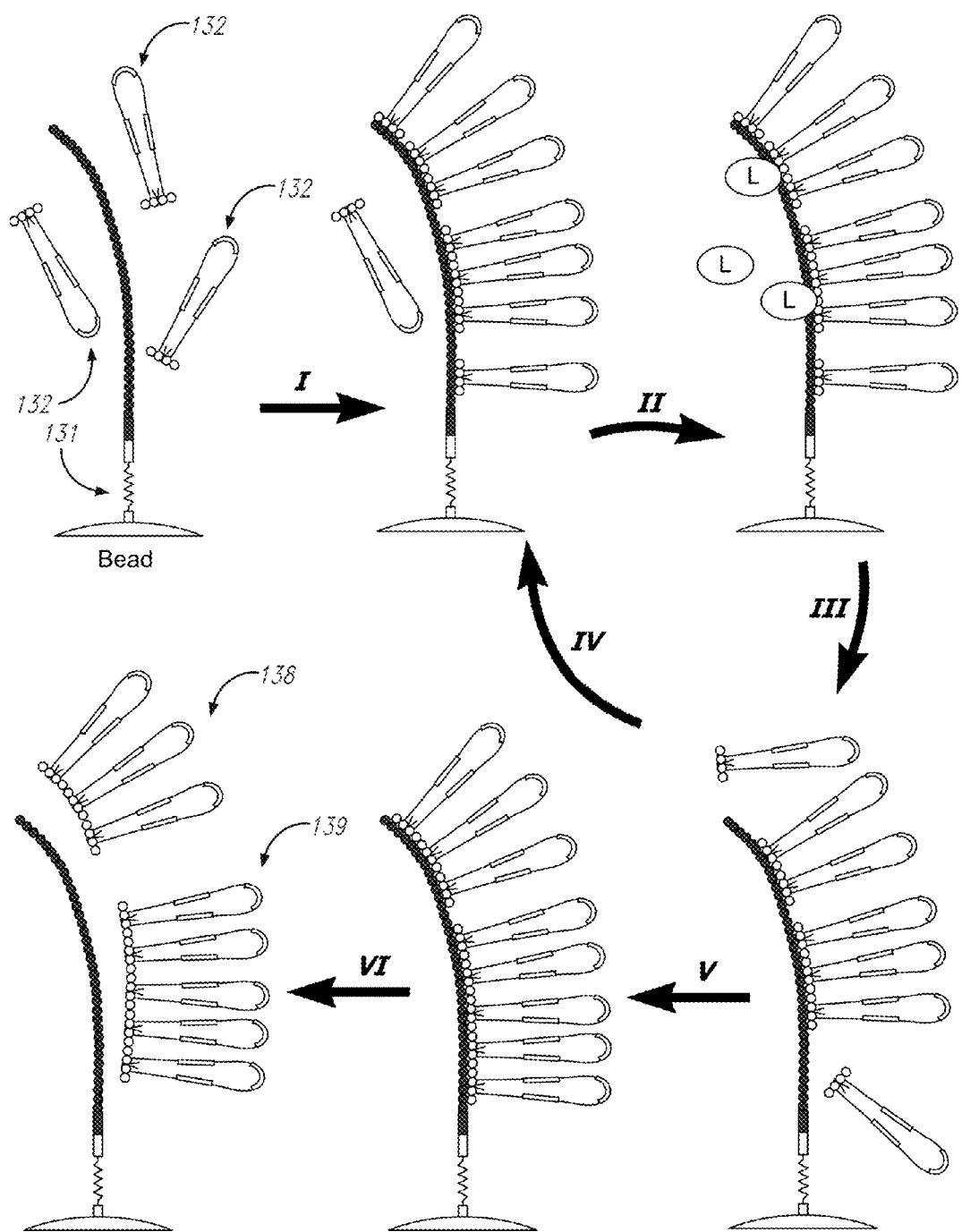
FIG. 13 is a condensed schematic of a method for synthesis of an Xpandomer by ligation on an immobilized template, without primers, using Class I substrate constructs.

In FIG. 13, a method relying on immobilized template strands is shown. Here the template strands are anchored to a bead (or other solid phase support) by an adaptor (131). The template is shown in contact with substrate constructs (132), and in Step I, the conditions are adapted so that hybridization occurs. It can be seen that "islands" of hybridized, abutting substrate constructs are formed. In Step II, addition of ligase, L, results in ligation of the abutting substrate constructs, thereby forming multiple contiguous sequences of ligated intermediates separated by gaps. In Step III, conditions are adjusted to favor dissociation of low molecular weight or mismatched hybridized material, and in Step IV, the reactions of Steps II through III are repeated one or more times to favor formation of longer extension products. This primerless process is referred to herein as "promiscuous ligation". Ligation can extend bidirectionally and nicked junctions can be sealed with ligase, thereby filling gaps. In Step V, after optimization of the desired product lengths, the immobilized duplexes are washed to remove unreacted substrate and ligase. Then, in Step VI, the daughter strands (here shown as a single-stranded Xpandomer intermediate) (138,139) are dissociated from the template. Selective cleavage of selectively cleavable bonds of the intermediate results in formation of the Xpandomer product (not shown). In this embodiment, the immobilized template can be reused. Once the Xpandomer products are sequenced, contigs can be assembled by well known algorithms for overlapping and aligning the data to build a consensus sequence.

Figure 14:
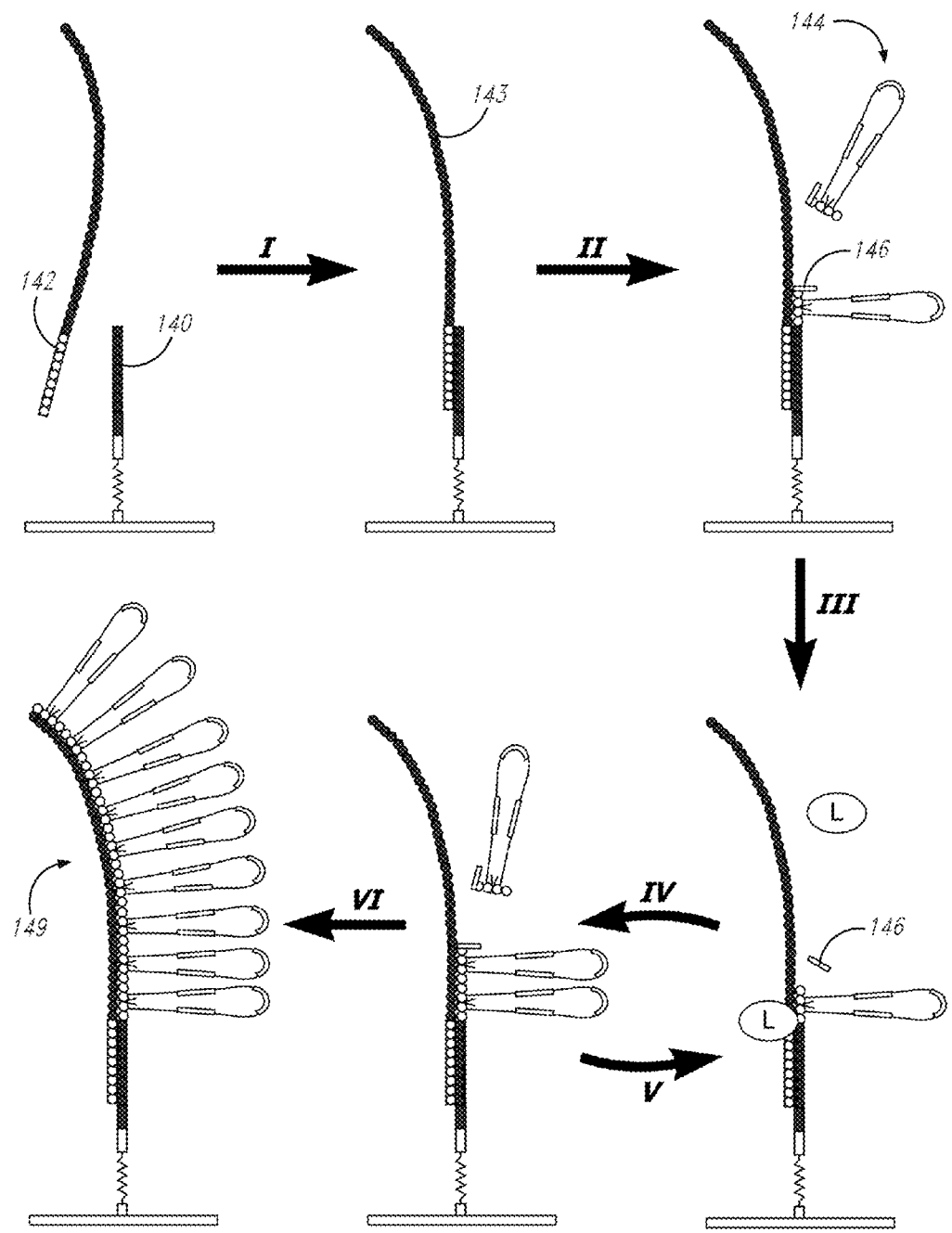
FIG. 14 is a condensed schematic of a method for synthesis of an Xpandomer by cyclical stepwise ligation using reversibly terminated Class I substrate constructs on templates annealed to immobilized primers.

Referring to FIG. 14, a method for using immobilized primers is shown. End-adapted (or random template sequences, depending on the nature of the immobilized primers) templates (142), are annealed to the immobilized primers (140) in Step I. In Step II, the immobilized templates (143) are contacted with a substrate construct library, members of which are shown as (144), and conditions are adjusted for template-directed hybridization. In this example, the substrate construct 3' OH termini of the probe members (R group) has been substituted (146) to reversibly block further extension. In Step III, the abutting ends of the adjacent substrate construct and primer, or free end of the nascent growing daughter strand, are ligated and the 3' OH end of the nascent daughter strand is activated by removing the blocking R group (146). As indicated in Steps IV and V, this process of stepwise cyclical addition can be repeated multiple times. Typically a wash step is used to remove unreacted substrates between each extension step.

The process is thus analogous to what is termed "cyclical single base extension", but would more properly be termed here "cyclical single probe extension". While ligase, L, is shown, the process can be performed with a ligase, polymerase, or by any chemical coupling protocol suitable for joining oligomers in a template-directed synthesis. The chemical coupling may occur spontaneously at the abutting ends of the hybridized probes, or a condensing agent may be added at the beginning of Step III and each ensuing Step V of the cycle. The terminally blocking R group is configured so that free run-on polymerization cannot occur on the template or in solution. Step VI shows the formation of a complete Xpandomer intermediate (149); no more substrate can be added. This intermediate can be dissociated from the template, the single-stranded product is then cleaved to open up the backbone as previously described.

This method can be adapted for selective sequencing of particular targets in a nucleic acid mixture, and for parsed sequencing methods on sequencing arrays, for example, by non-random selection of the immobilized primers. Alternatively, universal or random primers may be used as shown.

Figure 15:
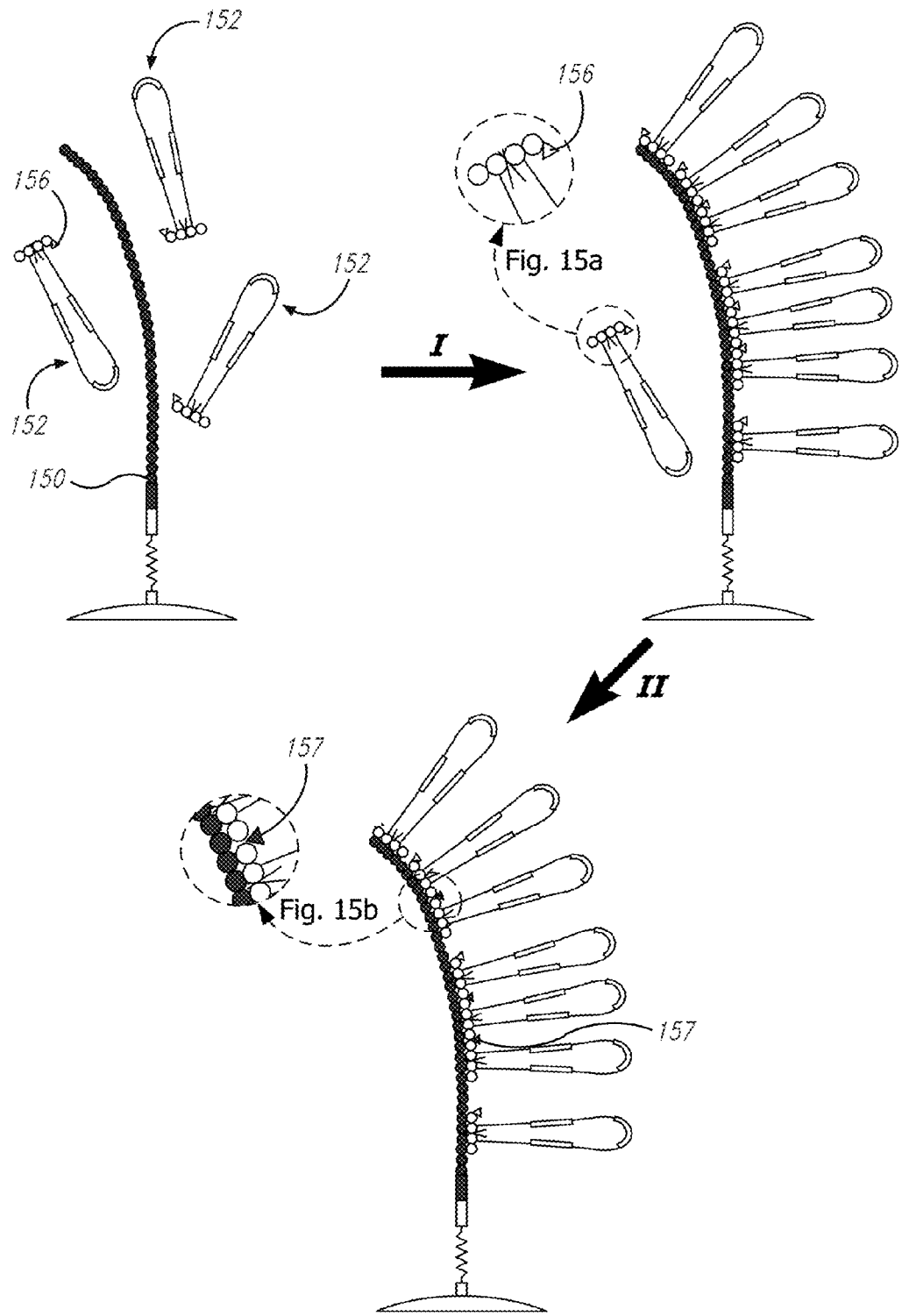
FIG. 15 is a condensed schematic of a method for synthesis of an Xpandomer by promiscuous assembly and chemical coupling using Class I substrate constructs without primers.

FIG. 15 describes a method for promiscuous hybridization on an immobilized template (150) (Step I), where the substrate constructs of the library (152) are modified with a chemical functional group that is selectively reactive (156), depicted as an open triangle, with an abutting probe. A detail of the chemical functional group of the substrate constructs is shown in the expanded portion shown by the hatched circle (FIG. 15a). At a certain density of hybridization, coupling is initiated as shown in Step II, resulting in high molecular weight Xpandomer intermediates linked by the crosslinked product (157), depicted as a filled triangle, of the coupling reaction. A detail of the crosslinked probes is shown in the expanded portion shown in the hatched circle (FIG. 15b) in the product of Step II. This process can be accompanied by steps for selective dissociation and removal of low molecular weight products and any possible mismatched products. Coupling chemistries for this method of promiscuous chemical coupling are known to someone skilled in the art and include, for example, the techniques disclosed in U.S. Pat. No. 6,951,720 to Burgin et al.

Figure 16:
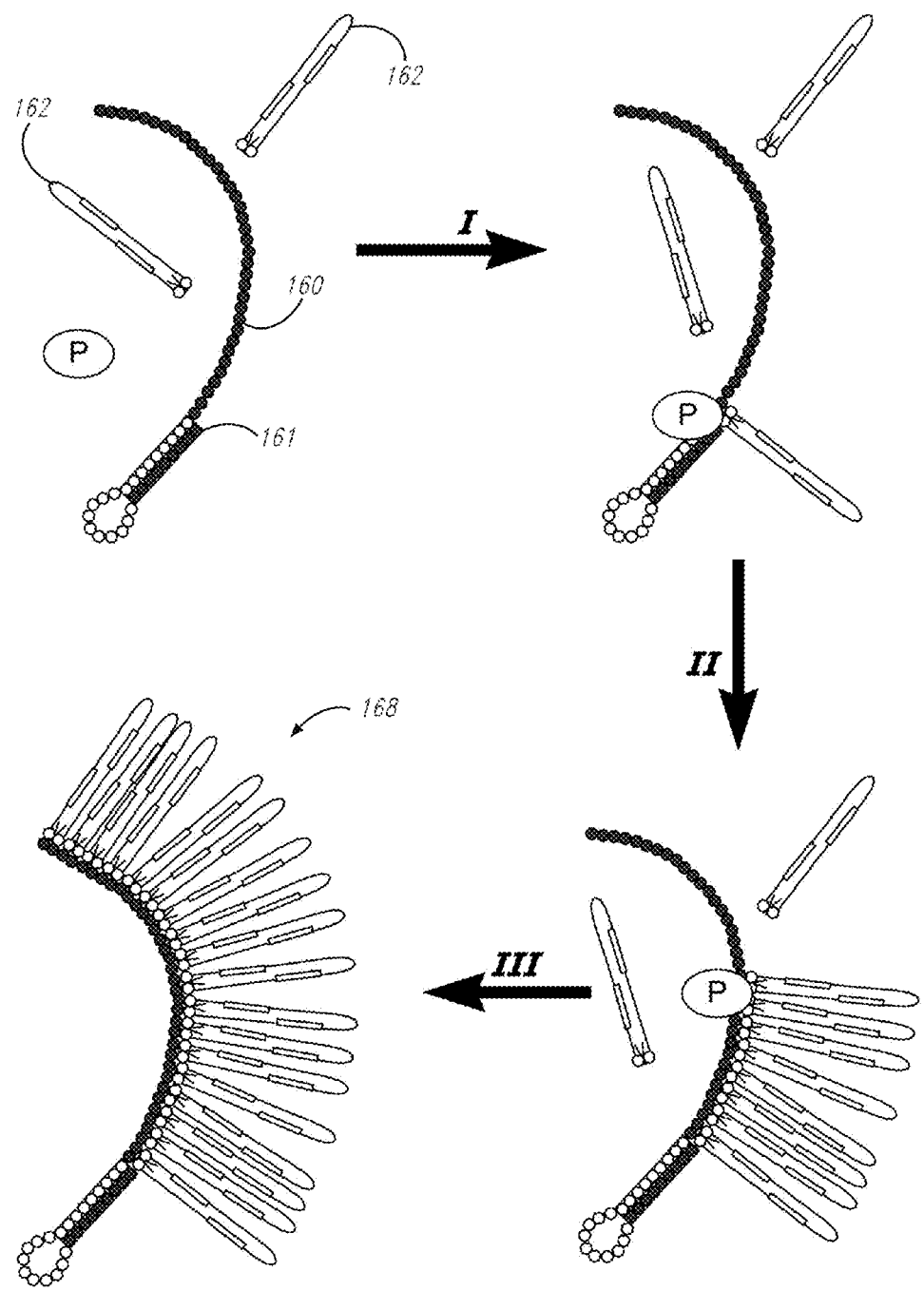
FIG. 16 is a condensed schematic of a method for synthesis of an Xpandomer by solution polymerization using a hairpin primer and Class I triphosphate substrate constructs.

In another embodiment, polymerase-based methods are disclosed for assembling product Xpandomers. Generally, substrate triphosphates (Xmers) are the appropriate substrate for reactions involving a polymerase. The selection of a suitable polymerase is part of a process of optimizing the experimental protocol. As shown in FIG. 16 for illustration, and while not intended to be limiting, a reaction mixture that contains a template (160) and a primer (161) is contacted with a library of substrate constructs (162) and a polymerase (P), under conditions optimized for template-directed polymerization. In Step I, the polymerase begins to processively add dinucleotide Xmers (tethers with two reporters) to the template strand. This process continues in Steps II and III. Each probe subunit added is a particular species selected by specific binding to the next adjacent oligomer of the template so as to form a contiguous complementary copy of the template. While not bound by theory, the polymerase is thought to assist in ensuring that incoming probe species added to the nascent chain are specifically complementary to the next available contiguous segment of the template. Loeb and Patel describe mutant DNA polymerases with increased activity and improved fidelity (U.S. Pat. No. 6,329,178). Williams for example, in U.S. Patent Application 2007/0048748 has shown that polymerases can be modified for increased speed of incorporation and reduction in error rate, clearly linking error rate not with hybridization accuracy but rather with polymerase processivity. Step III results in a completed Xpandomer intermediate (168). The single-stranded Xpandomer intermediate is then treated by a process that can involve denaturation of the template strand (not shown). The primary backbone of the daughter strand is selectively cleaved to expand the tethers, thereby forming an Xpandomer product suitable for use in a sequencing protocol, as previously explained.

Figure 17:
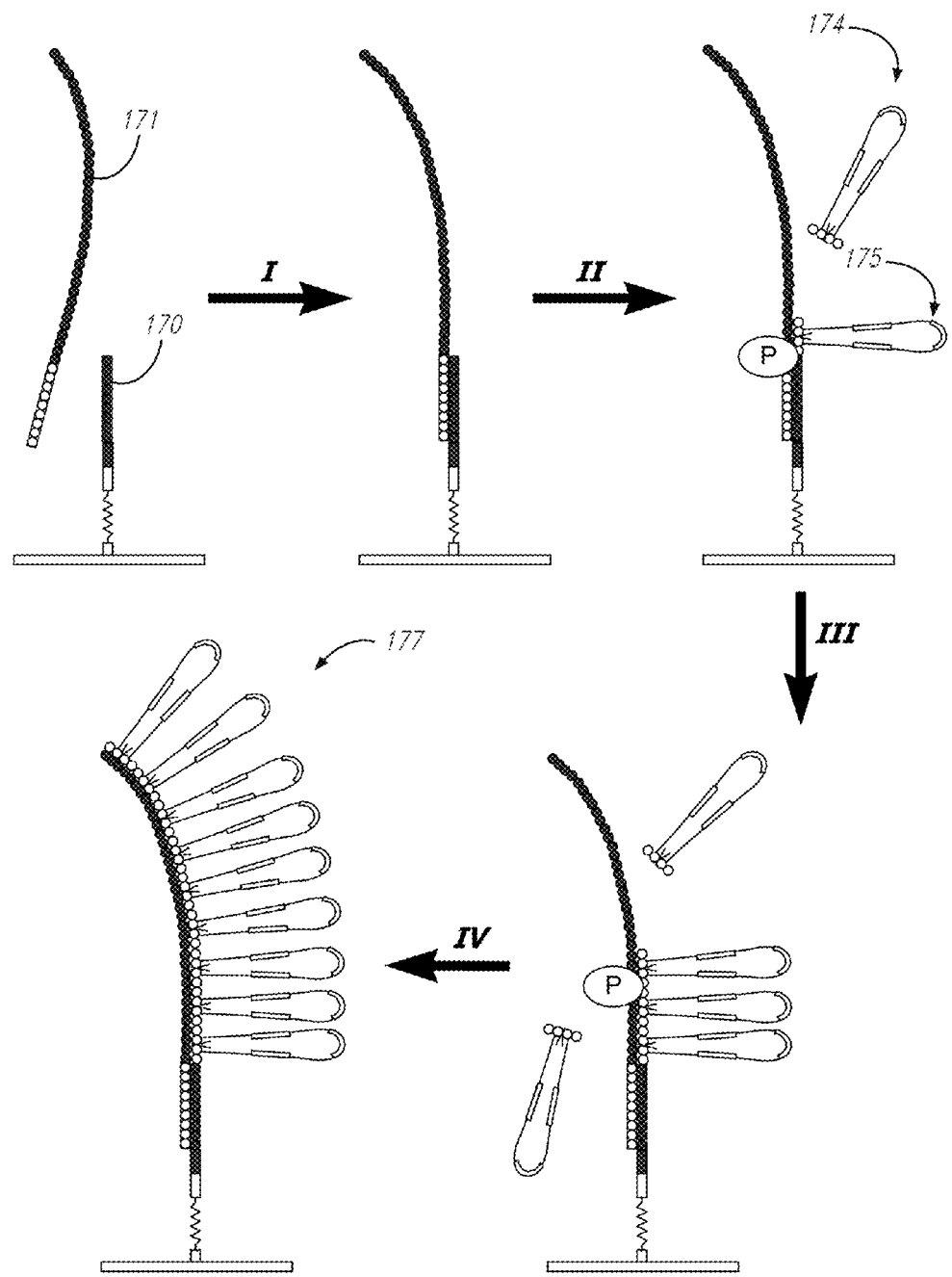
FIG. 17 is a condensed schematic of a method for synthesis of an Xpandomer on an immobilized template using Class I triphosphate substrate constructs and a polymerase.

As shown in FIG. 17, polymerase driven template-directed synthesis of an Xpandomer can be achieved by alternative techniques. Here, an immobilized primer (170) to which a processed template strand (171) is annealed in Step I. In Step II, polymerase, P, processively couples specifically complementary substrate constructs (175) from a library of such constructs (depicted by 174) in the reaction mixture. Conditions and reagent solutions are adjusted to favor processive polymerase activity. As shown here, hybridization in Step II and polymerization in Step III are separate activities, but the activities of the polymerase need not be isolated in that way. In Step IV, incremental processive addition of complementary substrate constructs continues cyclically (continuously without interruption), resulting in the fully loaded Xpandomer intermediate (177) as depicted resulting from Step IV. The Xpandomer intermediate can be dissociated and expanded in preparation for its use in a sequencing protocol as previously described. Note that this method also lends itself to parsed sequencing methods by selection of suitable immobilized primers. Further, methods for stretching the template to relief secondary structure are readily adapted to this method, and are discussed in subsequent sections.

Polymerases include, but are to limited to, DNA-dependent DNA polymerases, DNA-dependent RNA polymerases, RNA-dependent DNA polymerases, RNA-dependent RNA polymerases, T7 DNA polymerase, T3 DNA polymerase, T4 DNA polymerase, T7 RNA polymerase, T3 RNA polymerase, SP6 RNA polymerase, DNA polymerase I, Klenow fragment, *Thermophilus aquaticus* DNA polymerase, Tth DNA polymerase, VentR® DNA polymerase (New England Biolabs), Deep VentR® DNA polymerase (New England Biolabs), Bst DNA Polymerase Large Fragment, Stoeffel Fragment, 9° N DNA Polymerase, 9° N DNA polymerase, Pfu DNA Polymerase, Tfl DNA Polymerase, Tth DNA Polymerase, RepliPHI Phi29 Polymerase, Tli DNA polymerase, eukaryotic DNA polymerase beta, telomerase, Therminator™ polymerase (New England Biolabs), KOD HiFi™ DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting, and polymerases cited in US 2007/0048748, U.S. Pat. No. 6,329,178, U.S. Pat. No. 6,602,695, and U.S. Pat. No. 6,395,524 (incorporated by reference). These polymerases include wild-type, mutant isoforms, and genetically engineered variants.

Class II and III Oligomeric Constructs

Referring to FIGS. 18A through 18E, describe Class II oligomeric constructs in more detail, which (along with the isomeric Class III oligomeric constructs) can be either Xprobes or Xmers.

Figure 18A:
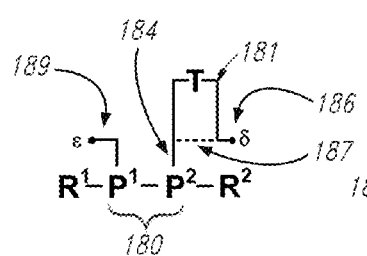
FIGS. 18A through 18E depict a Class II Xpandomer, Xpandomer intermediate, and substrate construct in a symbolic and graphical language.
Figure 18B:
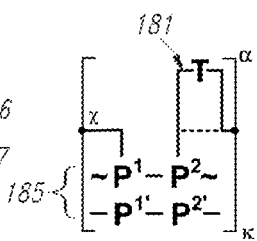
Figure 18C:
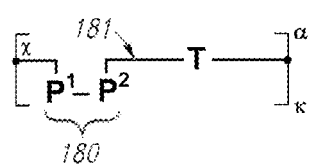

FIGS. 18A through 18C are read from left to right, showing first the probe substrate construct (oligomeric precursor of Xpandomer), then the intermediate duplex daughter strand in the center, and on the right the Xpandomer product prepared for sequencing.

As shown in FIG. 18A, a Class II substrate construct has an oligomeric probe member (-$P^1$-$P^2$-) (180) and a tether member, T (181). The tether is attached by a single end linkage (184) of a first end moiety to probe moiety $P^2$. At the distal end of the tether (186), a second end moiety has a linker group $\delta$ and is positioned proximate to $R^2$. The second end moiety also has a cleavable intra-tether crosslink (187) to constrain it to this location. Cleavable crosslink (187) is denoted by a dotted line, which can indicate, for example, a disulfide bond. These constraints prevent the tether from elongating or expanding and thus is in a constrained configuration. A second linker group $\epsilon$ is positioned near the distal end (189) of the probe member near $R^1$. Under template-directed assembly, substrates form a duplex with the target template such that the substrates are abutted. Under controlled conditions, linker groups $\delta$ and $\epsilon$ of the abutting substrates link to form a $\chi$-bond between the adjacent substrate constructs (shown in FIGS. 18B and 18C). These linkage groups are positioned on the substrate construct to limit these linkage reactions to adjacent abutted substrate constructs. The substrate construct preferentially does not link with itself. Suitable linkage and protection/deprotection chemistries for $\delta$, $\epsilon$, and $\chi$ are detailed in the general oligomeric construct description.

$R^1$ and $R^2$ are end groups configured as appropriate for the synthesis protocol in which the substrate construct is used. For example, $R^1$=5'-phosphate and $R^2$=3'-OH, would find use in a ligation protocol, and $R^1$=5'-triphosphate and $R^2$=3'-OH for a polymerase protocol. Optionally, $R^2$ can be configured with a reversible blocking group for cyclical single-substrate addition. Alternatively, $R^1$ and $R^2$ can be configured with linker end groups for chemical coupling or with no linker groups for a hybridization only protocol. $R^1$ and $R^2$ can be of the general type XR, wherein X is a linking group and R is a functional group.

Substrate constructs are reagents used for template-dependent assembly of a daughter strand, an intermediate composition for producing Xpandomers. FIG. 18B shows the duplex daughter strand, a hetero-copolymer with repeating subunits (shown in brackets). Shown are daughter strand primary backbone (~$P^1$-$P^2$~) and target template strand (-$P^{1'}$-$P^{2'}$-) as a duplex (185). Each subunit of the daughter strand is a repeating motif comprising a probe member and a tether member. The motifs have species-specific variability, indicated here by the α superscript. Each particular subunit in the daughter strand is selected from a library of motifs by a template-directed process and its probe binds to a corresponding sequence of complementary nucleotides on the template strand. In this way, the sequence of nucleobase residues of the probes forms a contiguous, complementary copy of the target template strand.

Each tilde (~) denotes a selectively cleavable bond. The internal bond between moieties $P^1$ and $P^2$ of a probe member are not selectively cleavable bonds but the inter-probe bonds (between subunits) are necessarily selectively cleavable as required to expand the tethers and the Xpandomer. In one embodiment, no direct bond is formed between the probes of separate subunits, thereby eliminating the need for subsequent selective cleavage.

The daughter strand is composed of the precursor Xpandomer called the "constrained Xpandomer" which is further composed of tethers in the "constrained configuration". When the tethers convert to their "expanded configuration", the constrained Xpandomer converts to the Xpandomer product. The tethers are constrained by the χ linkages formed by bridging to the probe members of adjacent subunits and, optionally, the intratether linkages if still present. The χ linkage attaches the tether member of a first subunit to the abutting end of an adjacent second subunit and is formed by linking the collocated linker groups δ, of the first subunit, and ε, of the second subunit.

The daughter strand can be seen to have two backbones, a "primary backbone", and the backbone of the "constrained Xpandomer. The primary backbone is composed of the contiguously abutted probe substrates. The "constrained Xpandomer backbone" bypasses the selectively cleavable linkage between the subunit substrates and is formed by χ bond linked backbone moieties, each backbone moiety being a linear linkage of tether, to $P^2$, to $P^1$, each χ bond linking $P^1$ to the tether of the next backbone moiety. It can be seen that the constrained Xpandomer backbone bridges or loops over the selectively cleavable bonds of the primary backbone, and will remain covalently intact when these selectively cleavable bonds are cleaved and the primary backbone is fragmented.

In FIG. 18B, the linker groups δ and ε have crosslinked and now form an inter-subunit bond χ. After the χ bond is formed the intra-tether bond may be broken, although it is shown here intact (dotted line in the substrate). Generally, the formation of the χ bond is dependent on proximity of the linker group δ on the first subunit and the position of the linker group ε of a second abutting subunit, so that they are collocated and are contacted during or after template-directed assembly of substrate constructs.

In further embodiments, the crosslinking is dependent only on hybridization to the template to bring the two linker groups together. In still other embodiments, the χ bond linkage is preceded by enzymatic coupling of the probe members P along the primary backbone, with formation of phosphodiester bonds between adjacent probes. In the structure shown here, the daughter strand primary backbone has been formed, and the inter-substrate bonds are depicted by a tilde (~) to indicate that they are selectively cleavable. After dissociating or degrading the target template strand, cleaving the selectively cleavable bonds (which include the intratether bonds), the constrained Xpandomer is released and becomes the Xpandomer product.

FIG. 18C is a representation of the Class II Xpandomer product after dissociation of the template strand and after cleavage of the selectively cleavable bonds (including those in the primary backbone and, if not already cleaved, the intratether links). Methods for dissociation of the template strand include heat denaturation, or selective digestion with a nuclease, or chemical degradation. The Xpandomer product strand contains a plurality of subunits where κ denotes the $κ^{th}$ subunit in a chain of m subunits making up the daughter strand, where κ=1, 2, 3 to m, where m>3, and generally m>20, and preferably m>50, and more preferentially m>1000. Each subunit is formed of a tether, and probe moieties $P^1$ and $P^2$. Tether, T (181), is seen in its expanded configuration and is stretched to its length between $P^2$ and $P^1$ of adjacent subunits. Each subunit, a subunit motif α, contains species-specific genetic information established by template directed assembly of the Xpandomer intermediate (daughter strand).

Figure 18D:
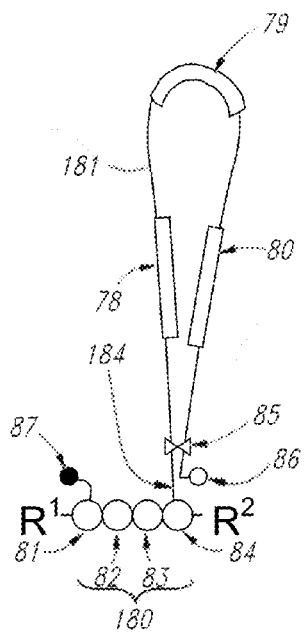

FIG. 18D shows the substrate construct of FIG. 18A as a molecular model, where the probe member (180), represented with four nucleobase residues (81,82,83,84), is joined to the tether (181) by a linkage of the first end moiety of the tether (184). An intra-tether bond (85) of a second end moiety is at the distal end of the tether. A linker group (δ) (86) is also disposed on the second end moiety and the corresponding second linker group (ε) (87) is anchored to the end of the probe opposing the linker group (δ). The tether loop shown here has three reporters (78,79,80), which can also be motif species specific.

Figure 18E:
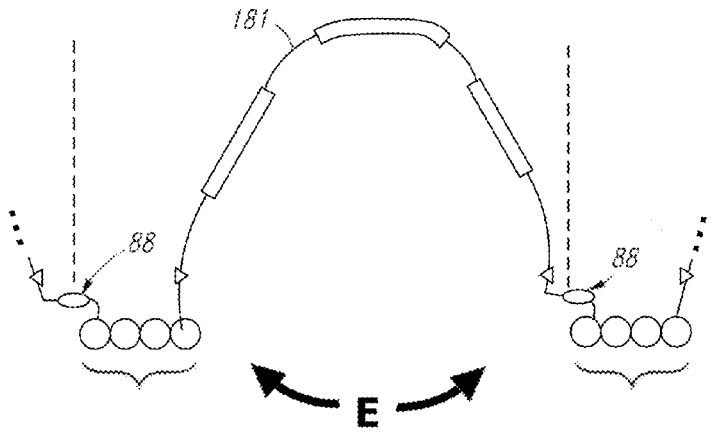
Figure 19A:
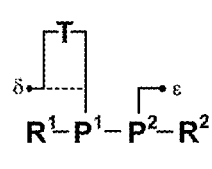
FIGS. 19A through 19E depict a Class III Xpandomer, Xpandomer intermediate and substrate construct in a symbolic and graphical language.
Figure 19B:
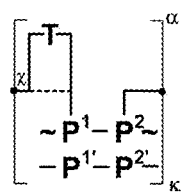
Figure 19C:
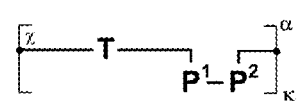
Figure 19D:
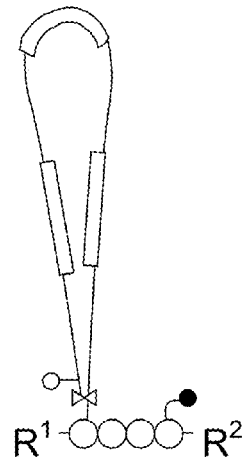
Figure 19E:
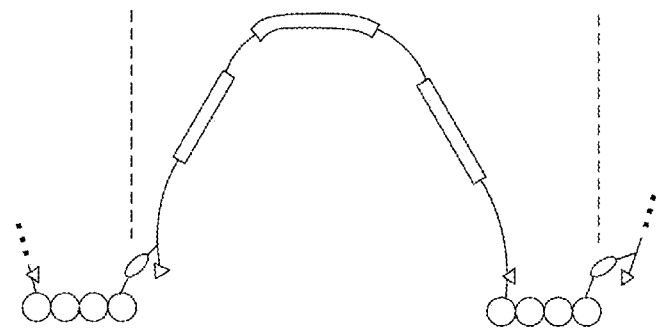

FIG. 18E shows the substrate construct after incorporation into the product Xpandomer. The subunits are cleaved and expanded and are linked by χ bonds (88), formed by linking the linker groups δ and ε referred to in FIG. 18A. A subunit is indicated by dotted lines vertically bracketing the repeating subunit, as represented by brackets in the accompanying FIG. 18C. "E" again denotes expansion.

In the Xpandomer product (FIG. 18E) the primary backbone has been fragmented and is not covalently contiguous because any direct bond between the probes of adjacent subunits has been cleaved. Through the cleavage process, the constrained Xpandomer is released to become the Xpandomer product. The tether members that were formerly in constrained configuration, are now in expanded configuration, thereby functioning to linearly stretch out the sequence information of the template target. Expanding the tethers lowers the linear density of the sequence information along the Xpandomer and provides a platform for increasing the size and abundance of reporters which in turn improves signal to noise for detection and decoding of the template sequence.

While the tether is depicted as a reporter construct with three reporter groups, various reporter configurations can be arrayed on the tether, and can comprise single reporters that identify probe constituents, single reporters that identify probe species, molecular barcodes that identify the probe species, or the tether can be a naked polymer. In some cases, one or more reporter precursors are arrayed on the tether, and reporters are affinity bound or covalently bound following assembly of the Xpandomer product.

Class III oligomeric constructs, illustrated in FIGS. 19A through 19E, are isomers to the Class II constructs discussed above. No further description is included because the description of Class II is adequate to understand this class.

This class can serve to emphasize that all classes can be reflected to mirror image application (i.e., exchanging the $R^1$ and $R^2$ groups). Furthermore this serves to illustrate that the classes described are not intended to be complete but to reflect a few of the many possible arrangements that this invention encompasses.

Figure 20:
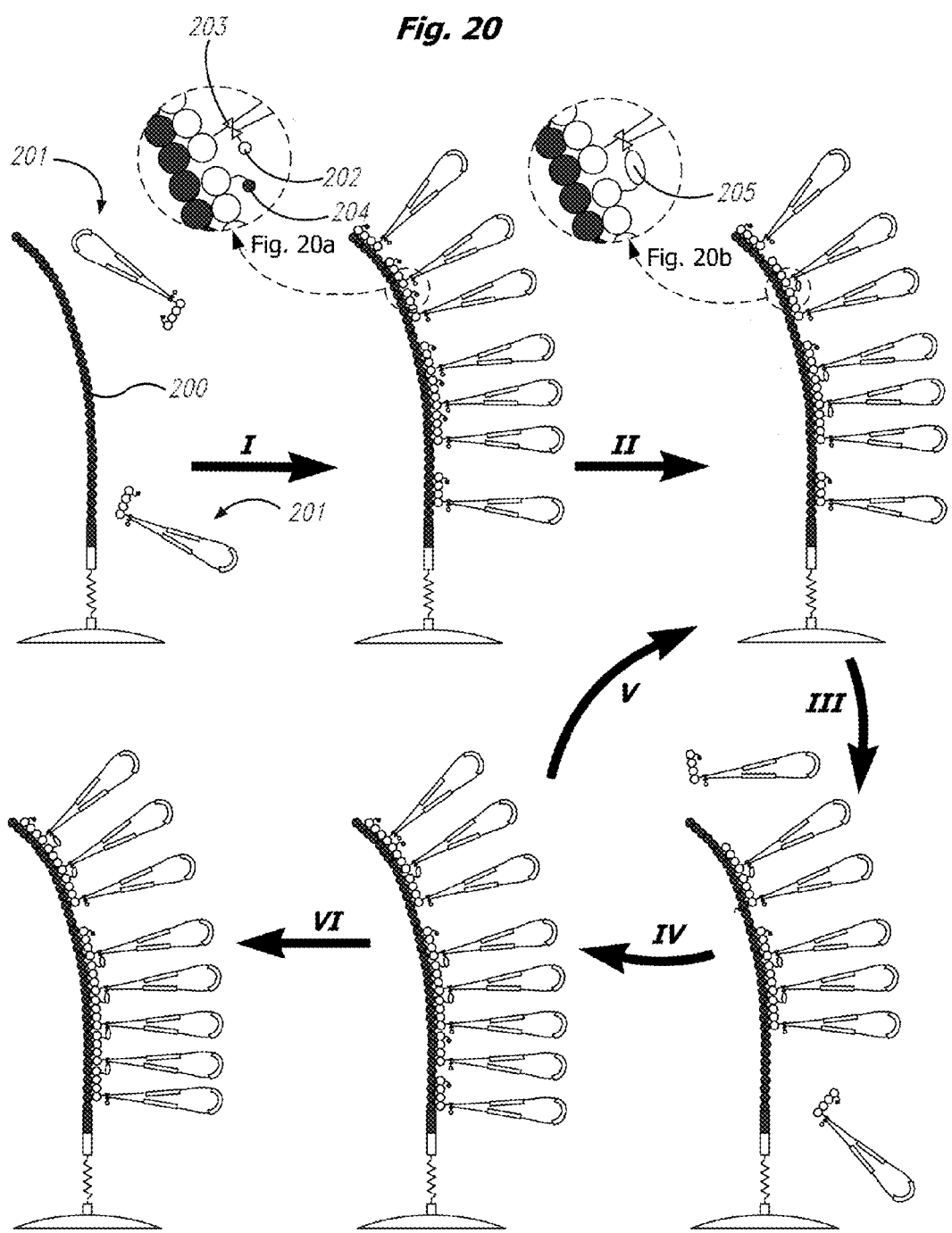
FIG. 20 is a condensed schematic of a method for synthesis of an Xpandomer on an immobilized template using Class II substrate constructs combining hybridization and primer-less chemical coupling.

FIG. 20 depicts a condensed schematic of a method for making a first embodiment of a Class II Xpandomer; the method illustrates the making and using of substrates and products shown in FIGS. 18D and 18E. The method is performed with solid-phase chemistries. Methods for relieving secondary structure in the template are discussed in a subsequent section. Suitable conditions adapted for hybridization and chemical coupling are well known in the art and the conditions can be readily optimized by one skilled in this field.

Step I of FIG. 20 shows a reaction mixture containing an immobilized template (200) and a library of substrate reagents (201). The substrate constructs are seen to specifically bind to the template in a template-directed hybridization. Conditions are adjusted to optimize the complementarity and fidelity of the binding. As shown in the figure insert (see FIG. 20a), each abutting substrate construct brings into proximity the functional group δ (202) on the distal aspect of the tether, shown here bound to the stem of the tether by an intra-tether crosslink (203), represented by the adjacent triangles, and the functional group ε (204) of the abutting probe member.

In Step II, a crosslinking reaction occurs between hybridized proximately abutted ends of the probe members involving the two functional groups δ and ε, thereby forming an inter-subunit tether-to-probe bond χ, (205), depicted as an open oval, as shown in the figure insert (see FIG. 20b). Hybridization occurs in parallel at various sites on the template, promiscuously, and chemical coupling can occur in a cycle of hybridization (Step III), stringent melt and/or wash (Step IV), and chemical coupling (Step V). The cycle can be repeated to increase the number of contiguous subunits assembled to form the Xpandomer intermediate. Step VI illustrates a completed Xpandomer intermediate with two contiguous product strands of varying length. A similar method may be employed with the Class III Xpandomers.

Figure 21:
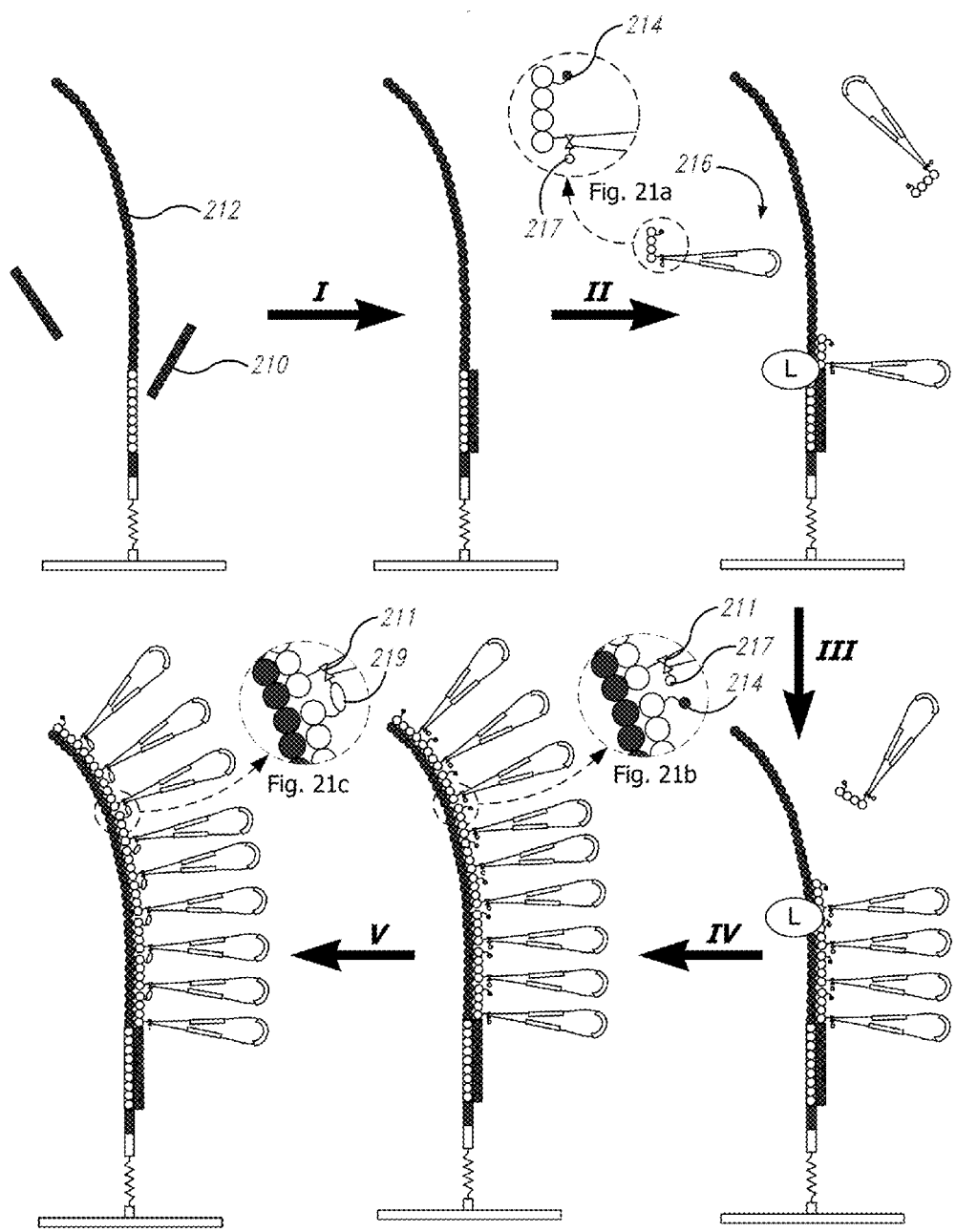
FIG. 21 is a condensed schematic of a method for synthesis of an Xpandomer on an immobilized template using a primer, Class II substrate constructs and a ligase.

FIG. 21 illustrates a method of processive ligation of Class II substrates on an immobilized template. Step I shows a primer (210) annealing to the template (212), the primer adapted with a chemically reactive functional group ε shown in the figure insert as (214) (see FIG. 21a). A reaction mixture containing Class II substrates (216) is then added in Step II. As shown in the figure insert (FIG. 21a), these substrate constructs have δ (217) and ε (214) reactivity on opposing ends of the probe-tether member. A first substrate construct is seen to specifically bind to the template in a template-directed hybridization. Conditions are adjusted to optimize the complementarity and fidelity of the binding. A ligase is then used to covalently bond the first probe to the primer (Step II).

In Steps III and IV, the process of processive hybridization and ligation of substrate constructs is continued in order to build up the Xpandomer intermediate shown formed in Step IV. Following this, in Step V, crosslinking is performed between the δ (217) and ε (214) groups (see FIG. 21b), resulting in a χ bond as depicted in FIG. 21c as (219). As shown in the figure inserts (FIGS. 21b and 21c), functional group δ (217) on the tether is constrained by an intra-tether crosslink (211), represented by the adjacent triangles, until the χ bond is formed. The completed Xpandomer intermediate is optionally dissociated from the template strand and is cleaved to form an Xpandomer product suitable for sequencing. A similar method may be employed with the Class III Xpandomers. This method is can also be adapted for use with a polymerase by substituting triphosphate substrate constructs.

Class IV and V Oligomeric Constructs

Referring to FIGS. 22A through 22E, describe Class IV oligomeric constructs in more detail.

Figure 22A:
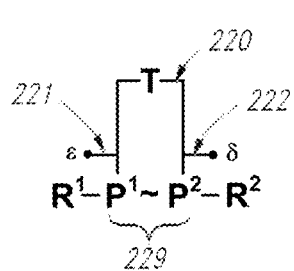
FIGS. 22A through 22E depict a Class IV Xpandomer, Xpandomer intermediate, and substrate construct in a symbolic and graphical form.
Figure 22B:
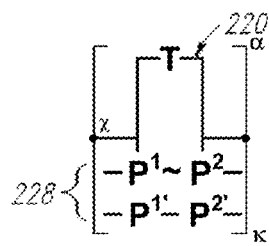
Figure 22C:
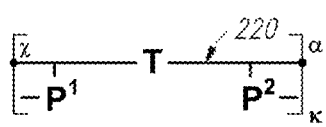

FIGS. 22A through 22C are read from left to right, showing first the probe substrate construct (Xprobe or Xmer precursors of Xpandomer), then the intermediate duplex daughter strand in the center, and on the right the Xpandomer product prepared for sequencing.

FIG. 22A, shows a Class IV substrate construct having oligomeric probe member (229) with probe moieties $P^1$ and $P^2$ attaching to tether, T (220). Tether T is attached to $P^1$ and $P^2$ by appropriate linkage with the first and second end moieties of the tether, respectively. Linker groups ε of the first end moiety and δ of the second end moiety are positioned near the $R^1$ and $R^2$ ends of the probe, respectively (in an alternative embodiment, the positions of the functional groups can be reversed). Under controlled conditions, functional groups δ (222) and ε (221) will react to form a linkage χ as shown in FIG. 22B. These linkage groups are positioned on the substrate construct to limit these linkage reactions to adjacent abutted substrate constructs. The substrate construct preferentially does not link with itself. Suitable linkage and protection/deprotection chemistries for δ, ε, and χ are detailed in the general oligomeric construct description.

$R^1$ and $R^2$ are end groups configured as appropriate for the synthesis protocol in which the substrate construct is used. For example, $R^1$=5'-phosphate and $R^2$=3'-OH, would find use in a ligation protocol, and $R^1$=5'-triphosphate and $R^2$=3'-OH for a polymerase protocol. Optionally, $R^2$ can be configured with a reversible blocking group for cyclical single-substrate addition. Alternatively, $R^1$ and $R^2$ can be configured with linker end groups for chemical coupling or with no linker groups for a hybridization only protocol. $R^1$ and $R^2$ can be of the general type XR, wherein X is a linking group and R is a functional group.

Substrate constructs are reagents used for template-directed assembly of a daughter strand, an intermediate composition for producing Xpandomers. FIG. 22B shows the duplex daughter strand, a hetero-copolymer with repeating subunits (shown in brackets). Shown are daughter strand primary backbone (-$P^1$~$P^2$-) and target template strand (-$P^{1'}$-$P^{2'}$-) as a duplex (228). Each subunit of the daughter strand is a repeating motif comprising a probe member and a tether member. The motifs have species-specific variability, indicated here by the α superscript. Each particular subunit in the daughter strand is selected from a library of motifs by a template-directed process and its probe binds to a corresponding sequence of complementary nucleotides on the template strand. In this way, the sequence of nucleobase residues of the probes forms a contiguous, complementary copy of the target template strand.

The tilde (~) denotes a selectively cleavable bond. The internal bond between moieties $P^1$ and $P^2$ of a probe member is necessarily selectively cleavable as required to expand the tethers and the Xpandomer. In one embodiment, no direct bond is formed between the probes of separate subunits.

The daughter strand is composed of an Xpandomer precursor called the "constrained Xpandomer" which is further composed of tethers in the "constrained configuration". When the tethers convert to their "expanded configuration", as shown in FIG. 22C, the constrained Xpandomer converts to the Xpandomer product. The tethers are constrained by the χ linkages formed by bridging to the tether member of adjacent subunits and by the probe linkages. The χ linkage attaches the tether member of a first subunit to the tether of an adjacent second subunit and is formed by linking the collocated linker groups, δ of the first subunit, and ε of the second subunit.

The daughter strand can be seen to have two backbones, a "primary backbone", and the backbone of the "constrained Xpandomer backbone". The primary backbone is composed of the contiguously abutted probe substrates. The "constrained Xpandomer backbone" is the linear linkage of the tethers in each subunit linked together by the $\chi$ linkages bypassing the subunit probe substrates. The $\chi$ linkage results from a reaction of the functional group $\epsilon$ of a first subunit with the functional group $\delta$ of an abutted second subunit. It can be seen that the constrained Xpandomer backbone bridges or loops over the selectively cleavable bonds of the primary backbone, and will remain covalently intact when these selectively cleavable bonds are cleaved and the primary backbone is fragmented.

In FIG. 22B, the linker groups $\delta$ and $\epsilon$ have crosslinked and now form an inter-subunit bond $\chi$. Generally, the formation of the $\chi$ bond is dependent on the collocation of the linker group $\delta$, on the first subunit, and the linker group $\epsilon$, of a second abutting subunit, so that they are contacted during or after template-directed assembly of substrate constructs.

In further embodiments, the $\chi$ bond crosslinking is dependent only on hybridization to the template to bring the two linker groups together. In still other embodiments, formation of the $\chi$ bond is preceded by enzymatic coupling of the probe members P along the primary backbone with phosphodiester bonds between adjacent probes. In the structure shown in FIG. 22B, the daughter strand primary backbone has been formed, and the bond between probe moieties is depicted by a tilde (~) to indicate that it is selectively cleavable. After dissociating or degrading the target template strand, cleaving the selectively cleavable bonds, the constrained Xpandomer is released and becomes the Xpandomer product as shown in FIG. 22C.

In this regard, FIG. 22C is a representation of the Class IV Xpandomer product after dissociation of the template strand and after cleavage of the selectively cleavable bonds of the primary backbone. Methods for dissociation of the template strand include heat denaturation, or selective digestion with a nuclease, or chemical degradation. The Xpandomer product strand contains a plurality of subunits $\kappa$, where $\kappa$ denotes the $\kappa^{th}$ subunit in a chain of m subunits making up the daughter strand, where m>3, and generally m>20, and preferably m>50, and more preferentially m>1000. Each subunit is formed of a tether (220), and pendant probe moieties $P^1$ and $P^2$. Tether, T, is seen in its expanded configuration and is stretched to its length between adjacent subunits. Each subunit, a subunit motif $\alpha$, contains species-specific genetic information established by template-directed assembly of the Xpandomer intermediate (daughter strand).

Figure 22D:
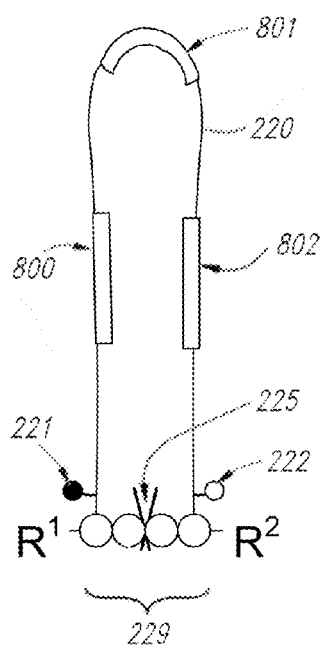

FIG. 22D shows the substrate construct of FIG. 22A as a molecular model, where the probe member, represented with four nucleobase residues (open circles), is joined to the tether by a linkage of the first end moiety of the tether. The linker group (221), shown as $\epsilon$ in FIG. 22A, is also of the first end moiety of the tether. A linker group (222), shown as $\delta$ in FIG. 22A, is disposed on a second end moiety at the distal end of the tether (220). The tether loop shown here has three reporters (800,801,802), which can also be motif species specific. A selectively cleavable bond, shown as a "V" (225), is located within probe member (229).

Figure 22E:
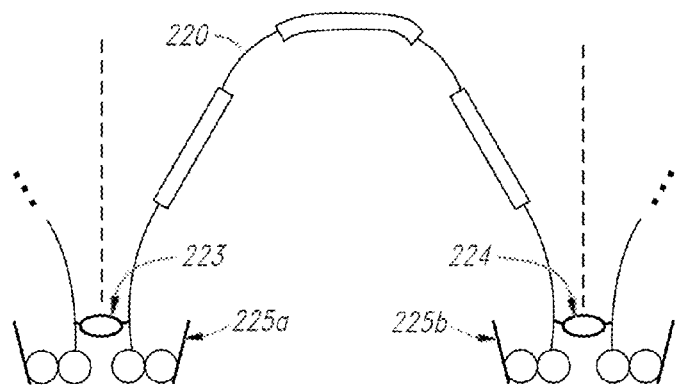

FIG. 22E shows the substrate construct after incorporation into the product Xpandomer. The subunits are cleaved, shown as lines (225a,225b), and expanded and are linked by $\chi$ bonds (223,224), formed by linking the linker groups $\delta$ and $\epsilon$ referred to in FIG. 22A. A subunit is indicated by dotted lines vertically bracketing the repeating subunit, as represented by brackets in the accompanying FIG. 22C.

In the Xpandomer product of FIG. 22E, the primary backbone has been fragmented and is not covalently contiguous because any direct bond between the probes of adjacent subunits has been cleaved. Through the cleavage process, the constrained Xpandomer is released to become the Xpandomer product. The tether members that were formerly in constrained configuration, are now in expanded configuration, thereby functioning to linearly stretch out the sequence information of the template target. Expanding the tethers lowers the linear density of the sequence information along the Xpandomer and provides a platform for increasing the size and abundance of reporters which in turn improves signal to noise for detection and decoding of the template sequence.

While the tether is depicted as a reporter construct with three reporter groups, various reporter configurations can be arrayed on the tether, and can comprise single reporters that identify probe constituents, single reporters that identify probe species, molecular barcodes that identify the probe species, or the tether can be a naked polymer. In some cases, one or more reporter precursors are arrayed on the tether, and reporters are affinity bound or covalently bound following assembly of the Xpandomer product.

Figure 23A:
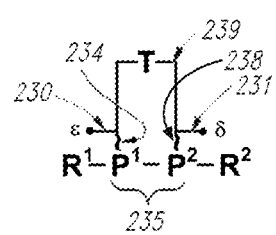
FIGS. 23A through 23E depict a Class V Xpandomer, Xpandomer intermediate, and substrate construct in a symbolic and graphical form.
Figure 23B:
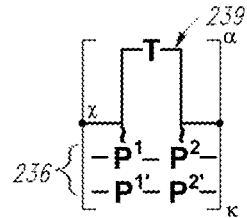
Figure 23C:
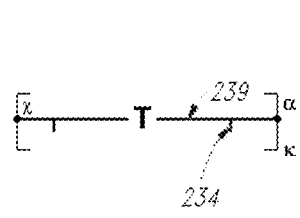

Class V substrate constructs are similar to the Class IV constructs, the primary difference being the position of the cleavable linkers. FIGS. 23A through 23C are read from left to right, showing first the probe substrate construct (Xprobe or Xmer precursors of Xpandomer), then the intermediate duplex daughter strand in the center, and on the right the Xpandomer product prepared for sequencing.

FIG. 23A illustrates a Class V substrate construct having first and second end moieties of tether T (239) attached with two selectively cleavable end linkages (234, 238) (depicted as two vertical "~"). These cleavable linkages are then attached to first and second probe moieties, $P^1$ and $P^2$, of an oligomeric probe member (235). Linker groups $\epsilon$ (230) and $\delta$ (231) of the said first and second end moieties are positioned near the $R^1$ and $R^2$ ends of the probe (again, the positions of these functional groups can be reversed). Under controlled conditions, functional groups $\delta$ and $\epsilon$ are reacted to form a linkage $\chi$. These linkage groups are positioned on the substrate construct to limit these linkage reactions to adjacent abutted substrate constructs. The substrate construct preferentially does not link with itself. Suitable linkage and protection/deprotection chemistries for $\delta$, $\epsilon$, and $\chi$ are detailed in the general oligomeric construct description.

$R^1$ and $R^2$ are end groups configured as appropriate for the synthesis protocol in which the substrate construct is used. For example, $R^1$=5'-phosphate and $R^2$=3'-OH, would find use in a ligation protocol as found in Xprobes, and $R^1$=5'-triphosphate and $R^2$=3'-OH for a polymerase protocol as found in Xmers. Optionally, $R^2$ can be configured with a reversible blocking group for cyclical single-substrate addition. Alternatively, $R^1$ and $R^2$ can be configured with linker end groups for chemical coupling or with no linker groups for a hybridization only protocol. $R^1$ and $R^2$ can be of the general type XR, wherein X is a linking group and R is a functional group.

Substrate constructs are reagents used for template-directed assembly of a daughter strand, an intermediate composition for producing Xpandomers. FIG. 23B shows the duplex daughter strand, a hetero-copolymer with repeating subunits (shown in brackets). Shown are daughter strand primary backbone (-$P^1$-$P^2$-) and target template strand (-$P^{1'}$-$P^{2'}$-) as a duplex (236). Each subunit of the daughter strand is a repeating motif comprising a probe member and a tether member. The motifs have species-specific variability, indicated here by the $\alpha$ superscript. Each particular subunit in the daughter strand is selected from a library of motifs by a template-directed process and its probe binds to a corresponding sequence of complementary nucleotides on the template strand. In this way, the sequence of nucleobase residues of the probes forms a contiguous, complementary copy of the target template strand.

The tilde (~) denotes a selectively cleavable bond. The bonds connect moieties $P^1$ and $P^2$ of a probe member with the tether and are necessarily selectively cleavable as required to expand the tethers and the Xpandomer. In one embodiment, no direct bond is formed between the probes of separate subunits.

The daughter strand is composed of an Xpandomer precursor called the "constrained Xpandomer" which is further composed of tethers in the "constrained configuration". When the tethers convert to their "expanded configuration", as shown in FIG. 23C, the constrained Xpandomer converts to the Xpandomer product. The tethers are constrained by the χ linkages formed by bridging to the tether members of adjacent subunits and by the selectively cleavable linkages (234, 238). The χ linkage attaches the tether member of a first subunit to the tether of an adjacent second subunit and is formed by linking the collocated linker groups, δ of the first subunit, and ε of the second subunit.

The daughter strand can be seen to have two backbones, a "primary backbone", and the backbone of the "constrained Xpandomer backbone". The primary backbone is composed of the contiguously abutted probe substrates. The "constrained Xpandomer backbone" is the linear linkage of the tethers in each subunit linked together by the χ linkages bypassing the subunit probe substrates. The χ linkage results from a reaction of the functional group ε of a first subunit with the functional group δ of an abutted second subunit. It can be seen that the constrained Xpandomer backbone bridges or loops over the selectively cleavable bonds connecting to the primary backbone, and will remain covalently intact when these selectively cleavable bonds are cleaved and the primary backbone is dissociated or otherwise fragmented.

In FIG. 23B, the linker groups δ and ε have crosslinked and now form an inter-subunit bond χ. Generally, the formation of the χ bond is dependent on the collocation of the linker group δ, on the first subunit, and the linker group E, of a second abutting subunit, so that they are contacted during or after template-directed assembly of substrate constructs.

In some protocols, the crosslinking reaction is dependent only on hybridization to the template to bring the two reactive groups together. In other protocols, the linking is preceded by enzymatic coupling of the probe members, with formation of phosphodiester bonds between adjacent probes. In the structure shown in FIG. 23B, the daughter strand primary backbone has been formed. The tether, now joined to adjacent subunits by χ-bonds, and comprises the constrained Xpandomer backbone. Upon cleavage of the selectively cleavable bonds (~), the constrained Xpandomer is separated from the primary backbone to become the Xpandomer product, and its now unconstrained tethers are linearly expanded to their full length as shown in FIG. 23C.

In this regard, FIG. 23C is a representation of the Class V Xpandomer product after cleavage of the selectively cleavable bonds that dissociates the primary backbone. The Xpandomer product strand contains a plurality of subunits κ, where κ denotes the $κ^{th}$ subunit in a chain of m subunits making up the daughter strand, where m>3, and generally m>20, and preferably m>50, and more preferentially m>1000. Each subunit is formed of a tether, T (239), as seen in its expanded configuration and is stretched to its length between adjacent subunits. Each subunit, a subunit motif α, contains species-specific genetic information established by template-directed assembly of the Xpandomer intermediate (daughter strand).

Figure 23D:
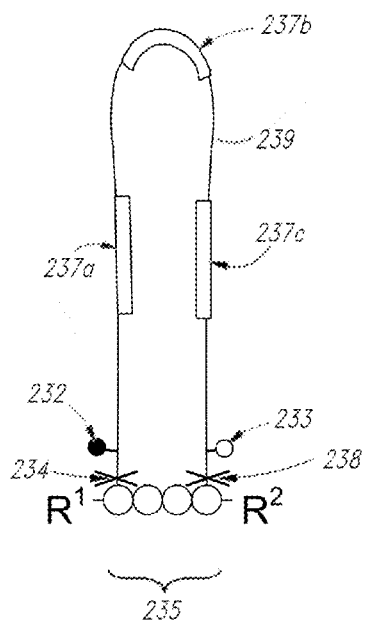

FIG. 23D shows the substrate construct of FIG. 23A as a molecular model, where the probe member (235), represented with four nucleobase residues (open circles), is joined to the first and second end moieties of the tether by two cleavable linkages (234,238). The linker group (232), shown as ε in FIG. 23A, is of the first end moiety of the tether and linker group (233), shown as δ in FIG. 23A, is of the tether second end moiety. The tether loop shown here has three reporters (237a, 237b, 237c), which can also be motif species specific.

Figure 23E:
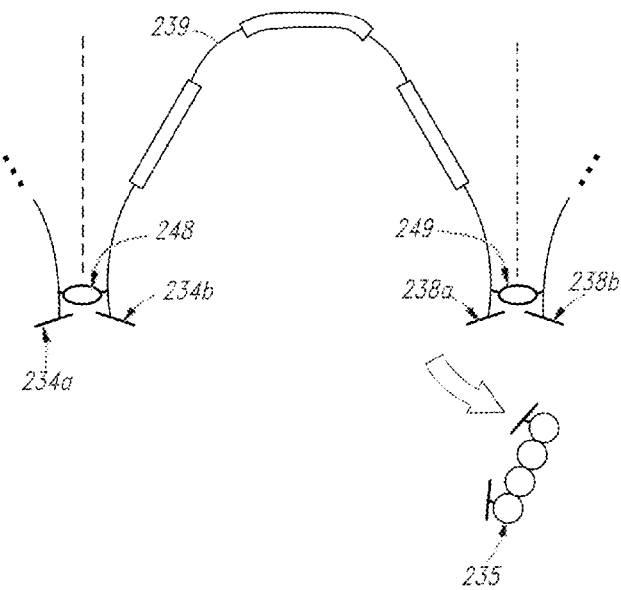

FIG. 23E shows the substrate construct after incorporation into the product Xpandomer. The subunits are cleaved (234a, 234b, 238a, 238b) and expanded and are linked by χ bonds (249,248), formed by linking the linker groups δ and ε referred to in FIG. 23A. A subunit is indicated by dotted lines vertically bracketing the repeating subunit, as represented by brackets in the accompanying FIG. 23C.

In the Xpandomer product of FIG. 23E, the primary backbone (235) has been cleaved off (dissociated). Through the cleavage process, the constrained Xpandomer is released to become the Xpandomer product. The tether members that were formerly in constrained configuration, are now in expanded configuration, thereby functioning to linearly stretch out the sequence information of the template target. Expanding the tethers lowers the linear density of the sequence information along the Xpandomer and provides a platform for increasing the size and abundance of reporters which in turn improves signal to noise for detection and decoding of the template sequence.

While the tether is depicted as a reporter construct with three reporter groups, various reporter configurations can be arrayed on the tether, and can comprise single reporters that identify probe constituents, single reporters that identify probe species, molecular barcodes that identify the probe species, or the tether can be a naked polymer. In some cases, one or more reporter precursors are arrayed on the tether, and reporters are affinity bound or covalently bound following assembly of the Xpandomer product.

Figure 24:
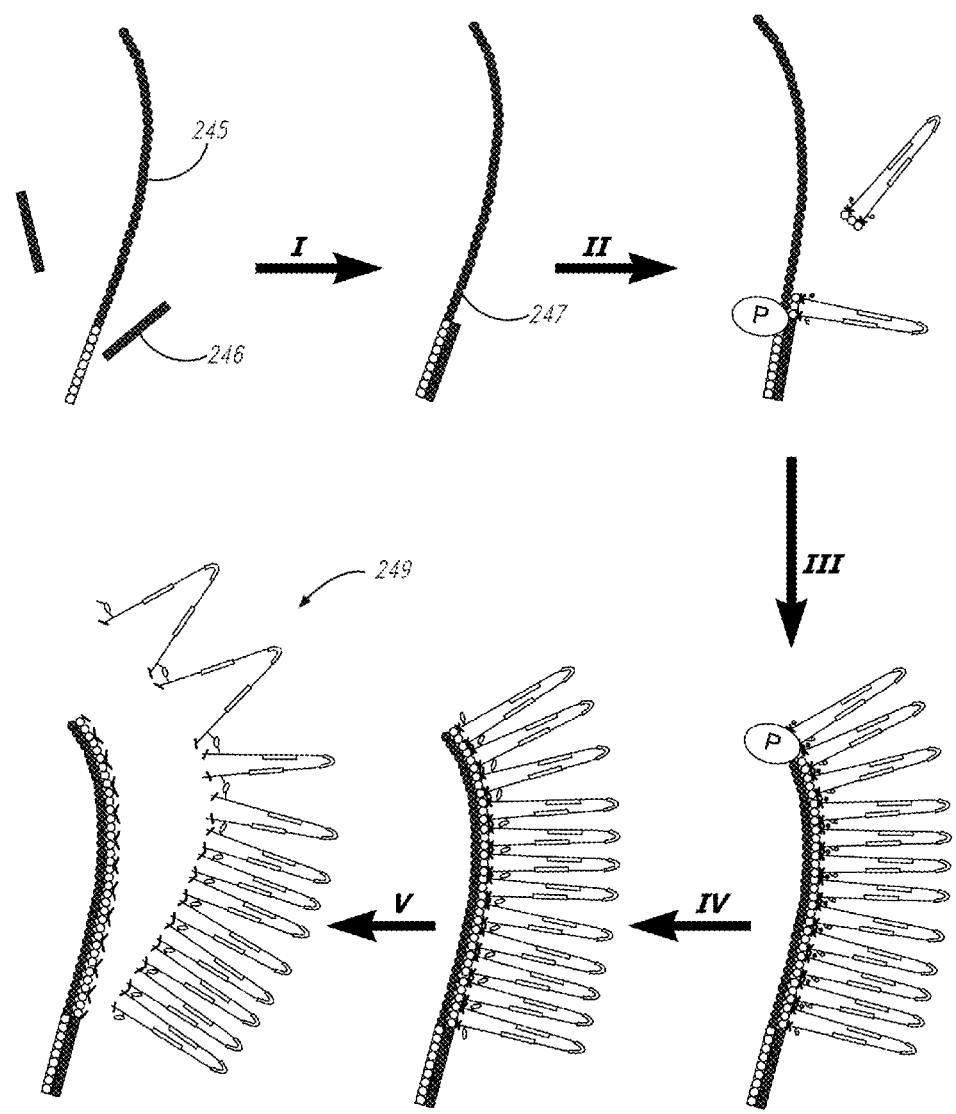
FIG. 24 is a condensed schematic of a method for synthesis of an Xpandomer by solution polymerization using an adapter primer and Class V triphosphate substrate constructs.

Making and use of a Class V Xpandomer is illustrated in FIG. 24. In setting up for the synthesis in Step I, a single stranded template (245) is contacted and annealed with sequencing primer (246). The primer assembly (247) is then contacted with a library of Class V substrate constructs and a polymerase (Step II). In Step III, the substrates have been added processively in a template-directed polymerization. In Step IV, polymerization of the primary backbone of the daughter strand is completed and the reactive functional groups of abutting tether side arms are crosslinked, forming the tether-to-tether χ bonds. Finally, in Step V, the cleavable bonds in the stems of the tether loops are cut, releasing the synthetic tether-to-tether backbone from the oligomeric daughter strand and template. This Xpandomer (249) is thus entirely constructed of tether linkages and is shown to spontaneously expand as it drifts away from the remainder of the synthetic intermediate. Here genetic information corresponding to the target polynucleotide sequence is encoded in the contiguous subunits of the tethers.

Making and Using Xmers

Class I embodiments include Xprobes and Xmers. Xprobes are monophosphates, while Xmers are triphosphates. "Xmers" are expandable oligonucleotide triphosphate substrate constructs that can be polymerized in an enzyme-dependent, template-directed synthesis of an Xpandomer. Like Xprobes, Xmer substrate constructs have a characteristic "probe-loop" form as illustrated in FIGS. 10A and 10C, where $R^1$ is 5'-triphosphate and $R^2$— is 3'-OH. Note that the substrate constructs are oligonucleobase triphosphates or oligomer analog triphosphates, but the probe members (i.e., the oligomer) have been modified with a tether construct and a selectively cleavable bond between the end linkages of the tether as shown in FIG. 10D, the function of which is further illustrated in FIG. 10E.

DNA and RNA polymerases can incorporate dinucleotide, trinucleotide, and tetranucleotide triphosphate oligonucleotides with a level of efficiency and fidelity in a primer-dependent, processive process as disclosed in U.S. Pat. No. 7,060,440 to Kless. Tether modified oligonucleotide triphosphates of length n (n=2, 3, 4, or more) can be used as substrates for polymerase-based incorporation into Xpandomers. Suitable enzymes for use in the methods shown in FIGS. 16 and 17 include, for example, DNA-dependent DNA polymerases, DNA-dependent RNA polymerases, RNA-dependent DNA polymerases, RNA-dependent RNA polymerases, T7 DNA polymerase, T3 DNA polymerase, T4 DNA polymerase, T7 RNA polymerase, T3 RNA polymerase, SP6 RNA polymerase, DNA polymerase I, Klenow fragment, *Thermophilus aquaticus* DNA polymerase, Tth DNA polymerase, VentR® DNA polymerase (New England Biolabs), Deep VentR® DNA polymerase (New England Biolabs), Bst DNA Polymerase Large Fragment, Stoeffel Fragment, 9° N DNA Polymerase, 9° N DNA polymerase, Pfu DNA Polymerase, Tfl DNA Polymerase, Tth DNA Polymerase, RepliPHI Phi29 Polymerase, Tli DNA polymerase, eukaryotic DNA polymerase beta, telomerase, Therminator™ polymerase (New England Biolabs), KOD HiFi™ DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting, and polymerases cited in US 2007/0048748, U.S. Pat. No. 6,329,178, U.S. Pat. No. 6,602,695, and U.S. Pat. No. 6,395,524 (incorporated by reference). These polymerases include wild-type, mutant isoforms, and genetically engineered variants.

Xmer polymerization is a method for Xpandomer synthesis and is illustrated in FIG. 16, for example, where the 2 mer substrate is provided as a triphosphate. Because Xmers are polymerized processively, the extension, crosslinking, end activation, and high stringency washing steps typically associated with cyclical sequencing by synthesis methods are optionally eliminated with this approach. Thus the reaction can be performed in solution. Xpandomer synthesis with Xmers can also be performed with immobilized templates, as illustrated in FIG. 17, where a 4 mer Xmer triphosphate is processively polymerized in a template-directed synthesis dependent on a primer.

A variety of methods can be employed for robust synthesis of 5' triphosphate Xmers. As described by Burgess and Cook ("Syntheses of Nucleoside Triphosphates", *Chem. Rev.* 100 (6):2047-2060, 2000), these methods include (but are not limited to) reactions using nucleoside phosphoramidites, synthesis via nucleophilic attack of pyrophosphate on activated nucleoside monophosphates, synthesis via nucleophilic attack of phosphate on activated nucleoside pyrophosphate, synthesis via nucleophilic attack of diphosphate on activated phosphate synthon, synthesis involving activated phosphites or phosphoramidites derived from nucleosides, synthesis involving direct displacement of 5'-O-leaving groups by triphosphate nucleophiles, and biocatalytic methods. A representative method for producing polymerase compatible dinucleotide substrates uses N-methylimidazole to activate the 5' monophosphate group; subsequent reaction with pyrophosphate (tributylammonium salt) produces the triphosphate (Abramova et al., "A facile and effective synthesis of dinucleotide 5'-triphosphates", *Bioorganic and Med Chem* 15, 6549-6555, 2007).

As is discussed in more detail below, the Xmer tether construct is related in design, composition and linkage to tether's used for Xprobes. In many embodiments, genetic information is encoded on the tether, and therefore each tether of each substrate construct is a species-specific tether. The information encoded on the tether is coded with a reporter code that digitizes the genetic information. For example, five bit, binary coding on the tethers would produce 32 unique sequence codes ($2^5$). This strategy can be used to uniquely code for all 16 combinations of two nucleobase residues per probe member of a 2 mer library, regardless of the tether's orientation. Similar to Xprobe coding, a variety of functionalization and labeling strategies can be considered for Xmers, including (but not limited to): functionalized dendrimers, polymers, branched polymers, nanoparticles, and nanocrystals as part of the tether scaffold, as well as reporter chemistries and reporter signals—to be detected with the appropriate detection technology. Base-specific labels can be introduced (via attachment to the tether) either prior to or after Xmer polymerization, by covalent or by affinity-directed binding.

Design and Synthesis of Xprobes and Xmers

An overview of synthetic and cleavage strategies are presented below, beginning with the probe oligomers with selectively cleavable bonds, followed by the tether and reporter tether constructs.

One objective of an Xprobe- or Xmer-based SBX method is to assemble a replica of the target nucleic acid as completely and efficiently as possible by a template-directed synthesis, generally a process or combination of processes selected from hybridizing, ligating, polymerizing, or chemically crosslinking of suitable precursor compositions, termed here "substrates". Xprobes and Xmers substrates are supplied as reagent libraries (e.g., as parts of kits for sequencing) for this purpose. The libraries are generally combinatorial in nature, and contain probe members selected to specifically bind to any or all of the complementary sequences such as would be found in a target polynucleotide. The number of probes required in a library for this purpose is a function of probe size. Each probe can be considered to be a sequence fragment, and sufficient variety of probe members must be present to form a contiguous copy of the contiguous sequence of complementary sequence fragments of the target polynucleotide. For probes in which each oligomer is a dimer, 16 possible species combinations of A, T, C and G exist. For probes in which each oligomer is a trimer, then 64 possible species combinations of A, T, C and G exist, and so forth. When sequencing random genomic fragments, it is likely that all such species are required in a reagent library.

Xprobes and Xmers are oligomeric substrate constructs that are divided into five different functional classes. Oligomeric substrate constructs have two distinct functional components: a modified oligonucleobase or "probe" member, and a tether member ("T"). The probe is joined to the tether member by a "probe-loop" construction, where the tether loop is a precursor of the linearized tether member of the final product Xpandomer. Each tether T can be encoded with reporters (commonly referred to as "tags" or "labels"), or combinations thereof, that uniquely identify the probe sequence to which it is tethered. In this way, the sequence information of the assembled Xpandomer is more readily detected.

The oligomer is the probe portion of the Xprobe. The probe is a modified oligonucleobase having a chain of x deoxyribonucleotides, ribonucleotides, or more generally, nucleobase residues (where x can 2, 3, 4, 5, 6, or more). In these discussions a probe with 2, 3, 4, 5 or 6 nucleobase residues in length can be referred to as a 2 mer, 3 mer, 4 mer, 5 mer, or timer, respectively.

Figure 25:
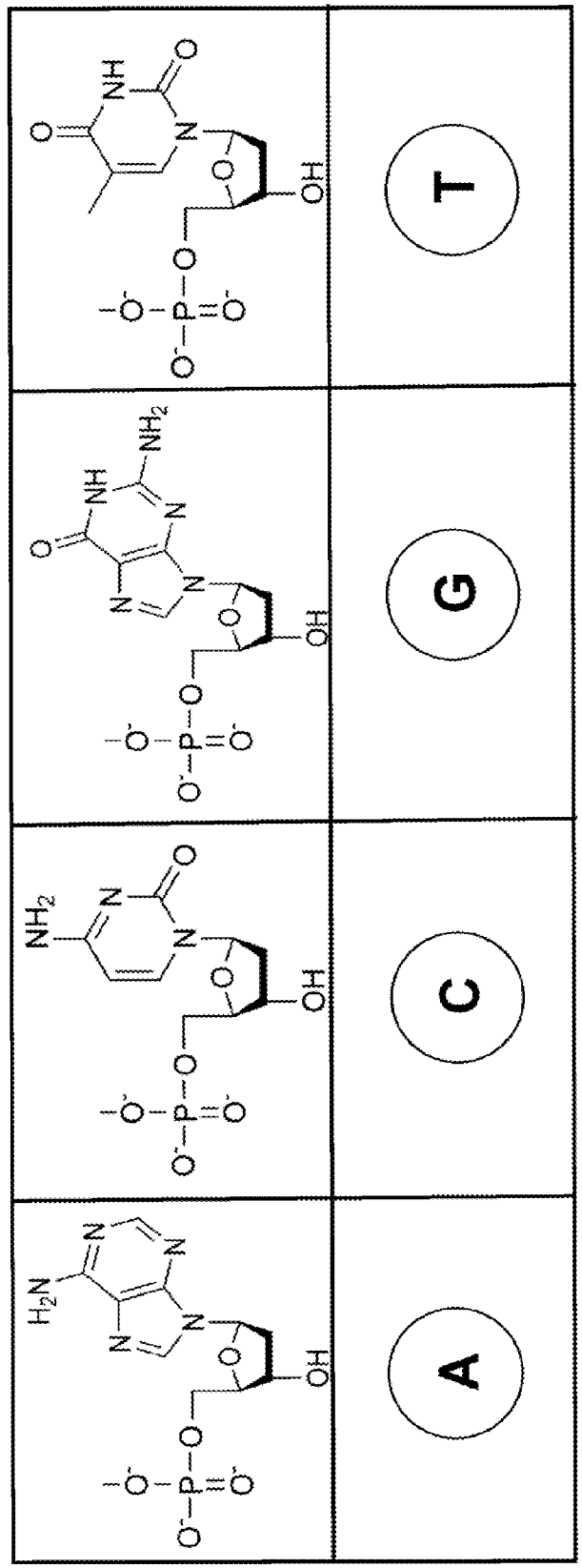
FIG. 25 illustrates structures of deoxyadenosine (A), deoxycytosine (C), deoxyguanosine (G), and deoxythymidine (T).

Substrate construct reagents can be synthesized with an oligonucleotide 5'-3' phosphodiester backbone, the oligomer having the nucleotides A, T, G and C (structures shown in the table of FIG. 25), or other hybridizable nucleic acid analogs such as those having a peptide backbone, phosphono-peptide backbone, serine backbone, hydroxyproline backbone, mixed peptide-phosphono-peptide backbone, mixed peptide-hydroxyproline backbone, mixed hydroxyproline-phosphono-peptide backbone, mixed serine-phosphono-peptide backbone, threose backbone, glycol backbone, morpholino-backbone, and the like, as are known in the art. Deoxyribonucleic acid oligomers and ribonucleic acid oligomers, and mixed oligomers of the two, may also be used as probes. Other bases may also be substituted, such as uracil for thymidine, and inosine as a degenerate base. Fragmentary residues of nucleobases having complementarity can also be used.

A more complete recitation of degenerate and wobbly bases known in the art includes, but is not limited to, xanthine, hypoxanthine, or a heterocyclic derivative, analog, or tautomer of xanthine and hypoxanthine, 8-azapurine, purines substituted at the 8 position with methyl- or bromo-, 9-oxo-$N^6$-methyladenine, 2-aminoadenine, 7-deazaxanthine, 7-deazaguanine, 7-deaza-adenine, $N^4$-ethanocytosine, 2,6-diaminopurine, $N^6$-ethano-2,6-diaminopurine, 5-methylcytosine, 5-(C3-C6)-alkynylcytosine, 5-fluorouracil, 5-bromouracil, thiouracil, 2-hydroxy-5-methyl-4-triazolopyridine, isocytosine, pseudoisocytosine, isoguanine, 7,8-dimethylalloxazine, 6-dihydrothymine, 5,6-dihydrouracil, 4-methyl-indole, ethenoadenine and the nucleobases described in U.S. Pat. Nos. 5,432,272 and 6,150,510, published PCTs WO 92/002258, WO 93/10820, WO 94/22892, and WO 94/22144, and in Fasman, Practical Handbook of Biochemistry and Molecular Biology, pp. 385-394, CRC Press, Boca Raton, La., 1989 (each of which are herein incorporated by reference in their entireties).

Figure 26A:
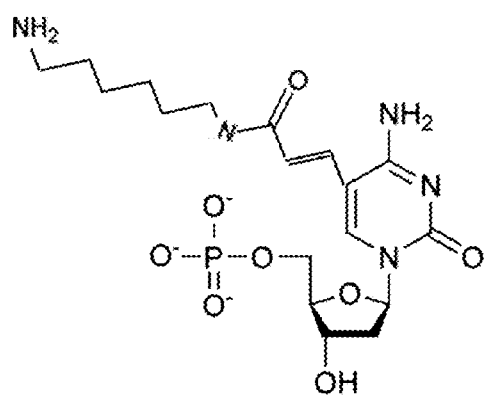
FIGS. 26A and 26B illustrate nucleotides derivatized with functional groups.
Figure 26B:
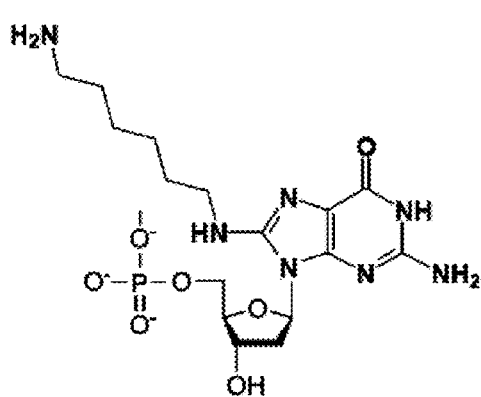

As is known in the art, oligomers can be designed to include nucleotide modifiers. In some embodiments, these serve as the attachment points for the tether member or members. Purine and pyrimidine derivatives suitable for synthesis of derivatized oligomers are well known in the art. Two such representative modified bases are shown in FIGS. 26A and 26B, wherein a 5-amino-modified cytosine derivative and an 8-amino-modified guanine residue are depicted.

Figure 27A:
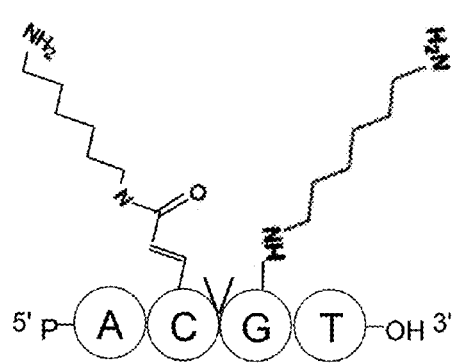
FIGS. 27A and 27B illustrate probe members incorporating derivatized nucleobases.
Figure 27B:
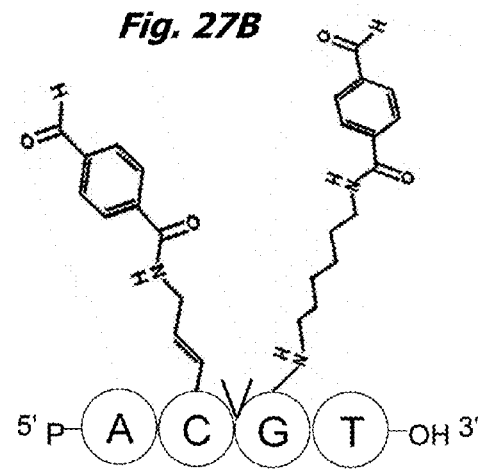

As illustrated in FIGS. 27A and 27B, taking a 4 mer oligomer as an example (here illustrated as 5'-monophosphate), any two of the four base positions on the oligomer can be modified to create attachment points by known chemistries. Modified nucleotides at probe residues 2 and 3 (on opposite sides of a selectively cleavable bond, depicted as "V") is illustrated in FIG. 27A. This figure illustrates a 4 mer oligomer with amino linkers attached to cytosine and guanosine of the oligomer. FIG. 27B illustrates a 4 mer oligomer with benzaldehyde functional groups to the cytosine and guanosine of the oligomer. The details are illustrative of methods well known in the art. For simplicity, most illustrations provided herein will assume 4 mers unless otherwise noted, but it is understood that other substrate construct libraries or library combinations may be employed in the practice of this invention.

Cleavage

Generally, Xprobes and Xmer substrate constructs have selectively cleavable bonds that allow for controlled expansion of the tether. As previously referenced, such selective cleavage may be achieved by any number of techniques known to one skilled in the art, including, but not limited to, phosphorothiolate backbone cleavage with metal cations, acid cleavage of phosphoramidate backbone modifications, selective nuclease cleavage of standard phosphodiester linkages using nuclease resistant phosphorothioate modifications for backbone protection, photocleavage of nitrobenzyl modified backbone linkers, and reduction of disulfide bonds.

Figure 28D:
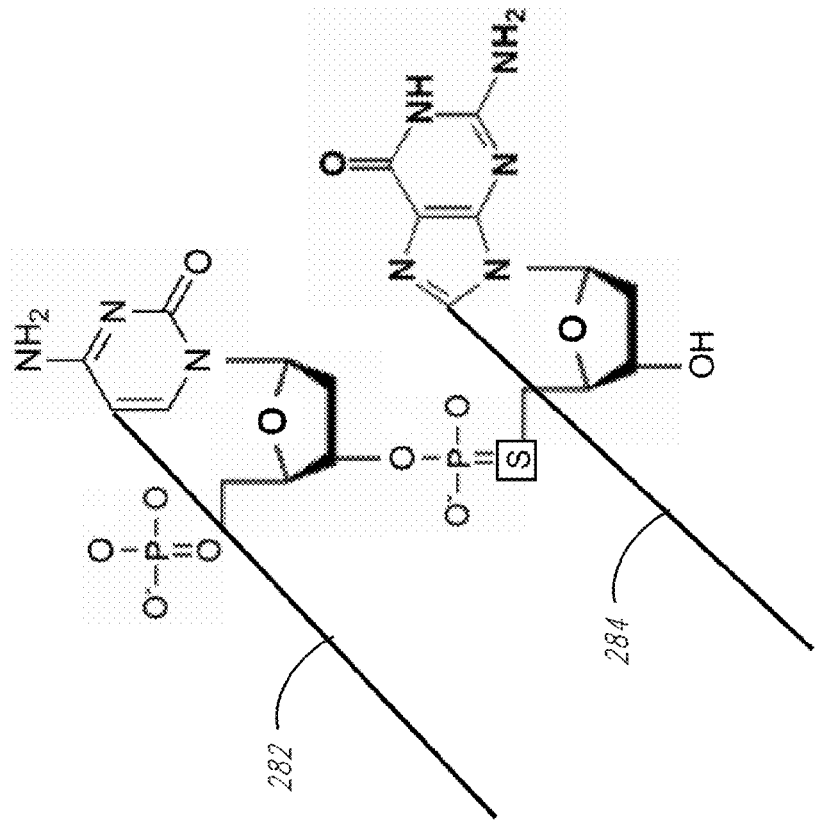

Modification of substrate probes to include selectively cleavable bonds are illustrated in FIGS. 28A through 28D and in FIGS. 29A through 29D. FIG. 28A shows an example of an Xprobe dimer with a ribosyl 2'-OH group susceptible to cleavage by Ribonuclease H in a DNA/RNA duplex Xpandomer intermediate. The bond is thus selectively cleavable, provided the other nucleotide(s) in the Xprobe are resistant to RNase cleavage (for example 2'-o-methyl pentose, 2' deoxyribose nucleobases, "locked" LNA nucleobases, and glycol- or peptide-linked nucleobases). These cleavage sites have other usages, for example, a ribonucleotide at the penultimate 5'-nucleobase and an adaptor provides a cleavable linker in between the Xpandomer and an immobilized support.

Figure 28C:
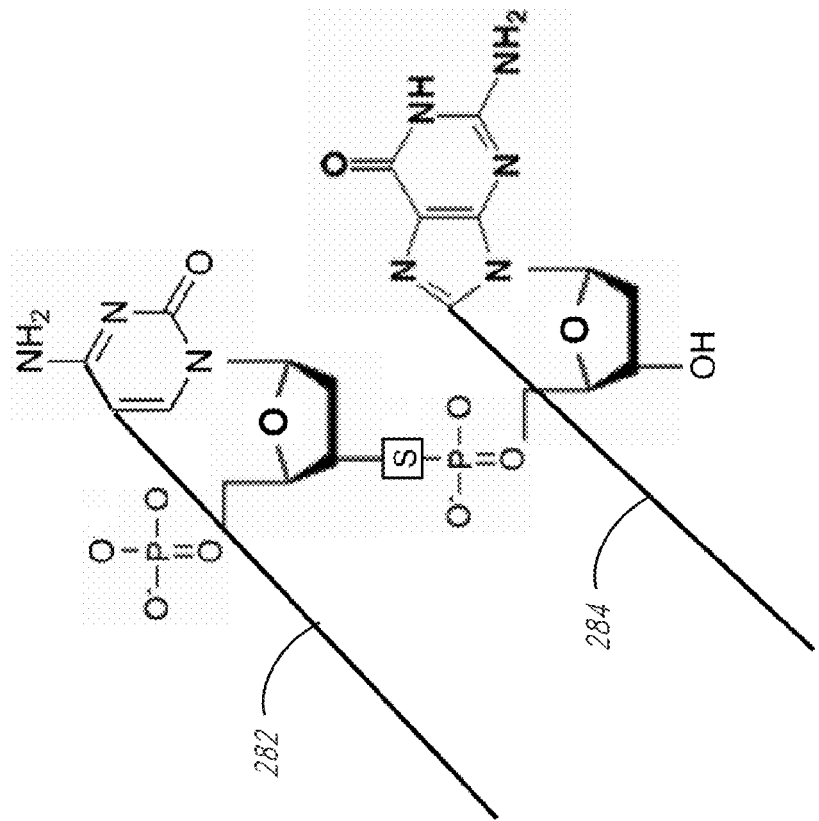

FIG. 28B shows an Xprobe with phosphodiester bond coupling two nucleotides. In this figure, as well as FIGS. 28A, 28C and 28D, tethers for bridging the selectively cleavable bond of the probe are indicated at (282) and (284). This bond is selectively cleavable with Mung Bean Nuclease, S1 Nuclease, DNase I, or other DNAases, for example, if other bonds joining the subunit tethers together are nuclease resistant. Synthesis of a 2 mer library, for example, with a standard phosphate linkage in between the tether attachment points and phosphorothioate linkage(s) at the nucleotide backbone position(s) that are to remain intact, provides the desired cleavage pattern. FIG. 28C is an Xprobe dimer held together by a 3'-phosphorothiolate bond, and in FIG. 28D is held together by a 5'-phosphorothiolate bond. These bonds are selectively cleavable by chemical attack, for example with iodoethanol as described by Gish et al. ("DNA and RNA sequence determination based on phosphorothioate chemistry", *Science* 240(4858): 1520-1522, 1988) or by cleavage with divalent metal cations as described by Vyle et al. ("Sequence- and strand-specific cleavage in oligodeoxyribonucleotides and DNA containing 3'-thiothymidine". *Biochemistry* 31(11): 3012-8, 1992). Other backbone cleavage options include, but are not limited to, UV induced photoredox cleavage (as by adaptation of nitrobenzyl photocleavage groups) as described by Vallone et al. ("Genotyping SNPs using a UV-photocleavable oligonucleotide in MALDI-TOF MS", *Methods Mol. Bio.* 297:169-78, 2005), acid cleavage of phosphoramidate linkages as described by Obika et al. ("Acid-Mediated Cleavage of Oligonucleotide P3'→N5' Phosphoramidates Triggered by Sequence-Specific Triplex Formation", *Nucleosides, Nucleotides and Nucleic Acids* 26(8, 9): 893-896, 2007), and periodate catalyzed cleavage of 3'-O-B-D-ribofuranosyl-2'-deoxy backbone modifications as disclosed by Nauwelaerts et al. ("Cleavage of DNA without loss of genetic information by incorporation of a disaccharide nucleoside", *Nucleic Acids Research* 31(23): 6758-6769, 2003).

Figure 29A:
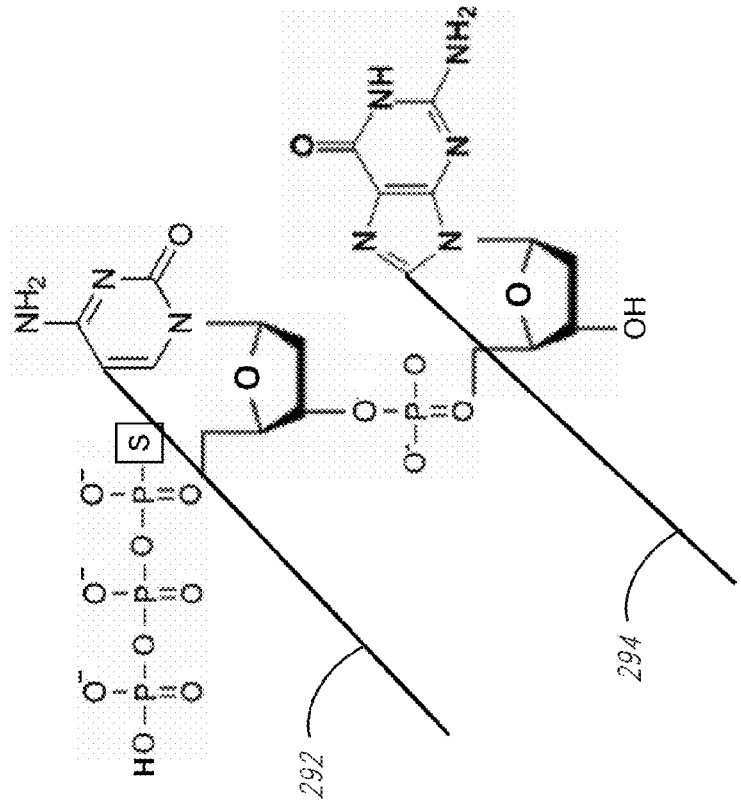
FIGS. 29A through 29D illustrate in more detail Class I-IV substrates of the invention, here showing examples of selectively cleavable bond cleavage sites in the probe backbone and indicating loop end linkages bridging the cleavage sites.
Figure 29B:
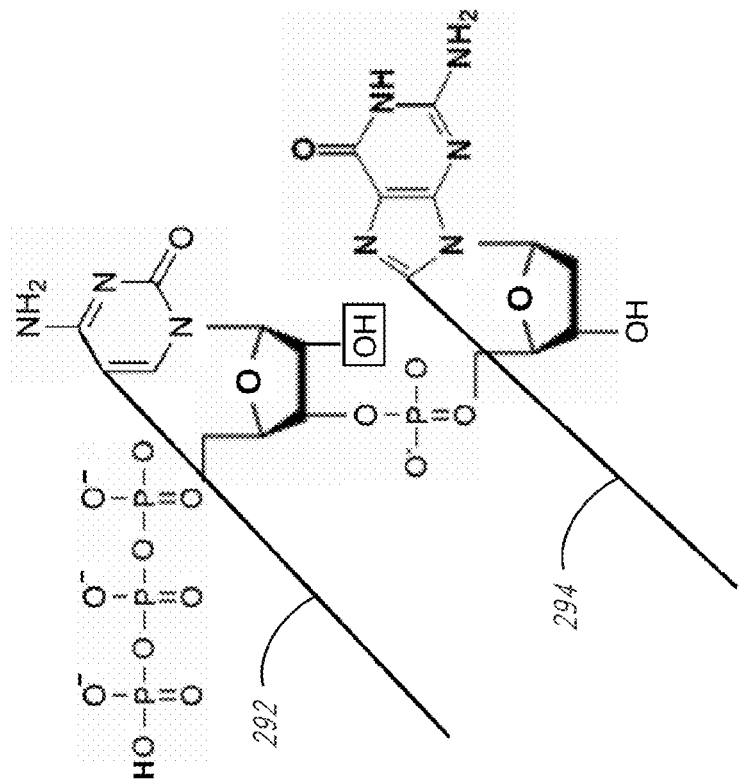
Figure 29D:
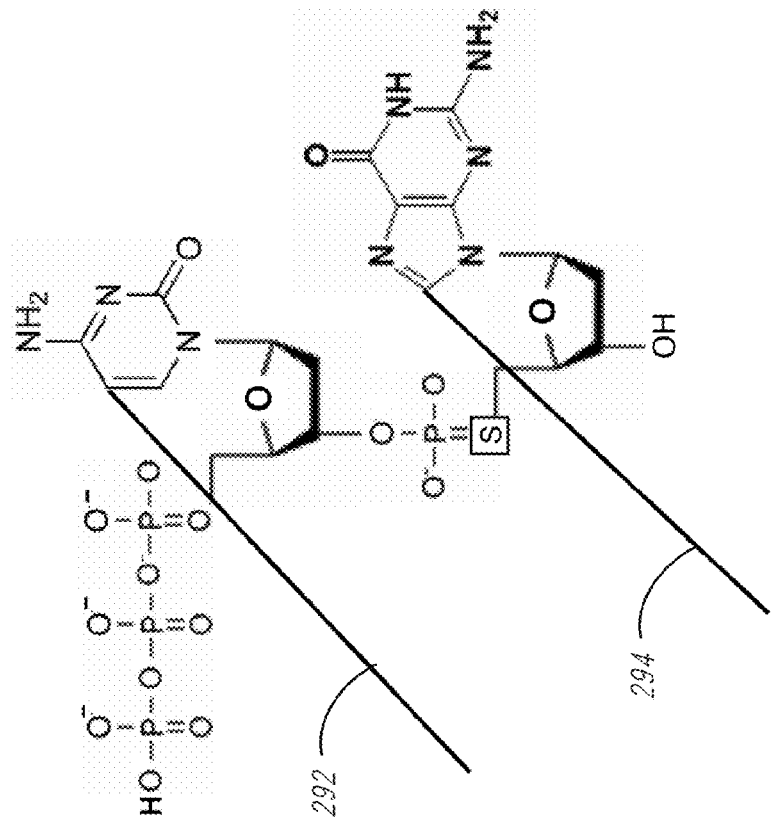
Figure 29C:
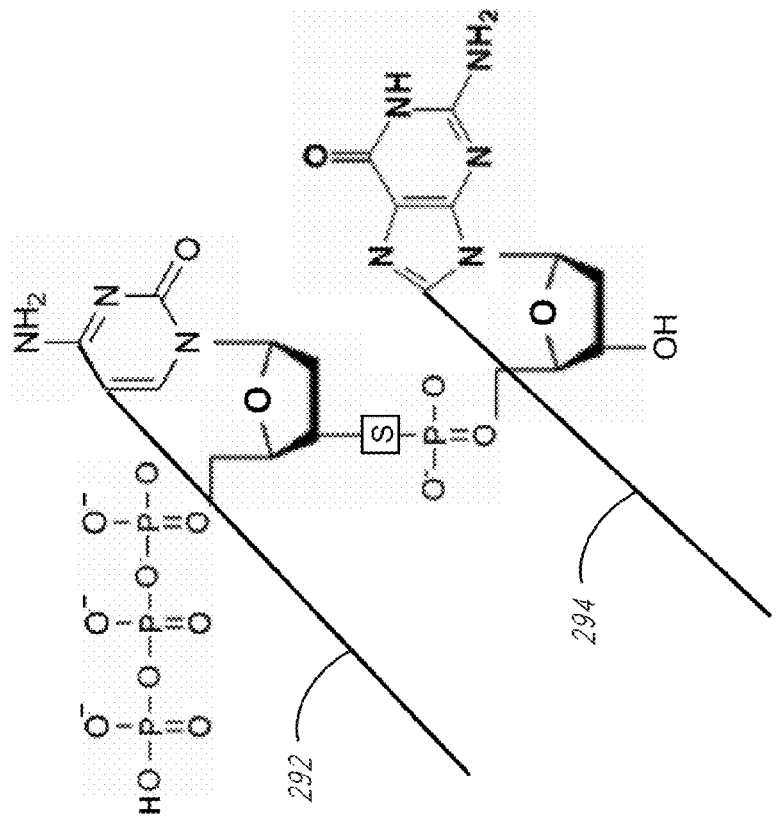

As with the Xprobes, cleavage of the poly-Xmer backbone to produce an Xpandomer is accomplished in a variety of ways. As shown in FIG. 29A, for example, an Xmer containing an RNase digestible ribonucleotide base can be selectively cleaved at that position provided the other nucleotide(s) in the Xmer are resistant to RNase cleavage (for example 2'-O-methyl pentose and 2' deoxyribose nucleobases, "locked" LNA nucleobases, and glycol- or peptide-linked nucleobases). For the Xmer described in FIG. 29A, the 5' base is a standard 2' hydroxyl ribonucleotide cytidine and the 3' base is an RNase resistant 2' deoxyribonucleotide guanine. The Xmer design allows for selective RNase cleavage of the Xmer backbone to expand an Xpandomer. Alternatively, as shown in FIG. 29B, DNase can be used to cleave all non-phosphorothioate protected backbone linkages. Accordingly, a 2 mer library, for example, with a standard phosphate linkage in between the tether attachment points and phosphorothioate linkage(s) at the nucleotide backbone position(s) that are to remain intact, provides the desired cleavage pattern. FIG. 29C is an Xmer dimer held together by a 3'-phosphorothiolate bond, and FIG. 29D is held together by a 5'-phosphorothiolate bond. These bonds are selectively cleavable by chemical attack, for example, with iodoethanol or by cleavage with divalent metal cations as previously referenced. Other backbone cleavage options include (but are not limited to) UV induced photoredox cleavage (as by adaptation of nitrobenzyl photocleavage groups) and acid cleavage of phosphoramidate linkages, both of which are cited above in FIG. 28. In FIGS. 29A through 29D, tethers for bridging the selectively cleavable bond of the probe are indicated at (292) and (294).

Figure 30:
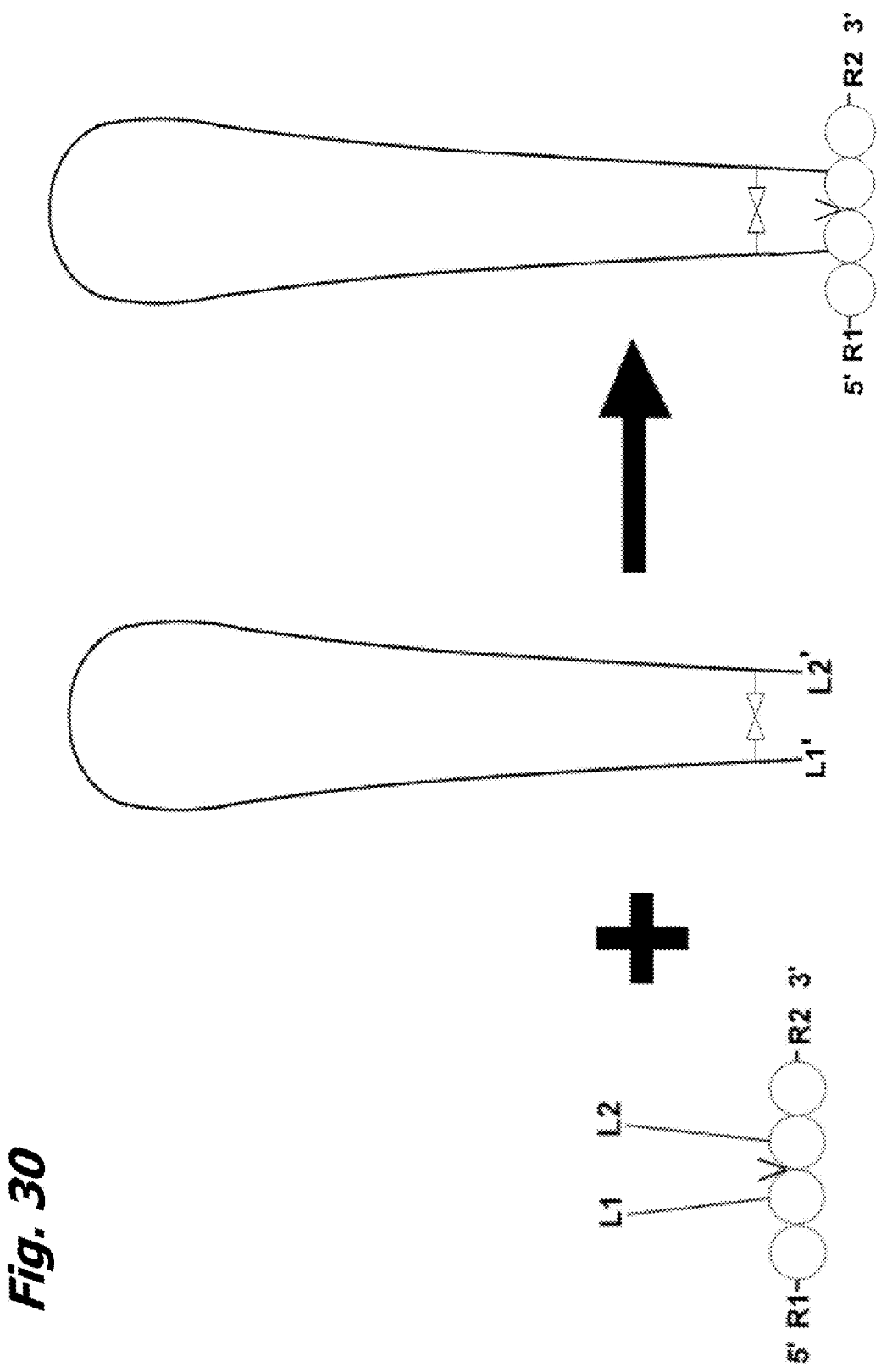
FIG. 30 illustrates one method of assembling a "probe-loop" construct, such as an Xprobe or an Xmer.

Turning now to FIG. 30, in a first general embodiment of a scheme for Class I "probe-loop" substrate construct synthesis, two nucleobase residues (circles) at the second and third positions on the probe are modified to create attachment points L1 and L2 for the two ends L1' and L2' of the tether. The tether is shown here as pre-assembled separately and is joined to the probe member in a synthetic step (arrow). Intra-tether disulfide bonds (depicted by the two triangles) may be used in the assembly and use of these substrate constructs. Introduction of a reducing agent to the Xpandomer product will selectively break the disulfide bridges that hold the tether together, thus allowing expansion of the Xpandomer backbone. Photocleavable bonds are also useful in folding tethers during assembly with subsequent release and unfolding upon exposure to light.

In other embodiments, the phosphodiester backbone of the substrate can be modified to create attachment points for the tether as disclosed by Cook et al. ("Oligonucleotides with novel, cationic backbone substituents: aminoethylphosphonates", *Nucleic Acids Research* 22(24): 5416-5424, 1994), Agrawal et al. ("Site specific functionalization of oligonucleotides for attaching two different reporter groups", *Nucleic Acids Research* 18(18): 5419-5423, 1990), De Mesmaeker et al., ("Amide backbone modifications for antisense oligonucleotides carrying potential intercalating substituents: Influence on the thermodynamic stability of the corresponding duplexes with RNA- and DNA-complements", *Bioorganic & Medicinal Chemistry Letters* 7(14): 1869-1874, 1997), Shaw et al. (Boranophosphates as mimics of natural phosphodiesters in DNA", *Curr Med. Chem.* 8(10):1147-55, 2001), Cook et al. (U.S. Pat. No. 5,378,825), and Agrawal ("Functionalization of Oligonucleotides with Amino Groups and Attachment of Amino Specific Reporter Groups", *Methods in Molecular Biology* Vol. 26, 1994). The nucleobase residues making up the probe member can be substituted with nucleobase analogs to alter Xprobe functionality. For example, Locked Nucleic Acids ("LNA") can be used to increase probe duplex stability. If chemical coupling of Xprobes is intended (instead of enzymatic ligation), probe 5' and 3' ends can be further derivatized to allow for chemical crosslinking.

Design, Composition and Synthesis of Reporter Constructs

In one embodiment, tethers are encoded with "reporter constructs" that uniquely identify the sequence of nucleobase residues (or "probe" of Xprobes, Xmers, and other oligomer substrates of FIG. 8) or nucleobase (as in XNTPs, RT-NTPs and monomeric substrates of FIG. 9) to which it is tethered. Reporters are reporters or combinations of reporters generally associated with the tethers which serve to "parse" or "encode" the sequence information inherent in the substrates and inherent in the order in which the substrates are incorporated into the Xpandomer. In some embodiments, the tether is only a spacer and the reporters are, or are associated with, the substrate.

Figure 31:
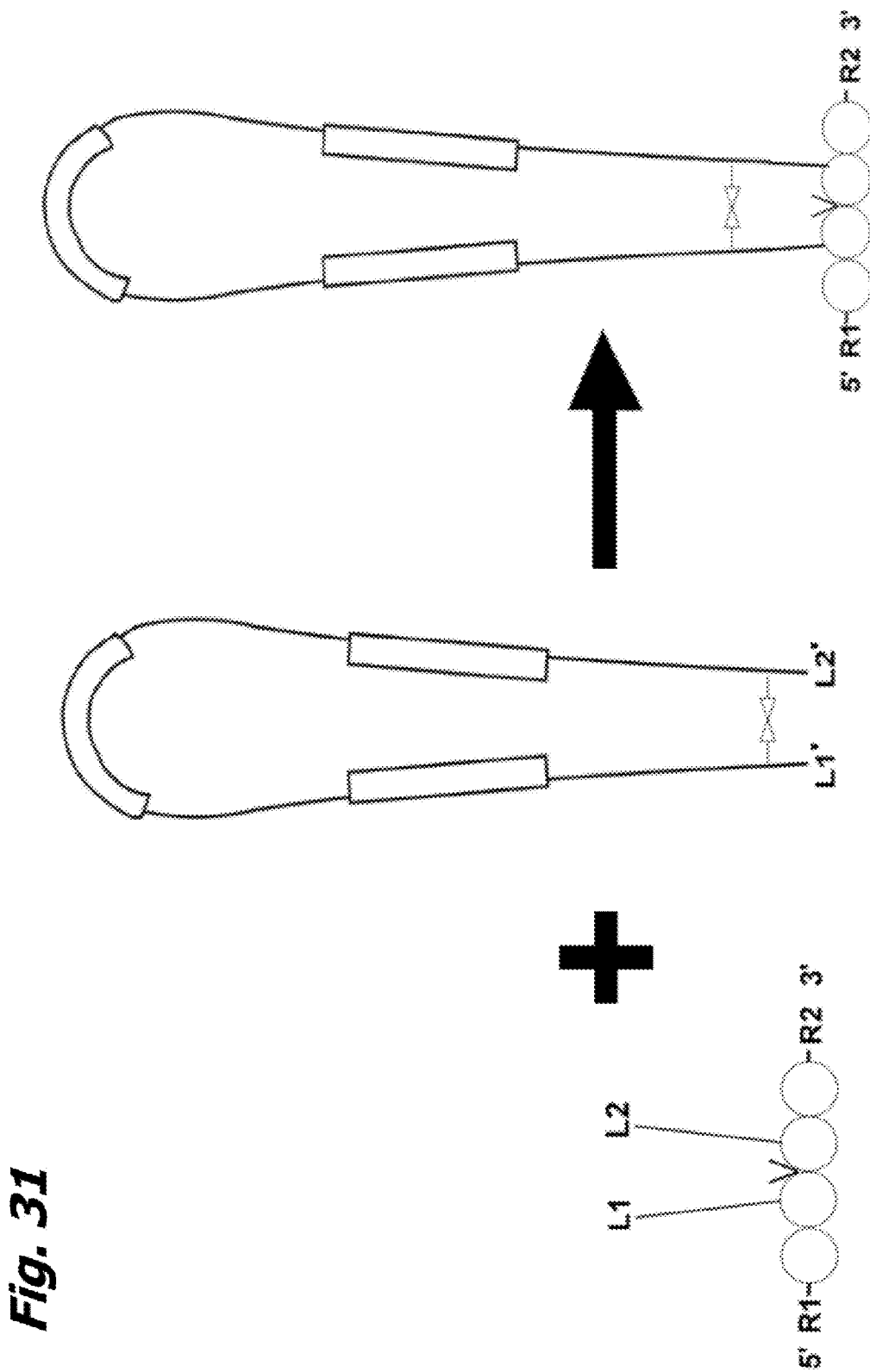
FIG. 31 illustrates a method of assembling a Class I substrate construct, where the loop contains reporter constructs.

FIG. 31 depicts a method for substrate tether assembly similar to that of FIG. 30 but the pre-assembled tether includes reporter groups (shown as the three rectangular portions of the tether) and is termed a "reporter construct". Reporter constructs and tethers may be made by a variety of polymer chemistries, and their use and synthesis is discussed in more detail here.

In the practice of this invention, tethers can serve a variety of functions, for example: (1) as a tether to sequentially link, directly or indirectly, adjacent tethers along the nucleobase backbone, (2) as a spacer to stretch out or expand so as to form an elongated chain of tethered subunits, referred to as an Xpandomer, upon cleavage of the backbone, and/or (3) optionally comprises reporter constructs or reporter precursors that encode the nucleobase or oligomeric sequence information of the individual substrate construct to which the tether is associated.

Reporter constructs are physical manifestations of reporter codes, which are bioinformational and digital in nature. Reporter codes parse or encode the genetic information associated with the probe or nucleobase sequence fragment to which the reporter construct and tether is attached. The reporter constructs are designed to optimize the detectability of the reporter code by adjusting spatial separations, abundance, and signal strength of the constituent reporters. The reporter constructs can incorporate a broad range of signal and structural elements including, but not limited to, polymers, dendrimers, beads, aptamers, ligands and oligomers. These reporter constructs are made by a variety of polymer chemistries and are discussed further below.

In one embodiment, the reporter constructs are attached to the probe or nucleobase by a polymer tether. The tethers can be constructed of one or more durable, aqueous- or solvent-soluble polymers including, but not limited to, the following segment or segments: polyethylene glycols, polyglycols, polypyridines, polyisocyanides, polyisocyanates, poly(tri-arylmethyl) methacrylates, polyaldehydes, polypyrrolinones, polyureas, polyglycol phosphodiesters, polyacrylates, polymethacrylates, polyacrylamides, polyvinyl esters, polystyrenes, polyamides, polyurethanes, polycarbonates, polybutyrates, polybutadienes, polybutyrolactones, polypyrrolidinones, polyvinylphosphonates, polyacetamides, polysaccharides, polyhyaluranates, polyamides, polyimides, polyesters, polyethylenes, polypropylenes, polystyrenes, polycarbonates, polyterephthalates, polysilanes, polyurethanes, polyethers, polyamino acids, polyglycines, polyprolines, N-substituted polylysine, polypeptides, side-chain N-substituted peptides, poly-N-substituted glycine, peptoids, side-chain carboxyl-substituted peptides, homopeptides, oligonucleotides, ribonucleic acid oligonucleotides, deoxynucleic acid oligonucleotides, oligonucleotides modified to prevent Watson-Crick base pairing, oligonucleotide analogs, polycytidylic acid, polyadenylic acid, polyuridylic acid, polythymidine, polyphosphate, polynucleotides, polyribonucleotides, polyethylene glycol-phosphodiesters, peptide polynucleotide analogues, threosyl-polynucleotide analogues, glycol-polynucleotide analogues, morpholino-polynucleotide analogues, locked nucleotide oligomer analogues, polypeptide analogues, branched polymers, comb polymers, star polymers, dendritic polymers, random, gradient and block copolymers, anionic polymers, cationic polymers, polymers forming stem-loops, rigid segments and flexible segments. Such polymers can be circularized at attachment points on a substrate construct as described in, for example, in FIG. 30 and FIG. 31.

The tether is generally resistant to entanglement or is folded so as to be compact. Polyethylene glycol (PEG), polyethylene oxide (PEO), methoxypolyethylene glycol (mPEG), and a wide variety of similarly constructed PEG derivatives (PEGs) are broadly available polymers that can be utilized in the practice of this invention. Modified PEGs are available with a variety of bifunctional and heterobifunctional end crosslinkers and are synthesized in a broad range of lengths. PEGs are generally soluble in water, methanol, benzene, dichloromethane, and many common organic solvents. PEGs are generally flexible polymers that typically do not non-specifically interact with biological chemicals.

Figure 32A:
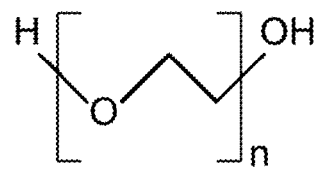
FIGS. 32A through 32C illustrate use of PEG as a polymeric tether.
Figure 32B:
Figure 32C:
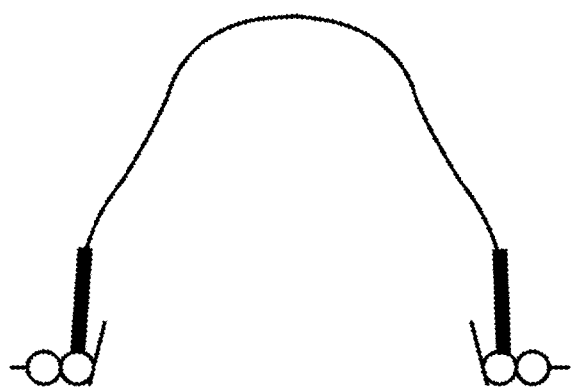

FIG. 32A illustrates the repeating structure of a PEG polymer. FIG. 32B shows an Xprobe or Xmer with a naked PEG tether secured to the probe backbone by, for example amine-terminated linkers (not shown) using standard linker chemistries. FIG. 32C shows the same substrate construct after cleavage of the probe backbone at a selectively cleavable bond ("V"), the PEG polymer flexibly accommodating elongation of the Xpandomer. In some embodiments, PEG polymer segments are assembled piecewise on the tether to provide expansion length or to minimize steric issues, such as, for example, at the stems of the tethers proximate to the terminal end linkages connecting the tether arms to the substrate.

Other polymers that may be employed as tethers, and provide "scaffolding" for reporters, include, for example, poly-glycine, poly-proline, poly-hydroxyproline, poly-cysteine, poly-serine, poly-aspartic acid, poly-glutamic acid, and the like. Side chain functionalities can be used to build functional group-rich scaffolds for added signal capacity or complexity.

Figure 33A:
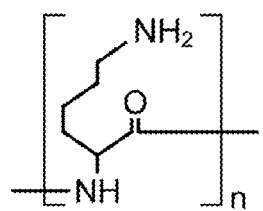
FIGS. 33A through 33D illustrate poly-lysine as a polymeric tether and dendrimeric constructs derived from poly-lysine scaffolds.
Figure 33B:
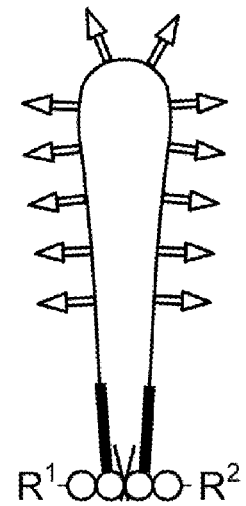
Figure 33C:
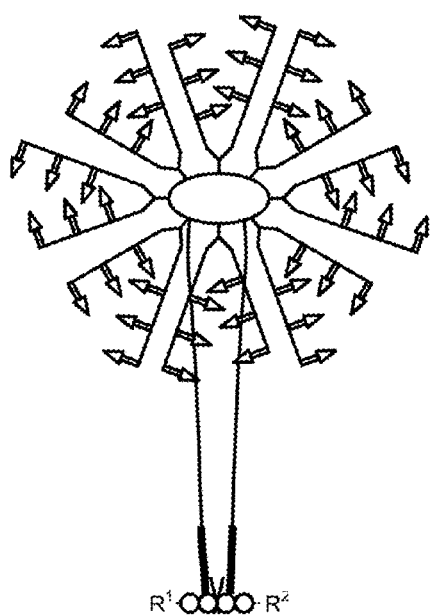

FIG. 33A shows the structure of poly-lysine. In the tether constructs embodiments described in FIG. 33B through 33D, the poly-lysine tether segments create a scaffolding for reporter attachment. In FIG. 33B, the e-amino groups of the lysine side chains (indicated by arrows) provide functionality for attachment of pluralities of reporter elements to a substrate construct, amplifying the reporter code. FIG. 33C illustrates a starburst dendrimer attached to a substrate construct) with poly-lysine side chains (arrows).

Figure 33D:
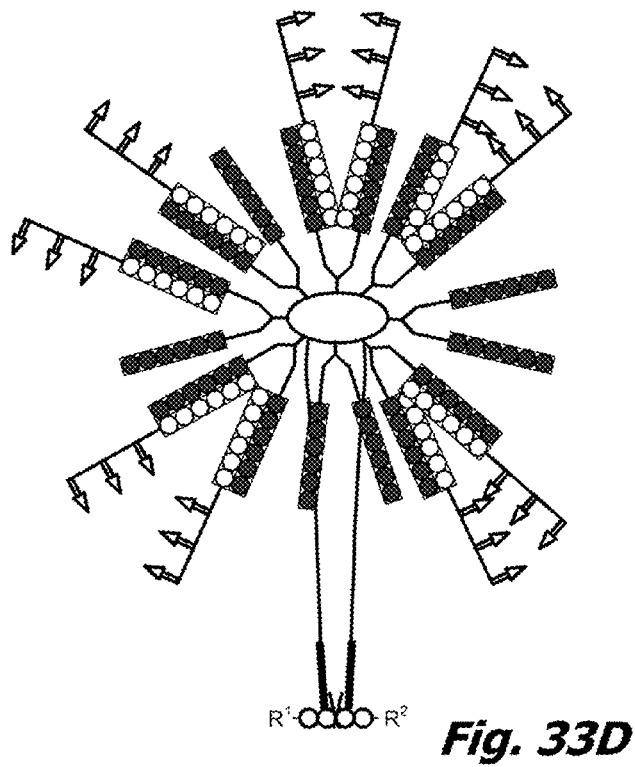

FIG. 33D illustrates loading of the dendrimer oligomers that can be detected by adding tagged complementary oligomers in a post-assembly labeling and "amplification of signal" step. This provides a useful method for preparing a universal tether—by attaching an untagged dendrimer complex with multiple oligomeric reporter groups to a probe, and then treating the probe-bound dendrimer with a selection of one or two complementary tagged probes, a "painted" dendrimer specific for the individual substrate species is obtained. Different probe/tether constructs can be painted with different complementary tagged probes.

In a further embodiment of this approach, the backbone of the reporter system comprises eight unique oligonucleotides which are spatially coded in a binary fashion using two discernable fluorescent reporters, each excited via the same FRET donor. Prior to or following coupling of the tether constructs to its respective substrate construct, the tether constructs are sequence coded by hybridizing the appropriate mixture of fluorescent reporter elements to create the proper probe-specific binary code. Variations of this approach are employed using coded, unlabeled dendrimers, polymers, branched polymers, or beads as the backbone of the reporter system. Oligonucleotides can again be used for the binary coding of the reporter construct. An advantage with this approach is that signal strength is significantly amplified and that coding is not reliant upon a single hybridization event, both of which decrease the possibility of measurement and/or coding error.

Still another embodiment replaces the above-described oligonucleotide coding strategy with affinity-bound heterospecific ligands to produce, for example, a similarly binary coded reporter construct. Using a 9 bit, binary coding strategy, this non-universal reporter construct, in its simplest form, employs only a single coupling chemistry to simultaneously label all of the tethers.

Given the flexibility of the SBX approach, a broad range of reporters are used to produce unique, measurable signals. Each tether is uniquely encoded by one or many distinct reporter segments. The scaffolding to which the reporter moieties are attached can be constructed using a broad range of existing structural features including, but not limited to dendrimers, beads, polymers, and nanoparticles. Depending on the coding scheme, one or many distinctly separated reporter scaffolds can be used for the reporter code of each tether. Any number of options are available for direct and indirect attachment of reporter moieties to the reporter scaffolding, including (but not limited to): reporter coding of chemically reactive polymer(s) integrated into the tether constructs; reporter coding of chemically reactive surface groups on dendrimer(s) integrated into the tether backbone; and reporter coding of chemically reactive surface groups on bead(s) integrated into the tether. In this context, a "bead" is taken broadly to indicate any crystalline, polymeric, latex, or composite particle or microsphere. For all three examples, reporter abundance can be significantly increased by attaching, to the reporter scaffolds, polymers that are loaded with multiples of reporters. These polymers can be as simple as a 100 residue poly-lysine or more advanced, such as labeled oligomeric probes.

Size reduced tether constructs can also be used. For example, the tether constructs can be lengthened in a post-processing step using directed methods for inserting spacing units, thus reducing the size of the reporter tether.

Reducing the size and mass of the substrate construct can also be achieved by using unlabeled tethers. By eliminating bulky reporters (and reporter scaffolding such as dendrimers, which for some encoding embodiments comprise over 90% of the tether mass), hybridization and/or coupling kinetics can be enhanced. Post-assembly tether labeling can then be employed. Reporters are bound to one or more linkage chemistries that are distributed along the tether constructs using spatial or combinatorial strategies to encode the base sequence information. A simple binary coding scheme can use only one reactive linkage chemistry for Xpandomer post-assembly labeling. More complicated labeling schemes, which can require hundreds of unique linkers, use an oligonucleotide based strategy for Xpandomer labeling. Another post labeling Xprobe or Xmer embodiment is to use the resulting nucleotide sequences derived from $P^1$ and $P^2$ (see FIG. 10) that remain following cleavage and expansion of the Xpandomer for reporter attachment by hybridization of a library of labeled probes. Similarly, other labeling and/or detection techniques can identify the more spatially resolved nucleotides directly.

The tethers and reporter constructs are employed that attach to the substrate constructs with a desired level of accuracy since inaccurate coupling leads to inefficiencies in detection, and can also lead to polymer termination or scrambling of the reporter code (e.g., if an asymmetrical reporter code is used).

The fidelity of the SBX process can be linked to the synthesis purity of the substrate constructs. Following purification of the tether/reporter construct to enrich for full length product, the construct can be directly coupled to a heterobifunctional (directional reporter coding) or homobifunctional (symmetrical or oriented reporter coding) oligonucleotide probe. As with all methods of polymer synthesis, purification (size, affinity, HPLC, electrophoresis, etc.) is utilized following completion of substrate construct synthesis and assembly to ensure high purity of full length, expandable probe constructs.

Synthesis of Class I Substrates Constructs Displaying Reporters

Synthesis of Class I substrate constructs with reporters or reporter precursors displayed on the tethers can be accomplished in a variety of ways. A stepwise process can be used to assemble a hairpin tether polymer that is connected near the tether attachment ends of the substrate construct via a disulfide bridge. This orients the reactive ends such that coupling of the tether to the probe is highly favored. Amino-Modifier C6 phosphoramidites are commercially available for all four nucleotides (Glen Research, USA) and are used to attach the tether to form the completed substrate construct, for example. Alternatively, linker chemistry in the form of benzaldehyde modified nucleotides can be employed. Size and/or affinity purification is useful to enrich for correctly assembled substrate constructs.

Probe heterobifunctionalization can advantageously be done on a solid support matrix, as is customary for oligo and peptide synthesis, or in solution with appropriate purification methods. A broad range of off-the-shelf heterobifunctional and homobifunctional crosslinking reagents are available for modifying, for example amine, carboxyl, thiol, and hydroxyl moieties, and to produce a variety of robust and selective linking chemistries. Since C6 amino modifiers are available for all four deoxy ribonucleotides, and can be made available for all four ribonucleotides, functionalization strategies described here use off-the-shelf amine based crosslinking methods along with well established amine protection/deprotection chemistries. However, given the broad range of phosphoramidite and crosslinking chemistries known in the art, methods not described here can be also considered and result in equivalent products.

The need for heterobifunctionalization of the probe can be eliminated if the reporter coding strategy produces digitally symmetrical coding or uses directional landmarks (parity bits) to identify code orientation. In this case, two internal amine probe modifiers are sufficient since either coupling orientations of the reporter constructs on the tether would produce a unique, probe specific sequence identification.

One or many polymer segments can be sequentially assembled using chemical, (e.g., crosslinkers) or enzyme (e.g., nucleic acid probe hybridization and ligation) catalyzed covalent linkages to form a circular, end functionalized tether. Given the current state of the art for polymer synthesis methods, the chemical crosslinking synthesis approach constitutes a representative embodiment. As is customary for many polymer synthesis methods, a solid support matrix can be used as a scaffold for synthesis. Polymer segments can be assembled one at a time on the basis of end functionalization, as mixed pair segments having different end functionalizations, or as bound pairs—two polymer segments with different homobifunctional end moieties (e.g., hydrazide and amine) paired via disulfide bridges.

Labeling chemistries, which includes both the linker and reporter element moieties, are developed and optimized on the basis of high signal yield and stability, low polymer cross reactivity and entanglement, and the structural rigidity (stiffening) which these chemistries impart to the Xpandomer backbone, which can be important for sample preparation and detection as discussed below.

Figure 34A:
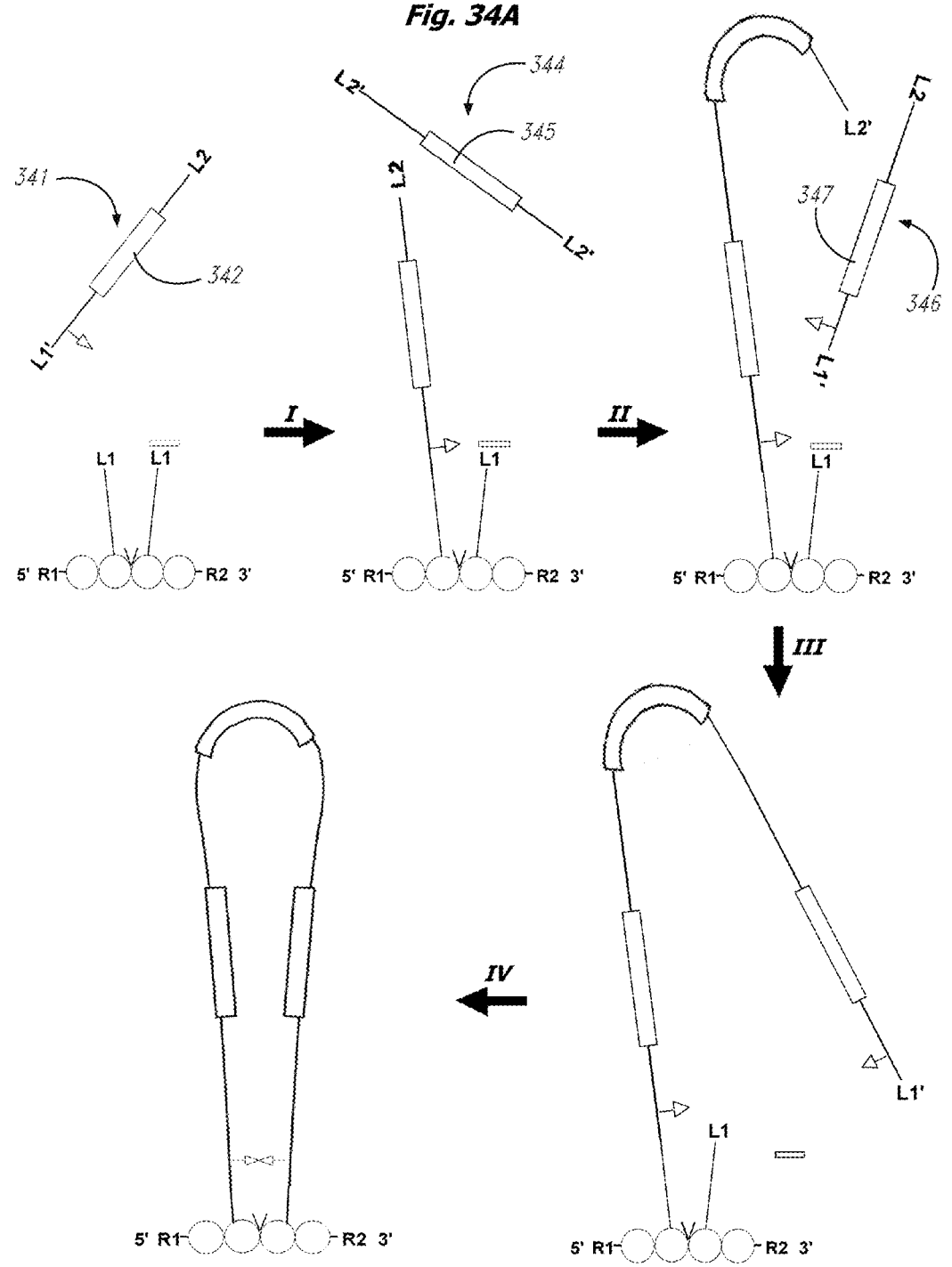

In FIG. 31 discussed above, the complete hairpin tether/reporter construct is assembled independently of the oligonucleotide probe and then joined by homobifunctional or heterobifunctional linker chemistries to the probe member. In an alternative embodiment, as shown in FIG. 34, tethers are circularized stepwise by construction on immobilized probe sequences. The reporter construct and tether are synthesized with heterobifunctional (directional) or homobifunctional (symmetrical or oriented) tether segments linked directly to an oligonucleotide probe. The probe sequence shown in FIG. 34A is a 4 mer and includes probe moieties $P^1$ and $P^2$ (the second and third circles) separated by a selectively cleavable bond ("V"). Solid state synthesis techniques are used in synthesis of the reporter construct. This synthesis is integrated with closure of the tether loop. In Step I of FIG. 34A, a first tether segment (341) with first reporter group (342) is added using specific functional group chemistry denoted by L1 and L1 (linker L1 on one of the probe moieties is blocked, as depicted by the small rectangle). In Step II, a second tether segment (344) with second reporter group (345) is added using specific functional group chemistry denoted by L2' and L2'. In Step III, a third tether segment (346) with reporter group (347) is added using specific functional group chemistry denoted by L2 and L1. In Step IV, and following removal of the blocking group from the L1 site on the $P^2$ moiety of the probe (again depicted by the small rectangle), the loop is closed after L1 and L1 coupling.

Figure 34B:
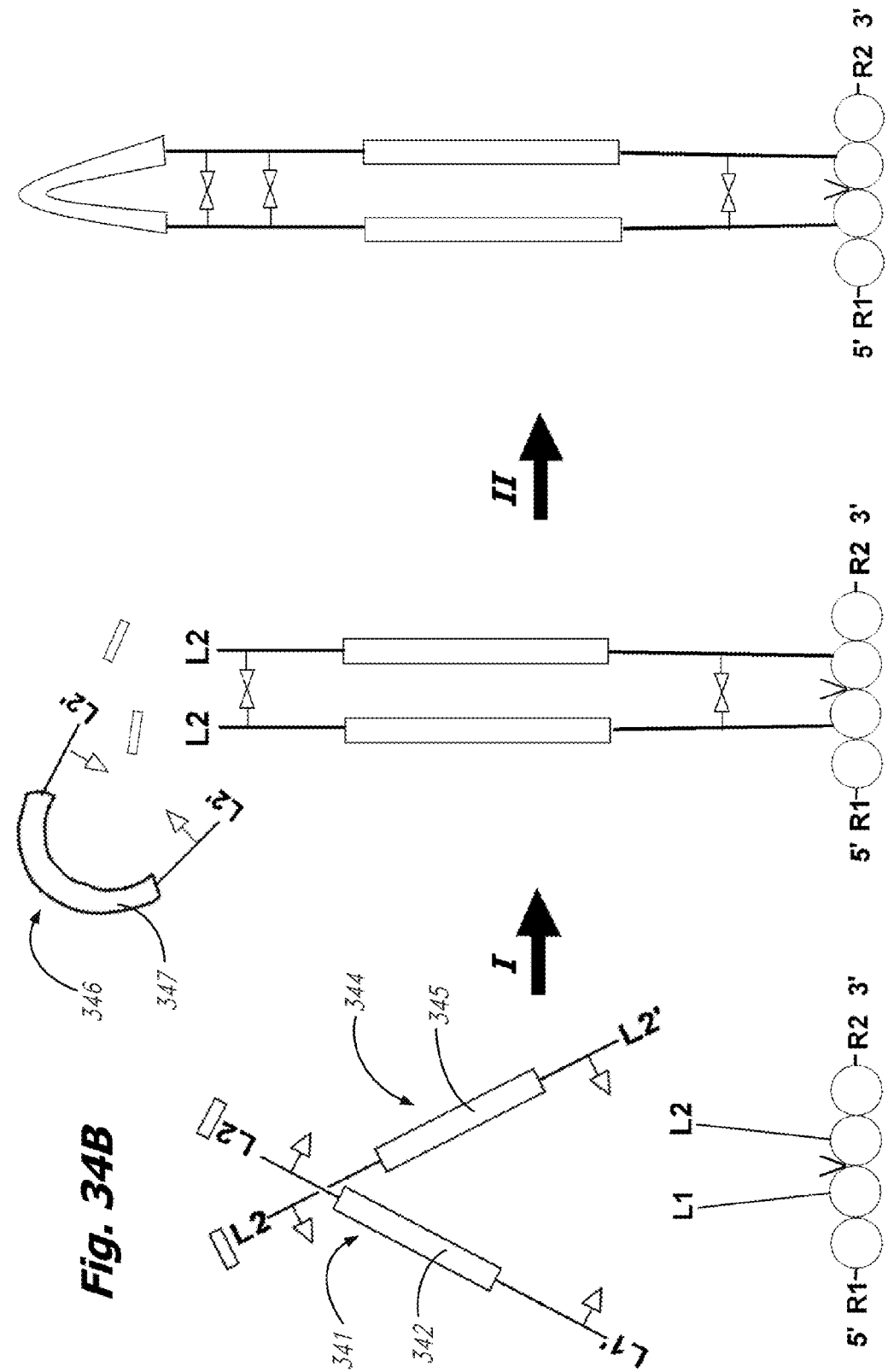

In yet another embodiment, as illustrated in FIG. 34B, heterobifunctional linker chemistry can again be used to ensure the tether is directionally positioned on the probe (although this is not necessary for all encoding strategies). A probe 4 mer is again depicted with probe moieties $P^1$ and $P^2$ (the second and third circles) separated by a selectively cleavable bond ("V"). In Step I, two tethers (341,344) with reporter segments (342,345) are contacted with functional groups L1 and L2 on $P^1$ and $P^2$; the chemistries are specific for each tether. The tethers at this stage may be stabilized with intra-tether bonds (depicted by the adjoining triangles). In Step II, a third tether (346) with reporter segment (347) is used to "cap" the tethers after removal of blocking groups (shown as the small rectangles) on the predecessor segments. The cap segment can also be stabilized with an intra-segment bond (again depicted as adjoining triangles).

Turning now to FIG. 34C, an embodiment based on addition of probe moieties $P^1$ and $P^2$ to separate end linkages of a preformed tether is shown. In step I, the preformed tether is first reacted with $P^1$ by contacting L1 to L1. In Step II, the tether is then reacted with $P^2$ by contacting L2 to L2'. The tether may be stabilized by an intra-tether bond (depicted by adjoining triangles), which brings $P^1$ into proximity with $P^2$. The two probe moieties are then ligated in Step III to form the selectively cleavable bond ("V") between $P^1$ and $P^2$ (the second and third circles). $P^1$ and $P^2$ ligation may optionally be facilitated by duplexing said probe moieties to a complementary template.

Figure 35A:
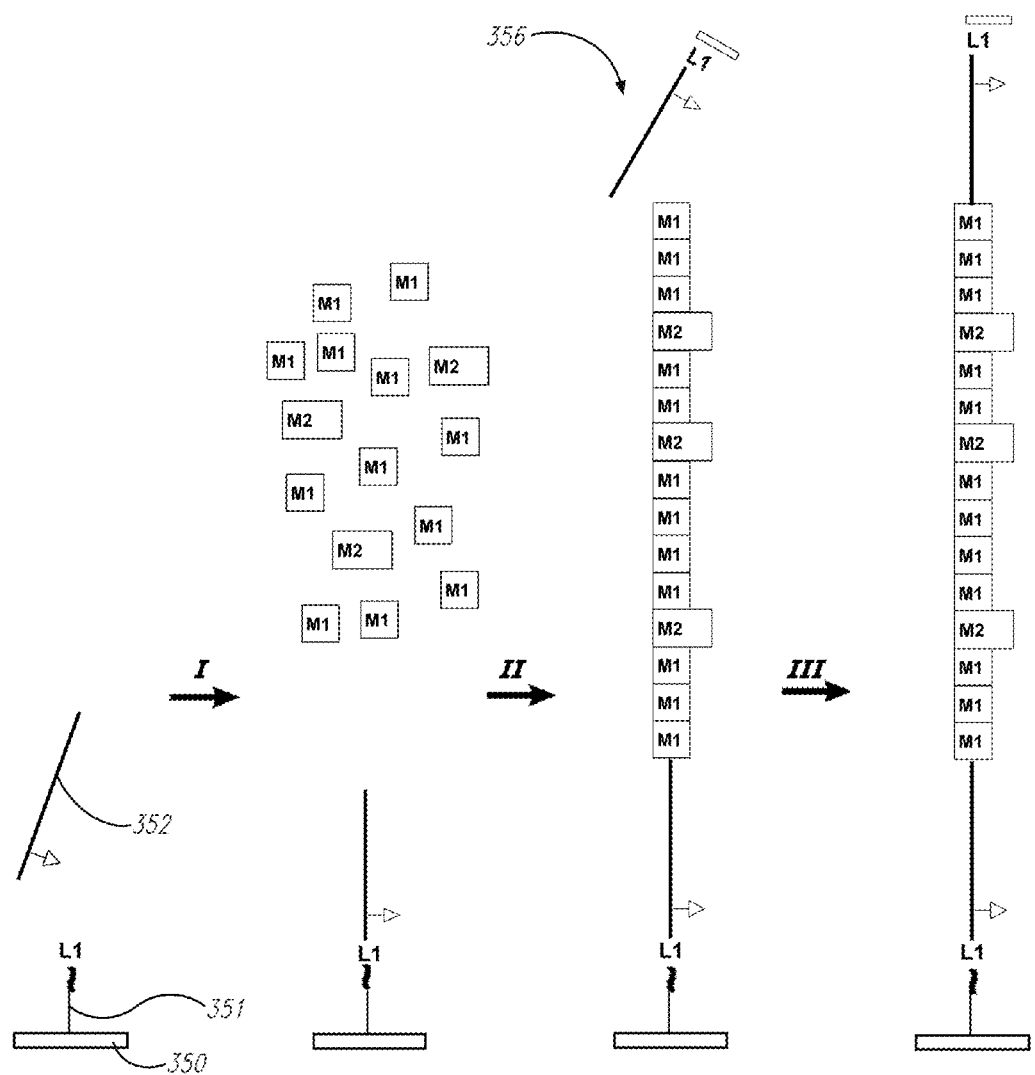
FIGS. 35A and 35B illustrate a method for synthesis of an individual reporter segment by randomized polymerization of precursor blocks.

In FIG. 35A, another embodiment is discloses for synthesis of a reporter construct segment. Using solid state chemical methods, a cleavable linker (351) is first anchored on a solid substrate (350). A first tether segment with a reversible linkage (352) is reacted with the linker in Step I, and then in Step II reacted with a combinatorial library of monomers M1 and M2, shown in this example as a 4:1 stoichiometric mix of the respective monomers. Random copolymer synthesis is done in this manner to produce unique tether segment compositions. If peptide or amino acid monomers are used, this can be done with mixed anhydride chemistry, for example, resulting in random copolymer peptide tethers of variable length (Semkin et al., "Synthesis of peptides on a resin by the mixed anhydride method", *Chemistry of Natural Compounds* 3(3): 182-183, 1968; Merrifield et al., "Solid Phase Peptide Synthesis. I. The Synthesis of a Tetrapeptide". *J. Am. Chem. Soc.* 85(14):2149-2154, 1963). In Step III, an end linker element (356) blocked at L1 (depicted as a small rectangle) is then added to the peptide segment. Following cleavage of the segment from the solid support (not shown), the tether segment can be incorporated into a reporter construct using a variety methods, some of which were described in FIG. 34.

Figure 35B:
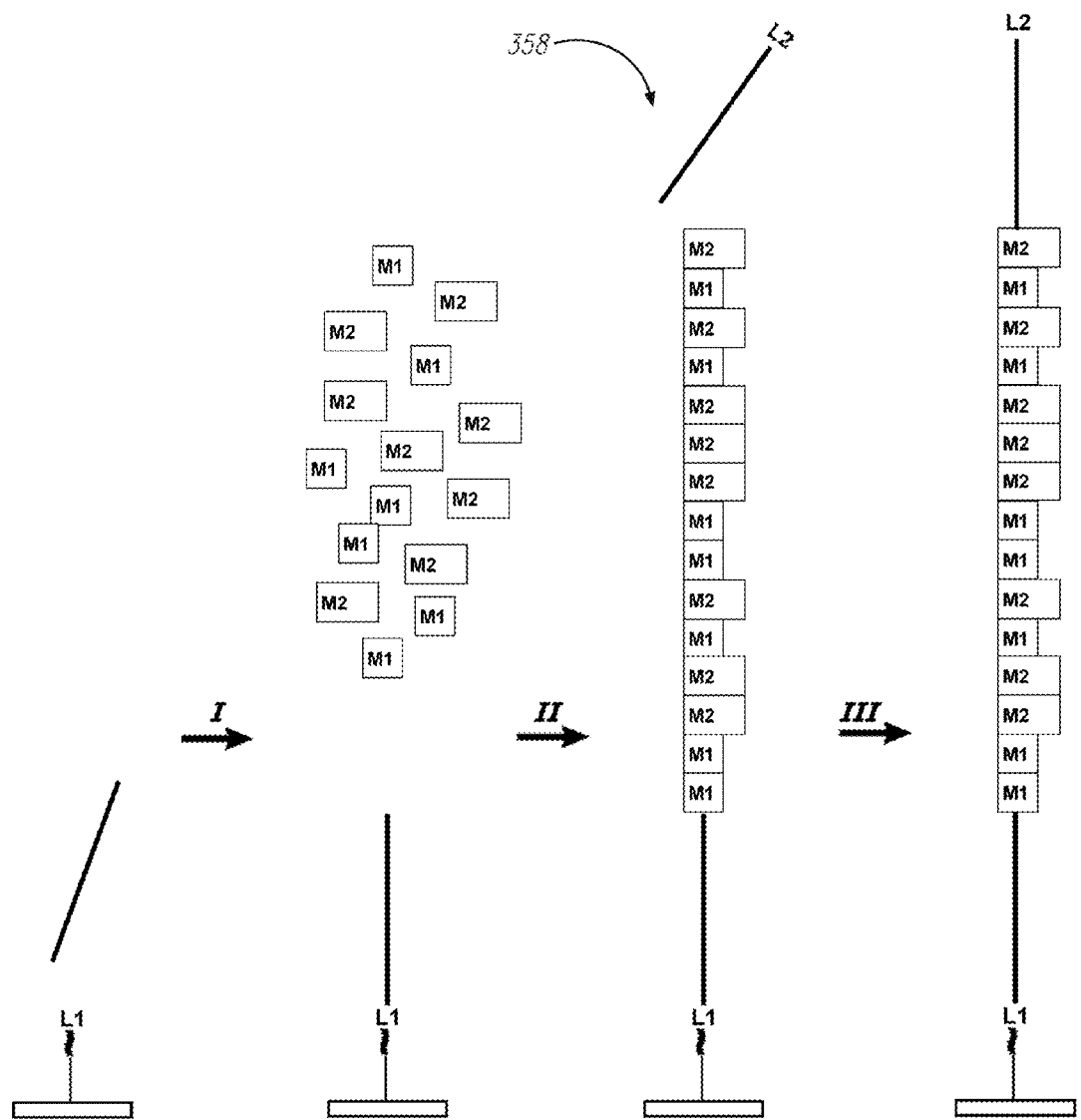

In FIG. 35B, an alternative to this embodiment is demonstrated. A reporter construct with randomly incorporated peptide fragments is synthesized as before in Steps I, II and III, but in Step III the end linker group (358) is provided with a heterofunctional linker L2. Different from the previous example, monomers are provided in equal proportions. After cleavage from the solid support (not shown), the reporter construct is available for further incorporation into tethers of the previous examples and is a heterobifunctional linker. Reporter constructs serve to encode the genetic information of the probe sequence fragment, as is described in more detail below.

Polypeptides are useful reporter constructs and also serve as tethers. Random, periodic, alternating, and block copolymers along with homopolymer, for example, can be utilized for tether segment and tether construct composition. Polypeptide segments can be end functionalized using succinimidyl containing heterobifunctional crosslinkers for amine conversion to a hydrazide or 4-formylbenzoate (4FB), for example. Polypeptides can be produced either by chemical synthesis or by cloning and over expression in biological systems (bacteria, yeast, baculovirus/insect, mammalian). Depending on the desired length of the segment, tether segments can range from N>2 (short segments) to N>1000 (long segments). Amine side group protection chemistries may be used as appropriate. As an alternative to using off the shelf crosslinkers, polypeptides can be chemically synthesized with hydrazide, 4FB, and NHS moieties directly attached.

Polypeptide segments end functionalized using maleimido-containing heterobifunctional crosslinkers for thiol conversion to a hydrazide or 4-formylbenzoate (4FB), can also be used in synthesis of tethers and reporter constructs. Polypeptide segments end functionalized using EDC crosslinkers for carboxyl conversion to a hydrazide (HZ) or 4-formylbenzoate can similarly be employed.

Synthesis of all five classes of oligomeric substrate construct having tethers modified with reporter constructs is achieved by use of the above synthetic methods. Similarly, synthesis of monomeric substrates having tethers modified with reporter constructs may also be achieved by the above synthetic mechanisms. The chemistries for these variants are generally applicable to the genera of Xpandomer species shown in FIGS. 8 and 9. We now turn to encoding strategies and rules for conveying genetic information in Xpandomers with reporter constructs.

Reporter Constructs and Reporter Code Strategies

A "reporter code" is a digital representation of a particular signal or signal sequence that is embodied in the reporters of a particular reporter construct. Whereas the "reporter construct" is a physical manifestation of extragenetic information, the reporter code is its digital equivalent.

Digital encoding requires reporter codes to follow certain rules. For example, at least 256 reporter codes are required to identify all the possible combinations of a 4 mer Xprobe library. Having more reporter codes than there are possible reporter construct combinations is advantageous because extra states can be used for other purposes such as tagging of gaps, providing positional information or identifying parity errors or high order errors.

A number of strategies can be considered for physically representing a reporter code. The tether can be divided into one or many codable segments, each of which can be labeled either before or after Xpandomer assembly. Variable signal levels (amount of label), lengths (duration of signal), and shapes of labeled tether constructs segments can be used to increase coding options. Coding can also be expanded by using multiplexable labels. For instance, using a mass tag label approach, a broad library of spectrally distinct tags can be used to uniquely encode a single reporter segment; 14 distinct mass tags used in combinations of three tags clustered on a single tether constructs segment would create 364 unique 3-mass spectra. For multi-segmented tether, post Xpandomer assembly labeling of most or all of the tether backbone can have the added benefit of increasing the rigidity of the Xpandomer, potentially making it easier to manipulate for detection and improving stability.

Figure 36B:
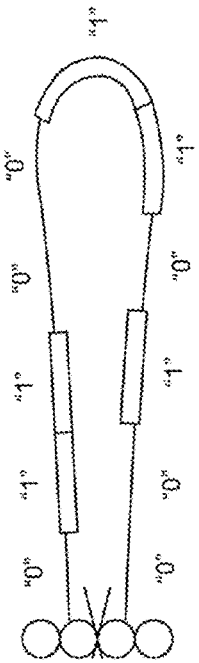
FIGS. 36A through 36I illustrate reporter constructs.
Figure 36D:
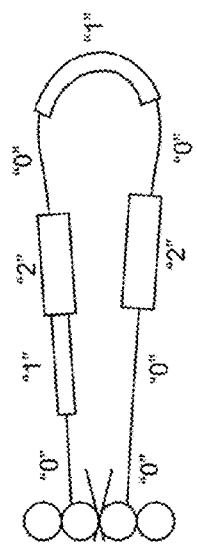
Figure 36F:
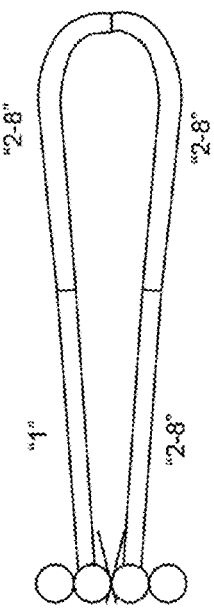
Figure 36A:

FIG. 36A (and also FIG. 2A) illustrates a tether with a single reporter segment of an Xprobe or an Xmer. This approach benefits from highly multiplexable reporter labeling, such as mass spectrometer tags, to produce a broad library of spectrally distinct outputs. A cleavable mass tag is a molecule or molecular complex of cleavable reporters that can be readily ionized to a minimum number of ionization states to produce precise mass spectra. When carefully controlled, a mass spectrometer can detect as little as a few hundred such mass tag reporters. This reporter code example needs no positional information of the reporter on the tether backbone to determine the code state (though positional information is required to distinguish one reporter code from the next). This characteristic simplifies the tether construction and potentially shortens the tether length requirements.

In one embodiment, using cleavable mass tag labels, the lengthened Xpandomer can be presented for detection via a nanopore ion source (electrospray ionization, atmospheric pressure chemical ionization, photoionization) or by surface deposition (nanocomb, nanochannel, laminar flow, electrophoretic, and the like) followed by desorption ionization with laser, ion beam, or electron beam sources (Matrix Assisted Laser Desorption Ionization "MALDI", Desorption Electrospray Ionization "DESI", Desorption Ionization on Silica "DIOS", Secondary Ion Mass Spectrometry "SIMS").

An example of a 9-bit tether constructs with 2 detection states ("1" and "0"), which produces 512 code identities, is described in FIG. 36B. In one embodiment, the tether constructs consists of segments "1" and "0" that produce two levels of electrical impedance as measured in a Coulter-like nanopore detector. In a second embodiment, the tether constructs consists of electrical conducting segments "1" and non-conducting segments "0". In a third embodiment the tether constructs consists of fluorescent segments "1" and non-fluorescent segments "0". A plurality of different reporter elements can be considered for this type of coding. For any of these approaches, the tether assembly and probe attachment chemistry can be identical—only the reporter segment composition would need to change. With this simple format, labeling can be done either before or after Xpandomer assembly. Post-labeling is desirable since the unlabeled reporter segment is significantly less massive and, as such, is usable at a much higher concentration than a fully labeled reporter construct. Depending on the strategy, the polymer segments can be: (1) coded via conjugatable or reactive surface chemistries (e.g., poly-lysine, poly-glutamic acid), (2) non-reactive (e.g., PEG, low reactivity polymers), or (3) a mixture of both reactive and non-reactive polymers. Reactive groups include, but are not limited to, primary amines (—$NH_3$), carboxyls (—COOH), thiols (—SH), hydroxyls (—OH), aldehydes (—RCOH), and hydrazide (—R—N—N) moieties. Labeling of reactive segments, which may include reactive group deprotection, can be done directly on the substrate constructs, after formation of the Xpandomer intermediate, after backbone cleavage to produce Xpandomer, or at any other time in the SBX process as appropriate to produce the best results.

Figure 36C:
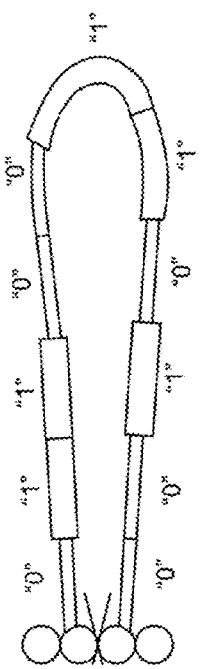

Additional levels may be possible, as shown in FIG. 36C. For example, a binary, directional (non-symmetrical reporter construct) coding strategy requires at least eight reporter coding segments and a ninth segment, a codable capping segment (for tether loop closure and as possible center substrate construct landmark) to produce the minimally required 256 codes for a four base substrate (512 codes if the capping segment is coded).

Turning to FIG. 36D, a 7-bit reporter construct, each reporter with three detection states, is shown to result in 2187 detectable code identities. Use of flexible polymer spacers may be used for steric reasons.

Figure 36E:
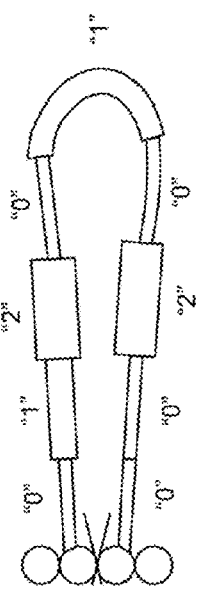

In FIG. 36E, a rigid equivalent of the previous 7-bit reporter construct is shown.

FIG. 36F describes an example of a rigid, 4-segment tether constructs with eight total distinct states or label combinations per segment. Using seven of the label combinations to label three of the tether constructs segments will produce 343 unique code identities and will leave 1 segment available for subunit boundary identification, parity, or other functional purpose. This embodiment can use a mixed labeling approach where 1 to 3 different labels can be incorporated on each segment to produce at least eight unique combinations per segment as shown in FIG. 37, where combinations of different reporter types and reporter construct chemistry are contemplated. Mass tag and fluorescent labeling options, among others, can be utilized as described. Post Xpandomer assembly tether constructs labeling is directed by the abundance and identity of three crosslinker moieties as described in FIG. 37. Tether segment lengths can be on the order of 100-1000 nm for diffraction limited measurements or <100 nm for near field measurements, if it is desired to use these detection technologies. Shorter tethers can be used for other detection methods.

Figure 36H:
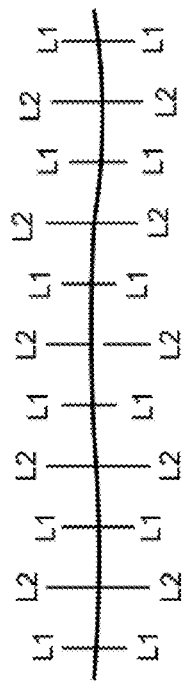
Figure 36I:
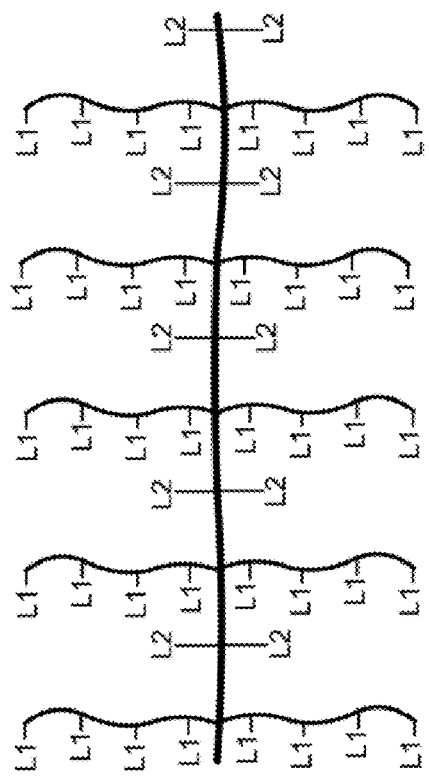
Figure 36G:
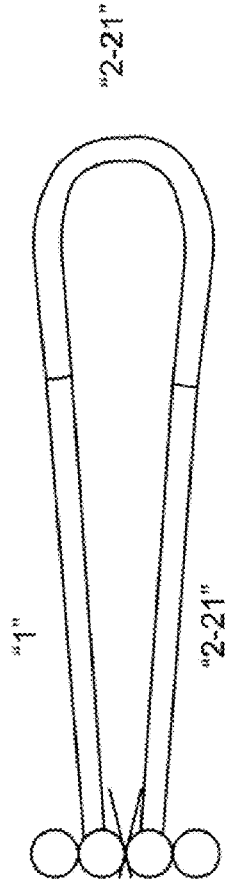

A rigid, 3-segment tether constructs with 22 total distinct label combinations per segment is described in FIG. 36G. Using 21 of the label combinations described in FIG. 37 to label two of the tether constructs segments will produce 441 unique tether constructs identities and will leave one segment available for Xprobe subunit boundary identification. This embodiment uses a mixed labeling approach where one to three different labels can be incorporated on each segment to produce up to 22 unique combinations per segment (FIG. 37). Mass tag and fluorescent labeling options, among others, can be utilized for this embodiment. As described in FIG. 37, post Xpandomer assembly tether construct labeling is directed by the abundance and identity of three chemical moieties.

By designing reporter/tether segments in which the reactive group abundance and spatial dimension (radial distance from polymer backbone) can be varied, coding levels can be achieved wherein at least three total code states are possible: High "2", Medium "1", and Low "0" (FIG. 36H). On the other hand, a three label, two level, coding strategy (i.e. 21 states per reporter) would require only two reporter coding segments to produce 441 codes and could use an additional segment for code orientation (FIG. 36I).

Reporter coding can be designed to reduce errors inherent with the reporter construct and associated detection technologies using several approaches. In the case of nanopore Coulter-like detection, the velocity that an Xpandomer passes through the pore and the current modulation it causes can depend on many factors including, but not limited to, the charge state of the portion of the Xpandomer within the pore, the electrolyte concentrations, the nanopore surface charge states, the applied potential, frictional effects limiting Xpandomer movement, and the relative dimensions of both the Xpandomer and the nanopore. If the velocity is not predictable, decoding the current modulation cannot use time (and constant velocity) to resolve the reporter measurement assignments. One encoding embodiment solves this issue using 3-state encoding. The reporter's signal is the impedance that a label causes to the electrolyte conductivity through the nanopore. By providing three possible levels of impedance for a reporter, one bit of information is encoded by the transition to the next label. By design, this transition is always a change to one of the other two states. If the three states are labeled A, B and C, then a sequence of reporters never has 2 As, 2 Bs, or 2 Cs together. In this way, information is encoded in level transitions and is therefore independent of velocity through the nanopore. One encoding scheme is to assign all transitions A to B, B to C, and C to A a value of "0" whereas transitions B to A, C to B and A to C are assigned the value "1". For example, the detected sequence ABACBCA decodes to 0,1,1,1,0,0.

Although timing cannot reliably resolve sequential labels, it can be sufficient to differentiate the separation of the label sequence on a single tether constructs from that of the next sequential tether. Additional spacer tether lengths at either end of the reporter label sequence (at the substrate construct attachment points) can provide a large timing gap that delineates the tether constructs codes in time.

In cases where such timing is insufficient, a frame shift error can occur. Frame shift errors result when the detector reads a series of labels from multiple tether constructs codes (frames) but does not correctly delineate the start-of-code (start of frame). This results in wrong codes. One embodiment to solve this is to add more bits in the code than are needed to identify the corresponding base sequences (which are typically 1 to 4 bases long). For example, eight bases are required to uniquely identify a 4 base sequence. Each 2 bit pair describes a single base. By adding a parity bit for each base, the tether constructs code is increased to 12 bits. A high parity error rate (near 50%) would indicate a frame shift error that would result from a missed state change. Besides a missed state change, another error type that can occur in this nanopore detection technology is that of a misread state. Single reporter errors can be isolated to the particular base using the parity bit and it can then be assigned the value "unknown base".

The Xpandomers labeled using either electrically impeding, electrically conducting or fluorescent segments can be measured in solution using a variety of nanopore, nanocomb, or nanochannel formats. Alternatively, the Xpandomers can be surface deposited as spatially distinct, linear polymers using nanocomb, nanochannel, laminar flow or electrophoretic deposition methods, among others. As with the solution approach, direct detection of surface elongated Xpandomer can be done by measuring the signal characteristics of labeled tether segments. Depending on the composition of the deposition material (conducting, insulating) and the underlying substrate (conduction, insulating, fluorescent), a variety of detection technologies can be considered for label detection.

Further SBX Methods

A number of SBX methods using class I-V oligomeric substrate constructs were illustrated in the previous figures (FIGS. 11-17, 20, 21, 24). We now consider optional methods that supplement these protocols.

End Functionalization

FIG. 38 illustrates preparation and use of target end adapters. FIG. 38A illustrates end functionalized complementary oligonucleotides duplexed to form an adapter with a bifunctional, conjugatable end ("L1" and "L2) and an enzymatically ligatable end (5' phosphate and 3'-OH). These adapters can also be designed with additional functionalities. For example, as shown in FIG. 38B, end functionalized adapters with nested, backbone crosslinkers ("L3") and a cleavable bond ("V") can be synthesized. For simplicity, the cleavable bond V can be the same cleavable bond chemistry (or enzymology) used to release or expand the Xpandomer, although other cleavable linkers can be utilized if desired to differentiate between independent cleavage steps. FIGS. 38C and 38D show steps for construction of a multifunctional adaptor of FIG. 38B. As shown, a magnetic bead with a surface tethered oligonucleotide complementary to each adapter strand (two different bead mixes) can be used to assemble differentially modified oligonucleotide segments. Once assembled, segments can be enzymatically ligated to covalently link the annealed segments. With this approach, each segment can be modified individually in a manner not available to standard oligonucleotide synthesis.

Manipulation of the Xpandomer can be useful for efficient sample presentation and detection. For example, terminal affinity labels can be used to selectively modify one end of the Xpandomer to allow for electrophoretic elongation. Attachment of a bulky, charge neutral, modifier to either the 3' or 5' end (not both) produces an electrophoretic drag on the Xpandomer that causes the non-modified end to elongate as it travels to the detector. End modifiers, which include but are not limited to microbeads, nanoparticles, nanocrystals, polymers, branched polymers, proteins and dendrimers, can be used to influence the structure (elongation), position, and rate at which the Xpandomer is presented to the detector by imparting unique, differentiating properties to its termini such as charge (+/−/neutral), buoyancy (+/−/neutral), hydrophobicity, and paramagnetism, to name a few. In the provided examples, the end modifications produce a drag force that enables the Xpandomer to elongate; however, the opposite strategy can also be employed wherein the end modification is used to pull the Xpandomer towards and through the detector. With this approach, pulling of the end modifier facilitates Xpandomer elongation. The end adaptor on the template strand may optionally also contain one or more nucleic acids that will be used to synthesize frame registration and validation signals in the finished Xpandomer (see FIG. 54).

Incorporation of an affinity modifier can be done either prior to, during, or after Xpandomer synthesis (hybridization, ligation, wash, cleavage). For example, terminal affinity tagged primers that are complementary to adapter sequence can be pre-loaded to ssDNA target under highly specific conditions prior to Xpandomer synthesis. The primer and its affinity tag can be incorporated into the full length Xpandomer and can be used to selectively modify its end. A potentially more elegant approach is to enzymatically incorporate end modifiers. Terminal transferase (TdT), for example, is a template independent polymerase that catalyzes the addition of deoxynucleotides to the 3' hydroxyl terminus of single or double stranded DNA molecules. TdT has been demonstrated to add modified nucleotides (Biotin) to the 3' terminus (Igloi et al., "Enzymatic addition of fluorescein- or biotin-riboUTP to oligonucleotides results in primers suitable for DNA sequencing and PCR", BioTechniques 15, 486-497, 1993). A wide range of enzymes are suitable for this purpose, including (but not limited to) RNA ligases, DNA ligases, and DNA polymerases.

Figure 38A:
FIGS. 38A through 38F are adaptors suitable for use in end-functionalization of target nucleic acids.
Figure 38B:
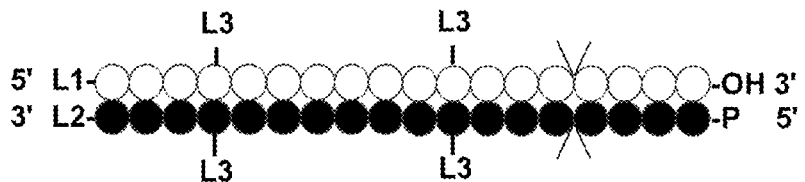
Figure 38C:
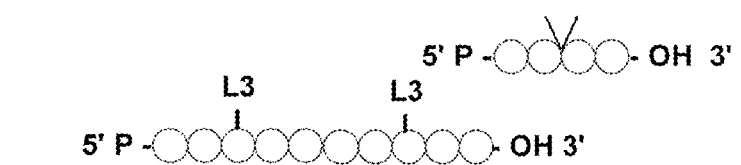
Figure 38D:
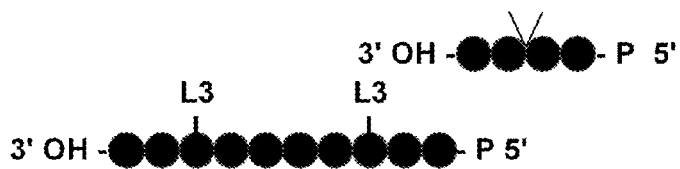
Figure 38E:
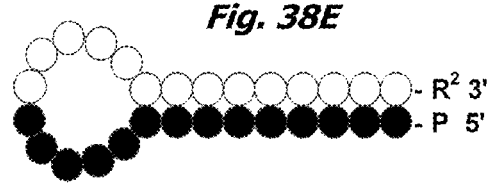
Figure 38F:
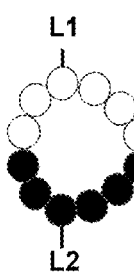

In FIGS. 38E and 38F, hairpin adaptors are illustrated. Hairpin adaptors find use in blunt ended ligation to yield self-priming template strands. One advantage of this approach is that the daughter strand remains covalently coupled to the template strand and more quickly re-anneals following a melt to remove unligated material and low molecular weight fragments. As shown in FIG. 38F, these adaptors can contain embedded pre-formed linker functionalities for purification or downstream handling, and can also contain cleavage sites for more efficient harvest of the Xpandomer daughter strands.

Target Template Preparation and Parsing

To perform whole genome sequencing of long, continuous DNA using the Xprobe based SBX methods presumes that the DNA is prepared in a manageable form for hybridization, ligation, gap filling if required, expansion and measurement. The Xpandomer assembly process can, in some embodiments, be improved by surface immobilization of the DNA target in order to (1) reduce complexity and cross hybridization effects, (2) improve washing, (3) enable target manipulation (elongation) in order to facilitate improved hybridization, and/or (4) if nanopore sensor is used, provide a seamless interface with the detection process. As described in detail below, methods for target template preparation, parsing, and surface attachment is expected to improve data quality and sequence assembly.

Most whole genome sequencing methods require fragmentation of the target genome into more manageable pieces. The largest chromosome in the human genome (Chromosome 1) is ~227 Mb and the smallest chromosome (Chromosome 22) is ~36 Mb. For most of the highly processive and continuous embodiments described herein, 36 Mb of continuous sequencing is far too long to be sequenced with high efficiency. However, to take advantage of the inherent long read length capability of SBX, DNA fragment lengths of >1 kb are targeted. Accordingly, a number of strategies can be employed to accomplish genome fragmentation and prepare a DNA target set compatible with the SBX method as disclosed herein.

One embodiment involves fragmenting the total genome into 1-10 Kb pieces (average 5 Kb). This can be done either by restriction enzymes or by hydrodynamic/mechanical shearing. The fragments are then blunt ended and repaired in preparation for blunt end ligation to a Sequence Adapter ("SA") or a Sequence Adapter-Dendrimer ("SAD") construct. The non-blunt end of the SA or SAD construct is designed to be incapable of ligation so as to prevent multimer assembly of said adapters. Any SA or SAD ligated target that is present can be affinity purified away from free adapters. At this point, if the capture dendrimer is not introduced with the SA construct then this can be done (using an efficient excess of dendrimer) followed by purification to isolate the target-SAD complex. Once purified, the complex is ready for attachment to the assay surface. To this end, it is desired that only a single target complex be attached per reaction location. Alternatively, the capture dendrimer can instead be associated with the assay surface, in which case the purified target-SA complex can be attached directly to the dendrimer that is already located and covalently attached to the surface. A similar method for DNA target assembly on surfaces is been disclosed by Hong et al. ("DNA microarrays on nanoscale-controlled surface", *Nucleic Acids Research,* 33(12): e106, 2005).

Another approach, called the "parsing" method, involves coarsely fragmenting the genome into 0.5-5 Mb pieces (using rare cutting restriction enzymes or by hydrodynamic/mechanical shearing), followed by capture of such fragments to a modified microarray (or partitioned surface) composed of gene/loci specific oligonucleotide capture probes. Custom microarrays and oligonucleotide capture probe sets are broadly available from a number of commercial sources (ArrayIt, Euorfins-Operon, Affymetric Inc.). This additional parsing can provide an advantage for backend sequence assembly. Capture of these large fragments involves either partial or complete target denaturation in order to allow the capture probes to bind or duplex with specific target DNAs. To reduce non-specific hybridization it can be necessary to load the capture array under dilute conditions so as to prevent cross hybridization between templates.

Each partitioned capture probe set, which can be arrayed on a large surface, is designed to provide linear genome resolution of ~3 Mb. To provide efficient genome parsing, each individual capture probe set can be composed of 3 to 5 gene/loci specific oligonucleotides, linearly separated on the genome by 0.5-1.5 Mb each. The capture probes are selected to be completely unique to the target fragment, thus providing both specificity and redundancy to the method. Given 3 Mb resolution of a 3 Gb genome, this approach requires a capture array composed of approximately a 1000 gene/loci specific probes. Microarray ready oligonucleotide capture probe sets specific to human gene targets are broadly available off the shelf (Operon Biotechnologies, Huntsville Ala., USA).

Once non-specific binding events have been washed away, each capture array can then proceed as independent reactions through the remainder of the genome preparation process in the same manner as discussed above for the non-parsing method. The primary difference being that the target sample can now be positionally parsed on an SBX assay surface or as individual solution based reactions, thus reducing the complexity of post data acquisition sequence assembly.

Another embodiment is to have non-tethered Xprobe-target hybridization and Xpandomer production. In this case, the SBX assay is performed in free solution. This approach can use one or a combination of physical manipulations such as using electrophoretic, magnetic, drag tags, or positive/negative buoyancy end functionalities under static or laminar flow conditions, as a means to elongate the target DNA prior to and during probe hybridization and ligation, for example, and, to lengthen or expand the cleaved Xpandomer prior to detection. Free solution synthesis of Xpandomers, without immobilization, can be done using polymerases and ligases (with and without primers) and can also be done using chemical ligation methods. Both triphosphate substrate constructs and monophosphate substrate constructs can be used. Simultaneous synthesis of Xpandomers from multiple and mixed nucleic acid targets is conceived. Generally, substrate triphosphate constructs are capable of continuous, processive polymerization in solution and can be adapted to single-tube protocols for massively parallel single-molecule sequencing in free solution, for example.

Surface Assembly of Nucleic Acid Targets

Figure 39:
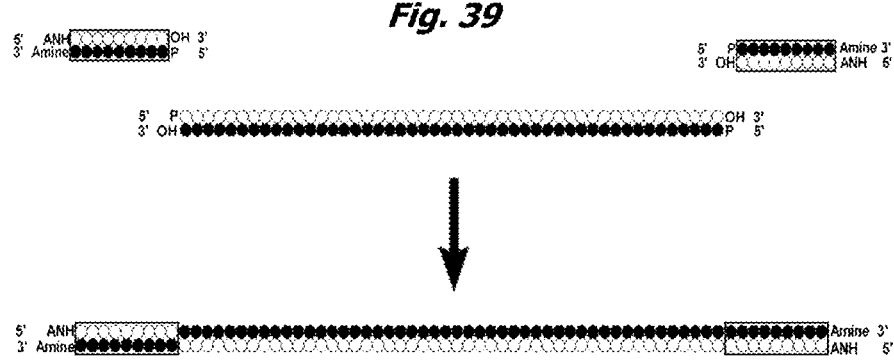
FIG. 39 is an adaptor cassette for introducing a terminal ANH functional group on a dsDNA template.

One method of preparing target nucleic acids for sequencing uses end functionalized double stranded DNA target as shown in FIG. 39. For this example, each adaptor is typically provided with an ANH group (reactive hydrazide) useful for further processing, for example, using succinimidyl 4-hydrazinonicotinate acetone hydrazone (SANH) linkage chemistry and an amine modified end adapter oligonucleotide duplex. Similarly, an amine reactive SANH can be used to, create reactive hydrazide moieties. SANH readily conjugates with aldehydes like 4-formylbenzoate (4-FB) to form stable, covalent hydrazone bonds. Amine reactive C6-succinimidyl 4-formylbenzoate (C6 SFB) can be used to create a reactive benzaldehyde moiety. End functionalized complementary oligonucleotides are duplexed to form a bifunctional, conjugatable end (SANH and amine) and an enzymatically ligatable end (3' OH and 5' phosphate). Ligation of adapter creates an end functionalized dsDNA target that can be crosslinked to surface tethered aldehyde groups. FIG. 39 illustrates dsDNA target end functionalized using SANH and amine modified end adapter oligonucleotide duplex.

For many of the described SBX methods, nucleic acid targets may be covalently tethered to a flat, coated solid support (stainless steel, silicon, glass, gold, polymer). As described in FIG. 40, target attachment points can be produced by 4FB derivatization of a SAM monolayer. The method utilizes the ANH adaptor of FIG. 39, and in Step I of FIG. 40, the ANH is reacted with the 4FB heads of the monolayer and the template is denatured (Step II). The other strand of the template, which is also end labeled, can be captured in a separate reaction. In Step III, the free amine on the 3' end of the single-stranded template is then reacted with a bead, for example, here shown as a buoyancy bead, so that the target template can be stretched. These capture complexes can be assembled either by random self assembly of a stoichiometrically balanced mix of end functionalized polymers (ex. thiol-PEG-hydrazide for target attachment; thiol-PEG-methoxy for Self Assembled Monolayer "SAM" capping) or by patterning spatially resolved reactive attachment points using lithographic techniques. The patterned lithographic method can produce consistently spaced target attachment points, although this is difficult to do for single molecule attachment, while the random self assembly method would likely produce more variable target attachment spacing, but has a high percentage of single molecule attachments. A broad range of monofunctional, bifunctional, and heterobifunctional crosslinkers are commercially available from a variety of sources. Crosslinker compatible monofunctional, bifunctional, and heterobifunctional polymers (polyethyleneglycol, poly-1-lysine) are also available from a wide range of commercial sources.

DNA target density of 1 Billion targets on a 100 $cm^2$ surface would require an average per target area of 10 $um^2$. Target spacing in this range provides sufficient target separation to prevent significant cross reaction of bead tethered 5000 base long target nucleic acids (100-1000 nm bead diameter; 5 Kb dsDNA=1700 um). Target area can be easily be expanded if target and/or bead (>1 bead/target) cross reactivity is determine to be unacceptably high.

Target Elongation Using Beads or Nanoparticles

Figure 40:
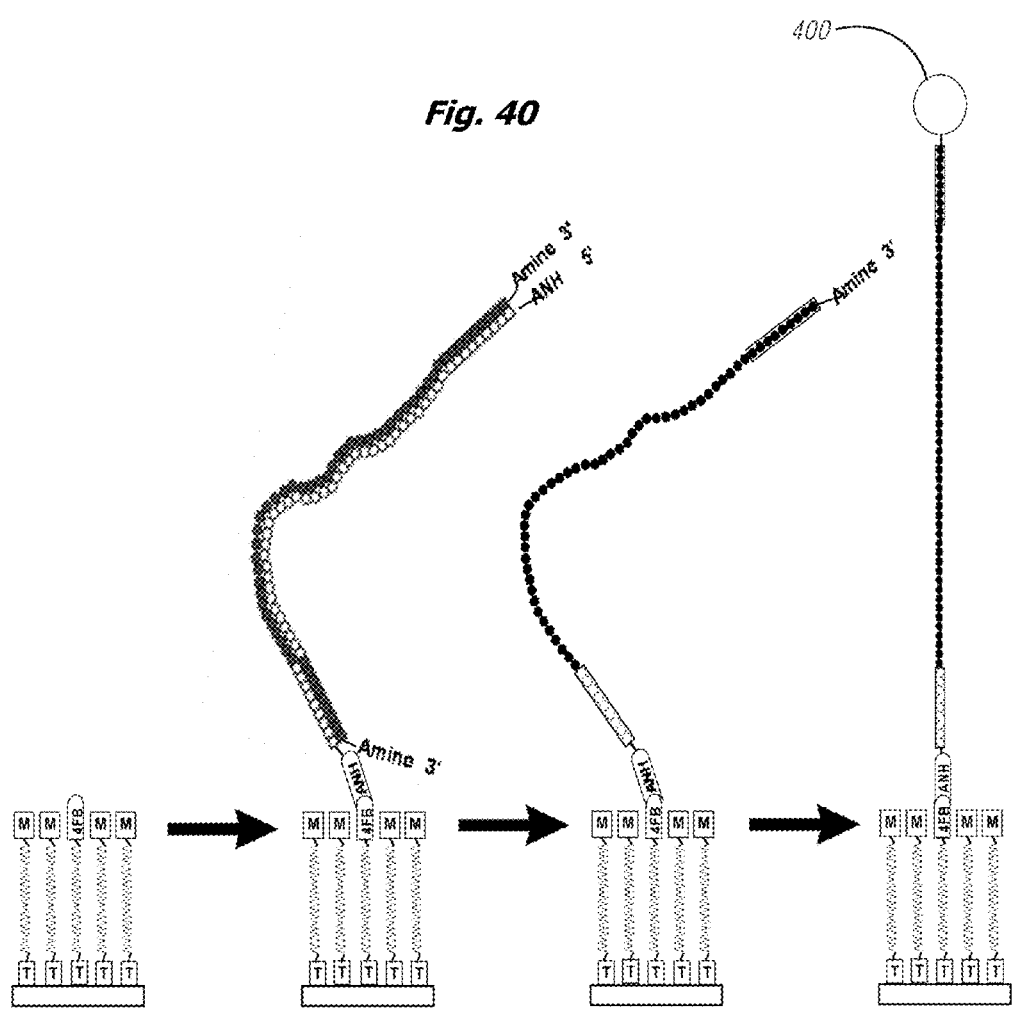
FIG. 40 is a schema for immobilizing and preparing a template for synthesis of an Xpandomer.

As shown in FIG. 40, a bead or nanoparticle (400) tethered on the free end of target DNA can be utilized to elongate and hold target in its single stranded conformation during, for example, Xprobe library hybridization. Retaining the target in an elongated conformation significantly reduces the frequency and stability of target intramolecular secondary structures that form at the lower temperatures. The reduction or even elimination of secondary structure influences promotes efficient, high-fidelity substrate construct assembly.

A variety of approaches for applying an elongational force to the single stranded target may be employed. For example, paramagnetic beads/nanoparticles/polymers enable the use of a magnetic field to deliver controlled, directional force to the surface tethered target. Further, by controlling the direction of the magnetic field lines, paramagnetic beads/particles can be used to guide and hold the Xprobe loaded target on the substrate surface during wash steps. By sequestering the targets along the surface, target loss due to shear forces can be minimized. As an alternative to magnetic field elongation, positive and negative buoyancy beads/particles that are either more or less dense than water, respectively, can be used to provide an elongational force. All beads/particles are surface coated as necessary to minimize non-specific interactions (bead aggregation, probe binding) and functionalized to enable covalent crosslinking to adapter modified targets.

FIG. 41A through 41D illustrates representative bead based target elongation strategies. Target elongation using end tethered paramagnetic beads/particles attracted to an external magnetic field (B) is illustrated in FIG. 41A. Target sequestering on the substrate surface (to reduce target shearing) using end tethered paramagnetic beads/particles attracted to an external magnetic field is illustrate in FIG. 41B. FIGS. 41C and 41D illustrate target elongation using end tethered negative buoyancy beads/particles (higher density than water) and positive buoyancy beads/particles (lower density than water), respectively. Free solution methods for target elongation using end tethered moieties, for example using both a positive and negative buoyancy bead to functionalize opposite ends of a target, provide an elegant alternative for reducing target secondary structure.

Figure 41E:
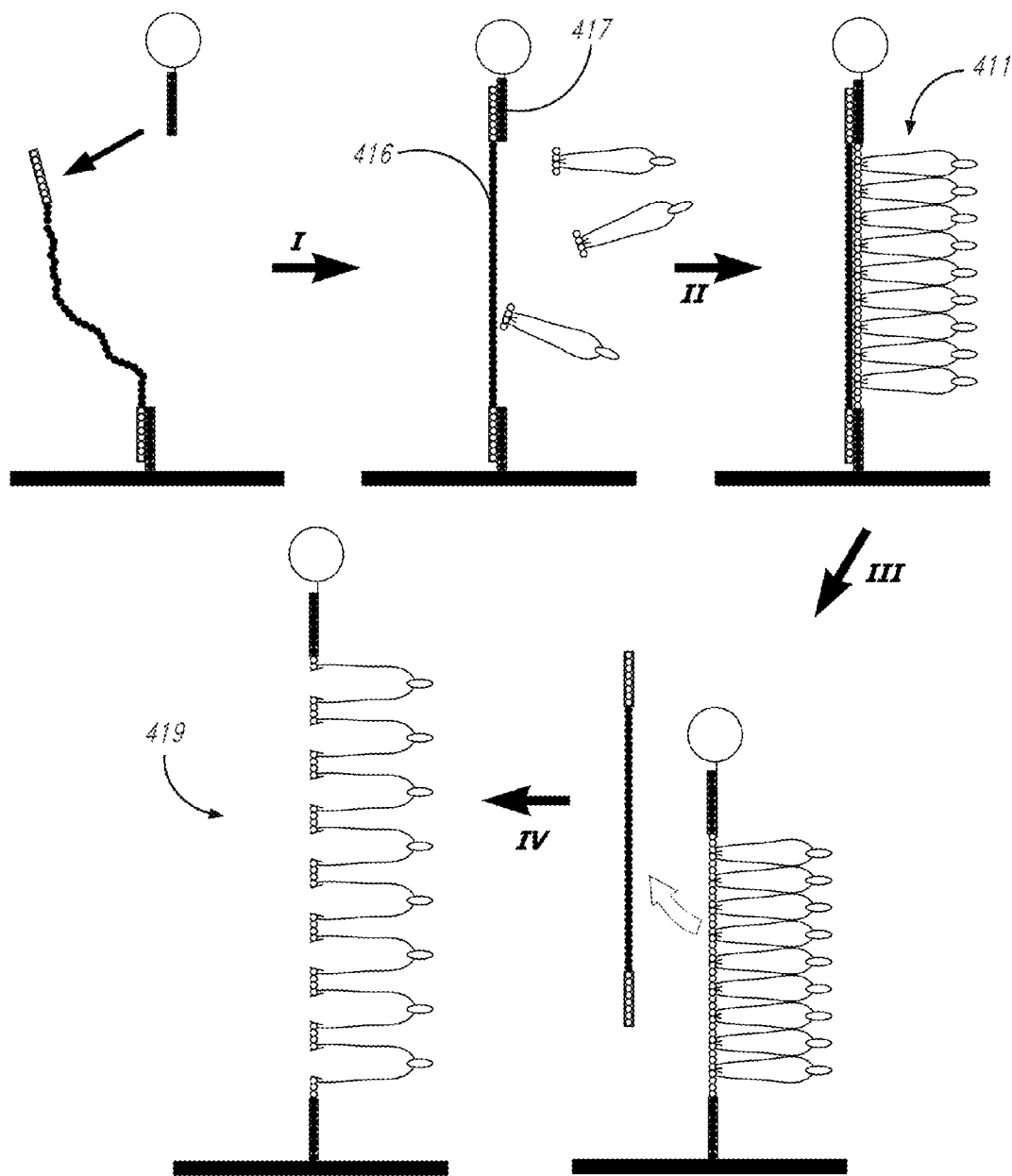

Use of these elongation strategies in preparation of Xpandomers is illustrated in FIG. 41E. Here, in Step I, the immobilized template (416) is stretched using a buoyant bead duplexed to the target via the adapter primer (417). The template is then contacted in Step II with substrate constructs and these are then ligated to the single stranded target, producing a double-stranded Xpandomer intermediate (411) with characteristic probe-loop construction and two backbones, one through the primary backbone of the polynucleotide and the other through constrained Xpandomer backbone. In Step III the template strand is denatured, and in Step IV the single-stranded Xpandomer intermediate is cleaved at selectively cleavable bonds in the primary backbone, resulting in an unfolding of the loops and elongation of the Xpandomer product with fully extended surrogate backbone (419).

DNA Target Elongation Using Polymer End Modifications

An alternative to the methods described in FIG. 40 utilizes long, functionalized polymers (instead of beads) covalently linked to the free ends of surface tethered DNA targets to elongate target. Electro-stretching and threading of polymer end modifications through porous substrate following by capture (sequestering) of polymer within substrate produces fully elongated single stranded target DNA significantly free of secondary structure. FIG. 42A illustrates this method, which shows threading of the target strands through pores in a substrate. Porous substrates include, but are not limited to, gel matrix, porous aluminum oxide, and porous membranes. Capture of fully elongated polymer can be achieved by controlled chemical functionalization wherein crosslinking or binding of polymer to porous substrate can be selectively initiated after full elongation of target. A variety of crosslinking or binding strategies are available. For example, crosslinking of carboxyl functionalized elongated polymer to amine functionalized porous substrate can be achieved with the introduction of the crosslinking agent 1-Ethyl-3-[3-dimethylamino propyl]carbodiimide Hydrochloride (EDC).

A further embodiment is illustrated in FIG. 42B, is to electrostretch the polymer towards a functionalized surface that crosslinks or binds to the polymer. In this case, the polymer is not necessarily threaded through the substrate but instead crosslinks or binds to functional groups on the surface. For this approach, the substrates include, but are not limited to, gel matrix, porous aluminum oxide, porous membranes, and non-porous, conductive surfaces like gold. Both the porous and non-porous substrates can be functionalized using a variety of off the shelf crosslinking (hydrazide-aldehyde; gold-thiol) or binding chemistries (biotin-streptavidin).

As an alternative, an enclosed electrical gating system may be employed that uses varying (high, low, ground) electric field regions to capture charged polymer segments. The method, which is illustrated in FIG. 42C, produces a Faraday Cage type of enclosure which can be used to hold the polymer and target DNA in its elongated position. This approach requires effective partitioning or confinement of electric fields, and has the advantage of allowing adjustable target elongation (throughout the SBX synthesis) by modifying the gating parameters. Outside of the Faraday Cage, electric field influences on substrate constructs are minimal.

In a related method, an elastic polymer is used to deliver a constant stretching force to the less elastic target nucleic acid. This method can be used as a supplement to any of the elongation methods described here, including magnetic bead, buoyancy deformation, density deformation (gravity), or electrostretching. The elastic force stored within the polymer provides a more consistent, buffered elongational force to the target strand.

Gel Matrix Based Target Substrate with Electro Straightening

In FIG. 43A, shows an alternative method for single stranded target DNA arraying (versus attachment to solid support) in which the target is covalently attached to a sieving gel matrix (430). In FIG. 43b (insert) substrate constructs can be seen associating with the anchored templates, which have been stretched straight. Electric fields can be used for target elongation and substrate construct presentation. This approach has advantages over other methods for DNA target array in terms of target density and target elongation (electro-straightening). For example, DNA crosslinking to acrylamide via acrylate modified end adapters (attached to oligonucleotides) is routinely done. Acrydite™ is an available phosphoramidite (Matrix Technologies, Inc., Hudson, N.H., USA) that has been extensively used to incorporate methacryl 5' terminal modifications to oligonucleotides: double bond in the Acrydite group reacts with activated double bonds of acrylamide (Kenney et al., "Mutation typing using electrophoresis and gel-immobilized Acrydite probes", *Biotechniques* 25(3):516-21, 1998). Amine functionalized agarose is also available off the shelf (G Biosciences, St. Louis, Mo., USA) and can similarly be used to crosslink to DNA using off the shelf amine reactive crosslinking chemistries (Spagna et al., "Stabilization of a β-glucosidase from *Aspergillus niger* by binding to an amine agarose gel", *J. of Mol. Catalysis. B: Enzymatic* 11(2, 3): 63-69, 2000).

As with the previously described solid support attachment methods, DNA fragments are usefully functionalized with end adapters, to produce, for example, a 5'-Acrydite modification. To ensure target uniformity, dsDNA targets are denatured (and maintained in a denatured state) while crosslinking to sieving matrix. Target can be denatured using a variety of existing techniques including, but not limited to, urea, alkaline pH, and thermal melt. Once crosslinked to a gel matrix, denatured target DNA can be straightened by applying an appropriate electric field (similar to electrophoresis). Diffusion, electrophoresis, and neutralization of the denaturants within the gel matrix along with tight temperature control, with the addition of hybridization compatible solutions, produces an environment conducive to substrate construct hybridization. For example, Xprobes can be presented continuously to tethered targets by electrophoresis. This format allows for probe recycling and provides good control over Xprobe flow rate.

Figure 43D:
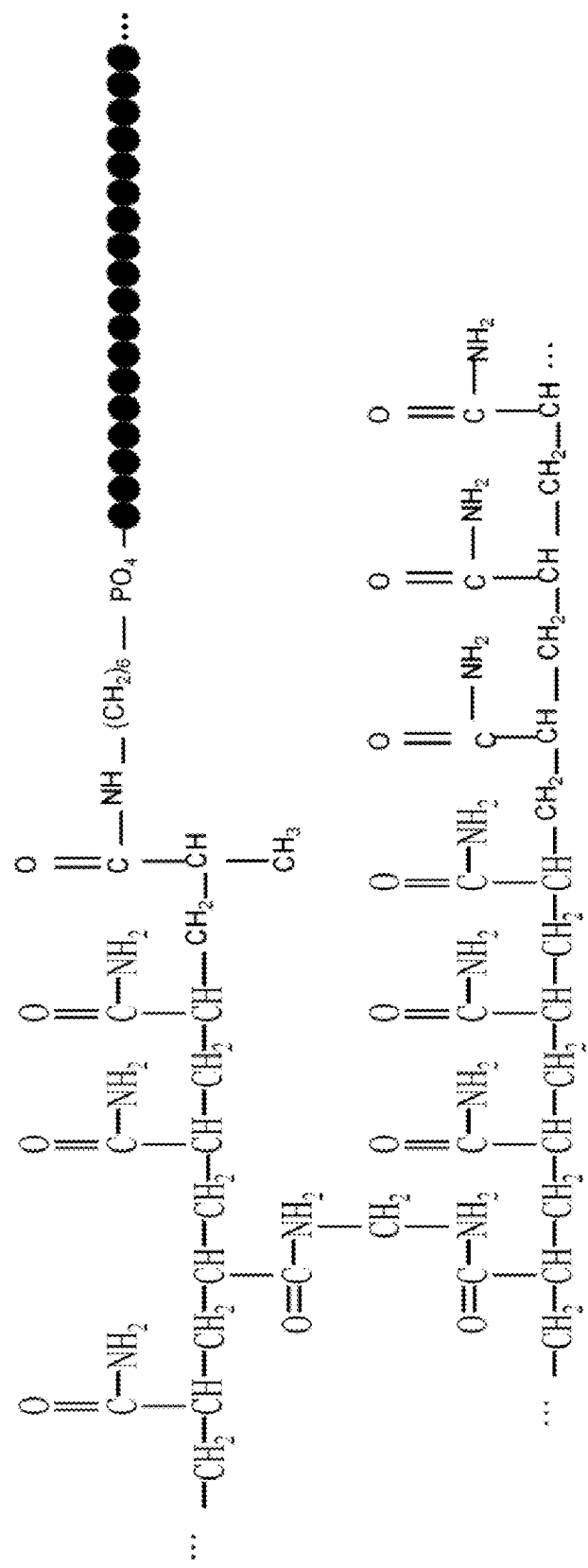

The target density of a 5 mm×50 mm×20 mm gel matrix array produces a $5.0 \times 10^{12}$ $\mu m^3$ reactive volume, which is substantially higher than what can be arrayed on a flat surface. FIG. 43C shows the chemical structures for acylamide, bisacrylamide, and the Acrydite oligonucleotide end modification. FIG. 43D illustrates a polyacrylamide gel matrix with covalently attached DNA target.

Enzymatic processing of substrate constructs can be done within the gel matrix. Enzymatic assays using polymerases (PCR) and ligases are routinely used for modification of oligonucleotides covalently coupled to acrylamide Gel Pads (Proudnikov et al., "Immobilization of DNA in Polyacrylamide Gel for the Manufacture of DNA and DNA-Oligonucleotide Microchips", *Analytical Biochemistry* 259(1): 34-41, 1998). Ligase, for example, is delivered to assembled Xprobe-targets within the gel matrix either by passive diffusion, electrophoresis, or a combination of both. A broad range of matrix densities and pore sizes are considered, however, passive diffusion benefits from relatively low density matrix and large pores. Active delivery of ligase by electrophoresis can be achieved by attachment of charge modifiers (polymers and dendrimers) to the enzyme to enhance its migration through the matrix.

A variation of the gel matrix method is to electrophorese end-modified single-stranded target polynucleotides through a gel matrix. End modifications can be used to create drag on one end of the target. A cationic end modification can be performed on the other end of the target so as to pull it through the gel. A temperature gradient or zone can also be induced in the gel so as to ramp or modulate hybridization stringency as the targets progress through the gel matrix. Enzymatic processing can be done within the gel matrix or after the hybridized target-substrate complexes exit the gel matrix. The process can be repeated as necessary to produce the desired average Xpandomer length.

Figure 44A:
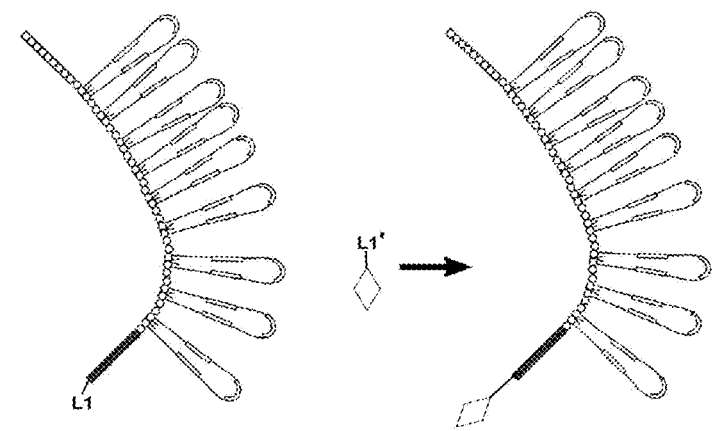
FIGS. 44A through 44C describes construction and use of "drag tags".
Figure 44B:
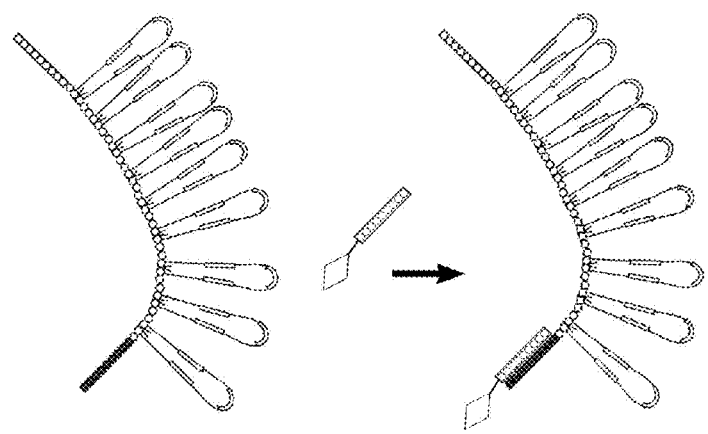
Figure 44C:
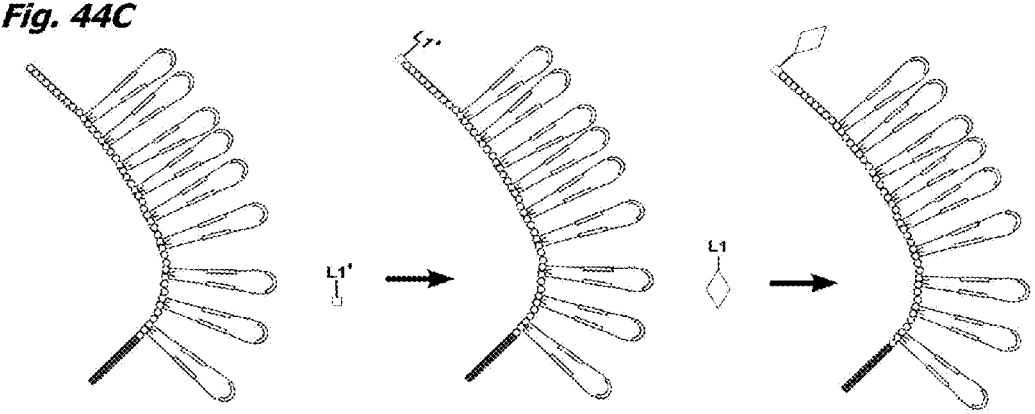

FIG. 44 illustrates the use of drag tags for Xpandomer manipulation post-synthesis. The drag tag (depicted as a diamond) serves as a solution-equivalent of a stretching and conveying technique (Meagher et al., "Free-solution electrophoresis of DNA modified with drag-tags at both ends", *Electrophoresis* 27(9):1702-12, 2006). In FIG. 44A, drag tags are attached by linker chemistry to adaptors functionalized on the 5' ends of the single stranded template (L1' of the drag tag combines with L1 of the template). In the step shown, processive addition of substrate constructs is shown already in progress. In FIG. 44B, the drag tag is added by annealing to a complementary adaptor. In FIG. 44C, the Xpandomer is first treated so as to attach a linker to a 3'-adaptor (shown as the small square with L1'), and the linker (L1) is then used in Step II to attach the drag tag thereto. Terminal transferase, which extends 3'-OH terminus of single or double stranded DNA, polymerizes linker-modified nucleotide triphosphates such as biotinylated nucleotides. Other enzymes can also be used to add modified bases or oligomers. In FIG. 44C, a drag-tag is added to the 3' end of the Xpandomer intermediate. Drag tags can include, but are not limited to, nanoparticles, beads, polymers, branched polymers and dendrimers.

Gaps and Gap Filling with Substrate Construct Hybridization and Ligation

Multiple variants on ligation methods can be employed to address gap management and gap filling. In one embodiment, cyclical stepwise ligation is used, where probes are sequentially assembled from a surface tethered primer duplexed to the target polynucleotide. In another embodiment, "promiscuous" hybridization and ligation of substrate constructs occur simultaneously across the entire target DNA sequence, generally without a primer.

For both the cyclical and promiscuous ligation approaches, it is possible that, for example, some portion of 4 mer substrate constructs (e.g., 25%) and some portion of 5 mer substrate constructs (e.g., 20%) will hybridize adjacently so as to allow for ligation. Of these adjacent duplexes, some percentage may contain mismatched sequences that will result in either measurement error (if ligated) or failure to ligate. Most instances of ligation failure (due to mismatch) is without consequence since unligated probes are removed prior to the next round of hybridization. The hybridization/wash/ligation/wash cycle can be repeated several hundred times if desired (6 minutes/cycle=220 cycles/day and 720 cycles/3 days; 10 minutes/cycle=144 cycles/day and 432 cycles/3 days).

In the cyclical process (illustrated with Xprobes in FIG. 14), Xprobes are sequentially assembled from one end of a surface tethered primer duplexed to the target DNA; one Xprobe per cycle. This being the case, the target read length can be calculated using the following assumptions: 25% adjacent hybridization (of 4 mers) with 20% perfect probe duplex fidelity would produce only 20 sequential 4 mer ligations (400×25%×20%) after 400 cycles. Using these assumptions, a 400 cycle assay (1.5 days at 6'/cycle) would produce an average product length 80 nucleotides.

In the promiscuous process (illustrated with Class I Xprobes in FIG. 45), if Xprobe hybridization and ligation reactions are allowed to occur spontaneously and simultaneously throughout the DNA target template, replication of a much longer DNA template can be achieved using much fewer cycles. Following each cycle of hybridization and wash, ligation can be used to connect the remaining duplexes that are both adjacent and 100% correct. Another, more stringent wash can be used to remove smaller ligation products (everything 8 mer and less; some 12 mers) as well as all unligated 4 mers. With ligation reactions occurring throughout the 1,000-10,000 nucleotide target sequence, assay processivity goes up dramatically. Since the promiscuous approach for Xprobe hybridization and ligation is independent of the DNA target template length, the majority of the target template can be replicated in a fraction of the cycles required for the serial method. Longer cycle times can be used to compensate for kinetic limitations if such an adjustment increases the fidelity and/or quantity of hybridization/ligation reactions.

Figure 45:
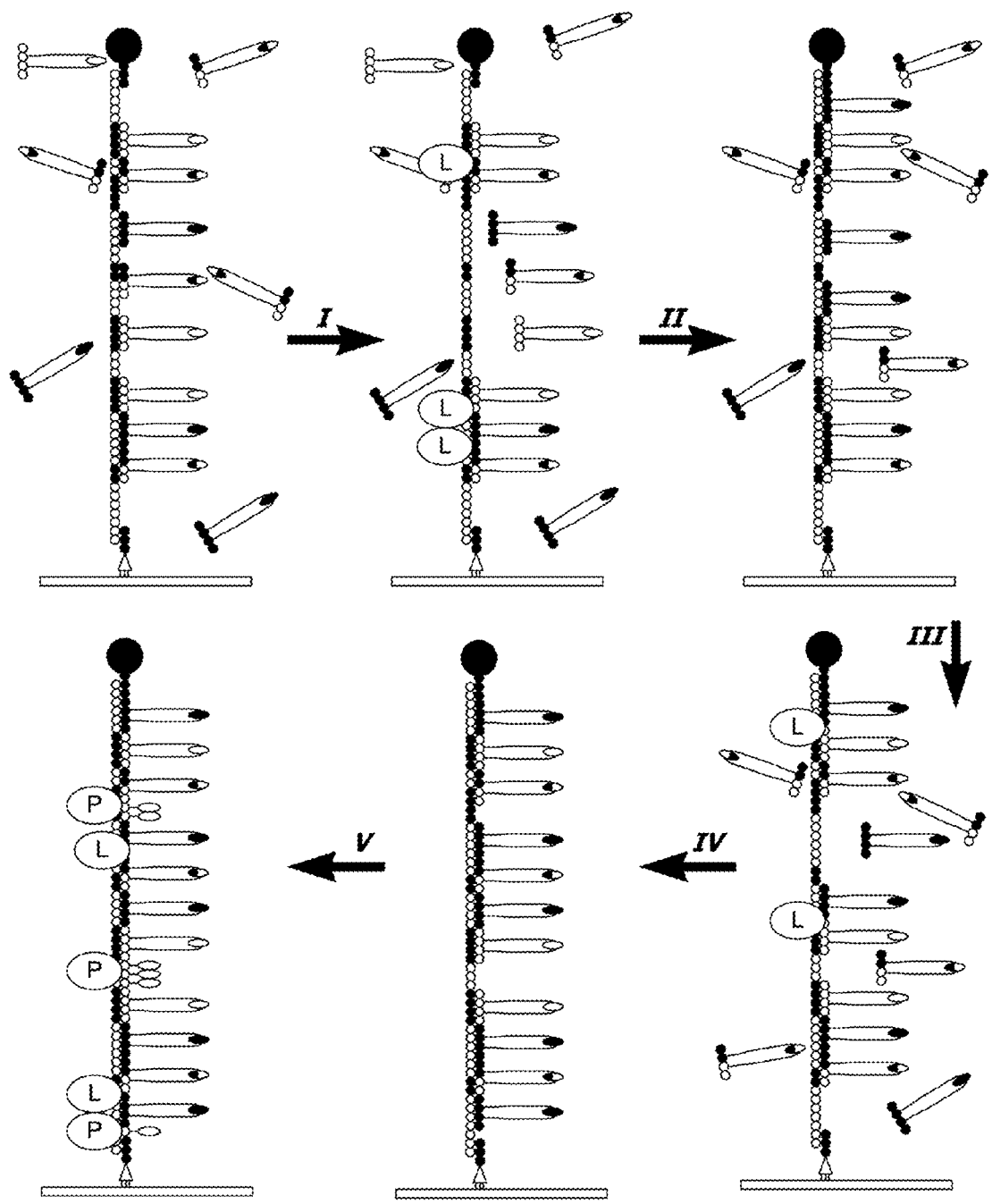
FIG. 45 describes a promiscuous hybridization/ligation based method for synthesizing an Xpandomer.

FIG. 45 illustrates a sequential progression of the promiscuous process. Step I illustrates 4 mer Xprobes hybridizing at multiple loci along the DNA target. Step II illustrates hybridization and ligation of adjacent Xprobes; ligated Xprobes are stabilized and thus remain hybridized while the unligated Xprobes are melted off. Step III and Step IV illustrate another thermal cycle of hybridization followed by ligation and thermal melting of unligated Xprobes. Each cycle preferentially extends the existing ligated Xprobe chains. As illustrated in Step IV, after repeated cycles, the DNA target is saturated with Xprobes leaving gaps, shorter than a probe length, where no duplexing has occurred. To complete the Xpandomer the Xprobes are linked across the gaps by enzymatic or chemical means as illustrated in Step V.

Standard Gap Filling

As illustrated with Xprobes in Step V of FIG. 45, after completion of the hybridization and ligation cycling process, sequence gaps can be filled to produce a continuous Xpandomer. Gaps along the target DNA backbone can be filled using well established DNA polymerase/ligase based gap filling processes (Stewart et al., "A quantitative assay for assessing allelic proportions by iterative gap ligation", *Nucleic Acids Research* 26(4):961-966, 1998). These gaps occur when adjacent chains of Xprobes meet each other and have a 1, 2 or 3 nucleotide gap length between them (assuming a 4 mer Class 1 Xprobe as illustrated in FIG. 45). Gap filling can also be done via chemical cross linking (Burgin et al.). After gap filling is completed, the target DNA compliment, which is composed principally of ligated Xprobes with periodic 1, 2 or 3 nucleotide fillers, can be processed (purification, cleavage, end modification, reporter labeling) as appropriate to produce a measurable Xpandomer. Since the SBX assay products are prepared and purified in batch processing prior to the detection step, detection is efficient and not rate limited by any concurrent biochemical processing.

Figure 46A:
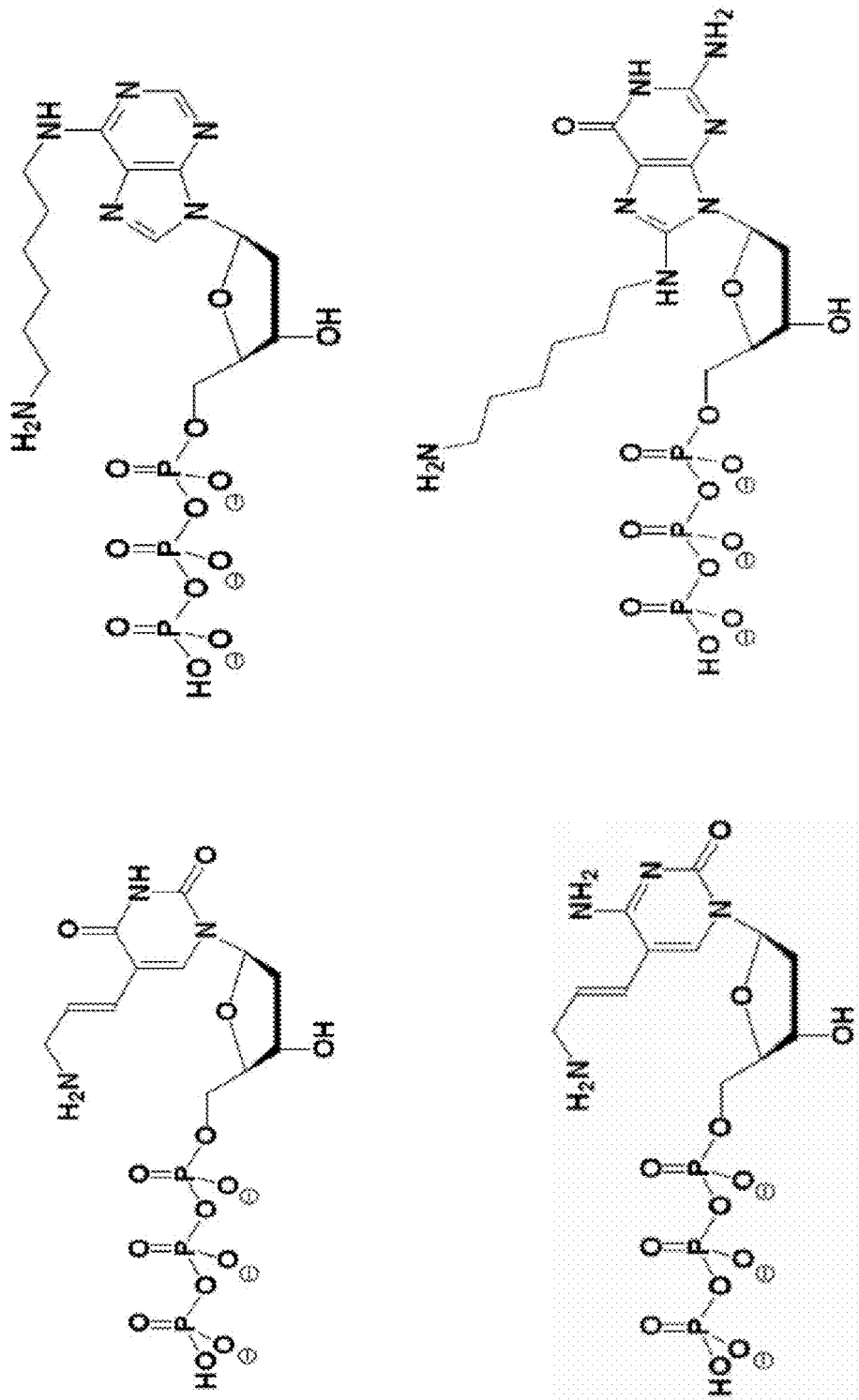
FIGS. 46A and B describe nucleobases used for gap filling.
Figure 46B:
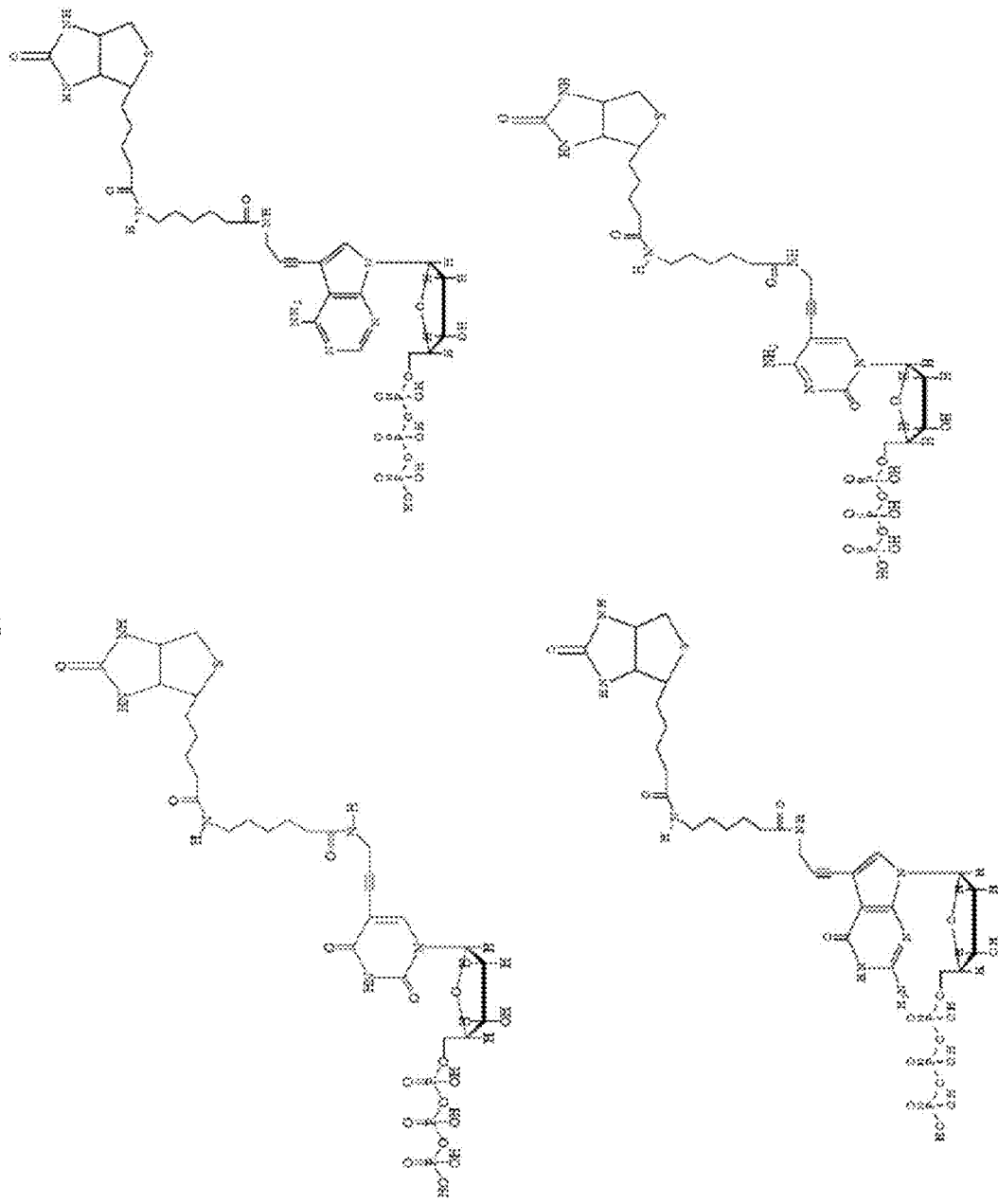

In order to differentiate the gaps from nucleotide specific reporter signal, modified deoxynucleotide triphosphates (that are either already labeled or capable of being labeled post assay) can be used to identify gap sequence. Suitable deoxynucleotide triphosphates are illustrated in FIGS. 46A (linker modified bases) and 46B (biotin modified bases).

Gap length and frequency are dependent upon a number of synthesis variables, including cycle number, hybridization stringency, library strategy (shotgun vs. sub-library with stoichiometric adjustment), target template length (100 b-1 Mb), and reaction density (0.1-10 B). Gap frequency and gap length can be significantly reduced by utilizing maximum stringency conditions, provided the conditions are compatible with the specified assay time range. Target length and reaction density are also important factors with respect to both alignment fidelity and gap filling probability.

The promiscuous process of hybridization can use thermal cycling methods to improve hybridization stringency and to increase the frequency of adjacent substrate construct alignments. The hybridization, ligation and thermal melting continue under a precise thermal cycling routine until the majority of the target sequence is duplexed with probe. Weakly-bound, non-specific probe-target duplexes can be removed by a simple wash step, again under precise thermal control. Enzymatic or chemical ligation can be performed to link any adjacently hybridized oligomeric constructs along the target DNA, generating longer and more stabilized sequences. Enzymatic ligation has the added benefit of providing an addition duplex fidelity crosscheck since mismatched probe-targets are not efficiently ligated. Using a second wash under precise thermal cycling conditions, unlinked substrate constructs can be melted off the DNA backbone; longer intermediates will remain. The longer ligated sequences grow at multiple loci along the target DNA until replication is mostly complete. The hybridization/wash/ligation/wash process is repeated zero to many times until the majority of target template has been replicated.

Temperature cycling coupled with substrate construct stabilization due to base stacking can be utilized to enrich for adjacent hybridization events. Thermal cycling conditions, similar in concept to "touchdown PCR", can be used to eliminate less stable, non-adjacent duplexes. For example, by repetitively cycling between the hybridization temperature and the upper melting temperature ("Tm") estimate for the oligo library (as determined by single probe melting—i.e., not base stack stabilized) adjacent probe hybridization events can be positively selected for. With sufficient enrichment efficiency, the number of cycles can be significantly reduced. This can be performed in single bath or multi-bath conditions.

With a small library size (256, 4 mer substrate constructs, for example), the library can be partitioned into sub-libraries on the basis of an even narrower range of melting temperature. This strategy can significantly benefit the method if Tm bias cannot be controlled through base modification, hybridization solution adjuvants, and the like. Further, the probe stoichiometry can be adjusted (up or down) to compensate for any residual biases that can still exist in the library/sub-libraries.

Computer modeling was performed to evaluate statistics of gap occurrence and the lengths of consecutively connected substrate constructs that are hybridized on a target DNA template. The model simulates a hybridization/ligation-thermal melt cycle with a complete library of 256, 4 mer Xprobes. The model results that are presented here are based upon the following model process:

i) The hybridization/ligation step simulates random 4 mer Xprobes randomly meeting a randomly sequenced DNA template at random positions and hybridizing if they match. No Xprobes can overlap any nucleotides. Hybridization continues until all locations on the target greater than 3 nucleotides long are hybridized.

ii) The thermal melt step is simulated by removing all Xprobes that are in chains shorter than M 4 mer Xprobes in length (where M=2, 3, 4, 5 . . . ). The longer chains remain on the DNA template. A "Chain" is defined here as multiple consecutive Xprobes with no gaps between them.

iii) Repeat the cycle defined by i) and ii) so that Xprobes randomly build off of the existing loci of multi-Xprobe chains. The cycling stops when no change occurs between 2 consecutive cycles.

Figure 47A:
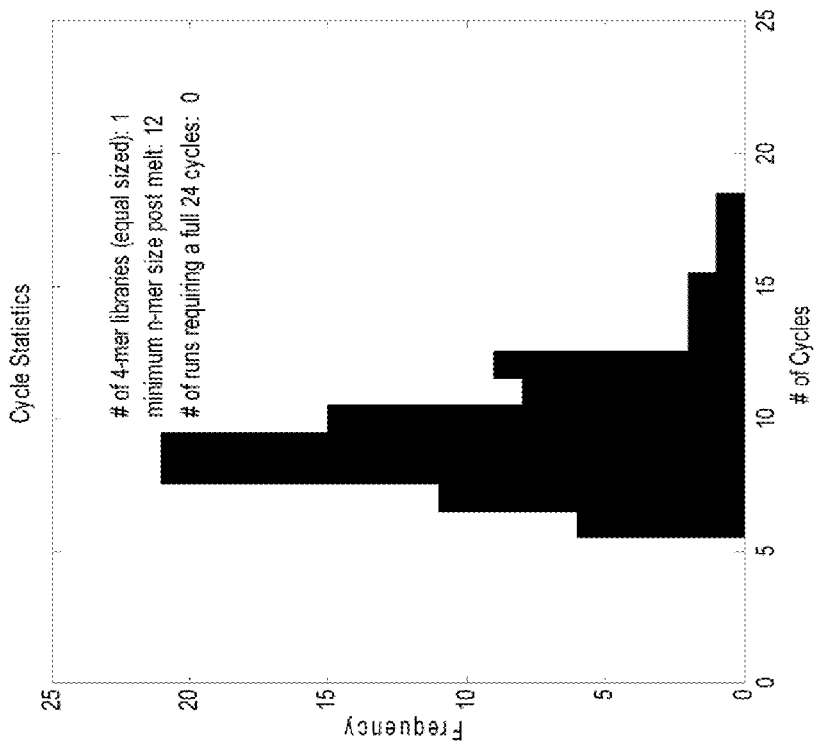
FIGS. 47A and B describe simulations of gap occurrence.
Figure 47B:
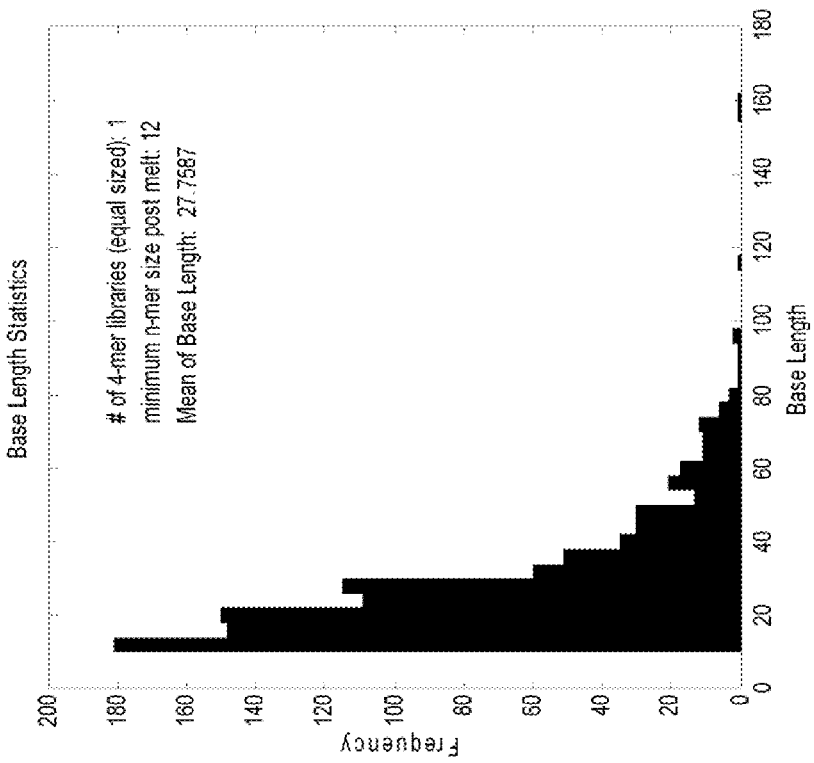
Figure 48B:
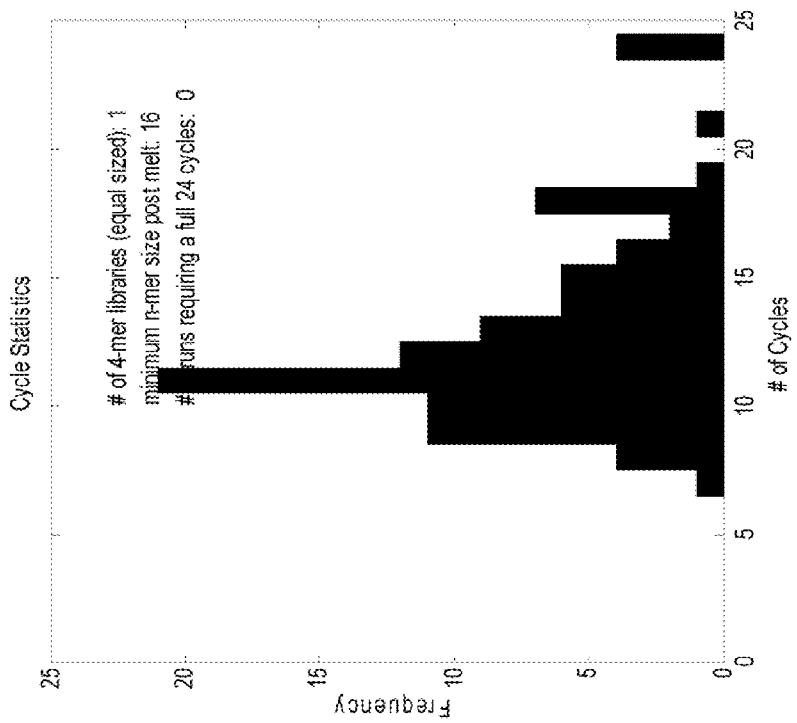
FIGS. 48A and B describe simulations of gap occurrence.
Figure 48A:
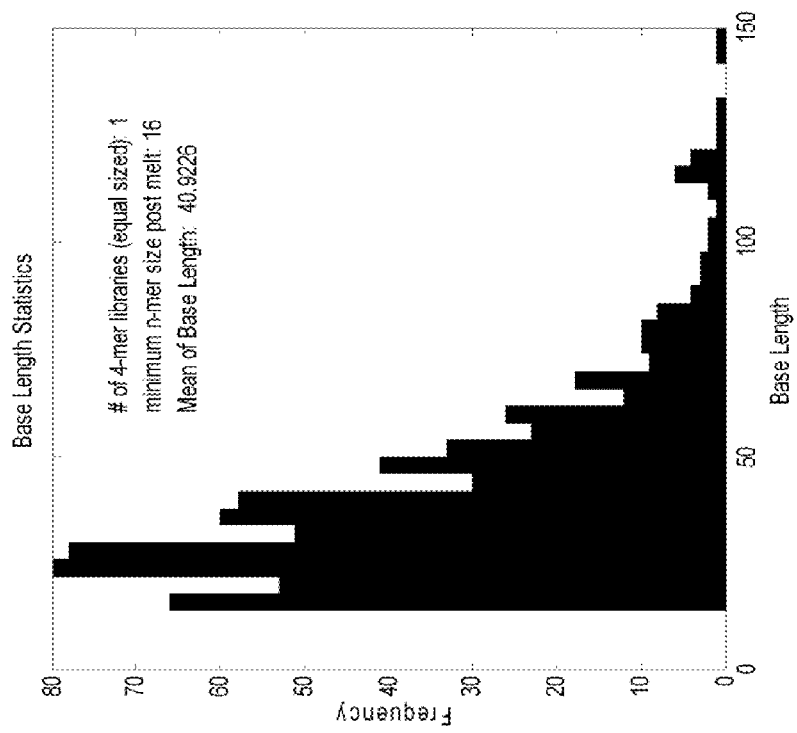

FIG. 47 and FIG. 48 each have two graphs that illustrate the statistics of running the model 100 times on a random DNA template. For processing purposes the DNA target was chosen to be 300 nucleotides long (but the statistics discussed here are not changed if the template length is 5000 nucleotides). FIG. 47 shows the results for M=3, where chains shorter than M=3 get "melted off" the DNA template. FIG. 47A shows the statistics of the chain lengths at the last cycle. The distribution appears to be quasi exponential ranging from 12 mer (M=3) up to some rare large 160 mers with a mean of ~28 nucleotides in length. FIG. 47B shows that a range of 5 to 20 cycles are needed to complete the DNA template using this method of chain "growth" and that 90% of the runs are complete after 12 cycles. FIGS. 48A and 48B show the same type of information for the case where M=4, a more stringent thermal melt. In this case the average chain length increases to ~40 nucleotides, but requires ~18 cycles to complete 90% of the runs. The longer chain lengths reduce the probability of having a gap as expected. The mean probability of not filling a nucleotide position for this M=4 data has a mean of 0.039 (approximately 1 in 25).

Gap Filling with 3 mer and 2 mer Substrate Constructs

Figure 49:
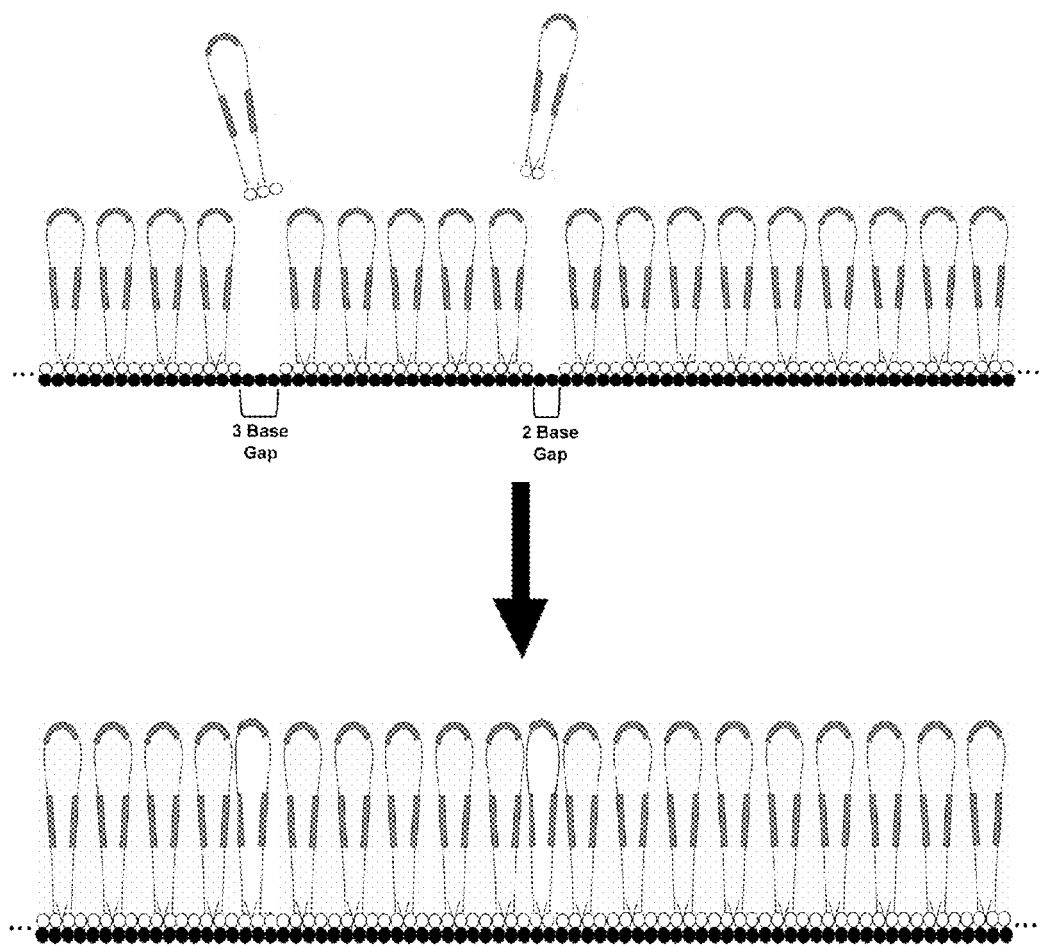
FIG. 49 illustrates how gaps are filled with 2 mers and 3 mers.

An extension of the basic 4 mer hybridization embodiment is to use 3 mer and 2 mer substrate constructs to fill 3 base and 2 base sequence gaps, respectively. FIG. 49 shows an example of gap filling by sequential or simultaneous addition of shorter Xprobes. If the majority of the target template is successfully duplexed with Xprobes following 4 mer hybridization, most of the remaining gaps are either 1, 2 or 3 bases in length. Average size of the Xpandomer can be increased significantly if a moderate to high percentage of the 2 and 3 base gaps can be filled and ligated with smaller Xprobes. Since hybridization of these smaller probes is done after most of the target is duplexed, temperature stringency can be reduced to allow for 3 mer and then 2 mer duplexing, respectively. Duplex stability of the smaller Xprobes is increased due to base stacking stabilization. Following ligation, remaining gaps are filled using a polymerase to insert nucleotides followed again by ligation to link all remaining adjacent 5' phosphates and 3' hydroxyls. The polymerase incorporated linker modified nucleotides, allow for gap labeling, either before or after incorporation. These labels can or cannot identify the base. On the basis of statistical models, summarized in the FIG. 50 charts, the full length Xpandomer polymers have greater than 95% target sequence coverage (greater than 16 bases). According to the model, the use of 3 mer/2 mer Xprobe gap filling drives down the unlabeled base percentage by a factor of 6 (assuming high efficiency incorporation), which, for a 5000 base target sequence, would result in 5000 bases of mostly contiguous sequence with less than 50 undiscriminated single base gaps throughout the target replicon. As such, at 16× coverage greater than 99% of the unidentified gap sequences is identified.

Gap filling with these smaller 3 mer and 2 mer Xprobes, for example, extends the average Xpandomer length by threefold. The charts summarizing the results of statistical modeling as shown in FIGS. 50A and 50B indicate that the average length 3 mer/2 mer gap filled Xpandomers, under the described conditions, are in the range of 130 bases of sequence. Further, with 5000 gigabases of Xpandomer sequence synthesized in this manner, which is the equivalent of converting only 2.5 ng target sequence to Xpandomer, size selection of the longest 10% of Xpandomer fragments from that population would produce 500 gigabases of sequence with average lengths in the range of 381 bases while size selection of the longest 2% of Xpandomer fragments would produce 100 gigabases of sequence with average lengths in the range of 554 bases. These fragment lengths can be achieved without the need for single base gap filling with polymerase. If 4 mer Xprobe hybridization is done without any gap filling, statistical models indicate that the average lengths for the longest 10% and 2% of the fragments would be 106 and 148 bases, respectively.

Addition of Adjuvants to Reduce Target Secondary Structure

Long, surface tethered single-stranded target DNA can present a challenging hybridization target due to intramolecular secondary structures. The addition of an end tethered bead, as described in FIG. 41E, reduces the occurrence of these intramolecular formations, and destabilizes them when they do occur. However, it can be found necessary to further diminish secondary structure formation, which can effectively block substrate construct hybridization, with the addition of adjuvants.

Figure 51:
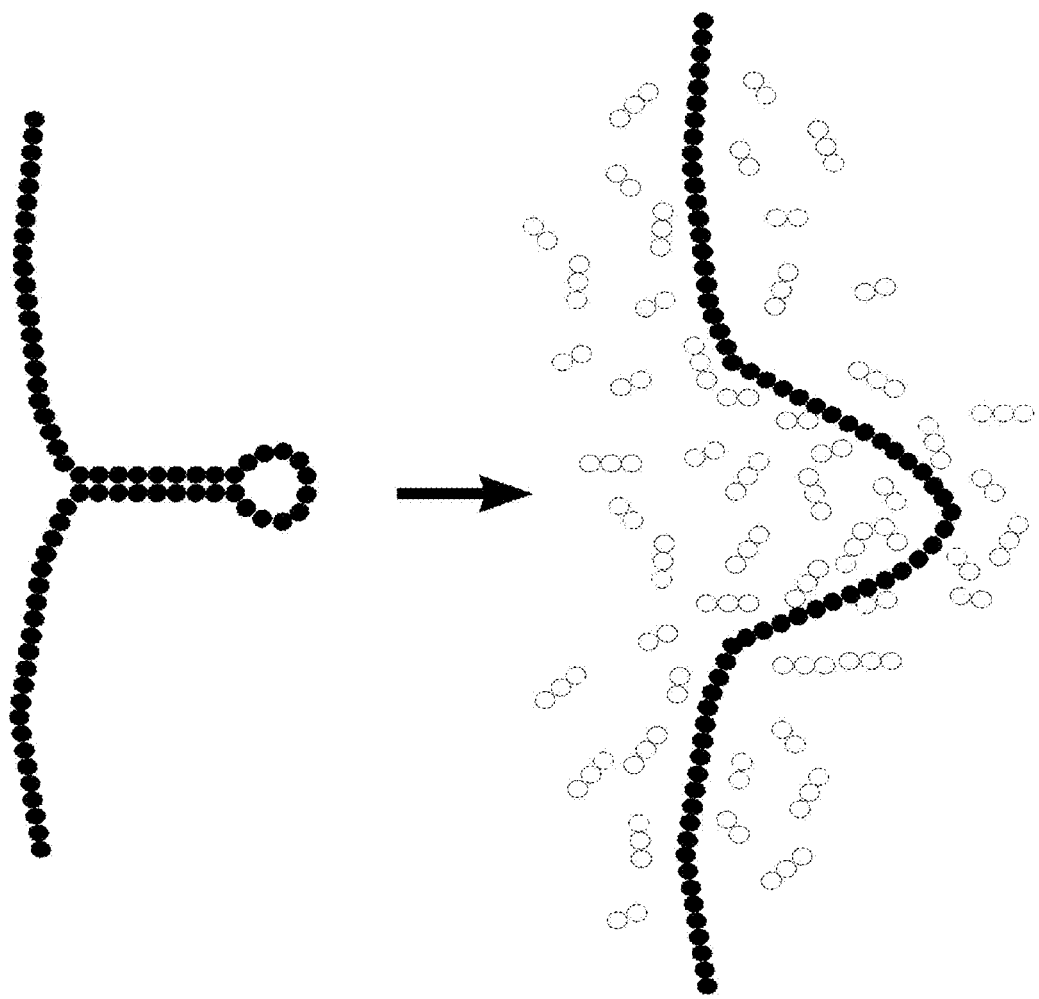
FIG. 51 illustrates the use of 2 mer and 3 mer adjuvants to disrupt secondary structure.

The addition of unlabeled 2 mer and/or 3 mer oligonucleotide probes to, for example, an Xprobe hybridization mix can serve this purpose. To eliminate the possibility of incorporation into the Xpandomer, these probes are synthesized to be un-ligatable (no 5' phosphate or 3' hydroxyl). Due to their small size, the 2 mer and/or 3 mer adjuvants are not likely to form stable duplexes at the 4 mer Xprobe hybridization temperatures; however, their presence in the reaction mix at moderate to high concentrations reduces the frequency and stability of target secondary structure by weakly and transiently blocking access of intramolecular nucleotide sequences that can otherwise duplex. FIG. 51 is an illustration of how the addition of 2 mer or 3 mer adjuvants inhibit secondary structure formation (for simplicity only, 4 mer Xprobes were not shown in the figure). Coupled with the elongational force provided by the bead tether, adjuvants significantly diminish the frequency of secondary structure formation.

Figure 52:
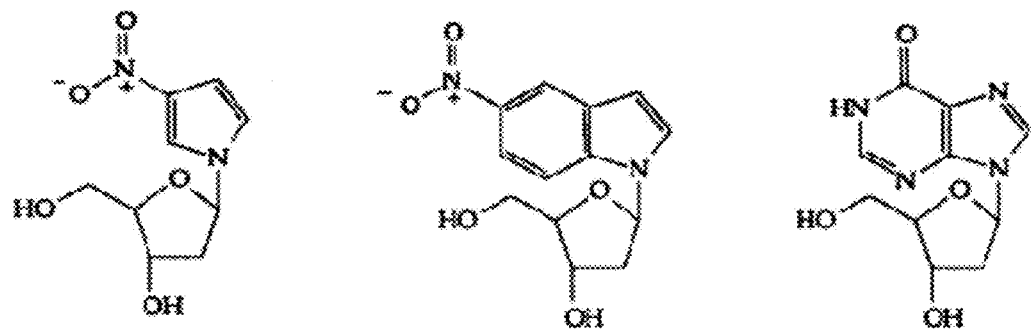
FIG. 52 describes bases useful as adjuvants.

These dinucleotide and/or trinucleotide adjuvants can be composed of standard nucleotides, modified nucleotides, universal nucleotides (5-nitroindole, 3-nitropyrrole and deoxyinosine), or any combination thereof to create all necessary sequence combinations. FIG. 52 shows common universal base substitutions that used for this purpose.

Another approach for reducing target secondary structure is to replicate target DNA to produce a synthetic cDNA target that has a reduced secondary structure stability as compared to native DNA. FIG. 53 lists some nucleotide analogs, as illustrated in US application 2005/0032053 ("Nucleic acid molecules with reduced secondary structure"), that can be incorporated into the described synthetic cDNA target. These analogs, which include (but are not limited to) N4-ethyldeoxycytidine, 2-aminoadenosine-5'-monophosphate, 2-thiouridine-mono phosphate, inosine-monophosphate, pyrrolopyrimidine-monophosphate and 2-thiocytidine-mono phosphate, have been demonstrated to reduce cDNA secondary structure. This approach can be used along with target elongation and hybridization adjuvants to reduce secondary structure.

Detection and Measurement

As mentioned previously, the Xpandomer can be labeled and measured by any number of techniques. The massive data output potential of the SBX method is well matched to sensor arrays based on nanopores or equivalent technologies. In one embodiment, the nanopore array can function as an ionization source on the front end of a mass spectrometer, wherein the reporter codes on the Xpandomer are cleavable mass spectroscopy tags. Other embodiments involve use of a nanopore sensor such as electrical impedance/conductance or FRET.

Figure 54:
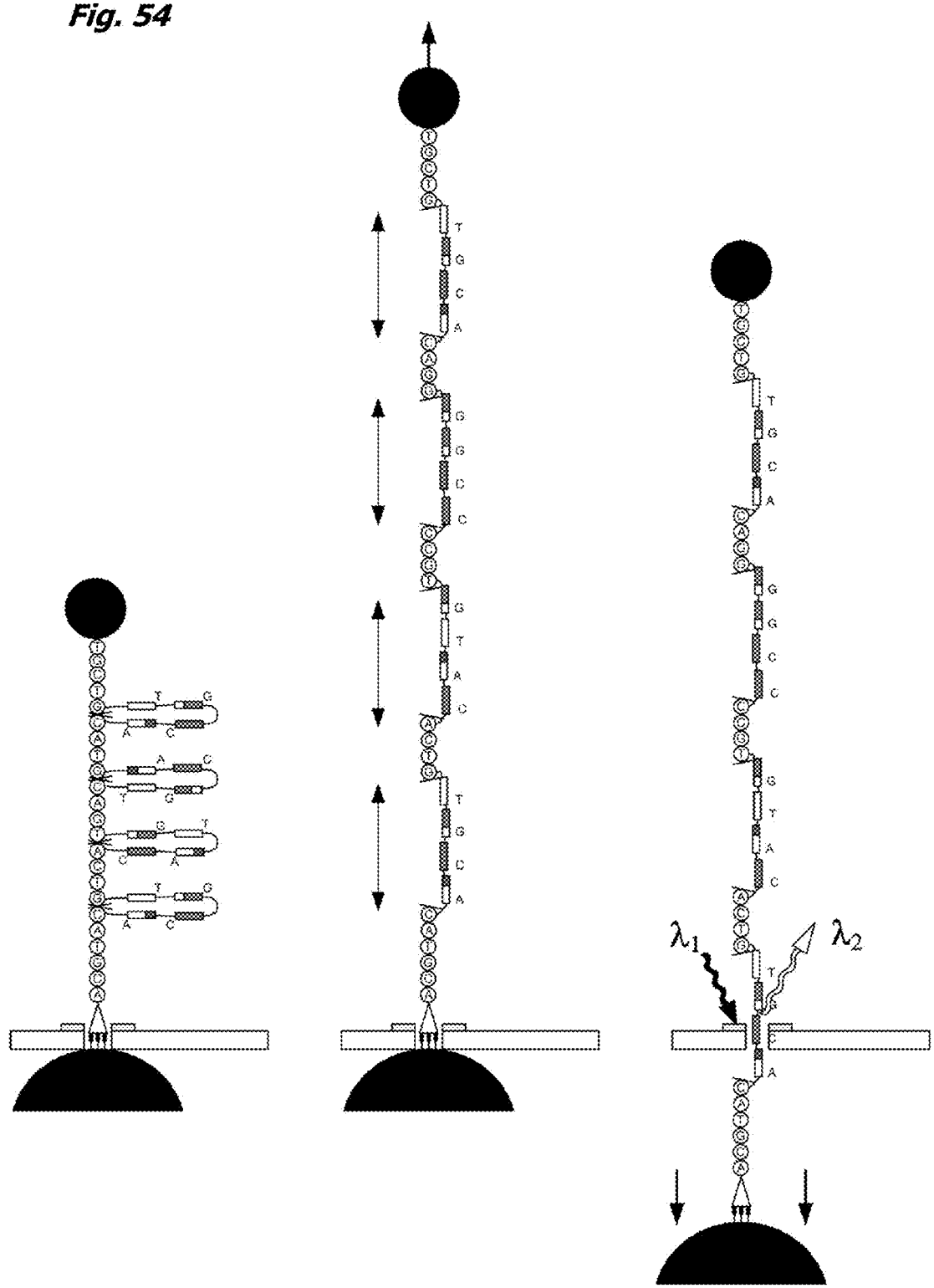
FIG. 54 describes a nanopore detection model with magnetic bead transport.

One detection embodiment uses a nanopore array as depicted in FIG. 54. In this embodiment, the Xpandomer is assembled using methods described previously, except that the DNA target is not anchored to an immobilized solid support but is anchored to a magnetic bead that has its anchoring probe threaded through a nanopore substrate. Furthermore, a multitude of FRET donor fluorophores, for two excitation wavelengths, are tethered to the nanopore entrance (shown as small squares). The FRET acceptor fluorophores constitute the reporters incorporated on the Xpandomer. After the linked Xprobes of the Xpandomer are cleaved, the Xpandomer is stretched by a force that can be electrostatic, magnetic, gravitational and/or mechanical and can be facilitated by the bead used to extend the original DNA target (shown attached to the top of the Xpandomer). In the final measurement step the Xpandomer is drawn through the nanopore by applying a magnetic force on the magnetic bead shown below the nanopore structure. The donor fluorophores at the nanopore entrance are excited with a light source ($\lambda_1$) and as the reporters pass proximal to the donor fluorophores, they are excited and emit their signature fluorescence ($\lambda_2$) that decodes to the associated nucleotide sequence.

FIG. 54 also illustrates one embodiment of encoding the sequence in the reporter codes. On each tether, there are 4 reporter sites, each loaded with a combination of two FRET acceptor fluorophore types. This provides four measurable states on each site using relative intensity level. If the acceptor fluorophores' fluorescence were red and green, the encoding of these states to the 4 nucleotides can be: A: green>red, C: only red, G: only green and T: red>green.

In another embodiment, the Xpandomer is labeled with mass tag reporters that are measured using a mass spectrometer. The Xpandomer is metered into a narrow capillary which feeds the reporters sequentially into an electrospray ionizer. To enable mass spectrometer measurement of the discrete mass tag reporters, the mass tags may be photocleaved from the reporter scaffolding just prior to, during, or after mass tag ionization. Magnetic sector, quadrupole, or time of flight ("TOF") based mass spectrometer can be used for mass tag detection. The instrument only requires distinguishing a limited number of mass-spaced tags. This can be used to improve sensitivity and throughput of the instrument. Also, employing an instrument having multiple channels for performing of ionization and detection in parallel increases throughput by orders of magnitude.

One embodiment of mass spectrometer approach detection is a multi-channel TOF mass detector that can read >100 channels simultaneously. A suitable instrument would use a multi-channel ionization source that feeds Xpandomer into multiple channels at a concentration and rate that maximizes the channel usage, thus maximizing the output rate of good quality data. Such an ionization source requires having adequate separation of the mass tag reporter segments. Mass tags can be photocleaved as they emerge from a nanopore and are ionized. The dispersion requirements are not high so that a short flight tube is all that is required. Extremely high measurement output is possible with a multi-channel mass spectrometer detection approach. For example, an array of 100 nanopore ion channels reading at the rate of 10,000 reporter codes per second (with 4 nucleotide measurements per reporter code) would achieve instrument throughput of >4 Mbases/second.

Figure 55:
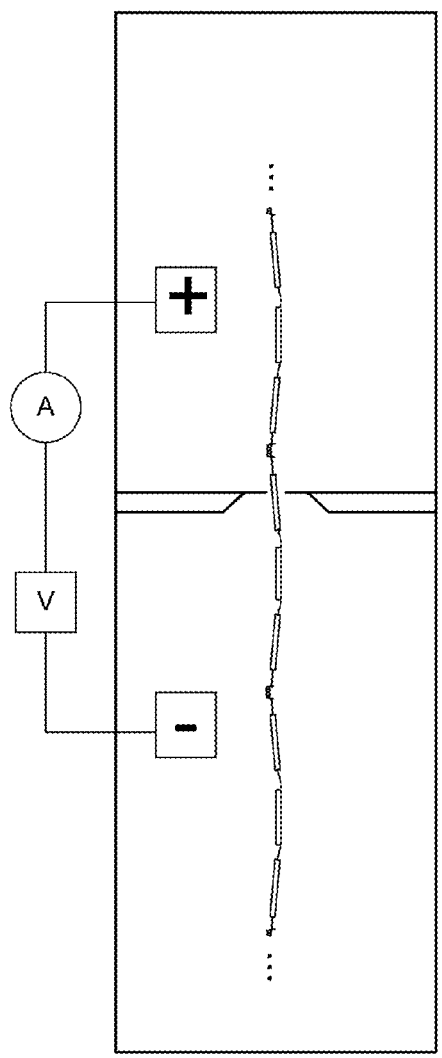
FIG. 55 illustrates a conventional nanopore detection method.

In another embodiment, the nanopore is used in a manner similar to a Coulter counter (FIG. 55). In this implementation, the charge density of the Xpandomer is designed to be similar to that of native DNA. The reporters are designed to produce 3 levels of impedance as measured in the nanopore detector, for example. The Xpandomers are presented in a free solution that has high concentrations of electrolyte, such as 1M KCl. The nanopore is 2 to 15 nm in diameter and is 4 to 30 nm long. To achieve good resolution of the tether constructs labels they are chosen to be close to the same length or longer. The diameter of the labels can be different for the 3 levels. The Xpandomer segment near the tether construct linkages have no reporters (for example PEG), this segment will have a particular impedance level. One of the three reporter levels can be equivalent. Different impedance signatures, which involve both level of impedance and temporal response, can be produced by varying segment lengths, charge density, and molecular density. For example, to achieve 3 different impedance levels, labeled tether constructs segments can be chemically coded to couple to one of three different polymer types, each with a different length and charge density.

When the Xpandomer passes through the nanopore detector the current is modulated according to which label type is present. The amount of charged polymer residing in the nanopore affects both the electrolyte species current and the translocation velocity.

Polymer-based detection by nanopores is demonstrated in U.S. Pat. Nos. 6,465,193 and 7,060,507, for example, and the physical parameters of a polymer are shown as expected to modulate electrical output from a nanopore. These patents and related arts are herein incorporated in full by reference.

Figure 56:
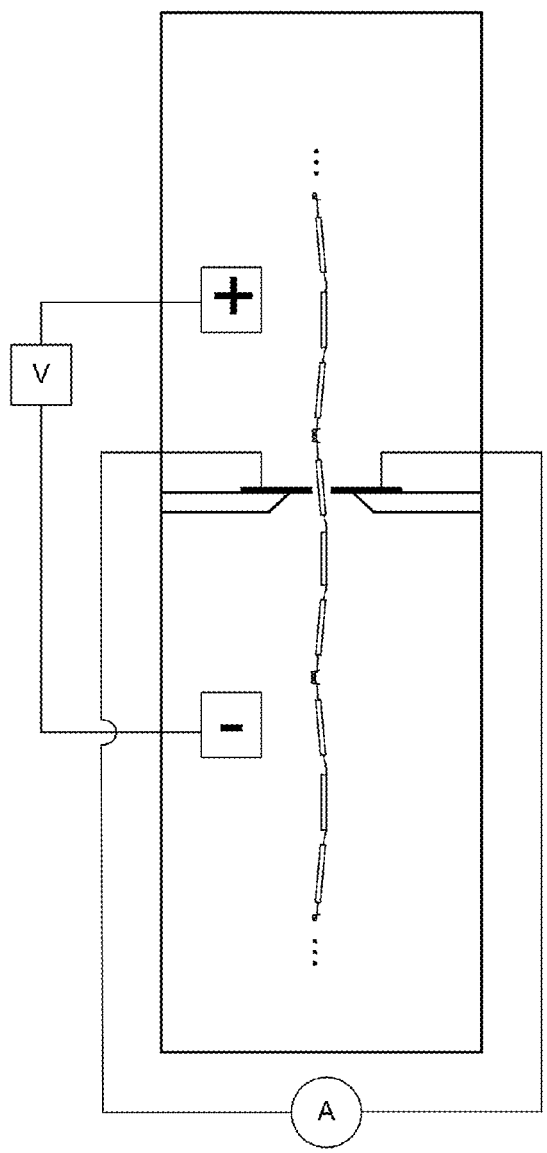
FIG. 56 illustrates a transverse electrode nanopore detection method.

In another embodiment of a nanopore-based detection apparatus (FIG. 56) lateral electrodes affixed to the nanopore are used to measure impedance or conductivity from side-to-side in the nanopore while a voltage is applied across the solid support film. This has an advantage of separating the translocation function from the impedance function. As the Xpandomer is conveyed through the nanopore, current modulation is again measured. Microfluidic and micropipetting techniques are employed, along with drag tags, magnetic beads, electrophoretic stretching techniques, and so forth, in order to convey the Xpandomer through the nanopore. For example, end-labeled free-solution electrophoresis, also termed ELFSE, is a method for breaking the charge to friction balance of free-draining DNA that can be used for free-solution Xpandomer electrophoresis (Slater et al., "End-labeled free-solution electrophoresis of DNA", *Electrophoresis* 26: 331-350, 2005).

Figure 57:
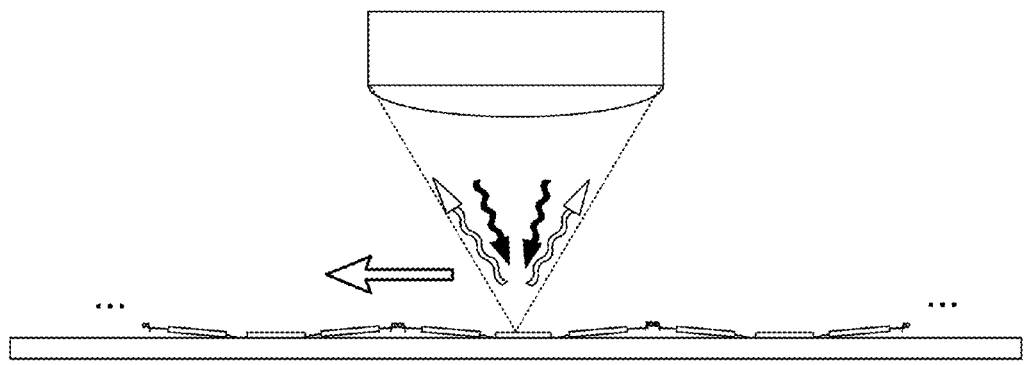
FIG. 57 illustrates a microscopic detection method.
Figure 58:
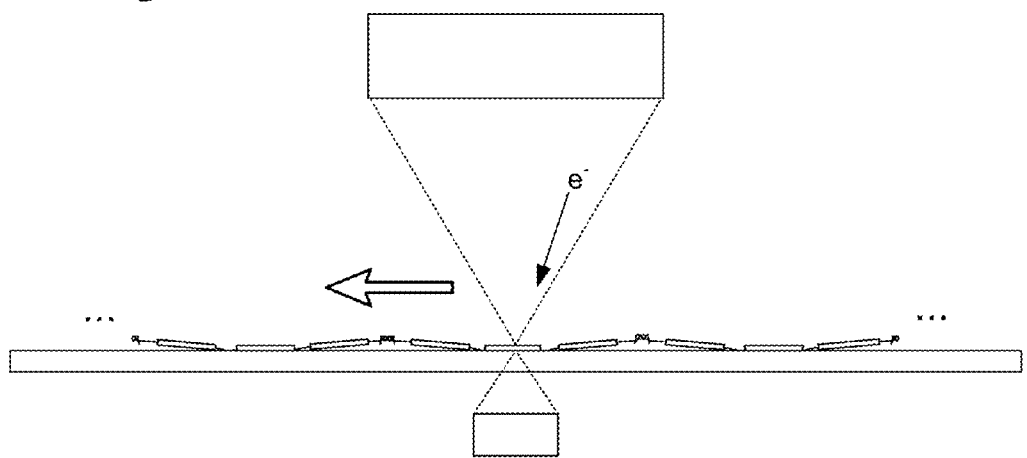
FIG. 58 illustrates detection by electron microscopy.
Figure 59:
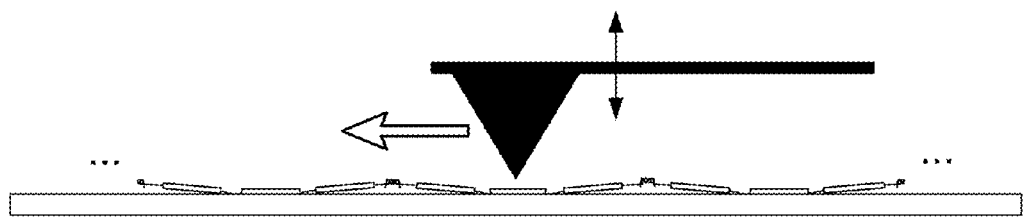
FIG. 59 illustrates detection using atomic force microscopy.

Methods for tethering, stretching, labeling, and measuring large DNA fragments are well established (Schwartz et al., "A single-molecule barcoding system using nanoslits for DNA analysis", *PNAS*, 104(8):2673-2678, 2007; and Blanch et al., "Electrokinetic Stretching of Tethered DNA", *Biophysical Journal* 85: 2539-2546, 2003). However, single nucleobase resolution for the purposes of whole genome sequencing of native nucleic acids is beyond the capabilities of these techniques. In FIG. 57 through 59, several "single-molecule" Xpandomer detection methods are pictured. In FIG. 57, a microscope is pictured and any of a variety of direct imaging techniques that take advantage of the greater spatial resolution of the Xpandomer structure can be conceived. An Xpandomer molecule is placed flat on a generally planar surface and scanned along its length. Examples include light microscopy and fluorescence microscopy. Using high resolution microscopy is limited in most cases to >100 nm resolution which is still possible with long tethers (100 nm per reporter for example). Higher resolution (requiring tethers <100 nm per reporter for example) can be achieved using techniques such as total internal reflection fluorescence microscopy (TIRF: Starr, T. E. et. al., *Biophys. J.* 80, 1575-84, 2001) zero-mode waveguides (Levine M. J. et al., *Science* 299, 682-85, 2003) or near field optical microscopy (NSOM: de Lang et al., *J. Cell Sci.* 114, 4153-60 2001) or Confocal laser scanning microscopy. In the case of localized FRET excitation interactions can be localized to <10 nm leading to tether lengths of ~10 nm/reporter.

Detection and analysis of large DNA molecules by electron microscopy is well established (Montoliu et al., "Visualization of large DNA molecules by electron microscopy with polyamines: application to the analysis of yeast endogenous and artificial chromosomes", *J. Mol. Bio.* 246(4):486-92, 1995), however, accurate and high-throughput sequencing of polynucleotides using these methods have proven difficult. In FIG. 58, transmission (TEM) and scanning electron microscopy (SEM) are indicated conceptually for detection of an Xpandomer. Here a focused electron beam is used to scan an Xpandomer, which is again generally flat on a surface. Aspects of the structure of the Xpandomer serve to decode the genetic information on the backbone. Specimen fixation and sputter coating techniques, which enable imaging of individual and atom-sized features of molecules, can be used to enhance magnification.

Also of interest are nanoelectrode-gated electron tunneling conductance spectroscopy, in which a tunneling electron beam between two nanoelectrode tips is modulated by conveyance of the Xpandomer between the tips (Lee et al., "Nanoelectrode-Gated Detection of Individual Molecules with Potential for Rapid DNA Sequencing", *Solid State Phenomena* 121-123: 1379-1386, 2007). The Xpandomer perturbs the tunneling current by its screening-conduction effect, which can be amplified over native DNA by use of suitable reporters. This technique has the advantage that specimen fixation and the requirement for vacuum is avoided, and in theory, massively parallel arrays of electrode gates can be employed to read many Xpandomers in parallel.

In FIG. 59, atomic force microscopy is illustrated conceptually. In a simple embodiment, a nanotube mounted on a sensitive cantilever swept across a surface and the attractive and repulsive forces between the probe and the sample surface are translated into a topological picture of the surface being scanned. This technique can achieve very high resolution but has relatively slow scan speeds (M. Miles, *Science* 277, 1845-1847 (1997)) Scanning tunneling electron microscopy (STM) is a related technology for imaging surfaces; the probe however does not touch the surface but rather a tunneling current between the surface and the probe is measured. Here the Xpandomer can be laid flat on a surface and physically scanned with the probe tip, much like a phonograph needle on a record.

Sequence Assembly

The published human genome reference sequence (or other reference sequence) can be used as an alignment tool to assist assembling the massive amounts of sequence data produced with SBX. Despite the likely inclusion of small, positionally identified sequence gaps, the long read length capabilities described for Xpandomer-based SBX simplifies and improves the fidelity of assembling whole genome sequences. As discussed above, the process can be further simplified by partitioning contiguous fragments in dimensionally confined locations on the assay reaction surface. In this embodiment the parsing method can dramatically reduce assembly time and error.

Monomeric Constructs

FIG. 9 provides an overview of monomeric constructs of the invention. A total of five classes are distinguished including four RT-NTP classes (VI, VII, VIII, and IX) and one XNTP class (X). Each class will be discussed individually below.

Monomeric constructs of Classes VI to X are distinguished from Class I to V oligomeric constructs in that they use a single nucleobase residue as a substrate. In the following description, N, refers to any nucleobase residue but is typically a nucleotide triphosphate or analog herein. It has attachment points on a tether (also described herein) for example, to the heterocyclic rings of the base, to the ribose group, or to the α-phosphate of the nucleobase residue. As described, the primary method for template-directed synthesis uses polymerase but any method that can perform template-directed synthesis is appropriate including methods of chemical and enzymatic ligation.

For the substrate constructs where ε and δ linker groups are used to create inter-subunit linkages, a broad range of suitable commercially available chemistries (Pierce, Thermo Fisher Scientific, USA) can be adapted for this purpose. Common linker chemistries include, for example, NHS-esters with amines, maleimides with sulfhydryls, imidoesters with amines, EDC with carboxyls for reactions with amines, pyridyl disulfides with sulfhydryls, and the like. Other embodiments involve the use of functional groups like hydrazide (HZ) and 4-formylbenzoate (4FB) which can then be further reacted to form linkages. More specifically, a wide range of crosslinkers (hetero- and homo-bifunctional) are broadly available (Pierce) which include, but are not limited to, Sulfo-SMCC (Sulfosuccinimidyl 4-[N-maleimidomethyl]cyclohexane-1-carboxylate), SIA (N-Succinimidyl iodoacetate), Sulfo-EMCS ([N-e-Maleimidocaproyloxy]sulfosuccinimide ester), Sulfo-GMBS (N-[g-Maleimido butyryloxy]sulfosuccinimide ester), AMAS N-(a-Maleimidoacetoxy)succinimide ester), BMPS(N EMCA (N-e-Maleimidocaproic acid) 4'-[β-Maleimidopropyloxy] succinimide ester), EDC (1-Ethyl-3-[3-dimethylaminopropyl]carbodiimide Hydrochloride), SANPAH (N-Succinimidyl-6-[4'-azido-2'-nitrophenylamino]hexanoate), SADP (N-Succinimidyl(4-azidophenyl)-1,3'-dithiopropionate), PMPI (N-[p-Maleimidophenyl] isocy, BMPH (N-[β-Maleimidopropionic acid]hydrazide, trifluoroacetic acid salt)anate), EMCH ([N-e-Maleimidocaproic acid]hydrazide, trifluoroacetic acid salt), SANH (succinimidyl 4-hydrazinonicotinate acetone hydrazone), SHTH (succinimidyl 4-hydrazidoterephthalate hydrochloride), and C6-SFB (C6-succinimidyl 4-formylbenzoate). Also, the method disclosed by Letsinger et al. ("Phosphorothioate oligonucleotides having modified internucleoside linkages", U.S. Pat. No. 6,242,589) can be adapted to form phosphorothiolate linkages.

Further, well established protection/deprotection chemistries are broadly available for common linker moieties (Benoiton, "Chemistry of Peptide Synthesis", CRC Press, 2005). Amino protection include, but are not limited to, 9-Fluorenylmethyl carbamate (Fmoc-NRR'), t-Butyl carbamate (Boc-NRR'), Benzyl carbamate (Z—NRR', Cbz-NRR'), Acetamide Trifluoroacetamide, Phthalimide, Benzylamine (Bn-NRR'), Triphenylmethylamine (Tr-NRR'), and Benzylideneamine p-Toluenesulfonamide (Ts-NRR'). Carboxyl protection include, but are not limited to, Methyl ester, t-Butyl ester, Benzyl ester, S-t-Butyl ester, and 2-Alkyl-1,3-oxazoline. Carbonyl include, but are not limited to, Dimethyl acetal 1,3-Dioxane, and 1,3-Dithiane N,N-Dimethylhydrazone. Hydroxyl protection include, but are not limited to, Methoxymethyl ether (MOM-OR), Tetrahydropyranyl ether (THP-OR), t-Butyl ether, Allyl ether, Benzyl ether (Bn-OR), t-Butyldimethylsilyl ether (TBDMS-OR), t-Butyldiphenylsilyl ether (TBDPS-OR), Acetic acid ester, Pivalic acid ester, and Benzoic acid ester.

Herein, the tether is often depicted as a reporter construct with three reporter groups, various reporter configurations can be arrayed on the tether, and can comprise a single reporter to identify the substrate, multiple reporters to identify the substrate, or the tether may be naked polymer (having no reporters). Note that reporters may be used for detection synchronization, error correction, redundancy, or other functions. In the case of the naked polymer, the reporters may be the substrate itself, or may be on a second tether attached to the substrate. In some cases, one or more reporter precursors are arrayed on the tether, and reporters are affinity bound or covalently bound following assembly of the Xpandomer product.

Reporter coding strategies are disclosed above, and further discussed below. For example, two bit, binary coding of each monomer would produce four unique code sequences (11, 10, 01, 00) which can be used to identify each sequence base (adenine "A", cytosine "C", guanine "G", thymidine "T"), assuming substrate coupling is directional. If non-direction, then a third bit provides unambiguous coding. Alternatively, a single 4-state multiplexed reporter construct provides a unique reporter code for each sequence base. A variety of functionalization and labeling strategies can be considered for tether constructs, including for examples functionalized dendrimers, polymers, branched polymers, nanoparticles, and nanocrystals as part of a reporter scaffold, as well as reporter chemistries with a detection characteristic to be detected with the appropriate detection technology including, for example, fluorescence, FRET emitters or exciters, charge density, size or length. Base specific labels can be incorporated into the tether as labeled substrates either prior to or after assembly of the Xpandomer. Once the Xpandomer is fully released and elongated, the reporter codes can be detected and analyzed using a range of detection methods.

Libraries of substrates suitable as monomeric substrates include (but are not limited to) modified ATP, GTP, CTP, TTP and UTP.

Class VI Monomeric Constructs

FIG. 60 describes Class VI monomeric substrate constructs (a type of RT-NTP) in more detail. FIGS. 60A through 60C are read from left to right, showing first the monomeric substrate construct (Xpandomer precursor having a single nucleobase residue), then the intermediate duplex daughter strand in the center, and on the right the Xpandomer product prepared for sequencing.

Figure 60A:
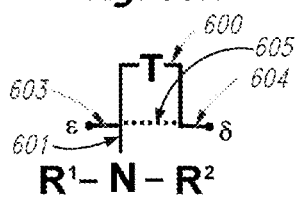
FIGS. 60A through 60E depict a Class VI Xpandomer, Xpandomer intermediate, and substrate construct in a symbolic and graphical language. These precursors are termed RT-NTPs.

As shown in FIG. 60A, the monomeric substrate constructs of Class VI have a tether, T (600), attached by a linkage (601) of a first end moiety to a substrate nucleobase residue, N. A linker group, $\epsilon$, is disposed on the first end moiety (603) of the tether proximate to $R^1$. At the distal end (604) of the tether, a second end moiety with a second linker group, $\delta$, is positioned proximate to $R^2$. The second end moiety of the tether is secured to the first end moiety in proximity to the nucleobase by an intra-tether selectively cleavable crosslink (or by other constraint). The intra-tether cleavable crosslink (605) is denoted here by dotted line, which can indicate, for example, a disulfide bond or a photocleavable linker.

This constraint prevents the tether from elongating or expanding and is said to be in its "constrained configuration". Under template-directed assembly, substrates form a duplex with the target template such that the substrates are abutted. Under controlled conditions, collocated linker groups $\delta$ and $\epsilon$ of the abutting substrates link to form a bond between the adjacent substrate constructs. Linker groups $\delta$ and $\epsilon$ of a monomeric substrate construct do not form an intra-substrate bond due to positioning constraints. Suitable linkage and protection/deprotection chemistries for $\delta$, $\epsilon$, and $\chi$ are detailed in the general monomeric construct description.

$R^1$ and $R^2$ are end groups configured as appropriate for the synthesis protocol in which the substrate construct is used. For example, $R^1$=5'-phosphate and $R^2$=3'-OH, would find use in a ligation protocol, and $R^1$=5'-triphosphate and $R^2$=3'-OH for a polymerase protocol. Optionally, $R^2$ can be configured with a reversible blocking group for cyclical single-substrate addition. Alternatively, $R^1$ and $R^2$ can be configured with linker end groups for chemical coupling or with no linker groups for a hybridization only protocol. $R^1$ and $R^2$ can be of the general type XR, wherein X is a linking group and R is a functional group.

Figure 60B:
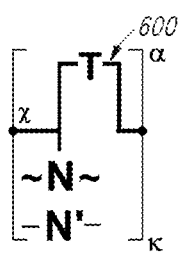

During assembly, the monomeric substrate construct is first polymerized on the extendable terminus of the nascent daughter strand by a process of template-directed polymerization using a single-stranded template as a guide. Generally, this process is initiated from a primer and proceeds in the 5' to 3' direction. Generally, a DNA polymerase or other polymerase is used to form the daughter strand, and conditions are selected so that a complementary copy of the template strand is obtained. Subsequently, linker group $\delta$, which is now collocated with the linker group $\epsilon$ of the adjacent subunit tether, are selectively crosslinked to form a $\chi$-bond, which is an inter-tether, inter-subunit bond. The $\chi$-bonds join the tethers in a continuous chain, forming an intermediate termed the "duplex daughter strand", as shown in FIG. 60B. After the $\chi$-bond is formed, the intra-tether bond may be broken.

The duplex daughter strand (FIG. 60B) is a hetero-copolymer with subunits shown in brackets. The primary backbone (~N~)$\kappa$, template strand (-N'-)$\kappa$, and tether (T) are shown as a duplexed daughter strand, where $\kappa$ denotes a plurality of repeating subunits. Each subunit of the daughter strand is a repeating "motif" and the motifs have species-specific variability, indicated here by the $\alpha$ superscript. The daughter strand is formed from monomeric substrate construct species selected by a template-directed process from a library of motif species, the monomer substrate of each substrate construct species binding to a corresponding complementary nucleotide on the target template strand. In this way, the sequence of nucleobase residues (i.e., primary backbone) of the daughter strand is a contiguous, complementary copy of the target template strand.

Each tilde (~) denotes a selectively cleavable bond shown here as the inter-substrate bonds. These are selectively cleavable to release and expand the tethers (and the Xpandomer) without degrading the Xpandomer itself.

The daughter strand is composed of an Xpandomer precursor called the "constrained Xpandomer" which is further composed of tethers in the "constrained configuration". When the tethers convert to their "expanded configuration", the constrained Xpandomer converts to the Xpandomer product. The tethers are constrained by the inter-subunit $\chi$ linkages, the substrate attachment and, optionally, the intra-tether linkages if still present. The $\chi$ linkage attaches the tether first end moiety of a first subunit to the tether second end moiety at the abutting end of a second subunit and is formed by linking the collocated linker groups, $\epsilon$ of the first subunit, and $\delta$ of the second subunit.

The daughter strand can be seen to have two backbones, a "primary backbone", and the backbone of the "constrained Xpandomer". The primary backbone is composed of the contiguously abutted and polymerized monomeric substrates. The "constrained Xpandomer backbone" bypasses the selectively cleavable linkage between the monomer substrates and is formed by $\chi$ bond-linked backbone moieties, each backbone moiety being a tether. It can be seen that the constrained Xpandomer backbone bridges over the selectively cleavable bonds of the primary backbone, and will remain covalently intact when these selectively cleavable bonds are cleaved and the primary backbone is fragmented.

The tether $\chi$ bond (crosslinking of linker groups $\delta$ and $\epsilon$) is generally preceded by enzymatic coupling of the monomer substrates to form the primary backbone, with, for example, phosphodiester bonds between adjacent bases. In the structure shown here, the daughter strand primary backbone has been formed, and the inter-substrate, are depicted by a tilde (~) to indicate that they are selectively cleavable. After dissociating or degrading the target template strand, cleaving the selectively cleavable bonds (which include the intra-tether bonds), the constrained Xpandomer is released and becomes the Xpandomer product. Methods for dissociation of the template strand include heat denaturation, or selective digestion with a nuclease, or chemical degradation. A method for selectable cleavage uses nuclease digestion where for example, phosphodiester bonds of the primary backbone are digested by a nuclease and tether-to-tether bonds are nuclease resistant.

Figure 60C:
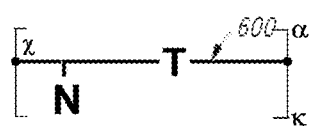

FIG. 60C is a representation of the Class VI Xpandomer product after dissociation of the template strand and after cleavage of the selectively cleavable bonds (including those in the primary backbone and, if not already cleaved, the intra-tether links). The Xpandomer product strand contains a plurality of subunits $\kappa$, where $\kappa$ denotes the $\kappa$th subunit in a chain of m subunits making up the daughter strand, where $\kappa$=1, 2, 3 to m, where m>10, generally m>50, and typically m>500 or >5,000. Each subunit is formed of a tether in its expanded configuration and is stretched to its length between the $\chi$ linkages of adjacent subunits. The pendant substrate is attached to the tether in each subunit. Each subunit, a subunit motif $\alpha$, contains species-specific genetic information established by template-directed assembly of the Xpandomer intermediate (daughter strand).

Figure 60D:
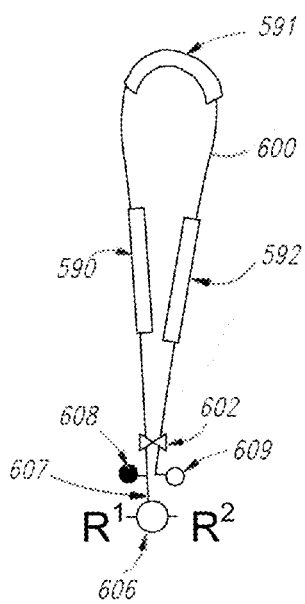

FIG. 60D shows the substrate construct of FIG. 60A as a molecular model, where the monomer substrate member, represented with a nucleobase residue (606), is joined to the tether by a linkage (607) of the tether first end moiety. Also disposed on the first end moiety is a linker group (608), shown as $\epsilon$ in FIG. 60A. A second linker group (609), shown as $\delta$ in FIG. 60A, is disposed on the second end moiety at the distal end of the tether. A selectively cleavable intra-tether linkage (602), depicted by the adjoining triangles, is shown that constrains the tether by linking the first and second end moiety. The linker groups $\epsilon$ and $\delta$ are positioned to not interact and to preferably align near the $R^1$ and $R^2$ sides of the substrate, respectively. The tether loop (600) shown here has three reporters (590,591,592), which can also be motif species specific.

Figure 60E:
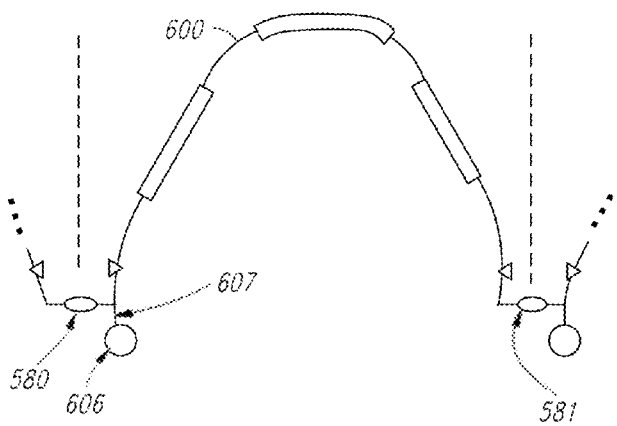

FIG. 60E shows the substrate construct after incorporation into the product Xpandomer. The subunits are cleaved and expanded and are linked by $\chi$ bonds (580,581), depicted as an open oval, formed by linking the linker groups $\delta$ and $\epsilon$ referred to in FIG. 60A. A subunit is indicated by dotted lines vertically bracketing the repeating subunit, as represented by brackets in the accompanying FIG. 60C.

In the Xpandomer product of FIG. 60E, the primary backbone has been fragmented and is not covalently contiguous because any direct bond between the substrates of adjacent subunits has been cleaved. Through the cleavage process, the constrained Xpandomer is released to become the Xpandomer product. The tether members that were formerly in constrained configuration are now in expanded configuration, thereby functioning to linearly stretch out the sequence information of the template target. Expanding the tethers lowers the linear density of the sequence information along the Xpandomer and provides a platform for increasing the size and abundance of reporters which in turn improves signal to noise for detection and decoding of the template sequence.

While the tether is depicted as a reporter construct with three reporter groups, various reporter configurations can be arrayed on the tether, and can comprise single reporters that identify monomer or the tether can be a naked polymer. In some cases, one or more reporter precursors are arrayed on the tether, and reporters are affinity bound or covalently bound following assembly of the Xpandomer product.

Figure 61:
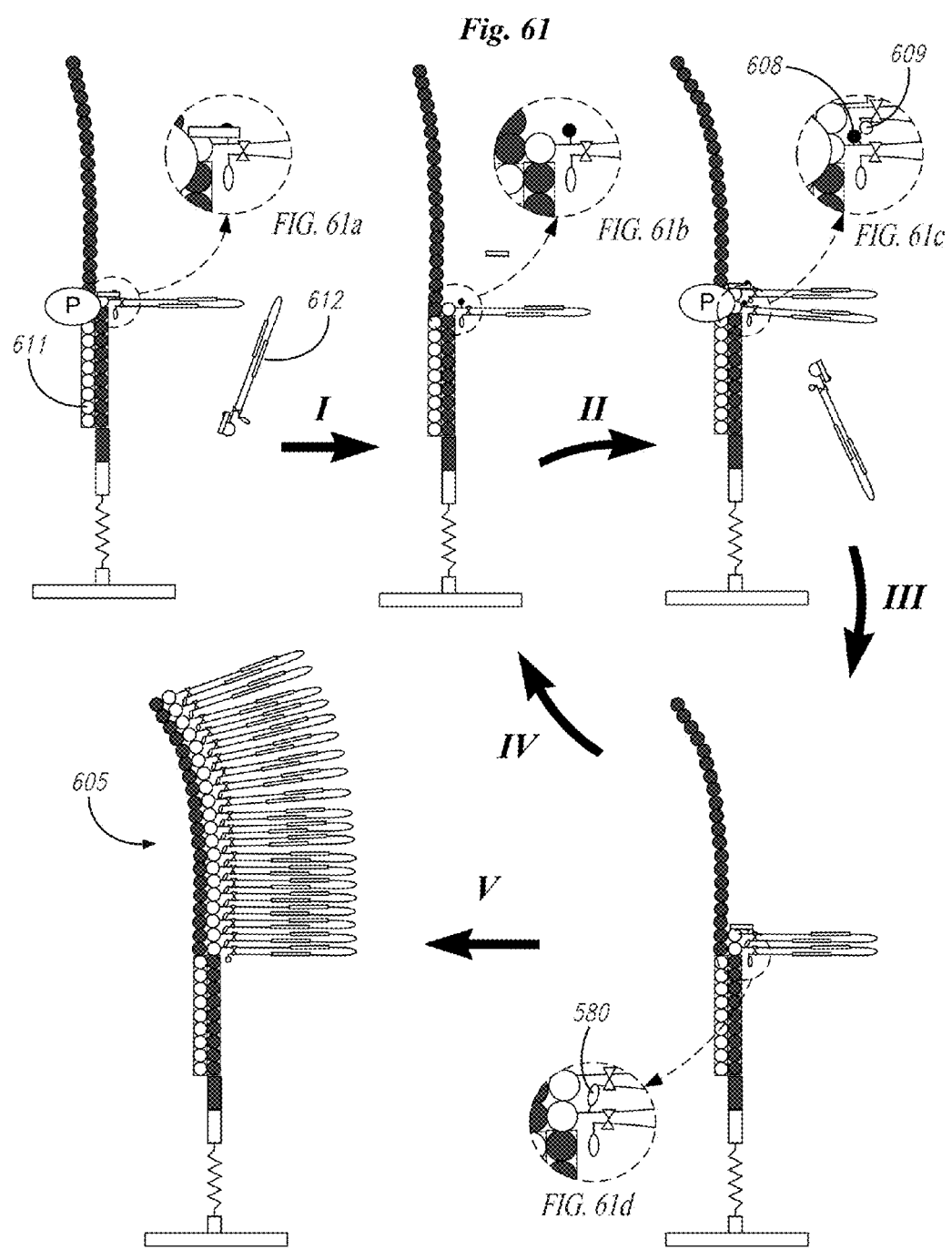
FIG. 61 is a condensed schematic of a method for synthesis of an Xpandomer on an immobilized template using reversibly terminated Class VI triphosphate substrate constructs and a polymerase.

Turning now to FIG. 61, a method for single base extension (SBE) with monomeric substrate constructs is shown. End-adapted target templates (or random target template sequences, depending on the nature of the immobilized primers), are first annealed to the immobilized primers. Before Step I, the immobilized templates (611) are contacted with a monomeric substrate construct library, a member of which is shown for illustration (612), and polymerase (P). Conditions are adjusted for template-directed polymerization. In this example, the 5' termini of the first monomeric substrate ($R^2$ of FIGS. 60A and 60D) is polymerized to initiate the nascent daughter strand. The substrate has been substituted at the 3' termini ($R^1$ of FIGS. 60A and 60D), to reversibly block further extension. This is shown in more detail in magnified FIG. 61a (dotted lines), where the monomeric substrate is shown abutting the primer. This substrate is a 5'-triphosphate, and a phosphodiester bond is formed with the primer by action of the polymerase. It should be noted that the reactive functional group ($\delta$ of FIG. 60A) shown in FIG. 61c is typically deactivated (by reaction or other means) in the first substrate added (as shown in FIG. 61a by the rectangle).

In step I of FIG. 61, the blocking group is removed (free rectangle) to enable the addition of another monomer (extension). Methods for reversibly blocking the 3' end include the use of Pd to catalyze removal of an allyl group to regenerate a viable 3' hydroxyl end, or the use of 3'-O-(2-Nitrobenzyl) terminated nucleotides, where active hydroxyls can be regenerated by exposure to a UV source to photocleave the terminating moiety as described by Ju et al. ("Four-color DNA sequencing by synthesis using cleavable fluorescent nucleotide reversible terminators", *PNAS* 26; 103(52): 19635-19640, 2006, and "Four-color DNA sequencing by synthesis on a chip using photocleavable fluorescent nucleotides", *PNAS* 26; 102(17):5926-31, 2005). The regenerated 3'-OH is shown in more detail in magnified view FIG. 61b. In this view, the abutting ends of the adjacent substrate construct and primer are polymerized and the 3'-OH end of the nascent daughter strand is activated by removing the blocking group. In step II, the template is contacted with a monomeric substrate construct library, where the functional $\delta$ groups are reactive under controlled conditions, and a monomer substrate is polymerized to the nascent daughter strand. This polymerization collocates the $\epsilon$ (608) and $\delta$ (609) groups of the abutted substrate constructs as shown in FIG. 61c. In step III, under controlled conditions, these groups react to form a $\chi$ bond (580), as shown in more detail in FIG. 61d.

As indicated, cycling through steps II, III and IV extends the nascent daughter each time by additional substrate (construct). Typically a wash step may be used to remove unreacted reagents between steps. The process is thus analogous to what is termed in the literature, cyclical "single base extension". The process is shown with polymerase, P, but may be adapted for a ligase or a chemical ligation protocol suitable for joining substrate constructs in a template-directed synthesis. Step V shows the daughter strand intermediate for the Xpandomer (605). This intermediate can be dissociated from the template and the primer, for example, with a nuclease that attacks the primary backbone of the daughter strand, thereby relieving the constrained tethers and releasing the Xpandomer product.

As with all SBE methods, efficient washing in between cycles is helpful for reducing undesirable side reactions. To further facilitate single base incorporation through template regions with high secondary structure, the extension temperature can be varied throughout each extension cycle and/or additives or adjuvants, such as betaine, TMACL, or PEG, can also be added to neutralize the effects of secondary structure (as is done in conventional polymerase extension protocols). And if necessary, stoichiometry of the substrate construct species can be varied to compensate for reaction bias favoring certain bases, such as C Or G.

An alternative method for producing Class VI Xpandomers is to do polymerase-based processive polymerization. DNA and RNA polymerases, as well as any similarly functioning enzymes demonstrated to catalyze accurate polymerization of RT-NTPs, absent reversibly terminal blocking R groups, can be considered for this approach.

A broad range of crosslinking chemistries are known in this field, and are useful for formation of $\chi$ bonds. These include use of NHS-esters with amines, maleimides with sulfhydryls, imidoesters with amines, EDC with sulfhydryls and carboxyls for reactions with amines, pyridyl disulfides with sulfhydryls, and so forth. Other embodiments involve the use of functional groups like hydrazide (HZ) and 4-formylbenzoate (4FB) which can then be further reacted to link subunits. In one option, two different linking chemistries, $\epsilon 1/\delta 1$ and $\epsilon 2/\delta 2$ (also referred to as L1/L1' and L2/L2' in other parts of this document) that react to form $\chi 1$ and $\chi 2$ bonds respectively, and can be used to differentially functionalize two sets of RT-NTP substrate constructs. For example, if one cycle of SBE is performed with a $\epsilon 1/\delta 2$ functionalized RT-NTP set, the following SBE cycle would use the $\epsilon 2/\delta 1$ set resulting in a reaction of the collocated $\delta 2/\epsilon 2$ pair to form $\chi 1$. Ordered activation of the crosslinking pairs is useful for minimizing crosslinking errors and undesired side reactions.

Class VII Monomeric Constructs

Figure 62A:
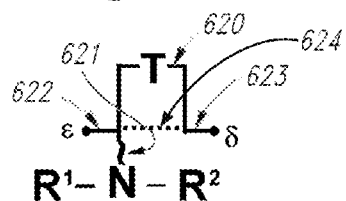
FIGS. 62A through 62E depict a Class VII Xpandomer, Xpandomer intermediate, and substrate construct in a symbolic and graphical language. These precursors are termed RT-NTPs.
Figure 62B:
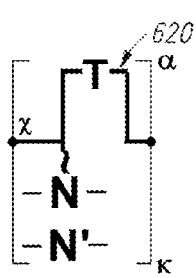
Figure 62C:
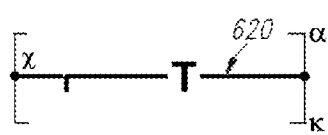

Class VII molecules are analogs of Class VI described previously. The primary difference is that the cleavable bond is between the tether and the substrate instead of between the substrates. In FIG. 62, Class VII monomeric substrate constructs (a type of RT-NTP) are disclosed in more detail. FIGS. 62A through 62C are read from left to right, showing first the monomeric substrate construct (Xpandomer precursor having a single nucleobase residue), then the intermediate duplex daughter strand in the center, and on the right the Xpandomer product prepared for sequencing.

As shown in FIG. 62A, the monomeric substrate constructs of Class VII have a tether, T (620), attached by a selectively cleavable linker (621) to a first end moiety to a substrate nucleobase residue, N. Another linker group, $\epsilon$ (622), is disposed on the first end moiety of the tether proximate to $R^1$. At the distal end of the tether T a second end moiety with a second linker group, $\delta$ (623), is positioned proximate to $R^2$. The second end moiety of the tether is secured to the first end moiety in proximity to the nucleobase by an intra-tether selectively cleavable crosslink (624) (or by other constraint). The intra-tether cleavable crosslink is denoted here by dotted line, which can indicate, for example, a disulfide bond or a photocleavable linker. This constraint prevents the tether from elongating or expanding and is in a "constrained configuration". Under template-directed assembly, substrates form a duplex with the target template such that the substrates are abutted. Under controlled conditions, collocated linker groups $\delta$ and $\epsilon$ of the abutting substrates link to form a bond between the adjacent substrate constructs. Linker groups $\delta$ and $\epsilon$ of a monomeric substrate construct do not form an intra-substrate bond due to positioning constraints. Suitable linkage and protection/deprotection chemistries for $\delta$, $\epsilon$, and $\chi$ are detailed in the general monomeric construct description.

$R^1$ and $R^2$ are end groups configured as appropriate for the synthesis protocol in which the substrate construct is used. For example, $R^1$=5'-phosphate and $R^2$=3'-OH, would find use in a ligation protocol, and $R^1$=5'-triphosphate and $R^2$=3'-OH for a polymerase protocol. Optionally, $R^2$ can be configured with a reversible blocking group for cyclical single-substrate addition. Alternatively, $R^1$ and $R^2$ can be configured with linker end groups for chemical coupling or with no linker groups for a hybridization only protocol. $R^1$ and $R^2$ can be of the general type XR, wherein X is a linking group and R is a functional group.

During assembly, the monomeric substrate construct is first polymerized on the extendable terminus of the nascent daughter strand by a process of template-directed polymerization using a single-stranded template as a guide. Generally, this process is initiated from a primer and proceeds in the 5' to 3' direction. Generally, a DNA polymerase or other polymerase is used to form the daughter strand, and conditions are selected so that a complementary copy of the template strand is obtained. Subsequently, linker group $\delta$, which is now collocated with the linker group $\epsilon$ of the adjacent subunit tether, is caused to crosslink and forms a $\chi$-bond, which is an inter-tether, inter-subunit bond. The $\chi$-bonds join the tethers in a continuous chain, forming an intermediate termed the "duplex daughter strand", as shown in FIG. 62B. After the $\chi$-bond is formed, the intra-tether bond may be broken.

The duplex daughter strand (FIG. 62B) is a hetero-copolymer with subunits shown in brackets. The primary backbone (-N-)$\kappa$, template strand (-N'-)$\kappa$, and Tether (T) are shown as a duplexed daughter strand, where $\kappa$ denotes a plurality of repeating subunits. Each subunit of the daughter strand is a repeating "motif" and the motifs have species-specific variability, indicated here by the $\alpha$ superscript. The daughter strand is formed from monomeric substrate construct species selected by a template-directed process from a library of motif species, the monomer substrate of each substrate construct species binding to a corresponding complementary nucleotide on the target template strand. In this way, the sequence of nucleobase residues (i.e., primary backbone) of the daughter strand is a contiguous, complementary copy of, the target template strand.

The tilde (~) denotes a selectively cleavable bond shown here as the tether to substrate linker. These are selectively cleavable to release and expand the tethers (and the Xpandomer) without degrading the Xpandomer itself.

The daughter strand is composed of an Xpandomer precursor called the "constrained Xpandomer" which is further composed of tethers in the "constrained configuration". When the tethers convert to their "expanded configuration", the constrained Xpandomer converts to the Xpandomer product. The tethers are constrained by the inter-subunit $\chi$ linkages, the cleavable linkage to the substrate and, optionally, the intra-tether linkages if still present. The $\chi$ linkage attaches the tether first end moiety of a first subunit to the tether second end moiety at the abutting end of a second subunit and is formed by linking the collocated linker groups, $\epsilon$ of the first subunit, and $\delta$ of the second subunit.

The daughter strand can be seen to have two backbones, a "primary backbone", and a "constrained Xpandomer backbone". The primary backbone is composed of the contiguously abutted and polymerized monomeric substrates. The constrained Xpandomer backbone bypasses the selectively cleavable linkage that connects to the substrate and is formed by $\chi$ bond linked backbone moieties, each backbone moiety being a tether. It can be seen that the constrained Xpandomer backbone bridges over the selectively cleavable bonds connected to the primary backbone, and will remain covalently intact when these selectively cleavable bonds are cleaved and the primary backbone is dissociated or fragmented.

The tether $\chi$ bond (crosslinking of linker groups $\delta$ and $\epsilon$) is generally preceded by enzymatic coupling of the monomer substrates to form the primary backbone with, for example, phosphodiester bonds between adjacent bases. In the structure shown here, the daughter strand primary backbone has been formed, and the inter-substrate, are depicted by a tilde (~) to indicate that they are selectively cleavable. After dissociating or degrading the target template strand, cleaving the selectively cleavable bonds (which include the intra-tether bonds), the constrained Xpandomer is released and becomes the Xpandomer product. Methods for dissociation of the template strand include heat denaturation, or selective digestion with a nuclease, or chemical degradation. A method for selectable cleavage uses nuclease digestion where for example, phosphodiester bonds of the primary backbone are digested by a nuclease and tether-to-tether bonds are nuclease resistant.

FIG. 62C is a representation of the Class VII Xpandomer product after dissociation of the template strand and after cleavage of the selectively cleavable bonds (including those attached to the primary backbone and, if not already cleaved, the intra-tether links). The Xpandomer product strand contains a plurality of subunits $\kappa$, where $\kappa$ denotes the $\kappa$th subunit in a chain of m subunits making up the daughter strand, where $\kappa$=1, 2, 3 to m, where m>10, generally m>50, and typically m>500 or >5,000. Each subunit is formed of a tether (620) in its expanded configuration and is stretched to its length between the $\chi$ linkages of adjacent subunits. The primary backbone has been removed completely. Each subunit, a subunit motif α, contains species-specific genetic information established by template-directed assembly of the Xpandomer intermediate (daughter strand).

Figure 62D:
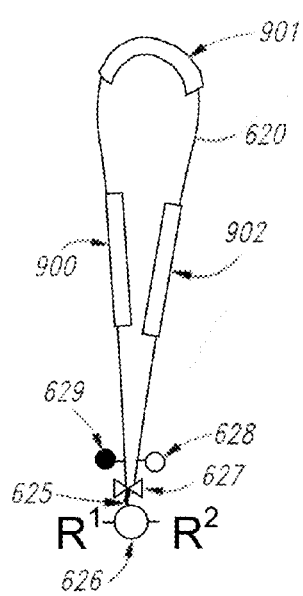

FIG. 62D shows the substrate construct of FIG. 62A as a molecular model, where the monomer substrate member, represented with a nucleobase residue (626), linked by a selectively cleavable linkage (625) to the tether first end moiety. Also disposed on the first end moiety is a linker group (629), shown as ε in FIG. 62A. A second linker group (628), shown as δ in FIG. 62A, is disposed on the second end moiety at the distal end of the tether. A selectively cleavable intra-tether linkage (627), represented by the adjoining triangles, is shown that constrains the tether by linking the first and second end moiety. The linker groups ε (629) and δ (628) are positioned to not interact and to preferably align near the $R^1$ and $R^2$ sides of the substrate, respectively. The tether loop shown here has three reporters (900,901,902), which can also be motif species specific.

Figure 62E:
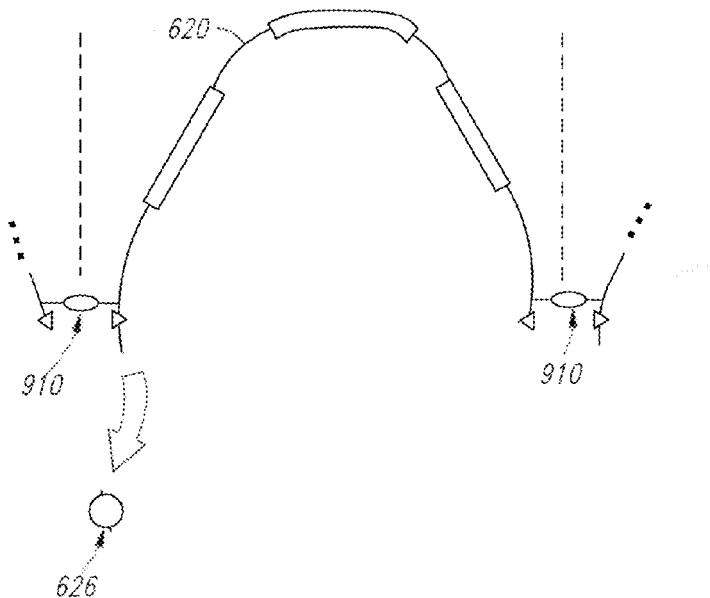

FIG. 62E shows the substrate construct after incorporation into the product Xpandomer. The subunits are cleaved and expanded and are linked by χ bonds (910), depicted as an open oval, formed by linking the linker groups δ and ε referred to in FIG. 62A. A subunit is indicated by dotted lines vertically bracketing the repeating subunit, as represented by brackets in the accompanying FIG. 62C.

In the Xpandomer product of FIG. 62E, the primary backbone has been dissociated or fragmented and is separated from the Xpandomer. Through the cleavage process, the constrained Xpandomer is released to become the Xpandomer product. The tether members that were formerly in constrained configuration are now in expanded configuration, thereby functioning to linearly stretch out the sequence information of the template target. Expanding the tethers lowers the linear density of the sequence information along the Xpandomer and provides a platform for increasing the size and abundance of reporters which in turn improves signal to noise for detection and decoding of the template sequence.

While the tether is depicted as a reporter construct with three reporter groups, various reporter configurations can be arrayed on the tether, and can comprise single reporters that identify monomer or the tether can be a naked polymer. In some cases, one or more reporter precursors are arrayed on the tether, and reporters are affinity bound or covalently bound following assembly of the Xpandomer product.

Class VIII Monomeric Constructs

Figure 63A:
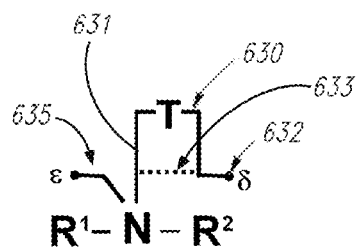
FIGS. 63A through 63E depict a Class VIII Xpandomer, Xpandomer intermediate, and substrate construct in a symbolic and graphical language. These precursors are termed RT-NTPs.
Figure 63B:
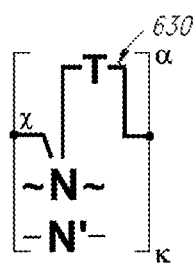
Figure 63C:
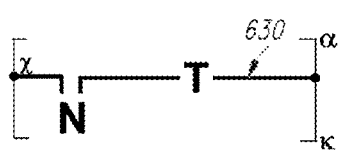

Class VIII molecules are analogs of Class VI described previously. The primary difference is that the linker group, E, is connected directly to the substrate instead of to the tether. In FIG. 63, we describe Class VIII monomeric substrate constructs (a type of RT-NTP), in more detail. FIGS. 63A through 63C are read from left to right, showing first the monomeric substrate construct (Xpandomer precursor having a single nucleobase residue), then the intermediate duplex daughter strand in the center, and on the right the Xpandomer product prepared for sequencing.

As shown in FIG. 63A, the monomeric substrate constructs of Class VIII have a tether, T (630), attached by a linkage (631) of a first end moiety to a substrate nucleobase residue, N. At the distal end of the tether (632), a second end moiety with a second linker group, δ, is positioned preferentially proximate to $R^2$. The second end moiety of the tether is secured to the first end moiety in proximity to the nucleobase by an intra-tether selectively cleavable crosslink (or by other constraint). The intra-tether cleavable crosslink (633) is denoted here by dotted line, which can indicate, for example, a disulfide bond or a photocleavable linker. This constraint prevents the tether from elongating or expanding and is said to be in its "constrained configuration". A linker group, ε (635), is attached to the monomer substrate preferentially proximate to $R^1$. Under template-directed assembly, substrates form a duplex with the target template such that the substrates are abutted. Under controlled conditions, linker groups δ and ε of the abutting substrates are collocated and link to form a bond between the adjacent substrate constructs. Linker groups δ and ε of a monomeric substrate construct do not form an intra-substrate bond due to positioning constraints. Suitable linkage and protection/deprotection chemistries for δ, ε, and χ are detailed in the general monomeric construct description.

$R^1$ and $R^2$ are end groups configured as appropriate for the synthesis protocol in which the substrate construct is used. For example, $R^1$=5'-phosphate and $R^2$=3'-OH, would find use in a ligation protocol, and $R^1$=5'-triphosphate and $R^2$=3'-OH for a polymerase protocol. Optionally, $R^2$ can be configured with a reversible blocking group for cyclical single-substrate addition. Alternatively, $R^1$ and $R^2$ can be configured with linker end groups for chemical coupling or with no linker groups for a hybridization only protocol. $R^1$ and $R^2$ can be of the general type XR, wherein X is a linking group and R is a functional group.

During assembly, the monomeric substrate construct is first polymerized on the extendable terminus of the nascent daughter strand by a process of template-directed polymerization using a single-stranded template as a guide. Generally, this process is initiated from a primer and proceeds in the 5' to 3' direction. Generally, a DNA polymerase or other polymerase is used to form the daughter strand, and conditions are selected so that a complementary copy of the template strand is obtained. Subsequently, linker group δ, which is now collocated with the linker group ε of the adjacent subunit tether, is caused to crosslink and forms a χ-bond, which is an inter-subunit bond. The χ-bonds provide a second linkage between subunits (polymerized inter-substrate linkages are the first) and form an intermediate termed the "duplex daughter strand", as shown in FIG. 63B.

The duplex daughter strand (FIG. 63B) is a hetero-copolymer with subunits shown in brackets. The primary backbone (-N-)κ, template strand (-N'-)κ, and tether (T) are shown as a duplexed daughter strand, where κ denotes a plurality of repeating subunits. Each subunit of the daughter strand is a repeating "motif" and the motifs have species-specific variability, indicated here by the α superscript. The daughter strand is formed from monomeric substrate construct species selected by a template-directed process from a library of motif species, the monomer substrate of each substrate construct species binding to a corresponding complementary nucleotide on the target template strand. In this way, the sequence of nucleobase residues (i.e., primary backbone) of the daughter strand is a contiguous, complementary copy of the target template strand.

Each tilde (~) denotes a selectively cleavable bond shown here as the inter-substrate bonds. These are necessarily selectively cleavable to release and expand the tethers (and the Xpandomer) without degrading the Xpandomer itself.

The daughter strand is composed of an Xpandomer precursor called the "constrained Xpandomer" which is further composed of tethers in the "constrained configuration". When the tethers convert to their "expanded configuration", the constrained Xpandomer converts to the Xpandomer product. The tethers are constrained by the inter-subunit χ linkages, the substrate attachments and, optionally, the intra-tether linkages if still present. The χ linkage attaches the substrate of a first subunit to the second end moiety tether at the abutting end of a second subunit and is formed by linking the collocated linker groups, $\epsilon$ of the first subunit, and $\mu$ of the second subunit.

The daughter strand can be seen to have two backbones, a "primary backbone", and the backbone of the "constrained Xpandomer". The primary backbone is composed of the contiguously abutted and polymerized monomeric substrates. The "constrained Xpandomer backbone" bypasses the selectively cleavable linkage between the monomer substrates and is formed by $\chi$ bond linked backbone moieties, each backbone moiety being a tether linked to a substrate which then links to the next backbone moiety tether with a $\chi$ bond. It can be seen that the constrained Xpandomer backbone bridges over the selectively cleavable bonds of the primary backbone, and will remain covalently intact when these selectively cleavable bonds are cleaved and the primary backbone is fragmented.

The tether $\chi$ bond (crosslinking of linker groups $\delta$ and $\epsilon$) is generally preceded by enzymatic coupling of the monomer substrates to form the primary backbone, with, for example, phosphodiester bonds between adjacent bases. In the structure shown here, the daughter strand primary backbone has been formed, and the inter-substrate linkages are depicted by a tilde (~) to indicate that they are selectively cleavable. After dissociating or degrading the target template strand, cleaving the selectively cleavable bonds (which include the intra-tether bonds), the constrained Xpandomer is released and becomes the Xpandomer product. Methods for dissociation of the template strand include heat denaturation, or selective digestion with a nuclease, or chemical degradation. A method for selectable cleavage uses nuclease digestion where for example, phosphodiester bonds of the primary backbone are digested by a nuclease and tether-to-tether bonds are nuclease resistant.

FIG. 63C is a representation of the Class VIII Xpandomer product after dissociation of the template strand and after cleavage of the selectively cleavable bonds (including those in the primary backbone and, if not already cleaved, the intra-tether links). The Xpandomer product strand contains a plurality of subunits $\kappa$, where $\kappa$ denotes the $\kappa^{th}$ subunit in a chain of m subunits making up the daughter strand, where $\kappa$=1, 2, 3 to m, where m>10, generally m>50, and typically m>500 or >5,000. Each subunit is formed of a tether in its expanded configuration and is stretched to its length between the $\chi$ linkages of adjacent subunits. The pendant substrate is attached to the tether in each subunit. Each subunit, a subunit motif $\alpha$, contains species-specific genetic information established by template-directed assembly of the Xpandomer intermediate (daughter strand).

Figure 63D:
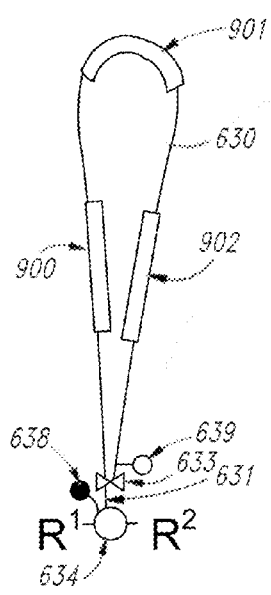
Figure 63E:
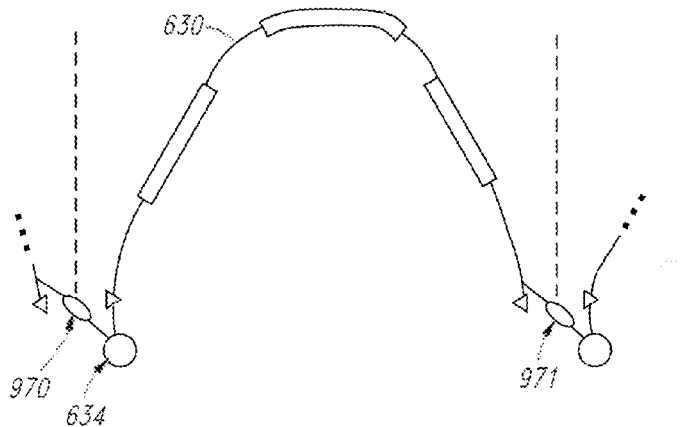

FIG. 63D shows the substrate construct of FIG. 63A as a molecular model, where the monomer substrate member, represented with a nucleobase residue (634), is joined to the tether by a linkage (631) of the tether first end moiety. A second linker group (639), shown as $\delta$ in FIG. 63A, is disposed on the second end moiety at the distal end of the tether. A selectively cleavable intra-tether linkage (633), depicted by the adjoining triangles, is shown that constrains the tether by linking the first and second end moiety. Also attached to the substrate is a linker group (638), shown as $\epsilon$ in FIG. 63A. The linker groups $\epsilon$ (638) and $\delta$ (639) are positioned to not interact and to preferably align near the $R^1$ and $R^2$ sides of the substrate respectively. The tether loop shown here has three reporters (900,901,902), which can also be motif species specific. The cleavable intra-tether crosslink (633) is shown in FIG. 63D and FIG. 63E to be positioned closer to the substrate than the $\delta$ (639). In FIG. 60D and FIG. 60E the positions are switched. This positioning can be in either place and in one embodiment both linker functions may be on a single multifunctional group.

FIG. 63E shows the substrate construct after incorporation into the product Xpandomer. The subunits are cleaved and expanded and are linked by $\chi$ bonds (970,971), depicted as an open oval, formed by linking the linker groups $\delta$ and $\epsilon$ referred to in FIG. 63A. A subunit is indicated by dotted lines vertically bracketing the repeating subunit, as represented by brackets in the accompanying FIG. 63C.

In the Xpandomer product of FIG. 63E, the primary backbone has been fragmented and is not covalently contiguous because any direct bond between the substrates of adjacent subunits has been cleaved. Through the cleavage process, the constrained Xpandomer is released to become the Xpandomer product. The tether members that were formerly in constrained configuration are now in expanded configuration, thereby functioning to linearly stretch out the sequence information of the template target. Expanding the tethers lowers the linear density of the sequence information along the Xpandomer and provides a platform for increasing the size and abundance of reporters which in turn improves signal to noise for detection and decoding of the template sequence.

While the tether (630) is depicted as a reporter construct with three reporter groups, various reporter configurations can be arrayed on the tether, and can comprise single reporters that identify monomer or the tether can be a naked polymer. In some cases, one or more-reporter precursors are arrayed on the tether, and reporters are affinity bound or covalently bound following assembly of the Xpandomer product.

Class IX Monomeric Constructs

Figure 64A:
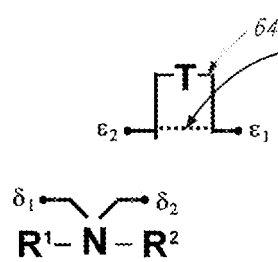
FIGS. 64A through 64E depict a Class IX Xpandomer, Xpandomer intermediate, and substrate construct in a symbolic and graphical language. These precursors are termed RT-NTPs.
Figure 64B:
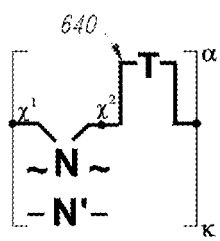
Figure 64C:
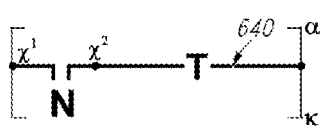

A class IX substrate construct is distinguished from the other RT-NTPs because it has two tether attachment points to which a free tether is attached after the primary backbone has been assembled. FIG. 64 describes Class IX monomeric substrate constructs (a type of RT-NTP), in more detail. FIGS. 64A through 64C are read from left to right, showing first the monomeric substrate construct (Xpandomer precursor having a single nucleobase residue), then the intermediate duplex daughter strand in the center, and on the right the Xpandomer product prepared for sequencing.

As shown in FIG. 64A, the monomeric substrate construct of Class IX has a substrate nucleobase residue, N, with two tether attachment sites, the linker groups $\delta_1$ and $\delta_2$. Also shown is a free tether, T (640), with linker groups $\epsilon_1$ and $\epsilon_2$ of a first and second tether end moiety. The first and second end moieties of the tether constrain the free tether by an intra-tether selectively cleavable crosslink (647) and serves to collocate linker groups $\epsilon_1$ and $\epsilon_2$. The cleavable crosslink is denoted here by dotted line, can indicate, for example, a disulfide bond or a photocleavable linker. This constraint prevents the tether from elongating or expanding and is said to be in its "constrained configuration". Linker groups, $\delta_1$ and $\delta_2$, are attached to the monomer substrate oriented proximate to $R^1$ and $R^2$, respectively. Under template-directed synthesis, substrates form a duplex with the target template and the linker group of one substrate construct, for example $\delta_1$, and the linker group of the abutted substrate construct, for example $\delta_2$, are collocated. Under controlled conditions, these collocated linkers contact the collocated $\epsilon$ linkers on the end of the free tether. Two selective linkages reactions occur, $\epsilon_1$ and $\delta_1$ to form $\chi^1$ and $\epsilon_2$ and $\delta_2$ to form $\chi^2$; the adjacent substrates are now bridged by the constrained tether. Suitable linkage and protection/deprotection chemistries for $\delta$, $\epsilon$, and $\chi$ are detailed in the general monomeric construct description.

$R^1$ and $R^2$ are end groups configured as appropriate for the synthesis protocol in which the substrate construct is used.

For example, $R^1$=5'-phosphate and $R^2$=3'-OH, would find use in a ligation protocol, and $R^1$=5'-triphosphate and $R^2$=3'-OH for a polymerase protocol. Optionally, $R^2$ can be configured with a reversible blocking group for cyclical single-substrate addition. Alternatively, $R^1$ and $R^2$ can be configured with linker end groups for chemical coupling or with no linker groups for a hybridization only protocol. $R^1$ and $R^2$ can be of the general type XR, wherein X is a linking group and R is a functional group.

During assembly, the monomeric substrate construct (without tether) is polymerized on the extendable terminus of the nascent daughter strand by a process of template-directed polymerization using a single-stranded template as a guide. Generally, this process is initiated from a primer and proceeds in the 5' to 3' direction. Generally, a DNA polymerase or other polymerase is used to form the daughter strand, and conditions are selected so that a complementary copy of the template strand is obtained. Linker group $\delta_1$ is now collocated with the linker group $\delta_2$ of the adjacent monomer substrate. After polymerization of the primary backbone, free tethers are crosslinked to form $\chi^1$-bonds and $\chi^2$-bonds between the two tether ends and two the adjacent substrates.

In one embodiment, the free tethers have no sequence information and are termed "naked". In this case, a single linker chemistry can be used so linker groups $\delta_1$ and $\delta_2$ are the same and linker groups $\epsilon_1$ and $\epsilon_2$ are the same with one $\chi$-bond type.

In the embodiment where the free tether comprises base type information (as in reporters) there are species-specific free tethers. Generally, there are four base types that would require four free tether types with the corresponding base information. Several methods can be used to link the correct free tether species to its correct base. In one method, four heterospecific linkage chemistries are used to further differentiate the linker pair $\delta_1$ and $\epsilon_1$, now expressed as $\delta_{1\alpha}$ and $\epsilon_{1\alpha}$ where $\alpha$ is one of four types and form bond types $\chi^{1\alpha}$. $\delta_{1\alpha}$ and $\epsilon_{1\alpha}$ of one $\alpha$ type will bond only with each other. In this method the linker pair $\delta_2$ and $\epsilon_2$ are caused to bond only after the $\delta_{1\alpha}$ and $\epsilon_{1\alpha}$ has been formed. In a second method, different selectively deprotectable protection groups, where each protection group is associated with one linker type, are used to selectively block linker groups. In a first cycle, there is no protection on one base type and its associated free tether type is bonded $\epsilon_1$ to $\delta_1$ to form a $\chi^1$-bond. In a second cycle, one type of protection group is removed from one base type and its associated free tether type is bonded $\epsilon_1$ to $\delta_1$ to form a $\chi$1-bond. This latter cycle is repeated for the next two base types and after it is completed, the linker pair $\delta_2$ and $\epsilon_2$ are caused to bond. Between each step wash steps are included to reduce bonding errors. Without loss of generality, the remaining description will be in terms of $\chi^1$-bonds and $\chi^2$-bonds. Note that after the tether is attached and the $\chi$-bonds are formed, the intra-tether bond may be broken.

As shown in FIG. 64B, the $\chi^1$-bonds provide a linkage between subunits (in addition to the polymerized inter-substrate linkages) and form an intermediate termed the "duplex daughter strand". The primary backbone (~N~)κ, template strand (-N'-)κ, and Tether (T) are shown as a duplexed daughter strand, where κ denotes a plurality of repeating subunits. Each subunit of the daughter strand is a repeating "motif" and the motifs have species-specific variability, indicated here by the α superscript. The daughter strand is formed from monomeric substrate construct species selected by a template-directed process from a library of motif species, the monomer substrate of each substrate construct species binding to a corresponding complementary nucleotide on the target template strand. In this way, the sequence of nucleobase residues (i.e., primary backbone) of the daughter strand is a contiguous, complementary copy of the target template strand.

Each tilde (~) denotes a selectively cleavable bond shown here as the inter-substrate bonds. These are necessarily selectively cleavable to release and expand the tethers (and the Xpandomer) without degrading the Xpandomer itself.

The daughter strand is composed of an Xpandomer precursor called the "constrained Xpandomer" which is further composed of tethers in the "constrained configuration". When the tethers convert to their "expanded configuration", the constrained Xpandomer converts to the Xpandomer product. The tethers are constrained by the $\chi$ linkages to adjacent substrates and optionally, the intra-tether linkages (if still present).

The daughter strand can be seen to have two backbones, a "primary backbone", and the backbone of the "constrained Xpandomer". The primary backbone is composed of the contiguously abutted and polymerized monomeric substrates. The "constrained Xpandomer backbone" bypasses the selectively cleavable linkage between monomer substrates and is formed by $\chi^1$-bond linked backbone moieties, each backbone moiety being a tether linked to a substrate (by a $\chi^2$-bond) which then links to the next backbone moiety tether with a $\chi^1$-bond. It can be seen that the constrained Xpandomer backbone bridges over the selectively cleavable bonds of the primary backbone, and will remain covalently intact when these selectively cleavable bonds are cleaved and the primary backbone is fragmented.

The tether $\chi$ bond (crosslinking of linker groups $\delta$ and $\epsilon$) is generally preceded by enzymatic coupling of the monomer substrates to form the primary backbone, with, for example, phosphodiester bonds between adjacent bases. In the structure shown here, the daughter strand primary backbone has been formed, and the inter-substrate linkages are depicted by a tilde (~) to indicate that they are selectively cleavable. After dissociating or degrading the target template strand, cleaving the selectively cleavable bonds (which include the intra-tether bonds), the constrained Xpandomer is released and becomes the Xpandomer product. Methods for dissociation of the template strand include heat denaturation, or selective digestion with a nuclease, or chemical degradation. A method for selectable cleavage uses nuclease digestion where for example, phosphodiester bonds of the primary backbone are digested by a nuclease and tether-to-tether bonds are nuclease resistant.

FIG. 64C is a representation of the Class IX Xpandomer product after dissociation of the template strand and after cleavage of the selectively cleavable bonds (including those in the primary backbone and, if not already cleaved, the intra-tether links). The Xpandomer product strand contains a plurality of subunits x, where κ denotes the $\kappa^{th}$ subunit in a chain of m subunits making up the daughter strand, where κ=1, 2, 3 to m, where m>10, generally m>50, and typically m>500 or >5,000. Each subunit is formed of a tether (640) in its expanded configuration linked to a monomer substrate and to the $\chi^1$ linkage with the next adjacent subunit. Each subunit, a subunit motif α, contains species-specific genetic information established by template-directed assembly of the Xpandomer intermediate (daughter strand).

Figure 64D:
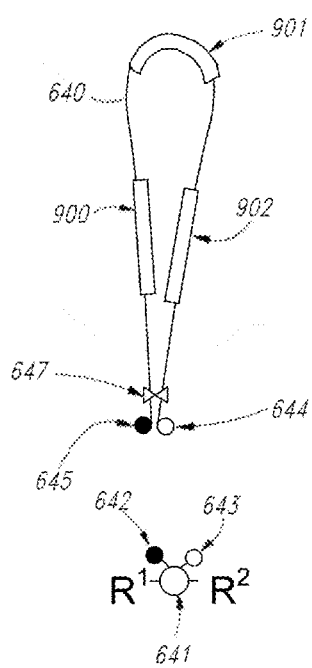

FIG. 64D shows the substrate construct of FIG. 64A as a molecular model, where the monomer substrate member, represented with a nucleobase residue (641), has two linkages (642,643), shown in FIG. 64a as $\delta_1$ and $\delta_2$, that will be attachment points for the free tether. The free tether is shown with two linker groups linker group (644,645), shown as $\epsilon_1$ and $\epsilon_2$ in FIG. 64A, on the first and second end moieties of the tether. A selectively cleavable intra-tether linkage (647) is shown that constrains the tether by linking the first and second end moieties. The linker groups are positioned to foster crosslinking of the tether ends between the monomer substrates and prevent crosslinking across a monomer substrate.

The tether loop shown here has three reporters (900,901, 902), which can also be motif species specific but requires a method to be correctly linked to the correct bases in the primary backbone.

Figure 64E:
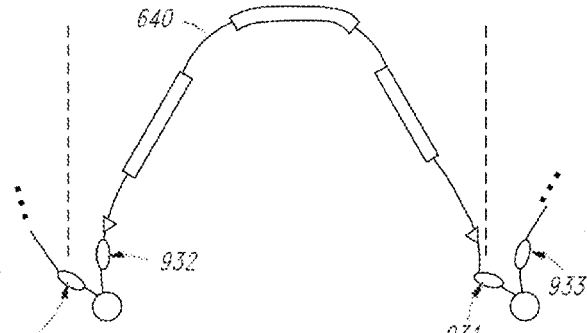

FIG. 64E shows the substrate construct after incorporation into the product Xpandomer. The subunits are cleaved and expanded and are linked by inter-tether $\chi^1$ bonds (930,931), and inter-tether $\chi^2$ bonds (932,933). Each subunit is a tether linked to a monomer substrate and connected on to the next $\chi^1$ bond. A subunit is indicated by dotted lines vertically bracketing the repeating subunit, as represented by brackets in the accompanying FIG. 64C.

In the Xpandomer product of FIG. 64E, the primary backbone has been fragmented and is not covalently contiguous because any direct bond between the substrates of adjacent subunits has been cleaved. Through the cleavage process, the constrained Xpandomer is released to become the Xpandomer product. The tether members that were formerly in constrained configuration are now in expanded configuration, thereby functioning to linearly stretch out the sequence information of the template target. Expanding the tethers lowers the linear density of the sequence information along the Xpandomer and provides a platform for increasing the size and abundance of reporters which in turn improves signal to noise for detection and decoding of the template sequence.

While the tether is depicted as a reporter construct with three reporter groups, various reporter configurations can be arrayed on the tether, and can comprise single reporters that identify monomer or the tether can be a naked polymer. In some cases, one or more reporter precursors are arrayed on the tether, and reporters are affinity bound or covalently bound following assembly of the Xpandomer product.

Figure 65:
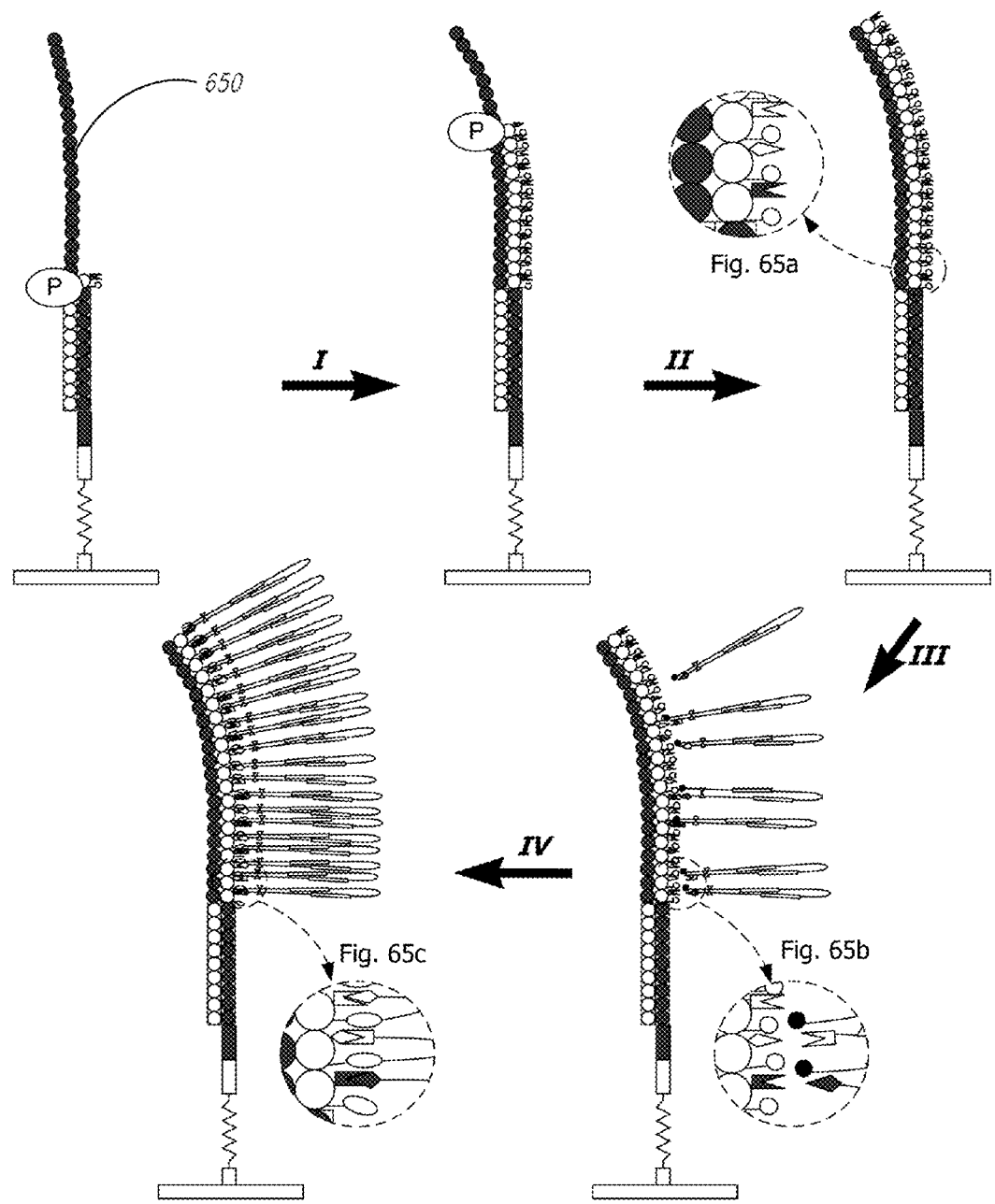
FIG. 65 is a condensed schematic of a method for synthesis of an Xpandomer on an immobilized template using Class IX triphosphate substrate constructs and a polymerase.

FIG. 65 demonstrates a method synthesizing Xpandomers using RT-NTP substrate constructs of Class IX. A target template (650) is first selected and annealed to an immobilized primer. In Step I, the primer is extended by template-directed synthesis of a daughter strand. This process continues in Step II, and in FIG. 65a, a magnified view (dotted arrow) is shown of the daughter strand. Illustrated are the template strand, primer, and polymerized Class IX nucleobase substrate constructs (without tethers), each substrate construct with chemical functionalities, depicted as the lock and key symbols, for chemical addition of tether reagents. The functionalities are selected so that each monomer has a base-specific tether attachment site and a universal attachment site. In step hairpin tethers with four species specific linkers are introduced. The tethers link to the primary backbone in a base specific manner according to the base specific linkers as shown in FIG. 65b, a magnified view (dotted arrow). Here, white and black circles indicate the universal chemical attachment chemistry and diamond and fork shapes indicate the base-specific attachment chemistries. In Step IV and FIG. 65c, a magnified view (dotted arrow), after all base specific linking is complete, the universal linkers are caused to form bonds. Note that the universal linkers on both the tethers and the primary backbone are in close proximity to their base specific linker counterpart to avoid linking errors. The chemical attachment of the tether reagents is shown as having been completed, and a constrained Xpandomer has been formed on the template. The Xpandomer is then released (not shown) by dissociating from the template, and cleaving the selectively cleavable bonds (of primary backbone and intra-tether bonds).

Class X Monomeric Constructs

Figure 66A:
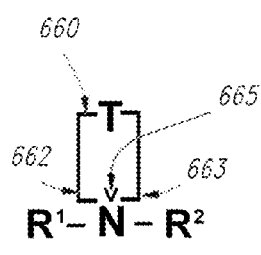
FIGS. 66A through 66E depict a Class X Xpandomer, Xpandomer intermediate, and substrate construct in a symbolic and graphical language. These precursors are termed XNTPs.
Figure 66B:
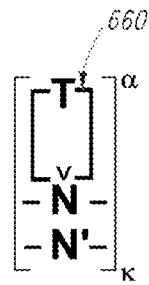
Figure 66C:
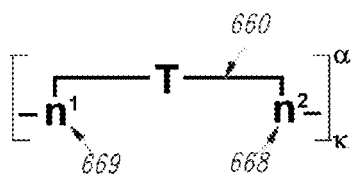

Class X substrate constructs, also called XNTPs, differ from the RT-NTPs in that the tether is contained within each monomer substrate to form an intra-substrate tether, each XNTP substrate having a selectively cleavable bond within the substrate which, once cleaved, enables the expansion of the constrained tether. In FIG. 66, we describe Class X monomeric substrate constructs in more detail. FIGS. 66A through 66C are read from left to right, showing first the monomeric substrate construct (Xpandomer precursor having a single nucleobase residue), then the intermediate duplex daughter strand in the center, and on the right the Xpandomer product prepared for sequencing.

As shown in FIG. 66A, the monomeric substrate construct of Class X has a substrate nucleobase residue, N, that has two moieties (662,663) separated by a selectively cleavable bond (665), each moiety attaching to one end of a tether (660). The tether ends can attach to the linker group modifications on the heterocycle, the ribose group, or the phosphate backbone. The monomer substrate also has an intra-substrate cleavage site positioned within the phosphororibosyl backbone such that cleavage will provide expansion of the constrained tether. For example, to synthesize a Class X ATP monomer, the amino linker on 8-[(6-Amino)hexyl]-amino-ATP or N6-(6-Amino)hexyl-ATP can be used as a first tether attachment point, and, a mixed backbone linker, such as the non-bridging modification (N-1-aminoalkyl)phosphoramidate or (2-aminoethyl)phosphonate, can be used as a second tether attachment point. Further, a bridging backbone modification such as a phosphoramidate (3' O—P—N 5') or a phosphorothiolate (3' O—P—S 5'), for example, can be used for selective chemical cleavage of the primary backbone.

$R^1$ and $R^2$ are end groups configured as appropriate for the synthesis protocol in which the substrate construct is used. For example, $R^1$=5'-triphosphate and $R^2$=3'-OH for a polymerase protocol. The $R^1$ 5' triphosphate may include mixed backbone modifications, such as an aminoethyl phosphonate or 3'-O—P—S-5' phosphorothiolate, to enable tether linkage and backbone cleavage, respectively. Optionally, $R^2$ can be configured with a reversible blocking group for cyclical single-substrate addition. Alternatively, $R^1$ and $R^2$ can be configured with linker end groups for chemical coupling. $R^1$ and $R^2$ can be of the general type XR, wherein X is a linking group and R is a functional group.

During assembly, the monomeric substrate construct is polymerized on the extendable terminus of the nascent daughter strand by a process of template-directed polymerization using a single-stranded template as a guide. Generally, this process is initiated from a primer and proceeds in the 5' to 3' direction. Generally, a DNA polymerase or other polymerase is used to form the daughter strand, and conditions are selected so that a complementary copy of the template strand is obtained.

As shown in FIG. 66B, the nucleobase residues are polymerized one subunit to the next and form an intermediate termed the "duplex daughter strand". The primary backbone (-N-)κ, template strand (-N'-)κ, and Tether (T) are shown as a duplexed daughter strand, where κ denotes a plurality of repeating subunits. Each subunit of the daughter strand is a repeating "motif" and the motifs have species-specific variability, indicated here by the α superscript. The daughter strand is formed from monomeric substrate construct species selected by a template-directed process from a library of motif species, the monomer substrate of each substrate construct species binding to a corresponding complementary nucleotide on the target template strand. In this way, the sequence of nucleobase residues (i.e., primary backbone) of the daughter strand is a contiguous, complementary copy of the target template strand.

The ("V") shown in FIG. 66B above the nucleobase residue denotes a selectively cleavable bond that divides the substrate into the first and second moieties. Upon cleaving, the first moiety (669) of one subunit will remain linked to the second moiety (668) of the adjacent subunit and within a subunit, each moiety will be bridged, one to the other by the tether. These are necessarily selectively cleavable to release and expand the tethers (and the Xpandomer) without degrading the Xpandomer itself.

The daughter strand has two backbones, a "primary backbone", and the backbone of the "constrained Xpandomer". The primary backbone is composed of the contiguously abutted and polymerized monomeric substrates. The "constrained Xpandomer backbone" bypasses the selectively cleavable linkage within the monomer substrate and is formed by the inter-substrate bonds linking the backbone moieties, each backbone moiety being a tether linked to two moieties of the still intact nucleobase residue. The constrained Xpandomer backbone bridges over the selectively cleavable bond within each monomer, and will remain covalently intact when these selectively cleavable bonds are cleaved and monomers are fragmented into portions $n^1$ and $n^2$ shown in FIG. 66C.

Cleaving is preceded by enzymatic coupling of the monomer substrates to form the primary backbone, with, for example, phosphodiester or mixed backbone bonds between adjacent bases. In the structure shown here, the daughter strand primary backbone has been formed. After dissociating or degrading the target template strand and cleaving the selectively cleavable bonds, the constrained Xpandomer is released and becomes the Xpandomer product. Methods for dissociation of the template strand include for example heat denaturation.

FIG. 66C is a representation of the Class X Xpandomer product after dissociation of the template strand and after cleavage of the selectively cleavable bonds. The Xpandomer product strand contains a plurality of subunits κ, where κ denotes the $κ^{th}$ subunit in a chain of m subunits making up the daughter strand, where κ=1, 2, 3 to m, where m>10, generally m>50, and typically m>500 or >5,000. Each subunit is formed of a tether in its expanded configuration linked to portions $n^1$ and $n^2$ of a monomer substrate, and each subunit is linked to the next by the monomer polymerization bonds. Each subunit, a subunit motif α, contains species-specific genetic information established by template-directed assembly of the Xpandomer intermediate (daughter strand).

Figure 66D:
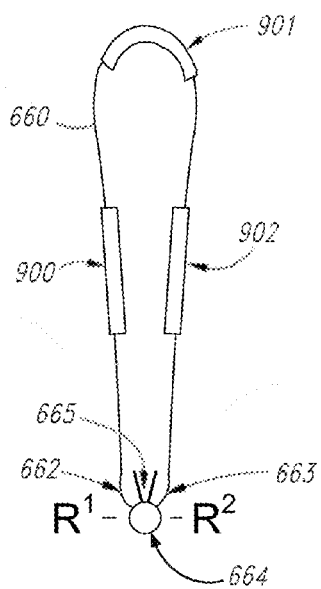

FIG. 66D shows the substrate construct as a molecular model, where the nucleobase member (664) is joined to a first and second moiety of the nucleobase, each moiety with an attachment site to the tether (662,663). The tether (660) comprises reporter groups (900,901,902). A selectively cleavable bond separating the two moieties of the nucleobase is denoted by a "V" (665).

Figure 66E:
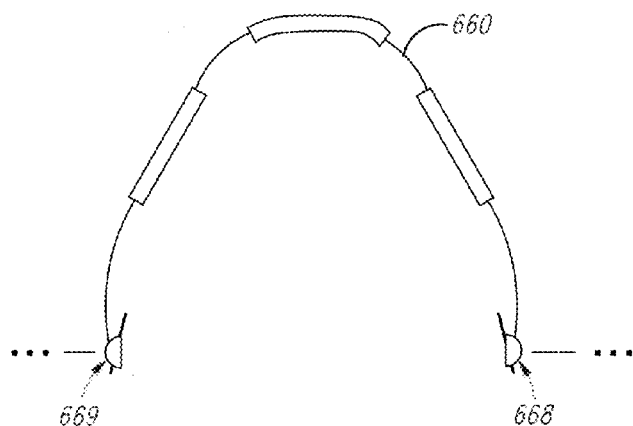

FIG. 66E shows the Xpandomer product. The subunits comprise the expanded tether (660) attached to nucleobase portions (669,668), shown as $n^1$ and $n^2$ in FIG. 66C, each subunit joined by inter-nucleobase bonds. Through the cleavage process, the constrained Xpandomer is released to become the Xpandomer product. The tether members that were formerly in constrained configuration, are now in expanded configuration, thereby functioning to linearly stretch out the sequence information of the template target. Expanding the tethers lowers the linear density of the sequence information along the Xpandomer and provides a platform for increasing the size and abundance of reporters which in turn improves signal to noise for detection and decoding of the template sequence.

While the tether is depicted as a reporter construct with three reporter groups, various reporter configurations can be arrayed on the tether, and can comprise single reporters that identify monomer or the tether can be a naked polymer. In some cases, one or more reporter precursors are arrayed on the tether, and reporters are affinity bound or covalently bound following assembly of the Xpandomer product.

Figure 67:
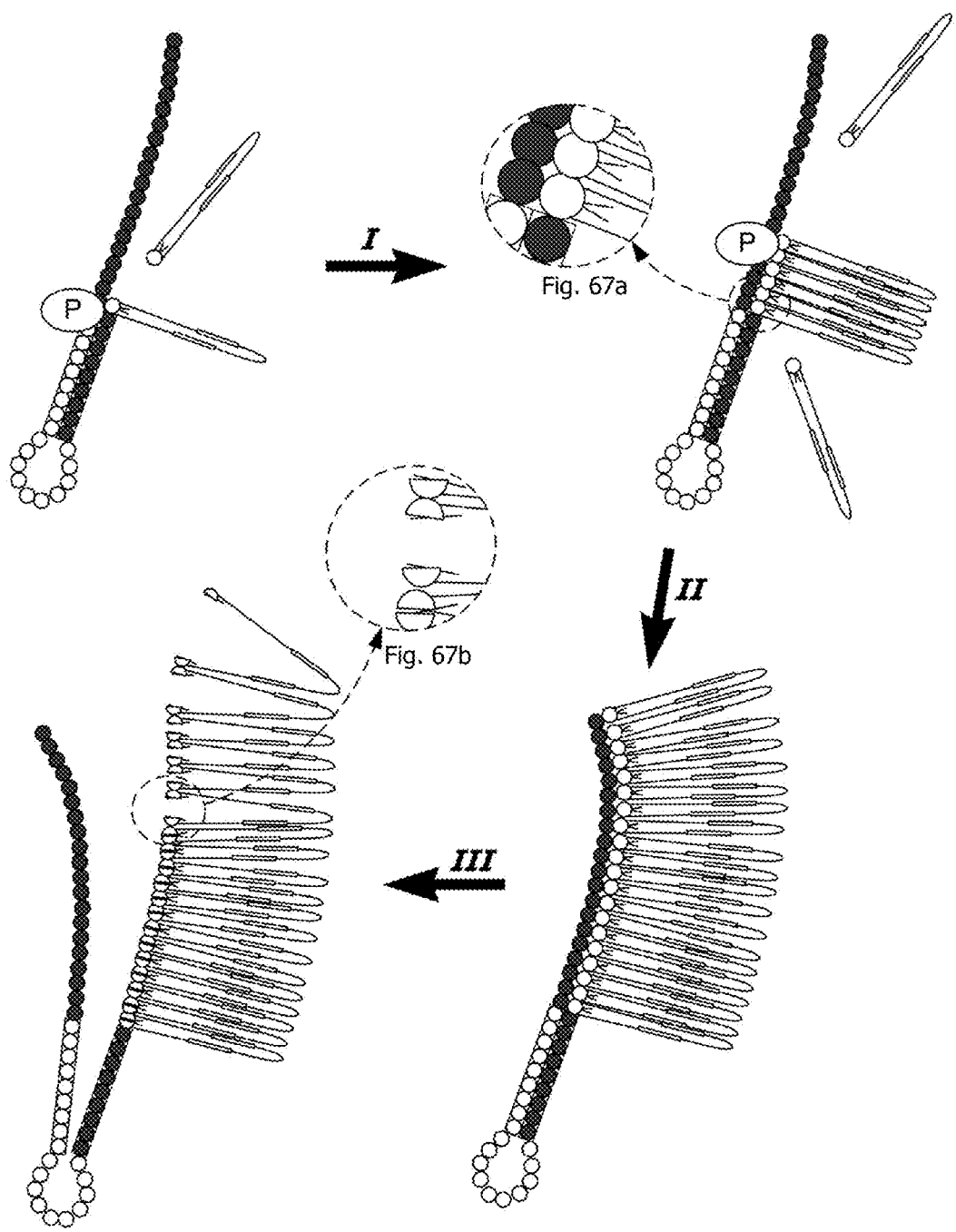
FIG. 67 is a condensed schematic of a method for synthesis of an Xpandomer by solution polymerization using a hairpin primer and Class X triphosphate substrate constructs.

FIG. 67 shows a method for assembling an Xpandomer with the XNTP substrate constructs of Class X. In the first view, a hairpin primer is used to prime a template and the template is contacted with a polymerase and Class X monomer substrates. Polymerization is shown in Step I to extend the nascent daughter strand processively by template-directed addition of monomer substrates. The magnified view (FIG. 67a) illustrates this in more detail. The daughter strand complementary to the template strand is shown to be composed of modified nucleobase substrates with internal cleavage site ("V"). In Step II, the process of forming the Xpandomer intermediate is completed, and in Step III, a process of cleavage, dissociation of the intermediate and expansion of the daughter strand is shown as underway. In the magnified view (FIG. 67b), internal cleavage of the nucleobase substrates is shown to relieve the constraint on the tethers, which expand, elongating the backbone of the Xpandomer.

EXAMPLE 1

Synthesis of a Chimeric 2 mer Xprobe "Ca" with Selectively Cleavable Ribosyl-5'-3' Internucleotide Bond Oligomeric Substrate constructs are composed of probe members and tether members and have a general "probe-loop" construction. Probe member synthesis is accomplished using well established methods of solid phase oligomer synthesis. In these methods, addition of nucleobases to a nascent probe chain on a resin is accomplished with phosphoramidite chemistry (U.S. Pat. Nos. 4,415,732 and 4,458,066) for example, and milligrams or grams of synthetic oligomer can be economically synthesized using readily available automated synthesizers. Typical solid-phase oligonucleotide synthesis involves reiteratively performing four steps: deprotection, coupling, capping, and oxidation. However, at least one bond in the probe of a class I Xprobe substrate construct is a selectively cleavable bond, and at least two probe moieties are modified for acceptance of a tether member. The selectively cleavable bond is located between the probe moieties selected for tether attachment (i.e., "between" should not be limited to mean "between adjacent nucleobase members" because the first and second points of tether attachment need only be positioned anywhere on a first and second moiety of the probe, respectively, the moieties being joined by the selectively cleavable bond). In this example, a ribosyl 5'-3' internucleotide bond, which is selectively cleavable by Ribonuclease H, is the selectively cleavable bond and the two points of tether attachment are the first and second nucleobase residues of a 2 mer probe.

Synthesis of linker modified Xprobes is achieved using commercially available phosphoramidites, for example, from Glen Research (Sterling, Va., USA), BioGenex (San Ramon, Calif., USA), Dalton Chemical Laboratories (Toronto, Canada), Thermo Scientific (USA), Link Technologies (UK), and others, or can be custom synthesized. Well established synthesis methods can be used to prepare the described probe wherein the 3' nucleobase, which for this example is an amino modifier C6 deoxyadenosine, is first attached to a universal support using 5'-Dimethoxytrityl-N-6-benzoyl-N8-[6-(trifluoroacetylamino)-hex-1-yl]-8-amino-2'-deoxyAdenosine-3'-[(2-cyanoethyl)-(N,N-diisopropyl)]-phosphoramidite followed by the addition of an amino modifier C6 cytidine using 5'-Dimethoxytrityl-N-dimethylformamidine-5-[N(trifluoroacetyl aminohexyl)-3-acrylimido]-Cytidine, 3'-[(2-cyanoethyl)-(N,N-diisopropyl)]-phosphoramidite, wherein the 5' cytidine is a ribonucleotide. The addition of a chemical phosphorylation reagent followed by standard cleavage, deprotection, and purification methods completes the synthesis. The dinucleotide product is a 5' phosphate (aminoC6-Cytosine)(aminoC6-deoxyAdenosine) 3' with a centrally cleavable ribosyl-5', 3' bond and amino linkers on each base.

The Xprobe tether for this example is constructed from bis-N-succinimidyl-[pentaethylene glycol]ester (Pierce, Rockford Ill.; Product No 21581). The linker amines of the modified pCA oligomer are crosslinked with bis(NHS)PEG5 according to the manufacturer's instructions. A product of the expected molecular weight for the circularized PEG-probe construct is obtained.

EXAMPLE 2

Synthesis of a 4 mer Xprobe "TATA" with Selectively Cleavable Phosphorothiolate Bond Xprobe 4 mers can be synthesized with a phosphorothiolate linkage as the selectively cleavable bond. For the following example, synthesis of a 5' phosphate (dT) (aminoC6-dA) (dT) (aminoC6-dA) 3' tetranucleotide is described.

A 5' mercapto-deoxyThymidine is first prepared as described by Mag et al. ("Synthesis and selective cleavage of an oligodeoxynucleotide containing a bridged internucleotide 5'-phosphorothioate linkage", Nucl Acids Res 19:1437-41, 1991). Thymidine is reacted with two equivalents of p-toluenesulfonyl chloride in pyridine at room temperature, and the resulting 5'-tosylate is isolated by crystallization from ethanol. The tosylate is converted to a 5'-(S-trityl)-mercapto-5'-deoxy-thymidine with five equivalents of sodium tritylthiolate (prepared in situ). The 5'-(S-trityl)-mercapto-thymidine nucleotide is purified and reacted with 2-cyanoethoxy-bis-(N,N-diisopropylamino-phosphane) in the presence of tetrazole to make the 3'-O-phosphoramidite building block.

To begin automated synthesis, amino modifier C6 deoxyadenosine is first attached to a universal support using 5'-Dimethoxytrityl-N-6-benzoyl-N8-[6-(trifluoroacetylamino)-hex-1-yl]-8-amino-2'-deoxyAdenosine-3'-[(2-cyanoethyl)-(N,N-diisopropyl)]-phosphoramidite followed by the addition of mercaptothymidine phosphoramidite prepared above. Prior to adding the next amino C6 dA phosphoramidite, the S-trityl group is first deprotected with 50 mM aqueous silver nitrate and the resin is washed with water. The resin is typically then treated with a reducing agent such as DTT to eliminate incidental disulfides formed during the cleavage. The column is then again washed with water and with acetonitrile, and the free thiol is reacted under standard conditions with the amino C6 deoxyAdenosine phosphoramidite in the presence of tetrazole, thereby forming "ATA" with a bridging S3'→P5' phosphorothiolate bond between the terminal deoxyAdenosine and the 3-mercapto-Thymidine. In the next cycle, standard deoxyThymidine phosphoramidite is added. Finally, the addition of a chemical phosphorylation reagent followed by standard cleavage, deprotection, and purification methods completes the synthesis. The tetranucleotide product is a 5' phosphate (dT) (aminoC6-dA) (dT) (aminoC6-dA) 3'.

The phosphorothiolate bond is selectively cleavable, for example, with AgCl, acid or with iodoethanol (Mag et al., "Synthesis and selective cleavage of an oligodeoxynucleotide containing a bridged internucleotide 5'-phosphorothioate linkage", Nucleic Acids Research, 19(7):1437-1441, 1991). Because the selectively cleavable bond is between the second and third nucleobases, the tether is designed to bridge this bond, and may be attached to any two nucleobases (or any two primary backbone attachment points) on either side of the selectively cleavable bond. Methods for zero linker and linker chemistries include, for example, provision of linkers with primary amines used in the synthesis of the oligomer, as described in Example 1. The amine modified linkers on the "TATA" oligomer are typically protected during oligomer synthesis and are deprotected in the normal course of completing oligonucleotide synthesis.

The Xprobe tether for this example is then constructed from bis-epoxide activated poly(ethylene glycol) diglycidyl ether (SigmaAldrich, St. Louis Mo., Product No 475696). The epoxide reaction of the amines with the activated PEG end groups is conducted in dilute solution to minimize any competing concatenation reaction. Similar reactivity is obtained with mixed anhydrides or even acid chlorides, and can employ heterobifunctional linkage groups so as to orient the attachment of the tether. Tethered reaction products are separated by preparative HPLC and characterized by mass spectroscopy. A product of the approximate molecular weight for the circularized 4 mer PEG-probe construct (about 2.5 Kd) is obtained. A distribution of PEG tethers with approximate $M_n$=500 is obtained with this method. This corresponds to a tether of about 40 Angstroms (at about 3.36 Å/PEG unit).

EXAMPLE 3

Synthesis of a 3 mer Xprobe "CTA" with Selectively Cleavable 5'-3' Phosphodiester Bond Xprobes can also be synthesized with a phosphodiester linkage as the selectively cleavable bond. For the following example, synthesis of a 5' phosphate (aminoC6-dC) (aminoC6-dT) (dA) 3' trinucleotide with a non-bridging phosphorothioate modification is described. Phosphodiester bonds are attacked by a variety of nucleases. A phosphorothioate bond, with non-bridging sulfur, is used as a nuclease-resistant bond in this example.

For automated synthesis in the 3' to 5' direction, a CPG immobilized deoxyAdenosine solid support is used (5'-Dimethoxytrityl-N-benzoyl-2'-deoxyAdenosine, 3'-succinoyl-long chain alkylamino-CPG 500). In the first cycle, amino modifier C6 deoxyThymidine phosphoramidite (5'-Dimethoxytrityl-5-[N-(trifluoroacetylaminohexyl)-3-acrylimido]-2'-deoxyUridine, 3'-[(2-cyanoethyl)-(N,N-diisopropyl)]-phosphoramidite) is coupled. Before capping, the immobilized dA is reacted with Sulfurizing Reagent (Glen Research, Sterling Va.; Cat No 40-4036), also known as Beaucage Reagent, following the manufacturer's protocol. The reagent is generally added through a separate port in the synthesizer. Following thiolation, amino modified C6 deoxy Cytidine (5'-Dimethoxytrityl-N-dimethylformamidine-5-[N-(trifluoroacetylaminohexyl)-3-acrylimido]-2'-deoxy Cytidine, 3'-[(2-cyanoethyl)-(N,N-diisopropyl)]-phosphoramidite) is coupled. Before capping, the immobilized dC is reacted with Sulfurizing Reagent (Glen Research, Sterling Va.; Cat No 40-4036), also known as Beaucage Reagent, following the manufacturer's protocol. The resulting "CTA" 3 mer has a phosphorothioate bond between the T and the A, and a phosphodiester bond between the C and the T. The addition of a chemical phosphorylation reagent followed by standard cleavage, deprotection, and purification methods completes the synthesis.

Resistance of phosphorothioate linkages to nuclease attack is well characterized, for example by Matsukura et al ("Phosphorothioate analogs of oligodeoxynucleotides: inhibitors of replication and cytopathic effects of human immunodeficiency virus", PNAS 84:7706-10, 1987), by Agrawal et al ("Oliogodeoxynucleoside phosphoramidates and phosphorothioates as inhibitors of human immunodeficiency virus", PNAS 85:7079-83, 1988), and in U.S. Pat. No. 5,770,713. Both C and T are linker or zero-linker modified, the derivatization serving for attachment of a tether member.

EXAMPLE 4

Synthesis of a 3 mer Xprobe "ATA" with Selectively Cleavable 5' N—P—O 3' Phosphoramidate Bond Amino modifier C6 deoxyadenosine, is first attached to a universal support using 5'-Dimethoxytrityl-N-6-benzoyl-N8-[6-(trifluoroacetylamino)-hex-1-yl]-8-amino-2'-deoxyAdenosine-3'-[(2-cyanoethyl)-(N,N-diisopropyl)]-phosphoramidite followed in the next cycle by the addition of MMT-blocked 5' amino-dT (5' monomethooxytritylamino-2'-deoxyThymidine). After deblocking, the 5'-amino end is reacted with amino modified C6 deoxyAdenosine phosphoramidite under standard conditions. The addition of a chemical phosphorylation reagent followed by standard cleavage, deprotection, and purification methods completes the synthesis. The trinucleotide 5' (aminoC6-dA) (O—P—N) (dT) (O—P—O) (aminoC6-dA) 3' has a phosphoramidate bond between the 5' aminoC6-dA and the penultimate dT.

This phosphoramidate bond is selectively cleavable under conditions in which phosphodiester bonds remain intact by treating the oligomer with 80% acetic acid as described by Mag et al. ("Synthesis and selective cleavage of oligodeoxynucleotides containing non-chiral internucleotide phosphoramidate linkages", Nucl. Acids Res. 17: 5973-5988, 1989). By attaching a tether to bridge the 5'N—P—O phosphoramidate bond, an Xpandomer containing dimers of this type can be expanded by selective cleavage of the phosphoramidate bonds of the primary backbone.

EXAMPLE 5

Synthesis of a 6 mer Xprobe "CACCAC" with an Internal Photocleavable Bond

After standard 3' to 5' synthesis with unmodified deoxyCytosine and deoxyAdenosine phosphoramidites, amino-modified C6 dC (5'-Dimethoxytrityl-N-dimethylformamidine-5-[N-(trifluoroacetylaminohexyl)-3-acrylimido]-2'-deoxy Cytidine, 3'-[(2-cyanoethyl)-(N,N-diisopropyl)]-phosphoramidite; Glen Research; Cat No 10-1019) is coupled, thereby forming a CAC trimer. For the next cycle, a photocleavable linker is coupled (3-(4,4'-Dimethoxytrityl)-1-(2-nitrophenyl)-propan-1-yl-[(2-cyanoethyl)-(N,N-diisopropyl)]-phosphor'amidite; Glen Research; Cat No 10-4920). In the next cycle, a second amino-modified dC is added followed by two final rounds of standard addition of dA and dC phosphoramidites, respectively. The resulting product, "CAC-pc-CAC" contains amino-linkers at the third and fourth base positions, and can be modified by addition of a tether that bridges the selectively cleavable bond formed by the photocleavable nitrobenzene construct between the two amino-modified bases. Selective cleavage of a photocleavable linker modified phosphodiester backbone is disclosed by Sauer et al. ("MALDI mass spectrometry analysis of single nucleotide polymorphisms by photocleavage and charge-tagging", Nucleic Acids Research 31, 11e63, 2003), Vallone et al. ("Genotyping SNPs using a UV-photocleavable oligonucleotide in MALDI-TOF MS", Methods Mol. Bio. 297:169-78, 2005), and Ordoukhanian et al. ("Design and synthesis of a versatile photocleavable DNA building block, application to phototriggered hybridization", J. Am. Chem. Soc. 117, 9570-9571, 1995), for example.

EXAMPLE 6

Synthesis of an Xmer Substrate Construct

Xmer substrate constructs are closely related in design and composition to Xprobes. An Xmer library is synthesized for example by 5'-pyrophosphorylation of Xprobes. Established procedures for pyrophosphate treatment of 5'-monophosphates include, for example, Abramova et al. ("A facile and effective synthesis of dinucleotide 5'-triphoshates", Bioorganic Medicinal Chemistry 15: 6549-55, 2007). In this method the terminal monophosphate of the oligomer is activated as necessary for subsequent reaction with pyrophosphate by first reacting the terminal phosphate as a cetyltrimethylammonium salt with equimolar quantities of triphenylphosphine ($Ph_3P$) and 2,2'-dipyridyl disulfide ($PyS)_2$ in DMF/DMSO, using DMAP (4-dimethylaminopyridine) or 1-MeIm (1-methylimidazole) as a nucleophilic catalyst. The product is precipitated with $LiClO_4$ in acetone and purified by anion exchange chromatography.

A variety of other methods can be considered for robust synthesis of 5' triphosphate Xmers. As described by Burgess and Cook (Chem Rev 100(6):2047-2060), these methods include, but are not limited to, reactions using nucleoside phosphoramidites, synthesis via nucleophilic attack of pyrophosphate on activated nucleoside monophosphates, synthesis via nucleophilic attack of phosphate on activated nucleoside pyrophosphate, synthesis via nucleophilic attack of diphosphate on activated phosphate synthon, synthesis involving activated phosphites or phosphoramidites derived from nucleosides, synthesis involving direct displacement of 5'-O-leaving groups by triphosphate nucleophiles, and biocatalytic methods. One specific method that produced polymerase compatible dinucleotide substrates uses N-methylimidazole to activate the 5' monophosphate group; subsequent reaction with pyrophosphate (tributylammonium salt) produces the triphosphate (Bogachev, 1996). In another procedure, trinucleotide phosphoramidates have been synthesized by Kayushin (Kayushin A L et al. 1996. A convenient approach to the synthesis of trinucleotide phosphoramidites. Nucl Acids Res 24:3748-55).

EXAMPLE 7

Xpandomer Synthesis with Polymerase-Phosphoramidate Cleavage

Synthesis of an Xpandomer is performed using a substrate construct prepared with 5'-triphosphate and 3'-OH ends. U.S. Pat. No. 7,060,440 to Kless describes use of polymerases to polymerize triphosphate oligomers, and the method is adapted here for synthesis of Xpandomers. The substrate construct consists of 2 mer probe member "pppCA" with inter-nucleotide 5' N—P—O phosphoramidate selectively cleavable bond and a PEG tether loop construct. A template strand and companion primer is synthesized and is purified before use. The sequence: "TGTGTGTGTGTGTGTGTGT-GATCTACCGTCCGTCCC" (SEQ ID NO:2) is used as a template. The sequence "5'GGGACGGACGGTAGAT" (SEQ ID NO:3) is used as a primer. A 5' terminal HEX (5' hexachloro-fluorescein) on the primer is used as a label. Annealing of the primer and template forms a template with duplex primer and free 3'-OH and 5' terminal single stranded overhang of twenty bases in length. The substrate constructs and Sequenase™ brand recombinant T7 DNA polymerase (US Biochemicals Corp., Cleveland, Ohio) are then added and polymerization is continued for 30 min under conditions adjusted for optimum polymerization. A sample of the polymerization reaction is mixed with gel loading buffer and is electrophoresed on a 20% TBE acrylamide gel (Invitrogen, USA) along with a no polymerase negative control and a MW marker to confirm Xmer polymerization.

The Xpandomer intermediate is treated with 80% acetic acid for 5 hrs at room temperature according to the procedure of Mag et al. ("Synthesis and selective cleavage of oligodeoxyribonucleotides containing non-chiral internucleotide phosphoramidate linkages", *Nucl. Acids Res.*, 17: 5973-88, 1989) to selectively cleave the phosphoramidate bonds, which is likewise confirmed by electrophoresis.

EXAMPLE 8

Xpandomer Synthesis with Polymerase-Phosphorothioate Cleavage

Synthesis of an Xpandomer is performed using a substrate construct prepared with 5'-triphosphate and 3'-OH ends. U.S. Pat. No. 7,060,440 to Kless describes use of polymerases to polymerize triphosphate oligomers. The substrate construct is a "pppCA". The substrate construct is designed with a selectively cleavable inter-nucleotide phosphorothiolate backbone linkage and a PEG 2000 tether loop construct. A template strand and companion primer is synthesized and is purified before use. The sequence: "TGTGTGTGTGTGT-GTGTGTGATCTACCGTCCGTCCC" (SEQ ID NO:2) is used as a target template. The sequence "5'GGGACGGACG-GTAGAT" (SEQ ID NO:3) is used as a primer. A 5' terminal HEX (5' hexachloro-fluorescein) on the primer is used as a label. Annealing of the primer and template forms a template with duplex primer and free 3'-OH and 5' terminal single stranded overhang of twenty bases in length. The substrate constructs and Therminator™ DNA Polymerase (New England Biolabs, USA) are then added with buffer and salts optimized for polymerization. Polymerization continued for 60 min under conditions adjusted for optimum polymerization. A sample of the polymerization reaction is mixed with gel loading buffer and is electrophoresed on a 20% TBE acrylamide gel (Invitrogen, USA) along with a no polymerase negative control and a MW marker to confirm Xmer polymerization.

The phosphorothiolate bonds of the Xpandomer intermediate are selectively cleavable, for example, with AgCl, acid or with iodoethanol (Mag et al., "Synthesis and selective cleavage of an oligodeoxynucleotide containing a bridged internucleotide 5'-phosphorothioate linkage", Nucleic Acids Research, 19(7):1437-1441, 1991). Cleavage is confirmed by gel electrophoresis.

EXAMPLE 9

Chimeric Xpandomer Synthesis with Ligase

Synthesis of an Xpandomer is performed using a substrate construct prepared with 5'-monophosphate and 3'-OH ends. The substrate construct is a chimeric "5' p dC rA~dC dA 3'" 4 mer where the 5' penultimate adenosine is a ribonucleotide and the rest of the substrate is deoxyribonucleotide. The substrate construct is designed with one selectively cleavable inter-nucleotide ribosyl 5'-3' phosphodiester bonds (as shown by the "~") and a PEG 2000 tether loop construct, where the tether is attached at the terminal "C" and "A" of the 4 mer. A template strand and companion primer is synthesized and is purified before use. The sequence: "TGTGTGTGTGTGT-GTGTGTG ATCTACCGTCCGTCCC" (SEQ ID NO:2) is used as a target template. The sequence "5'GGGACGGACG-GTAGAT" (SEQ ID NO:3) is used as a primer. A 5' terminal HEX (5' hexachloro-fluorescein) on the primer is used as a label. Annealing of the primer and template forms a template with duplex primer and free 3'-OH and 5' terminal single stranded overhang of twenty bases in length. The substrate constructs and T4 DNA ligase (Promega Corp, Madison, Wis., USA; Cat No M1801) are then added with temperature, buffer and salts optimized for transient probe hybridization and ligation. Ligation is continued for 6 hours. A sample of the ligation reaction is mixed with gel loading buffer and is electrophoresed on a 20% TBE acrylamide gel (Invitrogen, Carlsbad, Calif., USA) along with a no ligase negative control and a MW marker to confirm Xprobe ligation.

In a second step, the Xpandomer intermediate is treated with Ribonuclease H to cleave the RNase labile 5'-3' phosphodiester bond to produce an Xpandomer product which is likewise confirmed by gel electrophoresis.

EXAMPLE 10

Preparation of an Alpha-Phosphate Linker Construct

Tether linkers may also be attached to the phosphorothioate S diester or to a phosphoramidate N-amide, as is discussed by Agrawal ("Site specific functionalization of oligonucleotides for attaching two different reporter groups", *Nuc. Acids Res.* 18:5419-23, 1990). Disclosed is a method for functionalization of two different inter-nucleotide backbone linkages: aminohexyl phosphoramidate (N-1 amino alkyl) linker and phosphorothioate. The C6 amine prepared as described by Agrawal is used as a linker for synthesis of an inter-nucleobase tether construct of the present invention. Derivatization of N3'-P5' bonds has also been reported (Sinyakov et al., "Functionalization of the oligonucleotides containing an internucleotide phosphoramidate bond", *Russian J Bioorganic Chem*, 29:100-102, 2003).

EXAMPLE 11

Heterobifunctional Routes to Tether Constructs

Synthesis of modified oligomers containing a selectively cleavable bond are described in Examples 1-5. Here, a 4 mer with a C6-amino modified base in the second position and 4-formylbenzoate-linker modified base in the third position of the 4 mer is prepared by standard oligomer synthetic chemistry. The second and third bases are separated by a selectively cleavable bond selected from ribosyl 5'-3' phosphodiester bond, deoxyribosyl 5'-3' phosphodiester bond, phosphorothiolate bond (5' O—P—S 3' or 5' S—P—O 3'), phosphoramidate bond (5' O—P—N 3' or 5' N—P—O 3'), or a photocleavable bond. The amine of the C6 linker is reacted with Sulfo EGS to form an active ester NHS group. Heterobifunctional tether loop synthesis is then accomplished by reacting the modified probe member with a tether functionalized with amine and hydrazide end terminal groups. A tether-circularized end product is obtained.

EXAMPLE 12

Dye-Labeled Tether Construct

An Xprobe substrate construct with a single reporter is prepared. A 2 mer with C6 amines on the first and second bases is first synthesized using standard methods. The first and second bases are separated by a selectively cleavable bond selected from ribosyl 5'-3' phosphodiester bond, deoxyribosyl 5'-3' phosphodiester bond, phosphorothiolate bond (5' O—P—S 3' or 5' S—P—O 3'), phosphoramidate bond (5' O—P—N 3' or 5' N—P—O 3'), or a photocleavable bond. In this example, the tether is a species-specific, end-functionalized PEG 2000 molecule with a single internal linker group, which in this case is a maleimido-functionalized linker located mid-tether. The reporter is a dye-labeled dendrimer attached to the maleimido linker group on the tether via a sulfhydryl moiety on the dendrimer. The resulting reporter construct thereby contains one reporter on the tether. A cystamine dendrimer (Dendritic Nanotechnologies, Mt Pleasant, Mich., USA; Cat No DNT-294 G3) with a 5.4 nm diameter and 16 surface amines per half-dendrimer) is used as the reporter. By attaching specific dyes, or combinations of dyes to the amine groups on the dendrimer the substrate construct species is uniquely labeled for identification.

EXAMPLE 13

Peptide-Labeled Tether Construct

An Xprobe substrate construct with a single reporter is prepared. A 2 mer with C6 amines on the first and second bases is first synthesized using standard methods. The first and second bases are separated by a selectively cleavable bond selected from ribosyl 5'-3' phosphodiester bond, deoxyribosyl 5'-3' phosphodiester bond, phosphorothiolate bond (5' O—P—S 3' or 5' S—P—O 3'), phosphoramidate bond (5' O—P—N 3' or 5' N—P—O 3'), or a photocleavable bond. In this example, the tether is a species-specific, end-functionalized PEG 2000 molecule with a single internal linker group, which in this case is a maleimido-functionalized linker located mid-tether. The reporter is a dye-labeled dendrimer attached to the maleimido linker group on the tether via a sulfhydryl moiety on the dendrimer. The resulting reporter construct thereby contains one reporter on the tether. A cystamine dendrimer (Dendritic Nanotechnologies, Mt Pleasant, Mich., USA; Cat No DNT-294 G3) with a 5.4 nm diameter and 16 surface amines per half-dendrimer) is used as the reporter. By attaching specific dyes, or combinations of dyes to the amine groups on the dendrimer the substrate construct species is uniquely labeled for identification. By attaching specific peptides to the dendrimer, which is amine functionalized, the substrate construct species is tagged for later identification. The dimensions and the charge of the attached peptides are used as detection characteristics in a detection apparatus.

EXAMPLE 14

Heterobifunctional Route to Tether Reporter Constructs

Substrate constructs with multiple reporters are prepared. A library of 2 mers with C6-amino modified base in the first position and 4'-formylbenzoate modified base (4FB) in the second position of the 2 mer is prepared by standard organic chemistry. The first and second bases are separated by a selectively cleavable bond selected from ribosyl 5'-3' phosphodiester bond, deoxyribosyl 5'-3' phosphodiester bond, phosphorothiolate bond (5' O—P—S 3' or 5' S—P—O 3'), phosphoramidate bond (5' O—P—N 3' or 5' N—P—O 3'), or a photocleavable bond. The amine is reacted with Sulfo EGS to form an active ester NHS group. In a second step, a species-specific bifunctional amine reporter segment (segment 1) is reacted with the active NHS group and a species-specific bifunctional hydrazide reporter segment (segment 4) is reacted with 4FB. Next, the free amine on segment 1 is reacted with Sulfo EGS to form an active ester NHS. A species-specific heterobifunctional cap consisting of a pair of reporter segments (segments 2 and 3) with amine and 4FB end groups is then reacted with the construct, closing the tether loop.

The resulting reporter construct thereby contains four reporters on the tether construct. In this example, the reporters are polyamine dendrons with a cystamine linker to covalently bind to each polymer segment by thioether bonds (Dendritic Nanotechnologies, Mt Pleasant Mich., USA; Cat No DNT-294: G4, 4.5 nm diameter, 32 surface amines per half-dendrimer) and the polymer members are end-functionalized PEG 2000, each with an internal linker group. Each tether segment is comprised of a single reporter. With four directionally coupled segments, $2^4$ possible reporter code combinations are available.

EXAMPLE 15

Heterobifunctional Route to Reporter Constructs with Post-Synthesis Labeling Substrate constructs with multiple reporters are prepared. A 4 mer with C6-amino modified base in the first position and 4'-formylbenzoate modified base (4FB) in the second position of the 2 mer is prepared by standard organic chemistry. The second and third bases are separated by a selectively cleavable bond selected from ribosyl 5'-3' phosphodiester bond, deoxyribosyl 5'-3' phosphodiester bond, phosphorothiolate bond (5' O—P—S 3' or 5' S—P—O 3'), phosphoramidate bond (5' O—P—N 3' or 5' N—P—O 3'), or a photocleavable bond. The amine is reacted with Sulfo EGS to form an active ester NHS group. In a second step, a species-specific bifunctional amine reporter segment (segment 1) is reacted with the active NHS group and a species-specific bifunctional hydrazide reporter segment (segment 4) is reacted with 4FB. Next, the free amine on segment 1 is reacted with Sulfo EGS to form an active ester NHS. A species-specific heterobifunctional cap consisting of a pair of reporter segments (segments 2 and 3) with amine and 4FB end groups is then reacted with the construct, closing the tether loop.

The resulting reporter construct thereby contains four reporters on the tether construct. In this example, post labeling of the tether construct is described. Covalently bound to each tether segment is a 16 mer oligomer which is used for reporter attachment. Each tether segment is composed in part of a functionalized PEG molecule. The reporter is dye labeled polyamine dendrimer with a cystamine linker (Dendritic Nanotechnologies, Mt Pleasant Mich., USA; Cat No DNT-294: G5, 4.5 nm diameter, 64 surface amines per half-dendrimer) for coupling to the 16 mer oligomer probe. Following assembly of the Xpandomer, the dye-labeled dendrimers are hybridized to the oligomeric tether segments. This labeling approach is analogous to the method described by DeMattei et al. ("Designed Dendrimer Syntheses by Self-Assembly of Single-Site, ssDNA Functionalized Dendrons", *Nano Letters*, 4:771-77, 2004).

EXAMPLE 16

Dye-Labeled Reporter Elements

Referring to Examples 14 and 15, the surface amines of the dendrimeric reporter elements are labeled by active ester chemistry. Alexa Fluor 488 (green) and Alexa Fluor 680 (red) are available for one-step attachment as sNHS active esters from Molecular Probes (Eugene Oreg.). The density and ratio of the dyes are varied to produce a distinctive molecular tag on each reporter element.

EXAMPLE 17

Multi-State Reporter Elements

Various palettes of dyes are selected by techniques similar to those used in M-FISH and SKY, as is known to those skilled in the art, and conjugated to a dendrimeric reporter. Thus, the reporter element of each tether constitutes a "spectral address", whereby a single dendrimeric construct with a multiplicity of dye binding sites can create a plurality of reporter codes. Referring to the tether construct described in Examples 14 and 15, a 5-state spectral address results in 625 reporter code combinations.

EXAMPLE 18

PEG-5000 Spacer Tether

Tether segments are constructed of a durable, aqueous/organic solvent soluble polymer that possesses little to no binding affinity for SBX reactants. Modified PEG 5000 is used for the flexible tether spacers that flank a poly lysine 5000 reporter. The free PEG ends are functionalized for attachment to the probe member. The polymer is circularized by crosslinking to probe attachment points using heterobifunctional linker chemistry.

EXAMPLE 19

Preparation of a Mass Tag Reporter Composition

A tether is synthesized as follows: Cleavable mass tags are covalently coupled to poly-1-lysine peptide functionalized G5 Dendrimers (Dendritic Nanotechnologies, Mt Pleasant Mich.) using standard amine coupling chemistry. The G5 Dendrimers are ~5.7 nm in diameter and provide 128 reactive surface groups. A string of ten G5 Dendrimers functionalized with 10,000 Molecular Weight polylysine peptides provides about 100,000 reporter attachment sites collectively in a ~57 nm dendrimer segment. A total of about 10,000 mass tags are available for detection on the fully assembled segment, assuming only 10% occupancy of the available binding sites. Using the 3 mass tag reporter coding method described previously (FIG. 37), about 3,300 copies of each mass tag is available for measurement. As an alternative, a single G9 Dendrimer (with 2048 reactive groups) functionalized with 10,000 Molecular Weight poly-lysine has available about 170,000 mass tag attachment sites in a 12 nm segment of the reporter construct.

To detect a sequence with mass tags, a method for controlled release of the mass tag reporters at the point of measurement by use of photocleavable linkers is used. Sequential fragmentation of the tether is not necessary. Mass tag reporters associated with each subunit of the Xpandomer polymer are measured in one step. For example, a set of 13 mass tag reporters that range from 350 Daltons to 710 Daltons (i.e., a 30 Dalton ladder of mass tag reporters) has 286 combinations of three mass tags each. In this manner, any one of 256 different 4 mers is associated with only one particular combination of 3 mass tag reporters. The encoded sequence information of the Xpandomer is readily detected by mass spectroscopy of the subunits. Because the subunits of the Xpandomer are spatially well separated, the Xpandomer handling and detection technology need not be highly sophisticated.

EXAMPLE 20

Direct Analysis of Unlabelled Substrate Constructs

A substrate construct library is synthesized; the tethers contain no reporters. Following preparation of an Xpandomer product, the individual bases of the Xpandomer product are analyzed by electron tunneling spectroscopy.

EXAMPLE 21

Hybridization-Assisted Analysis of Unlabeled Substrate Constructs

An oligomeric substrate construct library is synthesized; the tethers contain no reporters. Following preparation of an Xpandomer product, a complete set of labeled probes are then hybridized to the Xpandomer product and the duplexed probes are analyzed sequentially.

EXAMPLE 22

Synthesis of a DeoxyAdenosine Triphosphate with Lys-Cys-PEG-Polyglutamate-Peg-Cys-COOH Tether Lysine with a BOC-protected amino side chain is immobilized on a resin and reacted with a cysteine residue using standard peptide synthesis methods. The amino sidechain of the lysine will be the epsilon reactive functional group of the RT-NTP tether (see Class VI, VII). The cysteine will form a first half of an intra-tether disulfide bond. The deprotected amine on the cysteine is modified with SANH (Pierce-Thermo Fisher, USA; Cat No 22400: Bioconjugate Toolkit) to form a hydrazide.

Separately, a spacer segment is prepared from bis-amino PEG 2000 (Creative PEGWorks, Winston Salem N.C.; Cat No PSB 330) by functionalization of the free amines with C6-SFB (Pierce-Thermo Fisher, USA; Cat No 22400: Bioconjugate Toolkit), forming a bis-4FB PEG spacer segment; the product is purified.

The bis-4FB PEG spacer segment is then coupled to the hydrazide linker on the cysteine, leaving a 4FB group as the terminal reactive group, and the resin is washed.

Separately, a polyglutamate segment (each glutamate derivatized at the gamma-carboxyl with 5 PEO units of methyl-capped PEG) is prepared. The c-terminus is converted to an amine with EDC coupling agent and diamino hexane. SANH is used to form a di-hydrazide terminated polyglutamate segment, and the product is purified. The dihydrazide-terminated polyglutamate segment is reacted with the terminal 4FB group on the resin, forming a terminal hydrazide, and the resin is washed.

Separately, a PEG-2000 spacer segment (with amine and carboxyl ends, Creative PEGWorks; PHB-930) is reacted with SFB to generate a 4FB terminal group. This spacer segment is reacted with the hydrazide group on the resin, forming a carboxyl-terminated chain. The resin is again washed.

A cysteine residue is coupled to the free carboxyl using standard peptide synthesis reagents. The terminal carboxyl of the cysteine is O-Benzyl protected. The resulting product is again washed and then cleaved from the resin. The free carboxyl generated by cleavage is then modified with EDC, aminohexyl, and SANH to form a reactive hydrazide.

Separately, a C6 amine modified deoxyAdenosine triphosphate (N-6-(6-amino)hexyl-dATP, Jena Bioscience, Jena D E; Cat No NU-835) is treated with SFB (Pierce Bioconjugate Toolkit, Cat No 22419) to form a 4FB functional group. By combining the modified base with the reactive hydrazide of the preceding steps, a tether-probe substrate construct is assembled. The BOC of the lysine side chain is removed before use. Under generally oxidizing conditions, the cysteines associate to form an intra-tether disulfide bond, stabilizing the tether in a constrained, compact form.

EXAMPLE 23

Synthesis of a RT-NTP Triphosphate Library

Tethered nucleotide triphosphate bases A, T, C and G with intra-tether —S—S— bond are prepared as described in Example 22, but charge and physical parameters of the PEGylated glutamate segments used for each base are selected to provide a distinct reporter characteristic.

EXAMPLE 24

Xpandomer Synthesis by SBE Using Polyglutamate tethered RT-NTPs

Modified RT-NTP Adenosine and Guanosine nucleotide triphosphates with disulfide intra-tether bonds are prepared. The bases are further modified so as to be reversibly blocked at the 3'-position. Allyl-based reversible blocking chemistry is as described by Ruparel ("Design and synthesis of a 3'-β-allyl photocleavable fluorescent nucleotide as a reversible terminator for DNA sequencing by synthesis" *PNAS*, 102: 5932-37, 2005). The tethers of the modified bases are constructed with delta functional group and epsilon functional group generally as shown in FIG. 61. The delta functional group is a carboxyl of a pendant cysteine of the tether and the epsilon functional group is a side chain amine of a lysine near the attachment of the tether to the purines. The tethers are further modified so as to contain nucleobase-specific modified polyglutamate segments.

The sequence TCTCTCTCTCTCTCATCTACCGTCCGTCCC" (SEQ ID NO:4) is used as a template. The sequence "5'GGGACGGACGGTAGAT" (SEQ ID NO:3) is used as a primer. A 5' terminal HEX (5' hexachloro-fluorescein) on the primer is used as a label. The method of Xpandomer synthesis is essentially as described for FIG. 61. In a first priming cycle of SBE, the modified nucleobase is added with Klenow polymerase under conditions adapted for polymerization and a single base is added to the nascent daughter strand on the 3' OH end of the primer. Because the substrate construct is blocked at the 3' position, no further polymerization occurs.

The amino side chain (epsilon) linker group on the first RT-NTP added is capped and will remain so throughout the SBE reaction. The terminal carboxyl group of the tether is deprotected and the 3' OH on the substrate is unblocked; the complex is washed before a next round of SBE.

In a second cycle of SBE, another nucleobase is polymerized to the nascent Xpandomer Intermediate. The $\chi$ bond is formed between the free amine of the epsilon linker group on the first nucleobase and the carboxyl linker group on the tether of the second nucleobase using EDC and Sulfo-NHS as a crosslinking agent (Pierce Cat No 22980 and 24510). The carboxyl on the delta linker group of the tether is deprotected and the 3' OH on the substrate is unblocked; the complex washed before a next round of SBE.

The cycle of SBE can be repeated multiple times, thereby forming an Xpandomer intermediate in the constrained configuration. Each tether in the growing chain of $\chi$-bonded nucleobases is in the constrained Xpandomer configuration.

EXAMPLE 25

Nuclease and TCEP Cleavage to Form Class X Xpandomer

The Xpandomer intermediate of Example 24 is cleaved with nuclease, forming an Xpandomer product composed of individual nucleobases linked by tether segments and $\chi$ bonds. The nuclease also degrades the template and any associated primer, freeing the product. The intra-tether disulfide linkages are cleaved by the addition of a reducing agent (TCEP, Pierce Cat. No. 20490).

The Xpandomer product is filtered and purified to remove truncated synthons and nuclease digestion side products. Detection and analysis of the linearized Xpandomer can be done using a wide variety of existing and next generation methods.

EXAMPLE 26

Synthesis of a DeoxyAdenosine Triphosphate with an Intratether Photocleavable Linker Glycine is immobilized on a resin and reacted with a cysteine. The cysteine amino group is then deprotected and reacted with a glutamate, the glutamate with a sidechain modified with a photolabile linker terminating in a OBenzyl protected carboxyl, such as a 2-nitroveratrylamine linker adapted from that described by Holmes et al. ("Reagents for combinatorial organic synthesis: development of a new O-nitrobenzyl photolabile linker for solid phase synthesis", *J Org Chem*, 60:2318-19, 1995). The cysteine will be the "epsilon functional group" of the RT-NTP tether. The deprotected amine on the glutamate is modified with SANH (Pierce-Thermo Fisher, USA; Cat No 22400: Bioconjugate Toolkit) to form a hydrazide. The sidechain of the glutamate will form a photocleavable intra-tether linker following synthesis of the tether.

Separately, a spacer segment is prepared from bis-amino PEG 2000

(Creative PEGWorks, Winston Salem, N.C., USA; Cat No PSB 330) by functionalization of the free amines with C6-SFB (Pierce Bioconjugate Toolkit, Cat No 22423), forming a bis-4FB PEG spacer segment, and the product is purified. The bis-4FB PEG spacer segment is then coupled to the hydrazide linker on the glutamate, leaving a 4FB group as the terminal reactive group, and the resin is washed.

Separately, a polyglutamate segment (with t-butyl protected sidechains) is prepared. The C-terminus is converted to an amine with EDC coupling agent and diamino hexane.

SANH is used to form a di-hydrazide terminated polyglutamate segment, and the product is purified. The dihydrazide-terminated polyglutamate segment is reacted with the terminal 4FB group on the resin, forming a terminal hydrazide on the resin, and the resin is washed.

A PEG-2000 spacer segment (with free amino and FMOC-protected amino ends; Cat No PHB-0982, Creative PEG-Works) is modified with C6 SFB to form a 4FB and FMOC-amino modified PEG spacer segment. The 4FB end is reacted with the hydrazide group on the resin, forming an FMOC amino-terminated chain. The resin is again washed.

A lysine residue is coupled to the free amine of the spacer by a peptide bond. The lysine residue is protected on the sidechain by BOC and the alpha-amine of the lysine is protected by FMOC. The OBenzyl terminal carboxyl of the photocleavable linker and the BOC-protected sidechain of the lysine are then deprotected and crosslinked with EDC/Sulfo-NHS to circularize the tether.

The resulting product is again washed and then cleaved from the resin. The free glycine carboxyl generated by cleavage is then modified with EDC, aminohexyl, and SANH to form a reactive hydrazide.

Separately, a C6 amine modified deoxyAdenosine triphosphate (N-6-(6-amino)hexyl-dATP, Jena Bioscience, Jena D E; Cat No NU-835) is treated with SFB (Pierce Bioconjugate Toolkit, Cat No 22419) to form a 4FB functional group. By combining the modified base with the reactive hydrazide of the preceding steps, a tether-probe substrate construct is assembled. The photocleavable intra-tether linker stabilizes the tether in a constrained, compact form. The FMOC is then removed and the free terminal amine is reacted with Sulfo-EMCS (Pierce; Cat No 22307) to introduce a terminal maleimido functional group.

EXAMPLE 27

Xpandomer Synthesis by SBE Using Photocleavable RT-NTPs

Modified RT-NTP Adenosine and Guanosine nucleotide triphosphates with photocleavable intra-tether bonds are prepared. The bases are further modified so as to be reversibly blocked at the 3'-position. Allyl-based reversible blocking chemistry is as described by Ruparel ("Design and synthesis of a 3'-O-allyl photocleavable fluorescent nucleotide as a reversible terminator for DNA sequencing by synthesis", PNAS, 102:5932-37, 2005). The tethers of the modified bases are constructed with delta functional group and epsilon functional group generally as shown in FIG. 61. The delta linker group is an amine of a terminal pendant lysine of the tether and the epsilon linker group is a sulfhydryl of a cysteine near the point of attachment of the tether. The tethers are further modified so as to contain species-specific modified polyglutamate segments.

The sequence TCTCTCTCTCTCTCTCATCTACCGTC-CGTCCC" (SEQ ID NO:4) is used as a template. The sequence "5'GGGACGGACGGTAGAT" (SEQ ID NO:3) is used as a primer. A 5' terminal HEX (5' hexachloro-fluorescein) on the primer is used as a label. The method of Xpandomer synthesis is essentially as described for FIG. 61. In a first priming cycle of SBE, the modified nucleobase (A) is added with Klenow polymerase under conditions adapted for polymerization and a single base is added to the nascent daughter strand on the 3'-OH end of the primer. Because the substrate construct is blocked at the 3' position, no further polymerization occurs. The immobilized primer-template complex is then washed to remove unreacted substrate.

The sulfhydryl side chain (epsilon) linker group on the first RT-NTP added is capped and will remain so throughout the SBE reaction. The terminal amino group of the tether is deprotected and the 3'-OH on the substrate is unblocked; the complex is washed before the next round of SBE.

In a second cycle of SBE, another nucleobase (G) is polymerized to the nascent Xpandomer intermediate. The χ-bond is formed between the amino (delta linker group) on the first nucleobase and the sulfhydryl (epsilon linker group) on the tether of the second base using crosslinking reagent GMBS (Pierce; Cat No 22309). The delta amino linker group on the second RT-NTP is deprotected and the 3' OH of the substrate is unblocked; the complex is washed before the next round of SBE.

The cycle of SBE can be repeated multiple times, thereby forming an Xpandomer intermediate in the constrained configuration. Each tether in the growing chain of χ-bonded nucleobases is in the constrained Xpandomer configuration.

EXAMPLE 28

Nuclease and Photo Cleavage to Form Class X Xpandomer

The Xpandomer intermediate of Example 27 is cleaved with nuclease, forming an Xpandomer product composed of individual nucleobases linked by tether segments and χ bonds. The nuclease also degrades the template and any associated primer, freeing the product. The intra-tether photocleavable linkages are cleaved by exposure to a UV light.

The Xpandomer product is filtered and purified to remove truncated synthons and nuclease digestion side products. Detection and analysis of the linearized Xpandomer can be done using a wide variety of existing and next generation methods.

EXAMPLE 29

Synthesis of an RT-NTP Tether In Situ

Using methods of standard peptide synthesis on a solid support, a peptide is prepared having the structure (Resin-C)-Glu-Cys-(Gly-Ala)$_{10}$-Pro-Ser-Gly-Ser-Pro-(Ala-Gly)$_{10}$-Cys-Lys (SEQ ID NO:5). The terminal amine is reacted with SANH (Pierce, Cat No 22400) to create a hydrazide linker.

Separately, a C6 amine modified deoxyAdenosine triphosphate (N-6-(6-amino)hexyl-dATP, Jena Bioscience, Jena D E; Cat No NU-835) is treated with SFB (Pierce Bioconjugate Toolkit, Cat No 22419) to form a 4FB functional group. By combining the modified base with the reactive hydrazide of the preceding steps, a tether-probe substrate construct is assembled.

The construct is then cleaved from the resin. Following deprotection and under generally oxidizing conditions, the cysteines associate to form an intra-tether disulfide bond, stabilizing the beta hairpin, which contains a terminal free carboxyl (a pendant delta linker group on the tether) and a lysine near the point of tether attachment (the sidechain amine an epsilon linker group).

The disulfide is representative of the intra-tether stabilization depicted in Classes II, III, VI, VII, and VIII substrate constructs (see FIGS. 8 and 9), although illustrated here with more specific reference to monomeric substrate constructs of Classes VI, VII and VIII. The length of the unfolded tether, assuming a residue C—C peptide bond length of 3.8 Å, is about 10 nm, but assumes a compact shape due to hydrogen bonding in the beta-hairpin.

As described by Gellman ("Foldamers, a manifesto", Acc Chem Res 31:173-80, 1998), a broad variety of polymers, not merely peptides, can be folded into compact shapes. Such polymers include oligopyridines, polyisocyanides, polyisocyanates, poly(triarylmethyl)methacrylates, polyaldehydes, polyproline, RNA, oligopyrrolinones, and oligoureas, all of which have exhibited the capacity to fold into compact secondary structures and expand under suitable conditions. Therefore, the peptide examples presented here are representative of a much larger class of tether chemistries, where constraints on the unexpanded tether can include hydrogen bonding and hydrophobic interactions, for example, as well as intra-tether crosslinks.

EXAMPLE 30

Xpandomer Synthesis Using Xprobes

In one SBX embodiment, an Xprobe library of 256 4 mer Xprobes is presented to a surface tethered and elongated single strand DNA target for hybridization. The hybridization step continues under a precise thermal cycling routine for promoting long Xprobe chains. Weakly-bound, non-specific probe-target duplexes are removed by a simple wash step, again under precise thermal control. Enzymatic ligation is performed to link any Xprobe chains along the target DNA followed by a second wash. By repeating the hybridization/wash/ligation/wash cycle, longer ligated sequences grow at multiple loci along the target DNA until replication of target template is mostly complete.

Unfilled gaps along the target DNA are filled using a well established DNA polymerase and ligase based gap filling process (Lee, "Ligase Chain Reaction", Biologicals, 24(3): 197-199, 1996). Nucleotides incorporated into the gaps have a unique reporter code to indicate a gap nucleotide. The completed Xpandomer intermediate, which is composed of the original DNA target with complementarily duplexed and ligated Xprobes with occasional 1, 2 or 3 nucleotide gap fillers, is cleaved to produce an Xpandomer. The cleavable linker for this example is a 3' O—P—N 5' substrate backbone modification. Selective cleavage is catalyzed by the addition of acetic acid at room temperature.

The Xpandomer is filtered and purified to remove truncated products and is subsequently elongated to form a linear structure of linked reporter codes. Detection and analysis of the Xpandomer product can be done using a wide variety of existing methods.

EXAMPLE 31

Xntp Xpandomer Synthesis Using Polymerase

Synthesis of a Class X Xpandomer is performed using a modified 8-[(6-amino)hexyl]-amino-deoxyAdenosine triphosphate substrate construct having a mixed backbone consisting of a non-bridging 2-aminoethyl phosphonate and a bridging phosphorothiolate (3' O—P—S 5') at the alpha phosphate. An intranucleotide tether is attached to the 2-aminoethyl phosphonate linker and to a C6 amino linker on the 8-[(6-amino)hexyl]-amino-deoxyATP. The sequence TTTTTTTTTTTTTTTTTTTATCTACCGTCCGTCCC" (SEQ ID NO:6) is used as a template. The sequence "5'GGGACGGACGGTAGAT" (SEQ ID NO:3) is used as a primer. A 5' terminal HEX (5' hexachloro-fluorescein) on the primer is used as a label. Annealing of the primer and template forms a template with duplex primer and free 3'-OH and 5' terminal single stranded overhang of twenty bases in length. The substrate constructs and polymerase are then added and polymerization is continued for 60 min under conditions adjusted for optimum polymerization. A sample of the polymerization reaction is mixed with gel loading buffer and is electrophoresed on a 20% TBE acrylamide gel (Invitrogen, USA) along with a no polymerase negative control and a MW marker to confirm XNTP polymerization.

The Xpandomer intermediate is treated with divalent cation (see Mag et al. 1991. "Synthesis and selective cleavage of an oligodeoxynucleotide containing a bridged internucleotide 5'-phosphorothioate linkage", Nucleic Acids Research, 19(7):1437-1441) to selectively cleave the phosphorothiolate bonds between the tether attachment and the deoxyribose, which is confirmed by electrophoresis.

EXAMPLE 32

Xntp Xpandomer Synthesis Using Polymerase

Synthesis of a Class X Xpandomer is performed using a modified $N^6$-(6-amino)hexyl-deoxyAdenosine triphosphate substrate construct having a mixed backbone consisting of a non-bridging (N-1-aminoalkyl) phosphoramidate and a bridging phosphorothiolate (3' O—P—S 5') at the alpha phosphate. An intranucleotide tether is attached to the N-1-aminoalkyl group and to a C6 amino linker on the $N^6$-(6-amino)hexyl-deoxyATP. The sequence TTTTTTTTTTTTTTTTTTTTATCTACCGTCCGTCCC" (SEQ ID NO:6) is used as a template. The sequence "5'GGGACGGACGGTAGAT" (SEQ ID NO:3) is used as a primer. A 5' terminal HEX (5' hexachloro-fluorescein) on the primer is used as a label. Annealing of the primer and template forms a template with duplex primer and free 3'-OH and 5' terminal single stranded overhang of twenty bases in length. The substrate constructs and polymerase are then added and polymerization is continued for 60 min under conditions adjusted for optimum polymerization. A sample of the polymerization reaction is mixed with gel loading buffer and is electrophoresed on a 20% TBE acrylamide gel (Invitrogen, USA) along with a no polymerase negative control and a MW marker to confirm XNTP polymerization.

The Xpandomer intermediate is treated with iodoethanol (see Gish et al ("DNA and RNA sequence determination based on phosphorothioate chemistry", Science, 240(4858): 1520-1522, 1988) or by cleavage with divalent metal cations as described by Vyle et al ("Sequence- and strand-specific cleavage in oligodeoxyribonucleotides and DNA containing 3'-thiothymidine". Biochemistry 31(11): 3012-8, 1992) to selectively cleave the phosphorothiolate bonds between the tether attachment and the deoxyribose, which is confirmed by electrophoresis.

EXAMPLE 33

Xntp Xpandomer Synthesis Using Ligase

Synthesis of an Class X Xpandomer is performed using a modified 8-[(6-amino)hexyl]-amino-deoxyAdenosine monophosphate substrate construct having a mixed backbone consisting of a non-bridging 2-aminoethyl phosphonate and a bridging phosphoramidate (3'-O—P—N-5') at the alpha phosphate. An intranucleotide tether is attached to the 2-aminoethyl linker and to a C6 amino linker on the 8-[(6-amino)hexyl]-amino-deoxyAMP. The sequence TTTTTTTTTTTTTTTTTTTTATCTACCGTCCGTCCC" (SEQ ID NO:6) is used as a template. The sequence "5'GGGACGGACGGTAGAT" (SEQ ID NO:3) is used as a primer. A 5' terminal HEX (5' hexachloro-fluorescein) on the primer is used as a label. Annealing of the primer and template forms a template with duplex primer and free 3'-OH and 5' terminal single stranded overhang of twenty bases in length. The substrate constructs and ligase are then added and ligation is continued for 5 hours under conditions adjusted for ligation. A sample of the ligation reaction is mixed with gel loading buffer and is electrophoresed on a 20% TBE acrylamide gel (Invitrogen, USA) along with a no polymerase negative control and a MW marker to confirm XNTP ligation.

The Xpandomer intermediate is treated with 80% acetic acid for 5 hrs at room temperature according to the procedure of Mag et al ("Synthesis and selective cleavage of oligodeoxyribonucleotides containing non-chiral internucleotide phosphoramidate linkages", *Nucl. Acids Res.* 17: 5973-88, 1989) to selectively cleave the phosphoramidate bonds between the tether attachment point and the deoxyribose, which is confirmed by electrophoresis.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for sequencing a target nucleic acid, comprising:
   a) providing a daughter strand produced by a template-directed synthesis, the daughter strand comprising a plurality of subunits coupled in a sequence corresponding to a contiguous nucleotide sequence of all or a portion of the target nucleic acid, wherein the daughter strand is formed from a plurality of oligomer or monomer substrate constructs, wherein the individual subunits of the daughter strand comprise a tether, at least one probe or nucleobase residue, and at least one selectively cleavable bond, wherein the tether is incorporated into the individual subunits of the daughter strand after formation of the daughter strand from the plurality of oligomer or monomer substrate constructs, and wherein the tether, upon cleavage of the at least one cleavable bond, permits lengthening of the subunits of the daughter strand;
   b) cleaving the at least one selectively cleavable bond to yield an Xpandomer of a length longer than the plurality of the subunits of the daughter strand, the Xpandomer comprising the tethers and reporter elements for parsing genetic information in a sequence corresponding to the contiguous nucleotide sequence of all or a portion of the target nucleic acid; and
   c) detecting the reporter elements of the Xpandomer.

2. The method of claim 1, wherein the reporter elements for parsing the genetic information are associated with the tethers of the Xpandomer.

3. The method of claim 1, wherein the reporter elements for parsing genetic information are associated with the daughter strand prior to cleavage of the at least one selectively cleavable bond.

4. The method of claim 1, wherein the reporter elements for parsing genetic information are associated with the Xpandomer after cleavage of the at least one selectively cleavable bond.

5. The method of claim 1, wherein the Xpandomer further comprises all or a portion of the at least one probe or nucleobase residue.

6. The method of claim 5, wherein the reporter elements for parsing the genetic information are or are associated with the at least one probe or nucleobase residue.

7. The method of claim 1, wherein the at least one selectively cleavable bond is a covalent bond.

8. The method of claim 1, wherein the at least one selectively cleavable bond is an intra-tether bond.

9. The method of claim 1, wherein the at least one selectively cleavable bond is a bond between or within probes or nucleobase residues of the daughter strand.

10. The method of claim 1, wherein the at least one selectively cleavable bond is a bond between the probes or nucleobase residues of the daughter strand and a target template.

11. The method of claim 1, wherein the Xpandomer comprises the following structure:

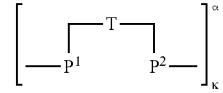

wherein

T represents the tether;

$P^1$ represents a first probe moiety;

$P^2$ represents a second probe moiety;

κ represents the $κ^{th}$ subunit in a chain of m subunits, where m is an integer greater than three; and α represents a species of a subunit motif selected from a library of subunit motifs, wherein each of the species comprises sequence information of the contiguous nucleotide sequence of a portion of the target nucleic acid.

12. The method of claim 11, wherein the daughter strand, prior to cleavage of the at least one selectively cleavable bond, comprises a template-daughter strand duplex having the following structure:

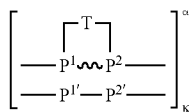

wherein
 T represents the tether;
 $P^1$ represents a first probe moiety;
 $P^2$ represents a second probe moiety;
 ~ represents the at least one selectively cleavable bond;
 $P^{1'}$ represents a contiguous nucleotide sequence of at least one nucleotide residue of the template strand to which $P^1$ is complementary;
 $P^{2'}$ represents a contiguous nucleotide sequence of at least one nucleotide residue of the template strand to which $P^2$ is complementary;
 $\kappa$ represents the $\kappa^{th}$ subunit in a chain of m subunits, where m is an integer greater than three; and
 $\alpha$ represents a species of a subunit motif selected from a library of subunit motifs, wherein each of the species is complementary to the contiguous nucleotide sequence of a portion of the target nucleic acid.

13. The method of claim 1, wherein the Xpandomer comprises the following structure:

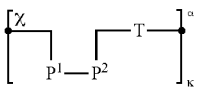

wherein
 T represents the tether;
 $P^1$ represents a first probe moiety;
 $P^2$ represents a second probe moiety;
 $\kappa$ represents the $\kappa^{th}$ subunit in a chain of m subunits, where m is an integer greater than three;
 $\alpha$ represents a species of a subunit motif selected from a library of subunit motifs, wherein each of the species comprises sequence information of the contiguous nucleotide sequence of a portion of the target nucleic acid; and
 $\chi$ represents a bond with the tether of an adjacent subunit.

14. The method of claim 13, wherein the daughter strand, prior to cleavage of the at least one selectively cleavable bond, comprises a template-daughter strand duplex having the following structure:

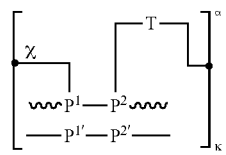

wherein
 T represents the tether;
 $P^1$ represents a first probe moiety;
 $P^2$ represents a second probe moiety;
 ~ represents the at least one selectively cleavable bond;
 $P^{1'}$ represents a contiguous nucleotide sequence of at least one nucleotide residue of the template strand to which $P^1$ is complementary;
 $P^{2'}$ represents a contiguous nucleotide sequence of at least one nucleotide residue of the template strand to which $P^2$ is complementary;
 $\kappa$ represents the $\kappa^{th}$ subunit in a chain of m subunits, where m is an integer greater than three;
 $\alpha$ represents a species of a subunit motif selected from a library of subunit motifs, wherein each of the species is complementary to the contiguous nucleotide sequence of a portion of the target nucleic acid; and
 $\chi$ represents a bond with the tether of an adjacent subunit.

15. The method of claim 1, wherein the Xpandomer comprises the following structure:

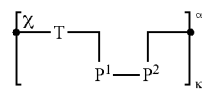

wherein
 T represents the tether;
 $P^1$ represents a first probe moiety;
 $P^2$ represents a second probe moiety;
 $\kappa$ represents the $\kappa^{th}$ subunit in a chain of m subunits, where m is an integer greater than three;
 $\alpha$ represents a species of a subunit motif selected from a library of subunit motifs, wherein each of the species comprises sequence information of the contiguous nucleotide sequence of a portion of the target nucleic acid; and
 $\chi$ represents a bond with the tether of an adjacent subunit.

16. The method of claim 15, wherein the daughter strand, prior to cleavage of the at least one selectively cleavable bond, comprises a template-daughter strand duplex having the following structure:

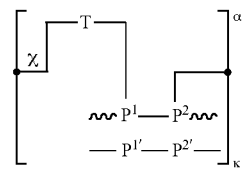

wherein
 T represents the tether;
 $P^1$ represents a first probe moiety;
 $P^2$ represents a second probe moiety;
 ~ represents the at least one selectively cleavable bond;
 $P^{1'}$ represents a contiguous nucleotide sequence of at least one nucleotide residue of the template strand to which $P^1$ is complementary;
 $P^{2'}$ represents a contiguous nucleotide sequence of at least one nucleotide residue of the template strand to which $P^2$ is complementary;
 $\kappa$ represents the $\kappa^{th}$ subunit in a chain of m subunits, where m is an integer greater than three;
 $\alpha$ represents a species of a subunit motif selected from a library of subunit motifs, wherein each of the species is complementary to the contiguous nucleotide sequence of a portion of the target nucleic acid; and
 $\chi$ represents a bond with the tether of an adjacent subunit.

17. The method of claim 1, wherein the Xpandomer comprises the following structure:

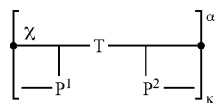

wherein
T represents the tether;
$P^1$ represents a first probe moiety;
$P^2$ represents a second probe moiety;
$\kappa$ represents the $\kappa^{th}$ subunit in a chain of m subunits, where m is an integer greater than three;
$\alpha$ represents a species of a subunit motif selected from a library of subunit motifs, wherein each of the species comprises sequence information of the contiguous nucleotide sequence of a portion of the target nucleic acid; and
$\chi$ represents a bond with the tether of an adjacent subunit.

18. The method of claim 17, wherein the daughter strand, prior to cleavage of the at least one selectively cleavable bond, comprises a template-daughter strand duplex having the following structure:

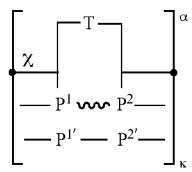

wherein
T represents the tether;
$P^1$ represents a first probe moiety;
$P^2$ represents a second probe moiety;
~ represents the at least one selectively cleavable bond;
$P^{1'}$ represents a contiguous nucleotide sequence of at least one nucleotide residue of the template strand to which $P^1$ is complementary;
$P^{2'}$ represents a contiguous nucleotide sequence of at least one nucleotide residue of the template strand to which $P^2$ is complementary;
$\kappa$ represents the $\kappa^{th}$ subunit in a chain of m subunits, where m is an integer greater than three;
$\alpha$ represents a species of a subunit motif selected from a library of subunit motifs, wherein each of the species is complementary to the contiguous nucleotide sequence of a portion of the target nucleic acid; and
$\chi$ represents a bond with the tether of an adjacent subunit.

19. The method of claim 1, wherein the Xpandomer comprises the following structure:

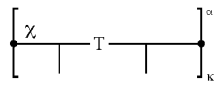

wherein
T represents the tether;
$\kappa$ represents the $\kappa^{th}$ subunit in a chain of m subunits, where m is an integer greater than three;
$\alpha$ represents a species of a subunit motif selected from a library of subunit motifs, wherein each of the species comprises sequence information of the contiguous nucleotide sequence of a portion of the target nucleic acid; and
$\chi$ represents a bond with the tether of an adjacent subunit.

20. The method of claim 19, wherein the daughter strand, prior to cleavage of the at least one selectively cleavable bond, comprises a template-daughter strand duplex having the following structure:

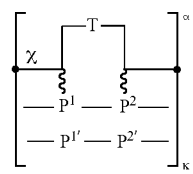

wherein
T represents the tether;
$P^1$ represents a first probe moiety;
$P^2$ represents a second probe moiety;
~ represents the at least one selectively cleavable bond;
$P^{1'}$ represents a contiguous nucleotide sequence of at least one nucleotide residue of the template strand to which $P^1$ is complementary;
$P^{2'}$ represents a contiguous nucleotide sequence of at least one nucleotide residue of the template strand to which $P^2$ is complementary;
$\kappa$ represents the $\kappa^{th}$ subunit in a chain of m subunits, where m is an integer greater than three;
$\alpha$ represents a species of a subunit motif selected from a library of subunit motifs, wherein each of the species is complementary to the contiguous nucleotide sequence of a portion of the target nucleic acid; and
$\chi$ represents a bond with the tether of an adjacent subunit.

21. The method of claim 1, wherein the Xpandomer comprises the following structure:

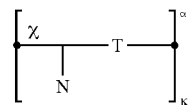

wherein
T represents the tether;
N represents a nucleobase residue;
$\kappa$ represents the $\kappa^{th}$ subunit in a chain of m subunits, where m is an integer greater than ten;
$\alpha$ represents a species of a subunit motif selected from a library of subunit motifs, wherein each of the species comprises sequence information of the contiguous nucleotide sequence of a portion of the target nucleic acid; and
$\chi$ represents a bond with the tether of an adjacent subunit.

22. The method of claim 21, wherein the daughter strand, prior to cleavage of the at least one selectively cleavable bond, comprises a template-daughter strand duplex having the following structure:

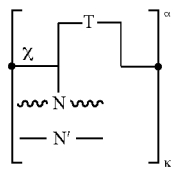

wherein
- T represents the tether;
- N represents a nucleobase residue;
- N' represents a nucleotide residue of the template strand to which N is complementary;
- ~ represents the at least one selectively cleavable bond;
- $\kappa$ represents the $\kappa^{th}$ subunit in a chain of m subunits, where m is an integer greater than ten;
- $\alpha$ represents a species of a subunit motif selected from a library of subunit motifs, wherein each of the species is complementary to the contiguous nucleotide sequence of a portion of the target nucleic acid; and
- $\chi$ represents a bond with the tether of an adjacent subunit.

23. The method of claim 1, wherein the Xpandomer comprises the following structure:

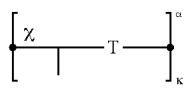

wherein
- T represents the tether;
- $\kappa$ represents the $\kappa^{th}$ subunit in a chain of m subunits, where m is an integer greater than ten;
- $\alpha$ represents a species of a subunit motif selected from a library of subunit motifs, wherein each of the species comprises sequence information of the contiguous nucleotide sequence of a portion of the target nucleic acid; and
- $\chi$ represents a bond with the tether of an adjacent subunit.

24. The method of claim 23, wherein the daughter strand, prior to cleavage of the at least one selectively cleavable bond, comprises a template-daughter strand duplex having the following structure:

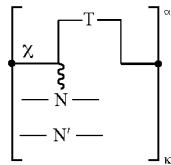

wherein
- T represents the tether;
- N represents a nucleobase residue;
- N' represents a nucleotide residue of the template strand to which N is complementary;
- ~ represents the at least one selectively cleavable bond;
- $\kappa$ represents the $\kappa^{th}$ subunit in a chain of m subunits, where m is an integer greater than ten;
- $\alpha$ represents a species of a subunit motif selected from a library of subunit motifs, wherein each of the species is complementary to the contiguous nucleotide sequence of a portion of the target nucleic acid; and
- $\chi$ represents a bond with the tether of an adjacent subunit.

25. The method of claim 1, wherein the Xpandomer comprises the following structure:

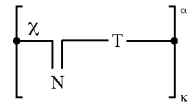

wherein
- T represents the tether;
- N represents a nucleobase residue;
- $\kappa$ represents the $\kappa^{th}$ subunit in a chain of m subunits, where m is an integer greater than ten;
- $\alpha$ represents a species of a subunit motif selected from a library of subunit motifs, wherein each of the species comprises sequence information of the contiguous nucleotide sequence of a portion of the target nucleic acid; and
- $\chi$ represents a bond with the tether of an adjacent subunit.

26. The method of claim 25, wherein the daughter strand, prior to cleavage of the at least one selectively cleavable bond, comprises a template-daughter strand duplex having the following structure:

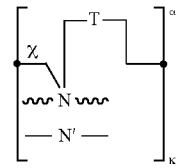

wherein
- T represents the tether;
- N represents a nucleobase residue;
- N' represents a nucleotide residue of the template strand to which N is complementary;
- ~ represents the at least one selectively cleavable bond;
- $\kappa$ represents the $\kappa^{th}$ subunit in a chain of m subunits, where m is an integer greater than ten;
- $\alpha$ represents a species of a subunit motif selected from a library of subunit motifs, wherein each of the species is complementary to the contiguous nucleotide sequence of a portion of the target nucleic acid; and
- $\chi$ represents a bond with the tether of an adjacent subunit.

27. The method of claim 1, wherein the Xpandomer comprises the following structure:

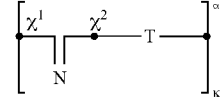

wherein
- T represents the tether;
- N represents a nucleobase residue;

κ represents the κ$^{th}$ subunit in a chain of m subunits, where m is an integer greater than ten;

α represents a species of a subunit motif selected from a library of subunit motifs, wherein each of the species comprises sequence information of the contiguous nucleotide sequence of a portion of the target nucleic acid;

$\chi^1$ represents a bond with the tether of an adjacent subunit; and $\chi^2$ represents an inter-tether bond.

28. The method of claim 27, wherein the daughter strand, prior to cleavage of the at least one selectively cleavable bond, is duplexed with a template strand to yield a duplex daughter strand having the following structure:

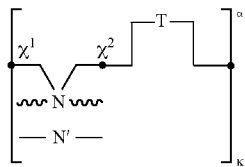

wherein
T represents the tether;
N represents a nucleobase residue;
N' represents a nucleotide residue of the template strand to which N is complementary;
~ represents the at least one selectively cleavable bond;
κ represents the κ$^{th}$ subunit in a chain of m subunits, where m is an integer greater than ten;
α represents a species of a subunit motif selected from a library of subunit motifs, wherein each of the species is complementary to the contiguous nucleotide sequence of a portion of the target nucleic acid;
$\chi^1$ represents a bond with the tether of an adjacent subunit; and
$\chi^2$ represents an inter-tether bond.

29. The method of claim 1, wherein the Xpandomer comprises the following structure:

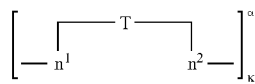

wherein
T represents the tether;
$n^1$ and $n^2$ represents a first portion and a second portion, respectively, of a nucleobase residue;
κ represents the κ$^{th}$ subunit in a chain of m subunits, where m is an integer greater than ten; and
α represents a species of a subunit motif selected from a library of subunit motifs, wherein each of the species comprises sequence information of the contiguous nucleotide sequence of a portion of the target nucleic acid.

30. The method of claim 29, wherein the daughter strand, prior to cleavage of the at least one selectively cleavable bond, is duplexed with a template strand to yield a duplex daughter strand having the following structure:

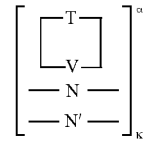

wherein
T represents the tether;
N represents a nucleobase residue;
N' represents a nucleotide residue of the template strand to which N is complementary;
V represents an internal cleavage site of the nucleobase residue;
κ represents the κ$^{th}$ subunit in a chain of m subunits, where m is an integer greater than ten; and
α represents a species of a subunit motif selected from a library of subunit motifs, wherein each of the species is complementary to the contiguous nucleotide sequence of a portion of the target nucleic acid.

\* \* \* \* \*

```
SEQUENCE LISTING

<160> NUMBER OF SEQ ID NOS: 6

<210> SEQ ID NO 1
<211> LENGTH: 12
<212> TYPE: DNA
<213> ORGANISM: Artificial Sequence
<220> FEATURE:
<223> OTHER INFORMATION: Three Xprobes encode entire contiguous sequence

<400> SEQUENCE: 1
actggccgaa at                                                           12

<210> SEQ ID NO 2
<211> LENGTH: 36
<212> TYPE: DNA
<213> ORGANISM: Artificial Sequence
<220> FEATURE:
<223> OTHER INFORMATION: Synthesized template sequence

<400> SEQUENCE: 2
tgtgtgtgtg tgtgtgtgtg atctaccgtc cgtccc                                 36

<210> SEQ ID NO 3
<211> LENGTH: 16
<212> TYPE: DNA
<213> ORGANISM: Artificial Sequence
<220> FEATURE:
<223> OTHER INFORMATION: Primer

<400> SEQUENCE: 3
gggacggacg gtagat                                                       16

<210> SEQ ID NO 4
<211> LENGTH: 32
<212> TYPE: DNA
<213> ORGANISM: Artificial Sequence
<220> FEATURE:
<223> OTHER INFORMATION: Synthesized template sequence

<400> SEQUENCE: 4
tctctctctc tctctcatct accgtccgtc cc                                     32

<210> SEQ ID NO 5
<211> LENGTH: 49
<212> TYPE: PRT
<213> ORGANISM: Artificial Sequence
```

```
<220> FEATURE:
<223> OTHER INFORMATION: Synthesized peptide on a solid support

<400> SEQUENCE: 5

Glu Cys Gly Ala Gly Ala Gly Ala Gly Ala Gly Ala Gly Ala Gly Ala
 1               5                  10                  15

Gly Ala Gly Ala Gly Ala Pro Ser Gly Ser Pro Ala Gly Ala Gly Ala
                20                  25                  30

Gly Ala Gly Ala Gly Ala Gly Ala Gly Ala Gly Ala Gly Ala Gly Cys
            35                  40                  45

Lys

<210> SEQ ID NO 6
<211> LENGTH: 36
<212> TYPE: DNA
<213> ORGANISM: Artificial Sequence
<220> FEATURE:
<223> OTHER INFORMATION: Synthesized template sequence

<400> SEQUENCE: 6
tttttttttt tttttttttt atctaccgtc cgtccc                              36
```